United States Patent [19]
Abood et al.

[11] Patent Number: 5,985,872
[45] Date of Patent: *Nov. 16, 1999

[54] 2-AMINO-BENZOXAZINONES FOR THE TREATMENT OF VIRAL INFECTIONS

[75] Inventors: Norman Anthony Abood, Morton Grove; Daniel L. Flynn, Libertyville; Daniel P. Becker, Glenview; Brian M. Bax, St. Charles; Hui Li, Skokie; Roger A. Nosal, Buffalo Grove; Lori A Schretzman, Gurnee; Clara I Villamil, Glenview, all of Ill.

[73] Assignee: G.D. Searle & Co., Chicago, Ill.

[*] Notice: This patent issued on a continued prosecution application filed under 37 CFR 1.53(d), and is subject to the twenty year patent term provisions of 35 U.S.C. 154(a)(2).

[21] Appl. No.: 08/448,795

[22] Filed: May 24, 1995

[51] Int. Cl.$^6$ ............ A61K 31/535; C07D 265/22
[52] U.S. Cl. .................... 514/230.5; 544/92
[58] Field of Search ............. 544/92; 514/230.5

[56] References Cited

U.S. PATENT DOCUMENTS

| | | | |
|---|---|---|---|
| 3,341,592 | 9/1967 | Sternbach et al. | 564/328 |
| 3,450,700 | 6/1969 | Sayigh et al. | 544/73 |
| 4,657,893 | 4/1987 | Krantz et al. | 514/18 |
| 4,745,116 | 5/1988 | Krantz et al. | 514/230.5 |
| 4,980,287 | 12/1990 | Kokubo et al. | 435/184 |
| 5,428,021 | 6/1995 | Hiebert et al. | 514/18 |
| 5,652,237 | 7/1997 | Augelli-Szafran et al. | 514/230.5 |

FOREIGN PATENT DOCUMENTS

| | | |
|---|---|---|
| 147211 | 7/1985 | European Pat. Off. . |
| 206323 | 12/1985 | European Pat. Off. . |
| 0317645 | 5/1989 | European Pat. Off. . |
| 466944 | 2/1992 | European Pat. Off. . |
| 514830 | 11/1992 | European Pat. Off. . |
| 2218302 | 4/1972 | Germany . |
| 2315303 | 3/1973 | Germany . |
| 91/12245 | 8/1991 | WIPO . |
| 92/18488 | 10/1992 | WIPO . |
| 93/01291 | 1/1993 | WIPO . |
| 96-07648 | 3/1996 | WIPO . |

OTHER PUBLICATIONS

Ljungman et al, *J. Infect. Dis.*, 162, 244 (1990).
Gately et al, *J. Infect. Dis.*, 161, 711 (1990).
Lui and Roizman, *J. Virol.*, 65, 5149 (1991).
A.R. Welch et al, *Proc. Natl. Acad. Sci. USA*, 88, 10792 (1991).
Teshima et al, *J. Biol. Chem.*, 257, 5085–5091 (1982).
Moorman and Abeles, *J. Amer. Chem. Soc.*, 104, 6785–86 (1982).
R. Stein et al, *Biochemistry*, 26, 4126–30 (1987).
A. Krantz et al, *J. Med. Chem.*, 33, 464–79 (1990).
Uejima et al, *J. Pharm. Exp. Ther.*, 265, 516–22 (1993).
F.L.M. Alvarez, *An. Quim.*, 79, 115–17 (1983).
J.G. Tercero et al, *An. Quim.*, 83, 247–50 (1987).
I. Butula et al, *Croat. Chem. Acta*, 54, 105–08 (1981).
H. Ulrich et al, *J. Org. Chem.*, 32, 4052–53 (1967).
E. Papadopoulos, *J. Heterocyclic. Chem.*, 21, 1411–14 (1984).
M. Badawy et al, *J. Heterocyclic. Chem.*, 21, 1403–04 (1984).
R. Khan and R. Rastogi, *J. Chem. Res.* (S), 342–43 (1992).
Von Dr. H. Herlinger, *Angew. Chem.*, 10:437 (1964).
Kurihara et al, *Tet. Lett.*, 30:2597–2606 (1965).
Sheehan et al, *J. Org. Chem.*, 3599–3601, (1964).
David J. Le Count, *J. Chem. Soc.*, 813–16 (1983).
Kurihara et al, *Bul. Chem. Soc. Japan*, 39:1942–48 (1966).
Krantz et al, STN printout of abstracts for EP–147,211 (1985) and U.S. 4,657,893 (1987).

*Primary Examiner*—Richard L. Raymond
*Attorney, Agent, or Firm*—Joseph W. Bulock

[57] ABSTRACT

A class of compounds for the treatment of viral infections. Compounds of particular interest are defined by Formula II

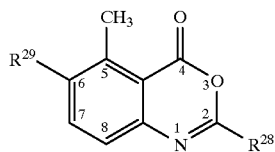

II wherein $R^{28}$ is selected from (a) amino substituted with one or two radicals selected from alkyl, aralkyl, heterocycoalkyl, heterocyclo, and aryl, and (b) amino acid residues and derivatives thereof; wherein $R^{29}$ is selected from hydrido, alkyl, halo,

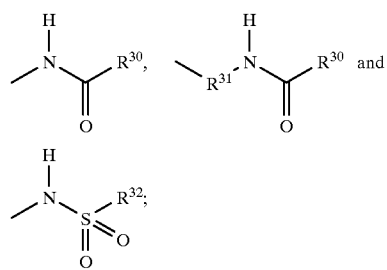

wherein $R^{30}$ is selected from alkyl, alkoxy, alkylamino, carboxyalkyl, alkoxyalkyl, alkylaminoalkyl, cycloalkyl, heterocyclo, heterocycloalkyl, heterocycloalkoxy, alkylaminoalkoxy, alkylaminoalkylamino, heterocycloalkylamino, and N-aralkylamino; wherein $R^{31}$ is alkyl; wherein $R^{32}$ is alkyl and aryl; or a pharmaceutically-acceptable salt thereof.

31 Claims, No Drawings

2-AMINO-BENZOXAZINONES FOR THE TREATMENT OF VIRAL INFECTIONS

FIELD OF THE INVENTION

This invention is in the field of antiviral agents and specifically relates to compounds, compositions and methods for treating herpes-related disorders.

BACKGROUND OF THE INVENTION

There is a great need for new therapies active in the treatment of viral diseases. Whereas there has been great progress in developing a variety of therapies for the treatment of bacterial infections, there are few viable therapies for the treatment of viruses. Zidovudine is the primary approved treatment for human immunodeficiency virus. Ganciclovir, acyclovir and foscarnet are currently utilized for the treatment of herpesvirus infections. However, these therapies can have substantial side effects based on their deleterious effects on host cell DNA replication or effect of a limited number of viral infections. In addition, viruses are known to develop resistance to therapies which causes a progressive decline in efficacy [Ljungman et al., *J. Infect. Dis.*, 162, 244 (1990) and Gately et al, *J. Infect. Dis.*, 161, 711 (1990)].

Viruses are classified into broad categories based on whether they incorporate RNA or DNA. Important virus families classified of RNA type include orthomyxoviridae, paramyxoviridae, picornaviridae, rhabdoviridae, coronaviridae, togaviridae, bunyaviridae, arenaviridae and retroviridae. Important virus families classified of DNA type include adenoviridae, poxviridae, papovaviridae and herpesviridae.

Herpesviridae is a family of DNA viruses which include herpes simplex virus type-1 (HSV-1), herpes simplex virus type-2 (HSV-2), cytomegalovirus (CMV), varicella-zoster virus (VZV), Epstein-Barr virus, human herpesvirus-6 (HHV6), human herpesvirus-7 (HHV7), human herpesvirus-8 (HHV8), pseudorabies and rhinotracheitis, among others.

It is known that herpesviruses express their genetic content by directing the synthesis of a number of proteins encoded by the herpesvirus DNA in the host cell. One of the important virus encoded proteins is made as a precursor consisting of an amino terminal-located protease and carboxyl terminal-located assembly protein. This precursor is proteolytically processed in an autocatalytic manner at a specific amino acid sequence known as the "release" site yielding separate protease and assembly protein. The assembly protein is cleaved further by the protease at another specific amino acid sequence known as the "maturation" cleavage site. Recently, EP No. 514,830, published Nov. 25, 1992, describes a virus-specific serine protease which has a role in herpesvirus replication. Additionally, Lui and Roizman [*J. Virol*, 65, 5149 (1991)] describe the sequence and activity of a protease and the associated assembly protein encoded by $U_L 26$ of HSV-1. A. R. Welch et al. [*Proc. Natl. Acad. Sci. USA*, 88, 10792 (1991) and WO93/01291, published Jan. 21, 1993] describe the related protease (also known as assemblin) and assembly protein encoded by $U_L 80$ of CMV. An approach currently being investigated for potential use in the treatment of herpesvirus infections is the development of inhibitors of herpesvirus proteases.

4H-3,1-Benzoxazinones have been described in the literature as having serine protease activity, among others. While compounds of this type have been reported to have serine protease inhibitory activity, none have been reported to inhibit viral assemblin protease. For example Teshima et al. [*J. Biol. Chem.*, 257, 5085–5091 (1982)] describe various 2-alkyl-4H-3,1-benzoxazin-4-ones as enzyme inhibitors. Moorman and Abeles [*J. Amer. Chem. Soc.*, 104, 6785–6786 (1982)] describe 4H-3,1-benzoxazin-2,4-dione as having some enzyme inhibitory activity. R. Stein, et al. [*Biochemistry*, 26, 4126–4130, (1987)] describe 2-alkyl-4H-benzoxazin-4-ones, with further substitution at the 5, 6 and 7 positions, as inhibiting the elastase enzyme. WO publication 92/18488 (published Oct. 29, 1992) describes 2-alkyl-4H-3,1-benzoxazin-4-ones with substitution at the 5 and 7 positions as selective inhibitors of elastase. European Application 206,323 (published Dec. 30, 1985) describes 2-alkoxy-, 2-aryloxy- and 2-aralkoxy-4H-3,1-benzoxazin-4-ones, having substitution at the 5, 6, 7, and 8 positions, as enzyme inhibitors. U.S. Pat. No. 4,745,116, to A. Kranz et al. claims 2-alkoxy, 2-aryloxy- and 2-aralkoxy-4H-3,1-benzoxazin-4-ones, having further substitution at the 5, 7 and 8 positions, as enzyme inhibitors.

2-Amino-4H-3,1-benzoxazinones have been described. A. Krantz et al. [*J. Med. Chem.*, 33, 464–479 (1990)] describe 4H-3,1-benzoxazin-4-ones substituted with alkyl, alkylamino, alkoxy and alkylthio substituents at the 2-position, and with further substitution at the 5, 6 and 7 positions, as elastase inhibitors. Uejima, et al. [*J. Pharm. Exp. Ther.*, 265, 516–522 (1993)] describe 2-alkylamino-5-methyl-7-acylamino-4H-3.1-benzoxazin-4-ones as highly selective elastase inhibitors with significant plasma stability. U.S. Pat. No. 4,657,893, to A. Krantz et al, describes 2-alkylamino- and 2-alkylurido-4H-3,1-benzoxazin-4-ones having further substitution at the 5, 7 and 8 positions, as enzyme inhibitors.

F. L. M. Alvarez [*An. Quim.*, 79, 115–17 (1983)] describes the preparation of 2-sulfonylamino-4H-3,1-benzoxazinones. J. G. Tercero et al. [*An. Quim.*, 83, 247–50 (1987)] describe the preparation of 2-arylsulfonylamino-4H-3,1-benzoxazinones.

I. Butula et al. [*Croat. Chem. Acta*, 54, 105–8 (1981)] describe the synthesis of 2-alkylamino-4H-3,1-benzoxazinones. H. Ulrich et al. [*J. Org Chem.*, 32, 4052–53 (1967)] describe the synthesis of 2-alkylamino-4H-3,1-benzoxazinones. E. Papadopoulos [*J. Heterocyclic. Chem.*, 21, 1411–14 (1984)] describes the use of 2-haloalkylamino-4H-3,1-benzoxazin-4-one as a starting material for the synthesis of phenylureas. European Patent Application 466,944 (published Jan. 22, 1992) describes 2-alkylamino-7-acylamino-5-alkyl-4H-benzoxazin-4-ones as selective enzyme inhibitors of elastase.

M. Badawy et al. [*J. Heterocyclic. Chem.*, 21, 1403–4 (1984)] describe the use of N-phenyl-2-amino-4H-3,1-benzoxazin-4-one as a starting material for the synthesis of quinazolines. R. Khan and R. Rastogi [*J. Chem. Research (S)*, 342–43 (1992)] describe the synthesis of 2-[5-aryl-1,3,4-oxadiazol-2-yl]amino-4H-3,1-benzoxazin-4-ones.

4H-3,1-Benzoxazin-4-ones have not previously been described as selective assemblin protease inhibitors or for the treatment and/or prophylaxis of viral infection.

DESCRIPTION OF THE INVENTION

The present invention relates to a class of substituted benzoxazinones, useful in the therapeutic and prophylactic treatment of viral infections, as defined by Formula I:

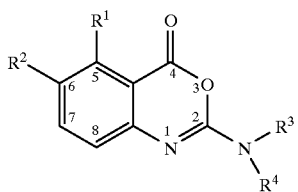

wherein R¹ is a substituent selected from hydrido, halo, alkoxy, and alkyl;

wherein R² is a substituent selected from hydrido, halo, alkyl,

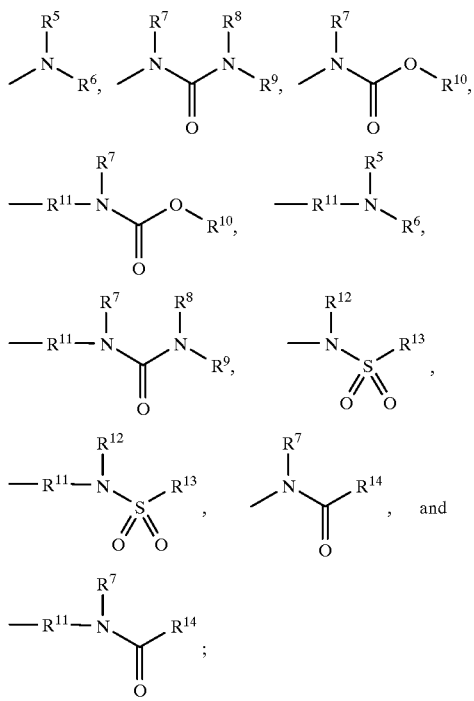

wherein R³ is selected from hydrido, alkyl, alkylaminoalkyl, aralkyl, and heterocycloalkyl;

wherein R⁴ is selected from hydrido, alkyl, cycloalkyl, cycloalkylalkyl, aryl, heterocyclo, aralkyl, heterocycloalkyl,

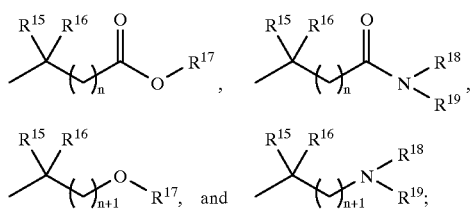

or wherein —NR³R⁴ form a heterocyclic ring of 5 to 7 members;

wherein n is 0–6, inclusive;

wherein R⁵ and R⁶ are independently selected from hydrido, alkyl, cycloalkyl, cycloalkylalkyl, aryl, aralkyl, heterocyclo, heterocycloalkyl, alkylaminoalkyl, aralkylaminoalkyl, alkoxyalkyl, and aralkoxyalkyl; or wherein —NR⁵R⁶ form a heterocyclic ring of 5 to 7 members;

wherein R⁷, R¹² and R²³ are independently selected from hydrido, alkyl, and aralkyl;

wherein R⁸, R⁹ and R¹⁴ are independently selected from hydrido, alkyl, cycloalkyl, cycloalkylalkyl, haloalkyl, aminoalkyl, alkylaminoalkyl, carboxyalkyl, aminocarbonylalkyl, alkylaminocarbonylalkyl, hydroxyalkyl, alkoxyalkyl, aralkoxyalkyl, alkylsulfonylalkyl, alkylsulfinylalkyl, alkylthioalkyl, aryl, aralkyl, heterocyclo, and heterocycloalkyl; or wherein —NR⁸R⁹ form a heterocyclic ring of 5 to 7 members;

wherein R¹⁰ is selected from alkyl, haloalkyl, alkylaminoalkyl, carboxyalkyl, aminocarbonylalkyl, alkylaminocarbonylalkyl, aralkoxyalkyl, alkoxyalkyl, cycloalkyl, cycloalkylalkyl, alkylsulfonylalkyl, alkylsulfinylalkyl, alkylthioalkyl, aryl, aralkyl, heterocyclo, and heterocycloalkyl;

wherein R¹¹ is alkyl;

wherein R¹³ is selected from amino, alkyl, alkylamino, alkylaminoalkyl and aryl;

wherein R¹⁵ is selected from hydrido, alkyl, hydroxyalkyl, alkoxyalkyl, aralkoxyalkyl, alkylaminoalkyl and N-aryl-N-alkylaminoalkyl;

wherein R¹⁶ is selected from hydrido, alkyl, cycloalkyl, cycloalkylalkyl, haloalkyl, guanidinylalkyl, carboxyalkyl, hydroxyalkyl, alkoxyalkyl, aralkoxyalkyl, alkylthioalkyl, alkylsulfinylalkyl, alkylsulfonylalkyl, aryl, heterocyclo, aralkyl, heterocycloalkyl,

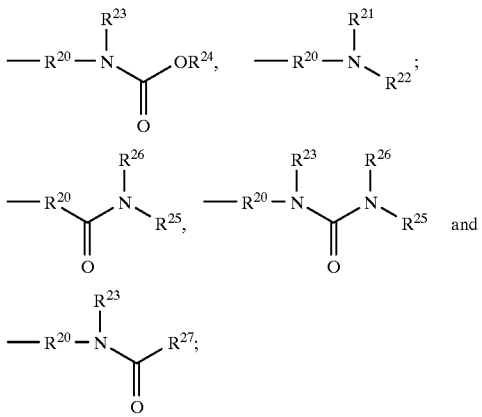

or wherein R¹⁵ and R¹⁶ together form cycloalkyl or heterocyclo;

wherein R¹⁷ is selected from hydrido, alkyl, cycloalkyl and aralkyl;

wherein R¹⁸ and R¹⁹ are independently selected from hydrido, alkyl, alkenyl, cycloalkyl, cycloalkylalkyl, aryl, heterocyclo, aralkyl, heterocycloalkyl, alkylaminoalkyl, and heterocycloalkyl; or wherein —NR¹⁸R¹⁹ together form a heterocyclic ring of 5 to 7 atoms;

or wherein R¹⁶ and R¹⁸ together form a saturated or partially unsaturated ring of 5 to 7 atoms;

wherein R²⁰ is alkyl;

wherein R²¹, R²², R²⁵, and R²⁶ are independently selected from hydrido, alkyl, cycloalkyl, cycloalkylalkyl, aminoalkyl, alkylaminoalkyl, hydroxyalkyl, alkoxyalkyl, aryl, heterocyclo, aralkyl, heterocycloalkyl; or wherein —NR²¹R²² together form a heterocyclic ring of 5 to 7 atoms; or wherein —NR²⁵R²⁶ together form a heterocyclic ring of 5 to 7 atoms;

wherein R²⁴ is selected from alkyl, cycloalkyl, cycloalkylalkyl, alkylaminoalkyl, aralkoxyalkyl, alkoxyalkyl, aryl, aralkyl, heterocyclo, and heterocycloalkyl; and wherein R²⁷ is selected from hydrido, alkyl, cycloalkyl, cycloalkylalkyl, alkylaminoalkyl, aminoalkyl, carboxyalkyl, aminocarbonylalkyl, hydroxyalkyl, aralkoxyalkyl, alkoxyalkyl, aryl, aralkyl, heterocyclo, and heterocycloalkyl;

provided R³ and R⁴ do not form benzotriazolyl when R² is hydrido and when R¹ is methyl; further provided R² is not methyl when R¹ is methyl and when R³ is benzyl or lower alkyl; further provided R² is not halo or methyl when R¹ is hydrido and when R³ is benzyl or lower alkyl; and further provided R² is not hydrido when R³ is lower alkyl or leucine methyl ester;

or a pharmaceutically-acceptable salt or tautomer thereof.

The compounds of this invention have been shown to be particularly effective against herpetoviridae. Thus they are particularly useful for the treatment of herpes simplex viruses (HSV-1, HSV-2), cytomegalovirus (CMV), herpes varicella-zoster, Epstein-Barr, HHV6, HHV7, pseudorabies and rhinotracheitis, among others.

The invention further involves a method of treating a subject having a viral infection with an effective amount of a compound which can inhibit a virus-specific protease. Preferably, the subject is treated with a herpesvirus protease inhibitor. More preferred is a method wherein the viral protease inhibitor is a CMV protease inhibitor or an HSV protease inhibitor. Even more preferred is a method wherein the subject is treated with an inhibitor of CMV protease, encoded by $U_L80$, HSV-1 protease or HSV-2 protease encoded by $U_L26$, such as the 4H-3,1-benzoxazin-4-one compounds of the present invention.

The phrase "further provided", as used in the above description, is intended to mean that the denoted proviso is not to be considered conjunctive with any of the other provisos.

A preferred class of compounds consists of those compounds of Formula I wherein R¹ is a substituent selected from hydrido, halo, lower alkoxy, and lower alkyl; wherein R² is a substituent selected from hydrido, halo, lower alkyl,

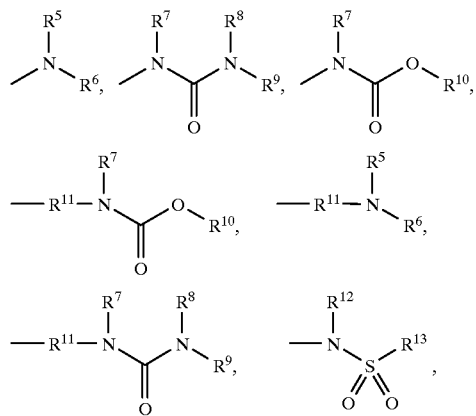

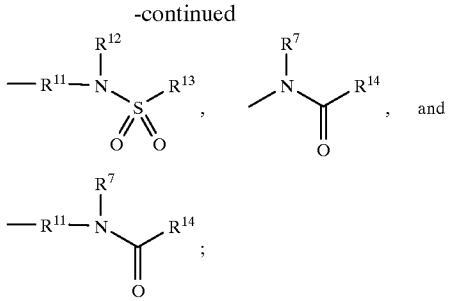

-continued

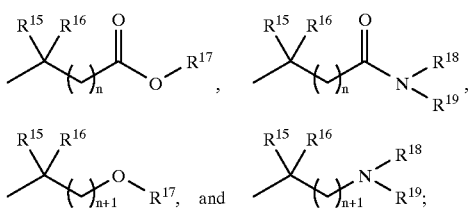

wherein R³ is selected from hydrido, lower alkyl, lower alkylaminoalkyl, lower aralkyl, and lower heterocycloalkyl; wherein R⁴ is selected from hydrido, lower alkyl, lower cycloalkyl, lower cycloalkylalkyl, aryl, heterocyclo, lower aralkyl, lower heterocycloalkyl, or wherein —NR³R⁴ form a heterocyclic ring of 5 to 7 members; wherein n is 0–6, inclusive; wherein R⁵ and R⁶ are independently selected from hydrido, lower alkyl, lower cycloalkyl, lower cycloalkylalkyl, aryl, lower aralkyl, heterocyclo, lower heterocycloalkyl, lower alkylaminoalkyl, lower aralkylaminoalkyl, lower alkoxyalkyl, and lower aralkoxyalkyl; or wherein —NR⁵R⁶ form a heterocyclic ring of 5 to 7 members; wherein R⁷, R¹² and R²³ are independently selected from hydrido, lower alkyl, and lower aralkyl; wherein R⁸, R⁹ and R¹⁴ are independently selected from hydrido, lower alkyl, lower cycloalkyl, lower cycloalkylalkyl, lower haloalkyl, lower aminoalkyl, lower alkylaminoalkyl, lower carboxyalkyl, lower aminocarbonylalkyl, lower alkylaminocarbonylalkyl, lower hydroxyalkyl, lower alkoxyalkyl, lower aralkoxyalkyl, lower alkylsulfonylalkyl, lower alkylsulfinylalkyl, lower alkylthioalkyl, aryl, lower aralkyl, heterocyclo, and lower heterocycloalkyl; or wherein —NR⁸R⁹ form a heterocyclic ring of 5 to 7 members; wherein R¹⁰ is selected from lower alkyl, lower haloalkyl, lower alkylaminoalkyl, lower carboxyalkyl, lower aminocarbonylalkyl, lower alkylaminocarbonylalkyl, lower aralkoxyalkyl, lower alkoxyalkyl, lower cycloalkyl, lower cycloalkylalkyl, lower alkylsulfonylalkyl, lower alkylsulfinylalkyl, lower alkylthioalkyl, aryl, lower aralkyl, heterocyclo, and lower heterocycloalkyl; wherein R¹¹ is lower alkyl; wherein R¹³ is selected from amino, lower alkyl, lower alkylamino, lower alkylaminoalkyl and aryl; wherein R¹⁵ is selected from hydrido, lower alkyl, lower hydroxyalkyl, lower alkoxyalkyl, lower aralkoxyalkyl, lower alkylaminoalkyl and lower N-aryl-N-alkylaminoalkyl; wherein R¹⁶ is selected from hydrido, lower alkyl, lower cycloalkyl, lower cycloalkylalkyl, lower haloalkyl, lower guanidinylalkyl, lower carboxyalkyl, lower hydroxyalkyl, lower alkoxyalkyl, lower aralkoxyalkyl, lower alkylthioalkyl, lower alkylsulfinylalkyl, lower alkylsulfonylalkyl, aryl, lower heterocyclo, lower aralkyl, lower heterocycloalkyl,

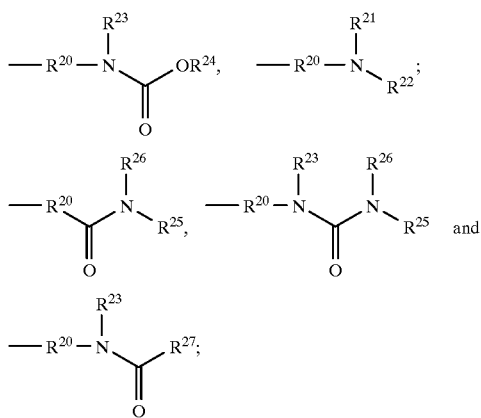

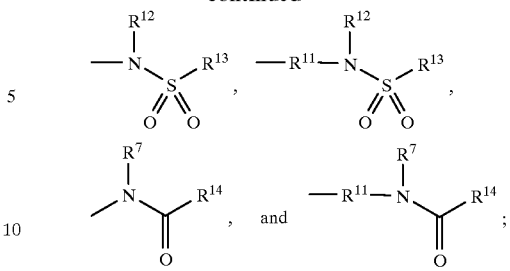

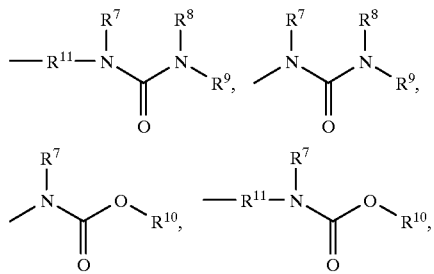

or wherein $R^{15}$ and $R^{16}$ together form cycloalkyl or heterocyclo; wherein $R^{17}$ is selected from hydrido, lower alkyl, lower cycloalkyl and lower aralkyl; wherein $R^{18}$ and $R^{19}$ are independently selected from hydrido, lower alkyl, lower alkenyl, lower cycloalkyl, lower cycloalkylalkyl, aryl, heterocyclo, lower aralkyl, lower heterocycloalkyl, lower alkylaminoalkyl, and lower heterocycloalkyl; or wherein —$NR^{18}R^{19}$ together form a heterocyclic ring of 5 to 7 atoms; or wherein $R^{16}$ and $R^{18}$ together form a saturated or partially unsaturated ring of 5 to 7 atoms; wherein $R^{20}$ is lower alkyl; wherein $R^{21}$, $R^{22}$, $R^{25}$, and $R^{26}$ are independently selected from hydrido, lower alkyl, lower cycloalkyl, lower cycloalkylalkyl, lower aminoalkyl, lower alkylaminoalkyl, lower hydroxyalkyl, lower alkoxyalkyl, lower, aryl, heterocyclo, lower aralkyl, lower heterocycloalkyl; or wherein —$NR^{21}R^{22}$ together form a heterocyclic ring of 5 to 7 atoms; or wherein —$NR^{25}R^{26}$ together form a heterocyclic ring of 5 to 7 atoms; wherein $R^{24}$ is selected from lower alkyl, lower cycloalkyl, lower cycloalkylalkyl, lower alkylaminoalkyl, lower aralkoxyalkyl, lower alkoxyalkyl, aryl, lower aralkyl, heterocyclo, and lower heterocycloalkyl; and wherein $R^{27}$ is selected from hydrido, lower alkyl, lower cycloalkyl, lower cycloalkylalkyl, lower alkylaminoalkyl, lower aminoalkyl, lower carboxyalkyl, lower aminocarbonylalkyl, lower hydroxyalkyl, lower aralkoxyalkyl, lower alkoxyalkyl, aryl, lower aralkyl, heterocyclo, and lower heterocycloalkyl; or a pharmaceutically-acceptable salt or tautomer thereof.

A more preferred class of compounds consists of those compounds of Formula I wherein $R^1$ is a substituent selected from hydrido, lower alkoxy and lower alkyl; wherein $R^2$ is a substituent selected from hydrido, halo, lower alkyl, wherein $R^3$ is selected from hydrido, lower alkyl, lower alkylaminoalkyl, lower aralkyl, and lower heterocycloalkyl; wherein $R^4$ is selected from hydrido, lower alkyl, lower cycloalkyl, lower cycloalkylalkyl, aryl, heterocyclo, lower aralkyl, lower heterocycloalkyl,

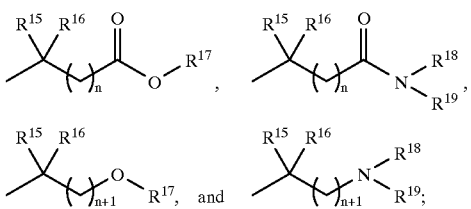

or wherein —$NR^3R^4$ form a heterocyclic ring of 5 to 7 members; wherein n is 0–6, inclusive; wherein $R^5$ and $R^6$ are independently selected from hydrido, lower alkyl, lower cycloalkyl, lower cycloalkylalkyl, aryl, lower aralkyl, heterocyclo, lower heterocycloalkyl, lower alkylaminoalkyl, lower aralkylaminoalkyl, lower alkoxyalkyl, and lower aralkoxyalkyl; or wherein —$NR^5R^6$ form a heterocyclic ring of 5 to 7 members; wherein $R^7$, $R^{12}$ and $R^{23}$ are independently selected from hydrido, lower alkyl and lower aralkyl; wherein $R^8$, $R^9$ and $R^{14}$ are independently selected from hydrido, lower alkyl, lower cycloalkyl, lower cycloalkylalkyl, lower haloalkyl, lower aminoalkyl, lower alkylaminoalkyl, lower carboxyalkyl, lower aminocarbonylalkyl, lower alkylaminocarbonylalkyl, lower hydroxyalkyl, lower alkoxyalkyl, lower aralkoxyalkyl, lower alkylsulfonylalkyl, lower alkylsulfinylalkyl, lower alkylthioalkyl, aryl, lower aralkyl, heterocyclo, and lower heterocycloalkyl; or wherein —$NR^8R^9$ form a heterocyclic ring of 5 to 7 members; wherein $R^{10}$ is selected from lower alkyl, lower haloalkyl, lower alkylaminoalkyl, lower carboxyalkyl, lower aminocarbonylalkyl, alkylaminocarbonylalkyl, lower aralkoxyalkyl, lower alkoxyalkyl, lower cycloalkyl, lower cycloalkylalkyl, lower alkylsulfonylalkyl, lower alkylsulfinylalkyl, lower alkylthioalkyl, aryl, lower aralkyl, heterocyclo, and lower heterocycloalkyl; wherein $R^{11}$ is lower alkyl; wherein $R^{13}$ is selected from amino, lower alkyl, lower alkylamino, lower alkylaminoalkyl and aryl; wherein $R^{15}$ is selected from hydrido, and lower alkyl; wherein $R^{16}$ is selected from hydrido, lower alkyl, lower cycloalkyl, lower cycloalkylalkyl, lower haloalkyl, lower guanidinylalkyl, lower carboxyalkyl, lower hydroxyalkyl, lower alkoxyalkyl, lower aralkoxyalkyl, lower alkylthioalkyl, lower alkylsulfinylalkyl, lower alkylsulfonylalkyl, aryl, heterocyclo, lower aralkyl, lower heterocycloalkyl,

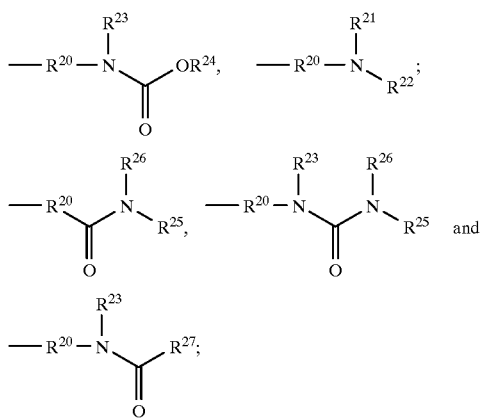

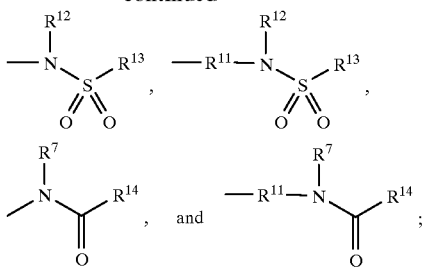

wherein $R^3$ is selected from hydrido, lower alkyl, and lower aralkyl; wherein $R^4$ is selected from

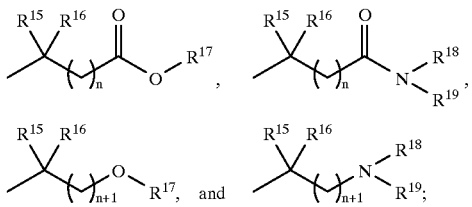

or wherein —$NR^3R^4$ form a heterocyclic ring of 5 to 7 members; wherein n is 0–5, inclusive; wherein $R^5$ and $R^6$ are independently selected from hydrido, lower alkyl, lower cycloalkyl, lower cycloalkylalkyl, aryl, lower aralkyl, heterocyclo, lower heterocycloalkyl, lower alkylaminoalkyl, lower aralkylaminoalkyl, lower alkoxyalkyl, and lower aralkoxyalkyl; or wherein —$NR^5R^6$ form a heterocyclic ring of 5 to 7 members; wherein $R^7$, $R^{12}$ and $R^{23}$ are independently selected from hydrido, lower alkyl and lower aralkyl; wherein $R^8$, $R^9$ and $R^{14}$ are independently selected from hydridon lower alkyl, lower cycloalkyl, lower cycloalkylalkyl, lower haloalkyl, lower aminoalkyl, lower alkylaminoalkyl, lower carboxyalkyl, lower aminocarbonylalkyl, lower alkylaminocarbonylalkyl, lower hydroxyalkyl, lower alkoxyalkyl, lower aralkoxyalkyl, lower alkylsulfonylalkyl, lower alkylsulfinylalkyl, lower alkylthioalkyl, aryl, lower aralkyl, heterocyclo, and lower heterocycloalkyl; or wherein —$NR^8R^9$ form a heterocyclic ring of 5 to 7 members; wherein $R^{10}$ is selected from lower alkyl, lower haloalkyl, lower alkylaminoalkyl, lower carboxyalkyl, lower aminocarbonylalkyl, alkylaminocarbonylalkyl, lower aralkoxyalkyl, lower alkoxyalkyl, lower cycloalkyl, lower cycloalkylalkyl, lower alkylsulfonylalkyl, lower alkylsulfinylalkyl, lower alkylthioalkyl, aryl, lower aralkyl, heterocyclo, and lower heterocycloalkyl; wherein $R^{11}$ is lower alkyl; wherein $R^{13}$ is selected from amino, lower alkyl, lower alkylamino, lower alkylaminoalkyl and aryl; wherein $R^{15}$ is selected from hydrido, and lower alkyl; wherein $R^{16}$ is selected from hydrido, lower alkyl, lower cycloalkyl, lower cycloalkylalkyl, lower haloalkyl, lower guanidinylalkyl, lower carboxyalkyl, lower hydroxyalkyl, lower alkoxyalkyl, lower aralkoxyalkyl, lower alkylthioalkyl, lower alkylsulfinylalkyl, lower alkylsulfonylalkyl, aryl, heterocyclo, lower aralkyl, lower heterocycloalkyl, or wherein $R^{15}$ and $R^{16}$ together form lower cycloalkyl or heterocyclo; wherein $R^{17}$ is selected from hydrido, lower alkyl, lower cycloalkyl and lower aralkyl; wherein $R^{18}$ and $R^{19}$ are independently selected from hydrido, lower alkyl, lower alkenyl, lower cycloalkyl, lower cycloalkylalkyl, aryl, heterocyclo, lower aralkyl, lower heterocycloalkyl, lower alkylaminoalkyl, and lower heterocycloalkyl; or wherein —$NR^{18}R^{19}$ together form a saturated, partially unsaturated or unsaturated ring of 5 to 7 atoms; or wherein $R^{16}$ and $R^{18}$ together form a saturated or partially unsaturated ring of 5 to 7 atoms; wherein $R^{20}$ is lower alkyl; wherein $R^{21}$, $R^{22}$, $R^{25}$, and $R^{26}$ are independently selected from hydrido, lower alkyl, lower cycloalkyl, lower cycloalkylalkyl, lower aminoalkyl, lower alkylaminoalkyl, lower hydroxyalkyl, lower alkoxyalkyl, lower, aryl, heterocyclo, lower aralkyl, lower heterocycloalkyl; or wherein —$NR^{21}R^{22}$ together form a heterocyclic ring of 5 to 7 atoms; or wherein —$NR^{25}R^{26}$ together form a heterocyclic ring of 5 to 7 atoms; wherein $R^{24}$ is selected from lower alkyl, lower cycloalkyl, lower cycloalkylalkyl, lower alkylaminoalkyl, lower aralkoxyalkyl, lower alkoxyalkyl, aryl, lower aralkyl, heterocyclo, and lower heterocycloalkyl; and wherein $R^{27}$ is selected from hydrido, lower alkyl, lower cycloalkyl, lower cycloalkylalkyl, lower alkylaminoalkyl, lower aminoalkyl, lower carboxyalkyl, lower aminocarbonylalkyl, lower hydroxyalkyl, lower aralkoxyalkyl, lower alkoxyalkyl, aryl, lower aralkyl, heterocyclo, and lower heterocycloalkyl; or a pharmaceutically-acceptable salt or tautomer thereof.

An even more preferred class of compounds consists of those compounds of Formula I wherein $R^1$ is a substituent selected from hydrido, lower alkoxy and lower alkyl; wherein $R^2$ is a substituent selected from hydrido, halo, lower alkyl,

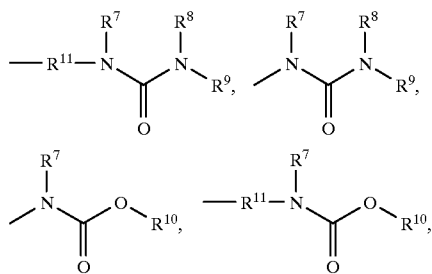

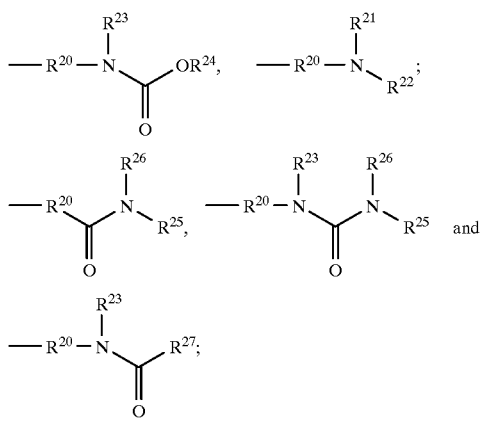

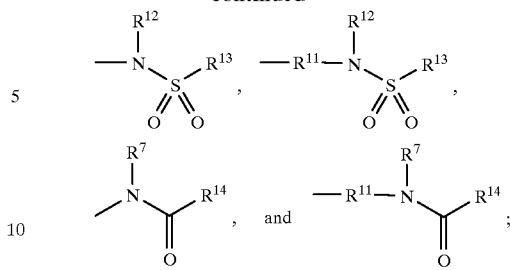

-continued

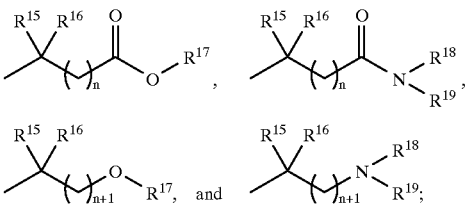

wherein $R^3$ is selected from hydrido, methyl, ethyl, n-propyl, isopropyl, n-butyl, isobutyl, sec-butyl, tert-butyl, pentyl, hexyl, benzyl, phenylethyl and diphenylmethyl; wherein $R^4$ is selected from or wherein $R^{15}$ and $R^{16}$ together form lower cycloalkyl or heterocyclo; wherein $R^{17}$ is selected from hydrido, lower alkyl, lower cycloalkyl and lower aralkyl; wherein $R^{18}$ and $R^{19}$ are independently selected from hydrido, lower alkyl, lower alkenyl, lower cycloalkyl, lower cycloalkylalkyl, aryl, heterocyclo, lower aralkyl, lower heterocycloalkyl, lower alkylaminoalkyl, and lower heterocycloalkyl; or wherein —$NR^{18}R^{19}$ together form a saturated, partially unsaturated or unsaturated ring of 5 to 7 atoms; or wherein $R^{16}$ and $R^{18}$ together form a saturated or partially unsaturated ring of 5 to 7 atoms; wherein $R^{20}$ is lower alkyl; wherein $R^{21}$, $R^{22}$, $R^{25}$, and $R^{26}$ are independently selected from hydrido, lower alkyl, lower cycloalkyl, lower cycloalkylalkyl, lower aminoalkyl, lower alkylaminoalkyl, lower hydroxyalkyl, lower alkoxyalkyl, lower, aryl, heterocyclo, lower aralkyl, lower heterocycloalkyl; or wherein —$NR^{21}R^{22}$ together form a heterocyclic ring of 5 to 7 atoms; or wherein —$NR^{25}R^{26}$ together form a heterocyclic ring of 5 to 7 atoms; wherein $R^{24}$ is selected from lower alkyl, lower cycloalkyl, lower cycloalkylalkyl, lower alkylaminoalkyl, lower aralkoxyalkyl, lower alkoxyalkyl, aryl, lower aralkyl, heterocyclo, and lower heterocycloalkyl; and wherein $R^{27}$ is selected from hydrido, lower alkyl, lower cycloalkyl, lower cycloalkylalkyl, lower alkylaminoalkyl, lower aminoalkyl, lower carboxyalkyl, lower aminocarbonylalkyl, lower hydroxyalkyl, lower aralkoxyalkyl, lower alkoxyalkyl, aryl, lower aralkyl, heterocyclo, and lower heterocycloalkyl; or a pharmaceutically-acceptable salt or tautomer thereof.

A class of compounds of particular interest consists of those compounds of Formula I wherein $R^1$ is a substituent selected from hydrido, methyl, ethyl, n-propyl, isopropyl, n-butyl, isobutyl, sec-butyl, tert-butyl, methoxy, ethoxy, propoxy, butoxy, and tert-butoxy; wherein $R^2$ is a substituent selected from hydrido, fluoro, chloro, bromo, iodo, methyl, ethyl, n-propyl, isopropyl, n-butyl, isobutyl, sec-butyl, tert-butyl, pentyl, hexyl,

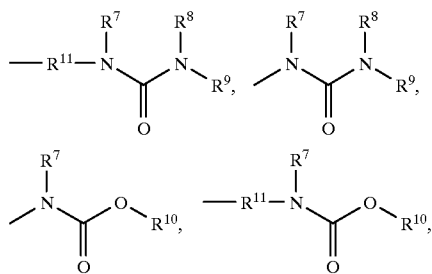

or wherein —$NR^3R^4$ form a heterocyclic ring selected from pyrrolidinyl, piperidinyl, morpholino, piperazinyl and azepinyl; wherein n is 0–4, inclusive; wherein $R^5$ and $R^6$ are independently selected from hydrido, methyl, ethyl, n-propyl, isopropyl, n-butyl, isobutyl, sec-butyl, tert-butyl, pentyl, hexyl, cyclopropyl, cyclobutyl, cyclopentyl, cyclohexyl, cyclopropylmethyl, cyclobutylmethyl, phenyl, benzyl, furyl, thienyl, thiazolyl, pyrrolyl, furylmethyl, thienylethyl, thiazolylmethyl, pyrrolylmethyl, methylaminomethyl, N,N-dimethylaminomethyl, N,N-dimethylaminoethyl, N,N-dimethylaminohexyl, N,N-diethylaminobutyl, benzylaminomethyl, methoxymethyl, methoxyethyl, ethoxyethyl, methoxybutyl, methoxypropyl, and benzyloxymethyl; or wherein —$NR^5R^6$ form a heterocyclic ring selected from pyrrolidinyl, piperidinyl, morpholino, piperazinyl and azepinyl; wherein $R^7$, $R^{12}$ and $R^{23}$ are independently selected from hydrido, methyl, ethyl, n-propyl, isopropyl, n-butyl, isobutyl, sec-butyl, tert-butyl, pentyl, hexyl, benzyl and phenylethyl; wherein $R^8$, $R^9$ and $R^{14}$ are independently selected from hydrido, methyl, ethyl, n-propyl, isopropyl, n-butyl, isobutyl, sec-butyl, tert-butyl, pentyl, hexyl, cyclopropyl, cyclobutyl, cyclopentyl, cyclohexyl, cyclopropylpropyl, cyclobutylethyl, cyclopentylmethyl, cyclohexylmethyl, fluoromethyl, difluoromethyl, trifluoromethyl, chloromethyl, dichloromethyl, trichloromethyl, trichloromethyl, pentafluoroethyl, heptafluoropropyl, difluorochloromethyl, dichlorofluoromethyl, difluoroethyl, difluoropropyl, dichloroethyl and dichloropropyl, methylamino, ethylamino, propylamino, N,N-dimethylaminomethyl, N,N-dimethylaminoethyl, N,N-dimethylaminopropyl, N,N-dimethylaminohexyl, N,N-diethylaminobutyl, N,N-diethylaminoethyl, N,N-diethylaminopropyl, carboxymethyl, carboxyethyl, carboxypropyl, aminocarbonylmethyl, N,N-dimethylaminocarbonylmethyl, hydroxymethyl, hydroxypropyl, methoxymethyl, methoxyethyl, ethoxyethyl, methoxybutyl, methoxypropyl, benzyloxymethyl, methylsulfonylmethyl, methylsulfinylmethyl, methylthiomethyl, phenyl optionally substituted at a substitutable position with one or more substituents selected independently from methyl, ethyl, n-propyl, isopropyl, n-butyl, isobutyl, sec-butyl, tert-butyl, pentyl, hexyl, methoxy, ethoxy, propoxy, isopropoxy, butoxy, tert-butoxy, amino, fluoro, chloro, bromo, iodo, N,N-dimethylaminomethyl, N,N-dimethylaminohexyl, N,N-diethylaminobutyl, N,N-dimethylaminoethyl, N,N-diethylaminoethyl, N,N-dimethylamino, and N,N-diethylamino, lower aralkyl selected from benzyl, naphthylmethyl, phenylethyl, and phenylisopropyl, wherein the phenyl ring is optionally substituted at a substitutable position with one or more substituents selected independently from methyl, ethyl, n-propyl, isopropyl, n-butyl, isobutyl, sec-butyl, tert-butyl, pentyl, hexyl, methoxy, ethoxy, propoxy, isopropoxy, butoxy, tert-butoxy, amino, fluoro, chloro, bromo, iodo, N,N-dimethylaminomethyl, N,N-dimethylaminohexyl, N,N-diethylaminobutyl, N,N-dimethylaminoethyl, N,N-diethylaminoethyl, N,N-dimethylamino, and N,N-diethylamino, heterocyclo selected from furyl, pyrrolyl, pyridyl, oxazolyl, pyrazolyl, isoxazolyl, thienyl, and thiazolyl, and lower heterocycloalkyl selected from thienylmethyl, morpholinylethyl, morpholinylmethyl, piperazinylethyl, piperdinylethyl, piperdinylmethyl, pyrrolidinylethyl, pyrrolidinylmethyl, pyrrolidinylpropyl, imidazolylethyl, oxazolylmethyl, thiazolylmethyl, furylmethyl, thienylethyl, and thiazolylmethyl, wherein the heterocyclo moiety may be substituted at a substitutable position with a radical selected from fluoro, chloro, bromo, iodo, methyl, ethyl, n-propyl, isopropyl, n-butyl, isobutyl, sec-butyl, tert-butyl, pentyl, and hexyl; or wherein $-NR^8R^9$ form a heterocyclic ring selected from pyrrolidinyl, piperidinyl, morpholinyl, piperazinyl and azepinyl; wherein $R^{10}$ is selected from methyl, ethyl, n-propyl, isopropyl, n-butyl, isobutyl, sec-butyl, tert-butyl, pentyl, hexyl, fluoromethyl, difluoromethyl, trifluoromethyl, chloromethyl, dichloromethyl, trichloromethyl, trichloromethyl, pentafluoroethyl, heptafluoropropyl, difluorochloromethyl, dichiorofluoromethyl, difluoroethyl, difluoropropyl, dichloroethyl and dichloropropyl, N,N-dimethylaminomethyl, N,N-dimethylaminoethyl, N,N-dimethylaminopropyl, N,N-dimethylaminohexyl, N,N-diethylaminoethyl, N,N-diethylaminopropyl, N,N-diethylaminobutyl, carboxymethyl, carboxyethyl, carboxypropyl, aminocarbonylmethyl, N,N-dimethylaminocarbonylmethyl, benzyloxymethyl, methoxymethyl, methoxyethyl, ethoxyethyl, methoxybutyl, methoxypropyl, cyclopropyl, cyclobutyl, cyclopentyl, cyclohexyl, cyclopropylpropyl, cyclobutylethyl, cyclopentylmethyl, cyclohexylmethyl, methylsulfonylmethyl, methylsulfinylmethyl, methylthiomethyl, phenyl optionally substituted at a substitutable position with one or more substituents selected independently from methyl, ethyl, n-propyl, isopropyl, n-butyl, isobutyl, sec-butyl, tert-butyl, pentyl, hexyl, methoxy, ethoxy, propoxy, isopropoxy, butoxy, tert-butoxy, amino, fluoro, chloro, bromo, iodo, N,N-dimethylaminomethyl, N,N-dimethylaminohexyl, N,N-diethylaminobutyl, N,N-dimethylaminoethyl, N,N-diethylaminoethyl, N,N-dimethylamino, and N,N-diethylamino, lower aralkyl selected from benzyl, phenethyl, naphthylmethyl, wherein the aryl ring is optionally substituted at a substitutable position with one or more substituents selected independently from methyl, ethyl, n-propyl, isopropyl, n-butyl, isobutyl, sec-butyl, tert-butyl, pentyl, hexyl, methoxy, ethoxy, propoxy, isopropoxy, butoxy, tert-butoxy, amino, fluoro, chloro, bromo, iodo, N,N-dimethylaminomethyl, N,N-dimethylaminoethyl, N,N-dimethylaminohexyl, N,N-diethylaminoethyl, N,N-diethylaminobutyl, N,N-dimethylamino, N,N-dimethylamino, and N,N-diethylamino, heterocyclo selected from furyl, thienyl, and thiazolyl, and lower heterocycloalkyl selected from thienylmethyl, morpholinylethyl, morpholinylmethyl, piperazinylethyl, piperdinylethyl, piperdinylmethyl, pyrrolidinylethyl, pyrrolidinylmethyl, pyrrolidinylpropyl, imidazolylethyl, oxazolylmethyl, thiazolylmethyl, furylmethyl, thienylethyl, and thiazolylmethyl, wherein the heterocyclo moiety may be substituted at a substitutable position with a radical selected from fluoro, chloro, bromo, iodo, methyl, ethyl, n-propyl, isopropyl, n-butyl, isobutyl, sec-butyl, tert-butyl, pentyl, and hexyl; wherein $R^{11}$ is selected from methyl, ethyl, n-propyl, isopropyl, n-butyl, isobutyl, sec-butyl, pentyl, and hexyl; wherein $R^{13}$ is selected from phenyl, amino, methyl, ethyl, n-propyl, isopropyl, n-butyl, isobutyl, sec-butyl, tert-butyl, pentyl, hexyl N,N-dimethylaminomethyl, N,N-dimethylaminoethyl, N,N-dimethylaminohexyl, N,N-diethylaminoethyl, N,N-diethylaminobutyl, N,N-dimethylamino, N,N-dimethylamino, and N,N-diethylamino; wherein $R^{15}$ is selected from hydrido, methyl, ethyl, n-propyl, isopropyl, n-butyl, isobutyl, sec-butyl, tert-butyl, pentyl, and hexyl; wherein $R^{16}$ is selected from hydrido, methyl, ethyl, n-propyl, isopropyl, n-butyl, isobutyl, sec-butyl, tert-butyl, pentyl, hexyl, hydroxymethyl, hydroxyethyl, hydroxypropyl, hydroxybutyl, mercaptoethyl, methoxymethyl, methoxyethyl, ethoxyethyl, methoxybutyl, methoxypropyl, phenylmethoxymethyl, aminomethyl, aminohexyl, aminobutyl, N,N-dimethylaminomethyl, N,N-dimethylaminoethyl, N,N-dimethylaminopropyl, N,N-dimethylaminohexyl, N,N-diethylaminopropyl, N,N-diethylaminobutyl, mercaptomethyl, methylthioethyl, methylsulfonylethyl, phenyl optionally substituted at a substitutable position with one or more substituents independently selected from methyl, ethyl, n-propyl, isopropyl, n-butyl, isobutyl, sec-butyl, tert-butyl, pentyl, hexyl, hydroxy, methoxy, ethoxy, propoxy, isopropoxy, butoxy, tert-butoxy, fluoro, chloro, bromo, iodo, nitro, amino, N,N-dimethylaminomethyl, N,N-dimethylaminoethyl, N,N-dimethylaminopropyl, N,N-dimethylaminohexyl, N,N-diethylaminopropyl, N,N-diethylaminobutyl, methylamino, and hexylamino, heterocyclo selected from pyridyl, thienyl, morpholinyl, piperidinyl, indolyl, quinolinyl, pyrrolidinyl, furyl, oxazolyl, thiazolyl, imidazolyl, pyrazolyl, and isoxazolyl, optionally substituted at a substitutable position with one or more substituents independently selected from methyl, ethyl, n-propyl, isopropyl, n-butyl, isobutyl, sec-butyl, tert-butyl, pentyl, hexyl, methoxy, ethoxy, propoxy, butoxy, tert-butoxy, fluoro, chloro, bromo, iodo, amino, oxo, N,N-dimethylamino, and N,N-diethylamino, lower aralkyl selected from benzyl, phenethyl and naphthylmethyl, wherein the aryl ring is optionally substituted at a substitutable position with one or more substituents independently selected from methyl, ethyl, n-propyl, isopropyl, n-butyl, isobutyl, sec-butyl, tert-butyl, pentyl, hexyl, hydroxy, methoxy, ethoxy, propoxy, butoxy, tert-butoxy, fluoro, chloro, bromo, iodo, nitro, amino, methylamino, N,N-dimethylaminomethyl, N,N-dimethylaminoethyl, N,N-dimethylaminopropyl, N,N-dimethylaminohexyl, N,N-diethylaminopropyl, N,N-diethylaminobutyl, ethylamino, N,N-dimethylamino, N,N-dimethylamino, and N,N-diethylamino, lower heterocycloalkyl selected from pyrrolidinylethyl, furylmethyl, pyrrolidinylmethyl, piperazinylmethyl, piperazinylethyl, imidazolylmethyl, indolylmethyl, morpholinylmethyl, morpholinylethyl, quinolinylmethyl, thienylmethyl, thiazolylethyl and thiazolylmethyl, wherein the heterocyclo moiety may be substituted at a substitutable position with a radical selected from fluoro, chloro, bromo, iodo, methyl, ethyl, n-propyl, isopropyl, n-butyl, isobutyl, sec-butyl, tert-butyl, pentyl, and hexyl,

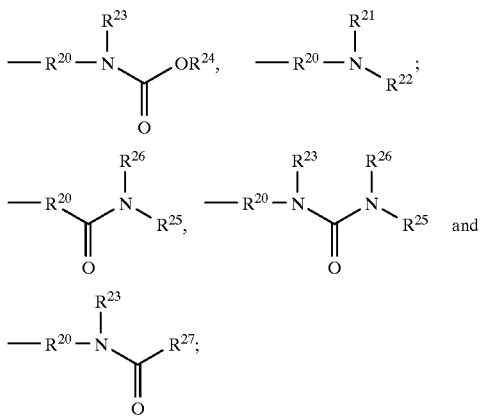

or wherein $R^{15}$ and $R^{16}$ together form a ring selected from cyclopropyl, cyclobutyl, cyclopentyl and cyclohexyl; wherein $R^{17}$ is selected from hydrido, methyl, ethyl, n-propyl, isopropyl, n-butyl, isobutyl, sec-butyl, tert-butyl, pentyl, hexyl, and benzyl; wherein $R^{18}$ and $R^{19}$ are independently selected from hydrido, methyl, ethyl, n-propyl, isopropyl, n-butyl, isobutyl, sec-butyl, tert-butyl, pentyl, hexyl, butenyl, propenyl, N,N-dimethylaminomethyl, N,N-dimethylaminoethyl, N,N-dimethylaminopropyl, N,N-dimethylaminohexyl, N,N-diethylaminopropyl, N,N-diethylaminobutyl, butenyl, phenyl, pyridyl, thienyl, morpholinyl, piperidinyl, indolyl, quinolinyl, pyrrolidinyl, furyl, oxazolyl, thiazolyl, imidazolyl, pyrazolyl, isoxazolyl, benzyl, phenethyl, lower heterocycloalkyl selected from furylmethyl, thienylmethyl, morpholinylethyl, piperazinylethyl, piperdinylethyl, pyrrolidinylethyl, pyrrolidinylpropyl, imidazolylethyl, oxazolylmethyl, and thiazolylmethyl, wherein the heterocyclo moiety may be substituted at a substitutable position with a radical selected from fluoro, chloro, bromo, iodo, methyl, ethyl, n-propyl, isopropyl, n-butyl, isobutyl, sec-butyl, tert-butyl, pentyl, hexyl, methylaminomethyl, methylaminohexyl, ethylaminobutyl, N,N-dimethylaminomethyl, N,N-dimethylaminoethyl, N,N-dimethylaminohexyl, and N,N-diethylaminobutyl; or wherein —$NR^{18}R^{19}$ together form a ring selected from piperazinyl, piperdinyl, pyrrolidinyl, azepinyl and morpholinyl, wherein the ring is optionally substituted at a substitutable position with one or more substituents independently selected from fluoro, chloro, bromo, iodo, methyl, ethyl, n-propyl, isopropyl, n-butyl, isobutyl, sec-butyl, tert-butyl, pentyl, and hexyl; or wherein $R^{16}$ and $R^{18}$ together form a ring selected from 2-oxo-pyrrolidinyl and 2-oxo-piperadinyl; wherein $R^{20}$ is selected from methyl, ethyl, n-propyl, isopropyl, n-butyl, isobutyl, sec-butyl, pentyl, and hexyl; wherein $R^{21}$, $R^{22}$, $R^{25}$, and $R^{26}$ are independently selected from hydrido, methyl, ethyl, n-propyl, isopropyl, n-butyl, isobutyl, sec-butyl, tert-butyl, pentyl, hexyl, propenyl, butenyl, phenyl optionally substituted at a substitutable position with one or more substituents selected independently from methyl, ethyl, n-propyl, isopropyl, n-butyl, isobutyl, sec-butyl, tert-butyl, pentyl, hexyl, methoxy, ethoxy, propoxy, isopropoxy, butoxy, tert-butoxy, amino, fluoro, chloro, bromo, iodo, N,N-dimethylaminomethyl, N,N-dimethylaminohexyl, N,N-diethylaminobutyl, N,N-dimethylaminoethyl, N,N-diethylaminoethyl, N,N-dimethylamino, and N,N-diethylamino, pyridyl, thienyl, morpholinyl, piperidinyl, indolyl, quinolinyl, pyrrolidinyl, furyl, oxazolyl, thiazolyl, imidazolyl, pyrazolyl, and isoxazolyl, benzyl, phenethyl, lower heterocycloalkyl selected from furylmethyl, thienylmethyl, morpholinylethyl, piperazinylethyl, piperdinylethyl, pyrrolidinylethyl, pyrrolidinylpropyl, imidazolylethyl, oxazolylmethyl, and thiazolylmethyl, wherein the heterocyclo moiety may be substituted at a substitutable position with a radical selected from fluoro, chloro, bromo, iodo, methyl, ethyl, n-propyl, isopropyl, n-butyl, isobutyl, sec-butyl, tert-butyl, pentyl, hexyl, methylaminomethyl, methylaminohexyl, ethylaminobutyl, N,N-dimethylaminomethyl, N,N-dimethylaminoethyl, N,N-dimethylaminohexyl, and N,N-diethylaminobutyl; or wherein —$NR^{21}R^{22}$ together form a ring selected from piperazinyl, piperdinyl, pyrrolidinyl, azepinyl and morpholinyl; or wherein —$NR^{25}R^{26}$ together form a ring selected from piperazinyl, piperdinyl, pyrrolidinyl, azepinyl and morpholinyl; wherein $R^{24}$ is selected from methyl, ethyl, n-propyl, isopropyl, n-butyl, isobutyl, sec-butyl, tert-butyl, pentyl, hexyl, N,N-dimethylaminomethyl, N,N-dimethylaminoethyl, N,N-dimethylaminopropyl, N,N-dimethylaminohexyl, N,N-diethylaminopropyl, N,N-diethylaminobutyl, methoxymethyl, methoxyethyl, ethoxyethyl, methoxybutyl, methoxypropyl, benzyloxyethyl, benzyloxymethyl, cyclopropyl, cyclobutyl, cyclopentyl, cyclohexyl, cyclopropylmethyl, cyclobutylmethyl, cyclopentylethyl, cyclohexylpropyl, phenyl optionally substituted at a substitutable position with one or more substituents selected independently from methyl, ethyl, n-propyl, isopropyl, n-butyl, isobutyl, sec-butyl, tert-butyl, pentyl, hexyl, methoxy, ethoxy, propoxy, isopropoxy, butoxy, tert-butoxy, amino, fluoro, chloro, bromo, iodo, N,N-dimethylaminomethyl, N,N-dimethylaminohexyl, N,N-diethylaminobutyl, N,N-dimethylaminoethyl, N,N-diethylaminoethyl, N,N-dimethylamino, and N,N-diethylamino, heterocyclo selected from pyridyl, thienyl, morpholinyl, pyrimidyl, indolyl, isoquinolyl, quinolyl, tetrahydroquinolinyl, piperidinyl, pyrrolidinyl, furyl, oxazolyl, thiazolyl, imidazolyl, pyrazolyl, and isoxazolyl, wherein the heterocyclo is optionally substituted at a substitutable position with one or more substituents selected independently from lower alkyl, lower alkoxy, amino, halo, lower dialkylaminoalkyl, and lower dialkylamino, lower aralkyl selected from benzyl, phenethyl, and naphthylmethyl, wherein the aryl ring is optionally substituted at a substitutable position with one or more substituents selected independently from methyl, ethyl, n-propyl, isopropyl, n-butyl, isobutyl, sec-butyl, tert-butyl, pentyl, hexyl, methoxy, ethoxy, propoxy, butoxy, tert-butoxy, amino, fluoro, chloro, bromo, iodo, N,N-dimethylaminomethyl, N,N-dimethylaminoethyl, N,N-dimethylaminopropyl, N,N-dimethylaminohexyl, N,N-diethylaminopropyl, N,N-diethylaminobutyl, N,N-dimethylamino, and N,N-diethylamino, and lower heterocycloalkyl selected from furylmethyl, pyrrolidinylmethyl, quinolinylmethyl, piperazinylmethyl, imidazolylmethyl, indolylmethyl, morpholinylmethyl, thienylmethyl, and thiazolylmethyl, wherein the heterocyclo moiety may be substituted at a substitutable position with a radical selected from fluoro, chloro, bromo, iodo, methyl, ethyl, n-propyl, isopropyl, n-butyl, isobutyl, sec-butyl, tert-butyl, pentyl, and hexyl; and wherein $R^{27}$ is selected from hydrido, methyl, ethyl, n-propyl, isopropyl, n-butyl, isobutyl, sec-butyl, tert-butyl, pentyl, hexyl, trifluoromethyl, N,N-dimethylaminomethyl, N,N-dimethylaminoethyl, N,N- dimethylaminopropyl, N,N-dimethylaminohexyl, N,N-diethylaminopropyl, N,N-diethylaminobutyl, hydroxymethyl, hydroxyethyl, hydroxypropyl, hydroxybutyl, methoxymethyl, methoxyethyl, ethoxyethyl, methoxybutyl, methoxypropyl, phenylmethoxymethyl, benzyloxyethyl, aminomethyl, aminohexyl, aminobutyl, carboxyethyl, carboxypropyl, carboxymethyl, cyclopropyl, cyclobutyl, cyclopentyl, cyclohexyl, cyclopropylmethyl, cyclobutylmethyl, cyclopentylethyl, cyclohexylpropyl, phenyl optionally substituted at a substitutable position with one or more substituents selected independently from methyl, ethyl, n-propyl, isopropyl, n-butyl, isobutyl, sec-butyl, tert-butyl, pentyl, hexyl, methoxy, ethoxy, propoxy, isopropoxy, butoxy, tert-butoxy, amino, fluoro, chloro, bromo, iodo, N,N-dimethylaminomethyl, N,N-dimethylaminohexyl, N,N-diethylaminobutyl, N,N-dimethylaminoethyl, N,N-diethylaminoethyl, N,N-dimethylamino, and N,N-diethylamino, heterocyclo selected from pyridyl, thienyl, morpholinyl, pyrimidyl, indolyl, isoquinolyl, quinolyl, tetrahydroquinolinyl, piperidinyl, pyrrolidinyl, furyl, oxazolyl, thiazolyl, imidazolyl, pyrazolyl, and isoxazolyl, wherein the heterocyclo is optionally substituted at a substitutable position with one or more substituents selected independently from lower alkyl, lower alkoxy, amino, halo, lower dialkylaminoalkyl, and lower dialkylamino, lower aralkyl selected from benzyl, phenethyl, and naphthylmethyl, wherein the aryl ring is optionally substituted at a substitutable position with one or more substituents selected independently from methyl, ethyl, n-propyl, isopropyl, n-butyl, isobutyl, sec-butyl, tert-butyl, pentyl, hexyl, methoxy, ethoxy, propoxy, butoxy, tert-butoxy, amino, fluoro, chloro, bromo, iodo, N,N-dimethylaminomethyl, N,N-dimethylaminoethyl, N,N-dimethylaminopropyl, N,N-dimethylaminohexyl, N,N-diethylaminopropyl, N,N-diethylaminobutyl, N,N-dimethylamino, and N,N-diethylamino, and lower heterocycloalkyl selected from furylmethyl, pyrrolidinylmethyl, quinolinylmethyl, piperazinylmethyl, imidazolylmethyl, indolylmethyl, morpholinylmethyl, thienylmethyl, and thiazolylmethyl, wherein the heterocyclo moiety may be substituted at a substitutable position with a radical selected from fluoro, chloro, bromo, iodo, methyl, ethyl, n-propyl, isopropyl, n-butyl, isobutyl, sec-butyl, tert-butyl, pentyl, and hexyl; or a pharmaceutically-acceptable salt or tautomer thereof.

Another more preferred class of compounds consists of those compounds of Formula I wherein $R^1$ is a substituent selected from hydrido, lower alkoxy and lower alkyl; wherein $R^2$ is a substituent selected from hydrido, halo, lower alkyl,

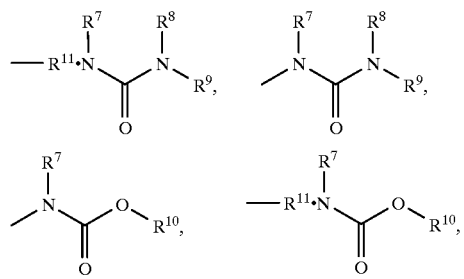

-continued

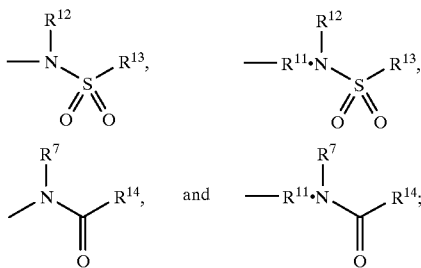

wherein $R^3$ is selected from hydrido, lower alkyl, and lower aralkyl; wherein $R^4$ is selected from hydrido, lower alkyl, lower cycloalkyl, lower cycloalkylalkyl, aryl, heterocyclo, lower aralkyl and lower heterocycloalkyl; or wherein —$NR^3R^4$ form a heterocyclic ring of 5 to 7 members; wherein n is 0–5, inclusive; wherein $R^5$ and $R^6$ are independently selected from hydrido, lower alkyl, lower cycloalkyl, lower cycloalkylalkyl, aryl, lower aralkyl, heterocyclo, lower heterocycloalkyl, lower alkylaminoalkyl, lower aralkylaminoalkyl, lower alkoxyalkyl, and lower aralkoxyalkyl; or wherein —$NR^5R^6$ form a heterocyclic ring of 5 to 7 members; wherein $R^7$, $R^{12}$ and $R^{23}$ are independently selected from hydrido, lower alkyl and lower aralkyl; wherein $R^8$, $R^9$ and $R^{14}$ are independently selected from hydrido, lower alkyl, lower cycloalkyl, lower cycloalkylalkyl, lower haloalkyl, lower aminoalkyl, lower alkylaminoalkyl, lower carboxyalkyl, lower aminocarbonylalkyl, lower alkylaminocarbonylalkyl, lower hydroxyalkyl, lower alkoxyalkyl, lower aralkoxyalkyl, lower alkylsulfonylalkyl, lower alkylsulfinylalkyl, lower alkylthioalkyl, aryl, lower aralkyl, heterocyclo, and lower heterocycloalkyl; or wherein —$NR^8R^9$ form a heterocyclic ring of 5 to 7 members; wherein $R^{10}$ is selected from lower alkyl, lower haloalkyl, lower alkylaminoalkyl, lower carboxyalkyl, lower aminocarbonylalkyl, alkylaminocarbonylalkyl, lower aralkoxyalkyl, lower alkoxyalkyl, lower cycloalkyl, lower cycloalkylalkyl, lower alkylsulfonylalkyl, lower alkylsulfinylalkyl, lower alkylthioalkyl, aryl, lower aralkyl, heterocyclo, and lower heterocycloalkyl; wherein $R^{11}$ is lower alkyl; and wherein $R^{13}$ is selected from amino, lower alkyl, lower alkylamino, lower alkylaminoalkyl and aryl; or a pharmaceutically-acceptable salt or tautomer thereof.

A class of compounds of particular interest consists of those compounds of Formula I wherein $R^1$ is a substituent selected from hydrido, methyl, ethyl, n-propyl, isopropyl, n-butyl, isobutyl, sec-butyl, tert-butyl, methoxy, ethoxy, propoxy, butoxy, and tert-butoxy; wherein $R^2$ is a substituent selected from hydrido, fluoro, chloro, bromo, iodo, methyl, ethyl, n-propyl, isopropyl, n-butyl, isobutyl, sec-butyl, tert-butyl, pentyl, hexyl,

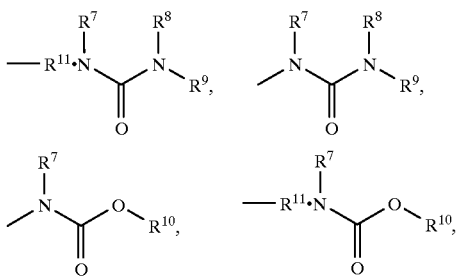

-continued

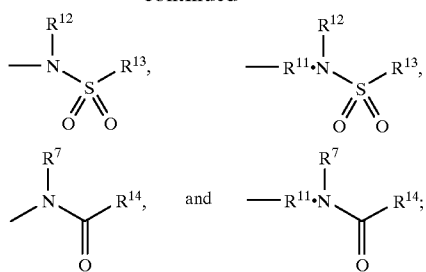

wherein R³ is selected from hydrido, methyl, ethyl, n-propyl, isopropyl, n-butyl, isobutyl, sec-butyl, tert-butyl, pentyl, hexyl, benzyl, phenylethyl and diphenylmethyl; wherein R⁴ is selected from hydrido, methyl, ethyl, n-propyl, isopropyl, n-butyl, isobutyl, sec-butyl, tert-butyl, pentyl, hexyl, cyclopropyl, cyclobutyl, cyclopentyl, cyclohexyl, cyclopropylmethyl, cyclobutylmethyl, cyclopentylethyl, cyclohexylpropyl, phenyl optionally substituted at a substitutable position with one or more substituents selected independently from fluoro, chloro, iodo, bromo, nitro, methyl, ethyl, n-propyl, isopropyl, n-butyl, isobutyl, sec-butyl, tert-butyl, pentyl, hexyl, lower alkoxy, N,N-dimethylaminoethyl, N,N-dimethylaminohexyl, N,N-diethylaminobutyl, N,N-dimethylaminoethoxy, N,N-dimethylaminohexyloxy, and N,N-diethylaminobutoxy, lower aralkyl selected from benzyl, naphthylmethyl, phenylethyl, and phenylisopropyl, wherein the phenyl ring is optionally substituted at a substitutable position with one or more substituents selected independently from methyl, ethyl, n-propyl, isopropyl, n-butyl, isobutyl, sec-butyl, tert-butyl, pentyl, hexyl, methoxy, ethoxy, propoxy, isopropoxy, butoxy, tert-butoxy, amino, fluoro, chloro, bromo, iodo, N,N-dimethylaminomethyl, N,N-dimethylaminohexyl, N,N-diethylaminobutyl, N,N-dimethylaminoethyl, N,N-diethylaminoethyl, N,N-dimethylamino, and N,N-diethylamino, heterocyclo selected from methylpiperidinyl, methylazabicyclooctanyl, morpholinyl, pyrrolidinyl, and piperazinyl, phenylmethyl, phenylethyl, and lower heterocycloalkyl selected from pyridylmethyl, pyridylethyl, furylmethyl, thienylmethyl, and thiazolylmethyl, where the heterocyclic rings are optionally substituted at a substitutable position with one or more substituents selected independently from fluoro, chloro, iodo, bromo, nitro, methyl, ethyl, n-propyl, isopropyl, n-butyl, isobutyl, sec-butyl, tert-butyl, pentyl, hexyl, lower alkoxy, N,N-dimethylaminoethyl, N,N-dimethylaminohexyl, N,N-diethylaminobutyl, N,N-dimethylaminoethoxy, N,N-dimethylaminohexyloxy, and N,N-diethylaminobutoxy; or wherein —NR³R⁴ form a heterocyclic ring selected from pyrrolidinyl, piperidinyl, morpholino, piperazinyl and azepinyl; wherein n is 0–4, inclusive; wherein R⁵ and R⁶ are independently selected from hydrido, methyl, ethyl, n-propyl, isopropyl, n-butyl, isobutyl, sec-butyl, tert-butyl, pentyl, hexyl, cyclopropyl, cyclobutyl, cyclopentyl, cyclohexyl, cyclopropylmethyl, cyclobutylmethyl, phenyl, benzyl, furyl, thienyl, thiazolyl, pyrrolyl, furylmethyl, thienylethyl, thiazolylmethyl, pyrrolylmethyl, methylaminomethyl, N,N-dimethylaminomethyl, N,N-dimethylaminoethyl, N,N-dimethylaminohexyl, N,N-diethylaminobutyl, benzylaminomethyl, methoxymethyl, methoxyethyl, ethoxyethyl, methoxybutyl, methoxypropyl, and benzyloxymethyl; or wherein —NR⁵R⁶ form a heterocyclic ring selected from pyrrolidinyl, piperidinyl, morpholino, piperazinyl and azepinyl; wherein R⁷, R¹² and R²³ are independently selected from hydrido, methyl, ethyl, n-propyl, isopropyl, n-butyl, isobutyl, sec-butyl, tert-butyl, pentyl, hexyl, benzyl and phenylethyl; wherein R⁸, R⁹ and R¹⁴ are independently selected from hydrido, methyl, ethyl, n-propyl, isopropyl, n-butyl, isobutyl, sec-butyl, tert-butyl, pentyl, hexyl, cyclopropyl, cyclobutyl, cyclopentyl, cyclohexyl, cyclopropylpropyl, cyclobutylethyl, cyclopentylmethyl, cyclohexylmethyl, fluoromethyl, difluoromethyl, trifluoromethyl, chloromethyl, dichloromethyl, trichloromethyl, trichloromethyl, pentafluoroethyl, heptafluoropropyl, difluorochloromethyl, dichlorofluoromethyl, difluoroethyl, difluoropropyl, dichloroethyl and dichloropropyl, methylamino, ethylamino, propylamino, N,N-dimethylaminomethyl, N,N-dimethylaminoethyl, N,N-dimethylaminopropyl, N,N-dimethylaminohexyl, N,N-diethylaminobutyl, N,N-diethylaminoethyl, N,N-diethylaminopropyl, carboxymethyl, carboxyethyl, carboxypropyl, aminocarbonylmethyl, N,N-dimethylaminocarbonylmethyl, hydroxymethyl, hydroxypropyl, methoxymethyl, methoxyethyl, ethoxyethyl, methoxybutyl, methoxypropyl, benzyloxymethyl, methylsulfonylmethyl, methylsulfinylmethyl, methylthiomethyl, phenyl optionally substituted at a substitutable position with one or more substituents selected independently from methyl, ethyl, n-propyl, isopropyl, n-butyl, isobutyl, sec-butyl, tert-butyl, pentyl, hexyl, methoxy, ethoxy, propoxy, isopropoxy, butoxy, tert-butoxy, amino, fluoro, chloro, bromo, iodo, N,N-dimethylaminomethyl, N,N-dimethylaminohexyl, N,N-diethylaminobutyl, N,N-dimethylaminoethyl, N,N-diethylaminoethyl, N,N-dimethylamino, and N,N-diethylamino, lower aralkyl selected from benzyl, naphthylmethyl, phenylethyl, and phenylisopropyl, wherein the phenyl ring is optionally substituted at a substitutable position with one or more substituents selected independently from methyl, ethyl, n-propyl, isopropyl, n-butyl, isobutyl, sec-butyl, tert-butyl, pentyl, hexyl, methoxy, ethoxy, propoxy, isopropoxy, butoxy, tert-butoxy, amino, fluoro, chloro, bromo, iodo, N,N-dimethylaminomethyl, N,N-dimethylaminohexyl, N,N-diethylaminobutyl, N,N-dimethylaminoethyl, N,N-diethylaminoethyl, N,N-dimethylamino, and N,N-diethylamino, heterocyclo selected from furyl, pyrrolyl, pyridyl, oxazolyl, pyrazolyl, isoxazolyl, thienyl, and thiazolyl, and lower heterocycloalkyl selected from thienylmethyl, morpholinylethyl, morpholinylmethyl, piperazinylethyl, piperdinylethyl, piperdinylmethyl, pyrrolidinylethyl, pyrrolidinylmethyl, pyrrolidinylpropyl, imidazolylethyl, oxazolylmethyl, thiazolylmethyl, furylmethyl, thienylethyl, and thiazolylmethyl, wherein the heterocyclo moiety may be substituted at a substitutable position with a radical selected from fluoro, chloro, bromo, iodo, methyl, ethyl, n-propyl, isopropyl, n-butyl, isobutyl, sec-butyl, tert-butyl, pentyl, and hexyl; or wherein —NR⁸R⁹ form a heterocyclic ring selected from pyrrolidinyl, piperidinyl, morpholinyl, piperazinyl and azepinyl; wherein R¹⁰ is selected from methyl, ethyl, n-propyl, isopropyl, n-butyl, isobutyl, sec-butyl, tert-butyl, pentyl, hexyl, fluoromethyl, difluoromethyl, trifluoromethyl, chloromethyl, dichloromethyl, trichloromethyl, trichloromethyl, pentafluoroethyl, heptafluoropropyl, difluorochloromethyl, dichlorofluoromethyl, difluoroethyl, difluoropropyl, dichloroethyl and dichloropropyl, N,N-dimethylaminomethyl, N,N-dimethylaminoethyl, N,N-dimethylaminopropyl, N,N-dimethylaminohexyl, N,N-diethylaminoethyl, N,N-diethylaminopropyl, N,N-diethylaminobutyl, carboxymethyl, carboxyethyl, carboxypropyl, aminocarbonylmethyl, N,N-dimethylaminocarbonylmethyl, benzyloxymethyl, methoxymethyl, methoxyethyl, ethoxyethyl, methoxybutyl, methoxypropyl, cyclopropyl, cyclobutyl, cyclopentyl, cyclohexyl, cyclopropylpropyl, cyclobutylethyl, cyclopentylmethyl, cyclohexylmethyl, methylsulfonylmethyl, methylsulfinylmethyl, methylthiomethyl, phenyl optionally substituted at a substitutable position with one or more substituents selected independently from methyl, ethyl, n-propyl, isopropyl, n-butyl, isobutyl, sec-butyl, tert-butyl, pentyl, hexyl, methoxy, ethoxy, propoxy, isopropoxy, butoxy, tert-butoxy, amino, fluoro, chloro, bromo, iodo, N,N-dimethylaminomethyl, N,N-dimethylaminohexyl, N,N-diethylaminobutyl, N,N-dimethylaminoethyl, N,N-diethylaminoethyl, N,N-dimethylamino, and N,N-diethylamino, lower aralkyl selected from benzyl, phenethyl, naphthylmethyl, wherein the aryl ring is optionally substituted at a substitutable position with one or more substituents selected independently from methyl, ethyl, n-propyl, isopropyl, n-butyl, isobutyl, sec-butyl, tert-butyl, pentyl, hexyl, methoxy, ethoxy, propoxy, isopropoxy, butoxy, tert-butoxy, amino, fluoro, chloro, bromo, iodo, N,N-dimethylaminomethyl, N,N-dimethylaminoethyl, N,N-dimethylaminohexyl, N,N-diethylaminoethyl, N,N-diethylaminobutyl, N,N-dimethylamino, N,N-dimethylamino, and N,N-diethylamino, heterocyclo selected from furyl, thienyl, and thiazolyl, and lower heterocycloalkyl selected from thienylmethyl, morpholinylethyl, morpholinylmethyl, piperazinylethyl, piperdinylethyl, piperdinylmethyl, pyrrolidinylethyl, pyrrolidinylmethyl, pyrrolidinylpropyl, imidazolylethyl, oxazolylmethyl, thiazolylmethyl, furylmethyl, thienylethyl, and thiazolylmethyl, wherein the heterocyclo moiety may be substituted at a substitutable position with a radical selected from fluoro, chloro, bromo, iodo, methyl, ethyl, n-propyl, isopropyl, n-butyl, isobutyl, sec-butyl, tert-butyl, pentyl, and hexyl; wherein $R^{11}$ is selected from methyl, ethyl, n-propyl, isopropyl, n-butyl, isobutyl, sec-butyl, pentyl, and hexyl; and wherein $R^{13}$ is selected from phenyl, amino, methyl, ethyl, n-propyl, isopropyl, n-butyl, isobutyl, sec-butyl, tert-butyl, pentyl, hexyl N,N-dimethylaminomethyl, N,N-dimethylaminoethyl, N,N-dimethylaminohexyl, N,N-diethylaminoethyl, N,N-diethylaminobutyl, N,N-dimethylamino, N,N-dimethylamino, and N,N-diethylamino; or a pharmaceutically-acceptable salt or tautomer thereof.

Within Formula I there is a subclass of compounds of high interest represented by Formula II:

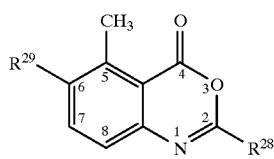

II wherein $R^{28}$ is selected from (a) amino substituted with one or two radicals selected from alkyl, aralkyl, heterocycloalkyl, heterocyclo, and aryl, and (b) amino acid residues and derivatives thereof;

wherein $R^{29}$ is selected from hydrido, alkyl, halo,

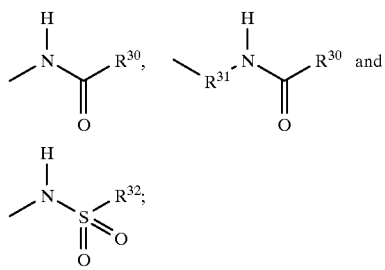

wherein $R^{30}$ is selected from alkyl, alkoxy, alkylamino, carboxyalkyl, alkoxyalkyl, alkylaminoalkyl, cycloalkyl, heterocyclo, heterocycloalkyl, heterocycloalkoxy, alkylaminoalkoxy, alkylaminoalkylamino, heterocycloalkylamino, and N-aralkylamino;
wherein $R^{31}$ is alkyl;
wherein $R^{32}$ is alkyl and aryl;
provided $R^{28}$ is not benzotriazolyl when $R^{29}$ is hydrido; further provided $R^{29}$ is not methyl when $R^{28}$ is amino substituted with benzyl or lower alkyl; and further provided $R^{29}$ is not hydrido when $R^{28}$ is leucine methyl ester or amino substituted with lower alkyl;
or a pharmaceutically-acceptable salt thereof.

An even more preferred class of compounds consists of those compounds of Formula II wherein $R^{28}$ is selected from (a) amino substituted with one or two radicals selected from lower alkyl, lower aralkyl, lower heterocycloalkyl, heterocyclo, and aryl, wherein $R^{24}$ is selected from hydrido, lower alkyl, halo,

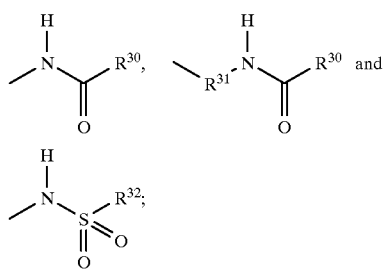

wherein $R^{30}$ is selected from lower alkyl, lower alkoxy, lower alkylamino, lower carboxyalkyl, lower alkoxyalkyl, lower alkylaminoalkyl, lower cycloalkyl, heterocyclo, lower heterocycloalkyl, lower heterocycloalkoxy, lower alkylaminoalkoxy, lower alkylaminoalkylamino, lower heterocycloalkylamino, and lower N-aralkylamino; wherein $R^{31}$ is lower alkyl; wherein $R^{32}$ is lower alkyl and aryl; or a pharmaceutically-acceptable salt thereof.

A family of specific compounds of particular interest within Formulas I and II consists of compounds and pharmaceutically-acceptable salts thereof as follows:
5-methoxy-2-[[(1R)-1-phenylethyl]amino]-4H-3,1-benzoxazin-4-one;
1,1-dimethylethyl[5-methyl-2-[(1-methylpiperidin-4-yl)amino]-4-oxo-4H-3,1-benzoxazin-6-yl]carbamate;
1,1-dimethylethyl[2-[[8-methyl-8-azabicyclo[3.2.1]octan-3-yl]amino]-5-methyl-4-oxo-4H-3,1-benzoxazin-6-yl]carbamate;
1,1-dimethylethyl[5-methyl-4-oxo-2-[(1S-phenyl ethyl)amino]-4H-3,1-benzoxazin-6-yl]carbamate;

1,1-dimethylethyl[5-methyl-4-oxo-2[[1S-(4-bromophenyl) ethyl]amino]-4H-3,1-benzoxazin-6-yl]carbamate;

1,1-dimethylethyl[5-methyl-4-oxo-2[[1S-(3-pyridinyl) ethyl]amino]-4H-3,1-benzoxazin-6-yl]carbamate;

1,1-dimethylethyl[2-[[1S-[2-[2-(dimethylamino)ethoxy] pyridin-5-yl]ethyl]amino]-5-methyl-4-oxo-4H-3,1-benzoxazin-6-yl]carbamate;

1,1-dimethylethyl[2-[[1S-4-[2-(dimethylamino)ethyl] phenyl]ethyl]amino]-5-methyl-4-oxo-4H-3,1-benzoxazin-6-yl]carbamate;

1,1-dimethylethyl N-methyl-[5-methyl-4-oxo-2-[(1S-phenylethyl)amino]4H-3,1-benzoxazin-6-yl]carbamate;

$N^1$-ethyl-$N^2$-[5-methyl-4-oxo-2-[(1S-phenylethyl)amino]-4H-3,1-benzoxazin-6-yl]urea;

$N^1$-[2-(dimethylamino)ethyl]-$N^2$-(5-methyl-4-oxo-2-[(1S-phenylethyl)amino]-4H-3,1-benzoxazin-6-yl]urea;

$N^1$-[2-(dimethylamino)ethyl]-$N^2$-[[5-methyl-4-oxo-2-[(1S-phenylethyl)amino]-4H-3,1-benzoxazin-6-yl]methyl] urea;

2-(dimethylamino)-N-[5-methyl-4-oxo-2-[(1S-phenylethyl)amino]-4H-3, 1-benzoxazin-6-yl]acetamide;

N-[5-methyl-4-oxo-2-[(1S-phenylethyl)amino]-4H-3,1-benzoxazin-6-yl]pyrrolidine-1-acetamide;

N-methyl-N-[5-methyl-4-oxo-2-[(1S-phenylethyl)amino]-4H-3,1-benzoxazin-6-yl]pyrrolidine-1-acetamide;

N-[5-methyl-4-oxo-2-[(1S-phenylethyl)amino]-4H-3,1-benzoxazin-6-yl]morpholine-4-acetamide;

4-methyl-N-[5-methyl-4-oxo-2-[(1S-phenylethyl)amino]-4H-3,1-benzoxazin-6-yl]piperazine-1-acetamide;

1-methyl-N-[5-methyl-4-oxo-2-[(1S-phenylethyl)amino]-4H-3,1-benzoxazin-6-yl]pyrrolidine-2S-carboxamide;

1,1-dimethylethyl[[5-methyl-4-oxo-2[(1S-phenyl ethyl) amino]-4H-3,1-benzoxazin-6-yl]methyl]carbamate;

1,1-dimethylethyl[[5-methyl-4-oxo-2[[1S-(3-pyridinyl) ethyl]amino]-4H-3,1-benzoxazin-6-yl]methyl]carbamate;

1,1-dimethylethyl[[2-[[1S[4-[2-(dimethylamino)ethyl] phenyl]ethyl]amino]-5-methyl-4-oxo-4H-3,1-benzoxazin-6-yl]methyl]carbamate;

2-(dimethylamino)-N-[[5-methyl-4-oxo-2-[(1S-phenylethyl)amino]-4H-3,1-benzoxazin-6-yl]methyl] acetamide;

N-[[5-methyl-4-oxo-2-[(1S-phenylethyl)amino]-4H-3,1-benzoxazin-6-yl]methyl]pyrrolidine-1-acetamide;

N-[[5-methyl-4-oxo-2-[(1S-phenylethyl)amino]-4H-3,1-benzoxazin-6-yl]methyl]morpholine-4-acetamide;

4-methyl-N-[[5-methyl-4-oxo-2-[(1S-phenylethyl)amino]-4H-3,1-benzoxazin-6-yl]methyl]piperazine-1-acetamide;

1-methyl-N-[[5-methyl-4-oxo-2[(1S-phenylethyl)amino]-4H-3,1-benzoxazin-6-yl]methyl]pyrrolidine-2S-carboxamide;

6-bromo-5-methyl-2-[[(1R)-1-phenylethyl]amino]-4H-3,1-benzoxazin-4-one;

2-ethylamino-5-methyl-4H-3,1-benzoxazin-4-one;

2-[(1-methylethyl)amino]-5-methyl-4H-3,1-benzoxazin-4-one;

5-methyl-2-[[(1S)-1-phenylethyl]amino]-4H-3,1-benzoxazin-4-one;

5-methyl-2-[[(1R)-1-phenylethyl]amino]-4H-3,1-benzoxazin-4-one;

5-methyl-2-(phenylamino)-4H-3,1-benzoxazin-4-one;

2-[(3-chlorophenyl)amino]-5-methyl-4H-3,1-benzoxazin-4-one;

2-[(2,6-dichlorophenyl)amino]-5-methyl-4H-3,1-benzoxazin-4-one;

5-methyl-2-[(2-nitrophenyl)amino]-4H-3,1-benzoxazin-4-one;

5-methyl-2-[(4-nitrophenyl)amino]-4H-3,1-benzoxazin-4-one;

6-iodo-2[[(1R)-phenylethyl]amino]-4H-3,1-benzoxazin-4-one;

2-[(2,6-dichlorophenyl)amino]-6-iodo-4H-3,1-benzoxazin-4-one;

2-[[(1S)-phenylethyl]amino]-6-iodo-4H-3,1-benzoxazin-4-one;

6-chloro-2-[[(1R)-phenylethyl]amino]-4H-3,1-benzoxazin-4-one;

6-methyl-2-[[(1R)phenylethyl]amino]-4H-3,1-benzoxazin-4-one;

6-methyl-2-[[(1S)-phenylethyl]amino]-4H-3,1-benzoxazin-4-one;

2-[[(1R)-(4-bromophenyl)ethyl]amino]-5-methyl-4H-3,1-benzoxazin-4-one;

2-(diethylamino)-5-methyl-4H-3,1-benzoxazin-4-one;

5-methyl-2-[N-methyl-N-(phenylmethyl)amino]-4H-3,1-benzoxazin-4-one;

5-methyl-2-[N-methyl-N-(2-pyridylmethyl)amino]-4H-3,1-benzoxazin-4-one;

6-bromo-5-methyl-2-[N-methyl-N-(phenylmethyl)amino-4H-3,1-benzoxazin-4-one;

6-[[[(1,1-dimethylethoxy)carbonyl]amino]-5-methyl-2-[[(1S)-phenylethyl]amino]-4H-3,1-benzoxazin-4-one;

6-[[[(1,1-dimethylethoxy)carbonyl]amino]-5-methyl-2-[[(1R)-phenylethyl]amino]-4H-3,1-benzoxazin-4-one;

6-[[[(1,1-dimethylethoxy)carbonyl]amino]methyl]-5-methyl-2-[[(1S)-phenylethyl]amino]-4H-3,1-benzoxazin-4-one;

6-amino-5-methyl-2-[[(1R)-phenylethyl]amino]-4H-3,1-benzoxazin-4-one;

6-amino-5-methyl-2-[[(1S)-phenylethyl]amino]-4H-3,1-benzoxazin-4-one;

6-amino-methyl-5-methyl-2-[[(1S)-phenylethyl]amino]-4H-3,1-benzoxazin-4-one;

6-[[[[dimethylaminomethyl]carbonyl]amino]methyl]-5-methyl-2-[[(1S)-phenylethyl]amino]-4H-3,1-benzoxazin-4-one;

5-methyl-2-[[(1R)-(4-iodophenyl)ethyl]amino]-4H-3,1-benzoxazin-4-one;

5-methyl-6-[[[(1-morpholinylmethyl)carbonyl]amino]-2-[[(1S)-phenylethyl]amino]-4H-3,1-benzoxazin-4-one;

6-[[[(2-furanyl)carbonyl]amino]-5-methyl-2-[[(1S)-phenylethyl]amino]-4H-3,1-benzoxazin-4-one;

5-methyl-2[[(1S)-phenylethyl]amino]-6-[[(1-pyrrolidinylmethyl)carbonyl]amino]-4H-3,1-benzoxazin-4-one;

5-methyl-6-[[[(dimethylaminomethyl)carbonyl]amino]-2-[[(1S)-phenylethyl]amino]-4H-3,1-benzoxazin-4-one;

5-methyl-6-[[[(3-dimethylaminopropyl)carbonyl]amino]-2-[[(1R)-phenylethyl]amino]-4H-3,1-benzoxazin-4-one;

6-[[[[(1R)-phenylethyl]amino]carbonyl]amino]-5-methyl-2-[[(1R)-phenylethyl]amino]-4H-3,1-benzoxazin-4-one;

1,1-dimethylethyl[2-[[2-(3,5-diiodo-4-methoxy phenyl)-1S-[(dimethylamino)methyl]ethyl]amino]-5-methyl-4-oxo-4H-3,1-benzoxazin-6-yl]carbamate;

1,1-dimethylethyl[2-[[1S-[(dimethylamino)methyl]-3-(methylsulfonyl)propyl]amino]-5-methyl-4-oxo-4H-3,1-benzoxazin-6-yl]carbamate;

1,1-dimethylethyl[2-[[2-(dimethylamino)-1S-methylethyl] amino]-5-methyl-4-oxo-4H-3,1-benzoxazin-6-yl] carbamate;

1,1-dimethylethyl[[2-[[2-(dimethylamino)-1S-methylethyl] amino]-5-methyl-4-oxo-4H-3,1-benzoxazin-6-yl]methyl] carbamate;

N-[5-methoxy-4-oxo-4H-3,1-benzoxazin-2-yl]-O-methyl-L-tyrosine, N-methyl-N-phenylmethylamide;

N-[6-[[(1,1-dimethylethoxy)carbonyl]amino]-5-methyl-4-oxo-4H-3,1-benzoxazin-2-yl]-3,5-diiodo-L-tyrosine, methyl ester;

N-[6-[[(1,1-dimethylethoxy)carbonyl]amino]-5-methyl-4-oxo-4H-3,1-benzoxazin-2-yl-]-3,5-diiodo-O-methyl-L-tyrosine, methyl ester;

N-[6-[[(1,1-dimethylethoxy)carbonyl]amino]-5-methyl-4-oxo-4H-3,1-benzoxazin-2-yl-]-3,5-diiodo-N,0-dimethyl-L-tyrosine, methyl ester;

3,5-dibromo-N-[6-[[(1,1-dimethylethoxy)carbonyl]amino]-5-methyl-4-oxo-4H-3,1-benzoxazin-2-yl-]-O-methyl-L-tyrosine, methyl ester;

methyl αS-[[6-[[(1,1-dimethylethoxy)carbonyl]amino]-5-methyl-4-oxo-4H-3,1-benzoxazin-2-yl]amino]thiazole-4-propanoate;

methyl αS-[[6-[[(1,1-dimethylethoxy)carbonyl]amino]-5-methyl-4-oxo-4H-3,1-benzoxazin-2-yl]amino]oxazole-4-propanoate;

methyl 4-[(aminocarbonyl)amino]-2S-[[6[[(1,1-dimethylethoxy)carbonyl]amino]-5-methyl-4-oxo-4H-3,1-benzoxazin-2-yl]amino]butanoate;

$N^2$-[6-[[(1,1-dimethylethoxy)carbonyl]amino]-5-methyl-4-oxo-4H-3,1-benzoxazin-2-yl]-L-asparagine, methyl ester;

$N^2$-[6-[[(1,1-dimethylethoxy)carbonyl]amino]-5-methyl-4-oxo-4H-3,1-benzoxazin-2-yl]-L-glutamine, methyl ester;

1,1-dimethylethyl[2-[[2-(diethylamino)-1S-[(4-hydroxy-3,5-diiodophenyl)methyl]-2-oxoethyl]amino]-5-methyl-4-oxo-4H-3,1-benzoxazin-6-yl]carbamate;

1,1-dimethylethyl[2-[[1S-[(4-hydroxy-3,5-diiodophenyl)methyl]2-(1-pyrrolidinyl)ethyl]amino]-5-methyl-4-oxo-4H-3,1-benzoxazin-6-yl]carbamate;

1,1-dimethylethyl[2-[[2-(diethylamino)-1S-methyl-2-oxoethyl]amino]-5-methyl-4-oxo-4H-3,1-benzoxazin-6-yl]carbamate;

1,1-dimethylethyl[2-[[1,1-dimethyl-2-oxo-2-(pyrrolidinyl)ethyl]amino]-5-methyl-4-oxo-4H-3,1-benzoxazin-6-yl]carbamate;

1,1-dimethylethyl[5-methyl-2-[[3-(methylsulfonyl)-1S-[(1-pyrrolidinyl)carbonyl]propyl]amino]-4-oxo-4H-3,1-benzoxazin-6-yl]carbamate;

1,1-dimethylethyl[2-[[2-(diethylamino)-1S-[(3,5-diiodo-4-methoxyphenyl)methyl]-2-oxoethyl]amino]-5-methyl-4-oxo-4H-3,1-benzoxazin-6-yl]carbamate;

1,1-dimethylethyl[5-methyl-2-[[1S-methyl-2-oxo-2-(1-pyrrolidinyl)ethyl]amino]-4-oxo-4H-3,1-benzoxazin-6-yl]carbamate;

1,1-dimethylethyl[2-[[1S[(3,5-diiodo-4-methoxy phenyl)methyl]-2-[(1-methylethyl)amino]-2-oxoethyl]amino]-5-methyl-4-oxo-4H-3,1-benzoxazin-6-yl]carbamate;

1,1-dimethylethyl[2-[[1S-[(4-hydroxy-3,5-diiodophenyl)methyl]-2-(4-morpholinyl)-2-oxoethyl]amino]-5-methyl-4-oxo-4H-3,1-benzoxazin-6-yl]carbamate;

1,1-dimethylethyl[2[[1S-[(4-hydroxy-3,5-diiodo phenyl)methyl]-2-(4-methylpiperazin-1-yl)-2-oxoethyl]amino]-5-methyl-4-oxo-4H-3,1-benzoxazin-6-yl]carbamate;

1,1-dimethylethyl[2-[[1S-[(4-hydroxy-3,5-diiodo phenyl)methyl]-2-[[2-(dimethylamino)ethyl]methylamino]-2-oxoethyl]amino]-5-methyl-4-oxo-4H-3,1-benzoxazin-6-yl]carbamate;

1,1-dimethylethyl[2-[[2-[[2-(dimethylamino)ethyl]methylamino]-1S-methyl-2-oxoethyl]amino]-5-methyl-4-oxo-4H-3,1-benzoxazin-6-yl]carbamate;

1,1-dimethylethyl[2-[[2-[[2-(dimethylamino)ethyl]methylamino]-1,1-dimethyl-2-oxoethyl]amino]-5-methyl-4-oxo-4H-3,1-benzoxazin-6-yl]carbamate;

1,1-dimethylethyl[2-[[1S[[[2-(dimethylamino)ethyl]methylamino]carbonyl]-3-(methylsulfonyl)propyl]amino]-5-methyl-4-oxo-4H-3,1-benzoxazin-6-yl]carbamate;

1,1-dimethylethyl[2-[[1S(3,5-diiodo-4-methoxy phenyl)methyl]-2-[methyl[2-(1-piperidinyl)ethyl]amino]-2-oxoethyl]amino]-5-methyl-4-oxo-4H-3,1-benzoxazin-6-yl]carbamate;

1,1-dimethylethyl[2-[[1S-methyl-2-(1-piperidinyl)ethyl]amino]-2-oxoethyl]amino]-5-methyl-4-oxo-4H-3,1-benzoxazin-6-yl]carbamate;

1,1-dimethylethyl[2-[[1S-[[methyl-[2-(1-piperidinyl)ethyl]amino]carbonyl]-3-(methylsulfonyl)propyl]amino]-5-methyl-4-oxo-4H-3,1-benzoxazin-6-yl]carbamate;

1,1-dimethylethyl[2-[[1S-[3,5-diiodo-4-methoxy phenyl)methyl]-2-[methyl[2-(4-morpholinyl)ethyl]amino]-2-oxoethyl]amino]-5-methyl-4-oxo-4H-3,1-benzoxazin-6-yl]carbamate;

1,1-dimethylethyl[2-[[1S-[[methyl-[2-(4-morpholinyl)ethyl]amino]carbonyl]-3-(methylsulfonyl)propyl]amino]-5-methyl-4-oxo-4H-3,1-benzoxazin-6-yl]carbamate;

1,1-dimethylethyl[5-methyl-2-[[1S-methyl-2-[methyl-[2-(4-methylpiperazin-1-yl)ethyl]amino]-2-oxoethyl]amino]-4-oxo-4H-3,1-benzoxazin-6-yl]carbamate;

1,1-dimethylethyl[5-methyl-2-[[1S-methyl-2-[methyl-[2-(4-methylpiperazin-1-yl)ethyl]amino]carbonyl]-3-(methylsulfonyl)propyl]amino]-4-oxo-4H-3,1-benzoxazin-6-yl]carbamate;

1,1-dimethylethyl[5-methyl-4-oxo-2-[[3-oxo-1S-(3-pyridinyl)-3-(1-pyrrolidinyl)propyl]amino]-4H-3,1-benzoxazin-6-yl]carbamate;

1,1-dimethylethyl[5-methyl-2-[1S-methyl-3-(4-methylpiperazin-1-yl)-3-oxopropyl]amino]-4-oxo-4H-3,1-benzoxazin-6-yl]carbamate;

methyl αS-[[6-[[1,1-dimethylethoxy)carbonyl]amino]-5-methyl-4-oxo-4H-3,1-benzoxazin-2-yl]amino]morpholine-4-butanoate;

methyl αS-[[6-[[(1,1-dimethylethoxy)carbonyl]amino]-5-methyl-4-oxo-4H-3,1-benzoxazin-2-yl]amino]pyrrolidine-1-butanoate;

1,1-dimethylethyl[6-[[1S-[(4-hydroxy-3,5-diiodo phenyl)methyl]-1-methyl-2-oxo-2-(1-pyrrolidinyl)ethyl]amino]-5-methyl-4-oxo-4H-3,1-benzoxazin-6-yl]carbamate;

N-[2-(dimethylamino)ethyl]-αS-[[6-[[(ethylamino)carbonyl]amino]-5-methyl-4-oxo-4H-3,1-benzoxazin-2-yl]amino]-3,5-diiodo-4-methoxy-N-methylbenzenepropanamide;

N-[2-dimethylamino)ethyl]-αS-[[6-[[ethyl amino)carbonyl]amino]-5-methyl-4-oxo-4H-3,1-benzoxazin-2-yl]amino]-N-methylpropanamide;

N-[2-(dimethylamino)ethyl]-3,5-diiodo-4-methoxy-N-methyl-αS[[5-methyl-4-oxo-6-[(propylsulfonyl)amino]-4H-3,1-benzoxazin-2-yl]amino]-N-methylpropanamide;

$N^1$[2-(dimethylamino)ethyl]-$N^2$-[2-[[1S-[(4-hydroxy-3,5-diiodophenyl)methyl]-2-oxo-2-(1-pyrrolidinyl)ethyl]amino]-5-methyl-4-oxo-4H-3,1-benzoxazin-6-yl]urea;

2-(dimethylamino)ethyl[2-[[1S-[(3,5-diiodo-4-methoxyphenyl)ethyl]-2-oxo-2(1-pyrrolidinyl)ethyl]amino]-5-methyl-4-oxo-4H-3,1-benzoxazin-6-yl]carbamate;

$N^1$-[2-(dimethylamino)ethyl]-$N^2$-[5-methyl-4-oxo-2-[[1S-methyl-2-oxo-2-(1-pyrrolidinyl)ethyl]amino]]-4H-3,1-benzoxazin-6-yl]urea;

$N^1$-[2-(dimethylamino)ethyl]-$N^2$-[5-methyl-2-[[3-(methylsulfonyl)-1S-[(1-pyrrolidinyl)carbonyl]propyl]amino]-4-oxo-4H-3,1-benzoxazin-6-yl]urea;

(3-pyridinyl)methyl[2-[[1S[3,5-diiodo-4-methoxy phenyl]methyl]-2-oxo-2-(1-pyrrolidinyl)ethyl]amino]-5-methyl-4-oxo-4H-a3,1-benzoxazin-6-yl]carbamate;

2-(dimethylamino)-N-[2-[[1S[(3,5-diiodo-4-methoxyphenyl)methyl]-2-oxo-2-(4-morpholinyl)ethyl]amino]-5-methyl-4-oxo-4H-3,1-benzoxazin-6-yl]acetamide;

2-(dimethylamino)-N-[5-methyl-2[[1S-methyl-2-oxo-2-(1-pyrrolidinyl)ethyl]amino]-4-oxo-4H-3,1-benzoxazin-6-yl]acetamide;

N-[2-[[1S-[(3,5-diiodo-4-methoxyphenyl)methyl]-2-oxo-2-(1-pyrrolidinyl)ethyl]amino]-5-methyl-4-oxo-4H-3,1-benzoxazin-6-yl]morpholine-4-acetamide;

N-[2-[[1,1-dimethyl-2-oxo-2-(1-pyrrolidinyl)ethyl]amino]-5-methyl-4-oxo-4H-3,1-benzoxazin-6-yl]morpholine-4-acetamide;

N-[5-methyl-2-[[3-(methylsulfonyl)-1S-[(1-pyrrolidinyl)carbonyl]propyl]amino]-4-oxo-4H-3,1-benzoxazin-6-yl]morpholine-4-acetamide;

4-methyl-N-[5-methyl-2-[[1S-methyl-2-oxo-2-(1-pyrrolidinyl)ethyl]amino]-4-oxo-4H-3,1-benzoxazin-6-yl]piperazine-1-acetamide;

N-[2-[[1S-[(3,5-diiodo-4-methoxyphenyl)methyl]-2-oxo-2-(1-pyrrolidinyl)ethyl]amino]-5-methyl-4-oxo-4H-3,1-benzoxazin-6-yl]-1-methylpyrrolidine-2S-carboxamide;

N-[5-methyl-2-[[1S-methyl-2-oxo-(4-morpholinyl)ethyl]amino]-4-oxo-4H-3,1-benzoxazin-6-yl]pyrrolidine-1-acetamide;

N-[5-methyl-2-[[3-(methylsulfonyl)-1S-[(1-pyrrolidinyl)carbonyl]propyl]amino]-4-oxo-4H-3,1-benzoxazin-6-yl]pyrrolidine-1-acetamide;

N-[5-methyl-2-[[3-(methylsulfonyl)-1S-[(4-methylpiperazin-1-yl)carbonyl]propyl]amino]-4-oxo-4H-3,1-benzoxazin-6-yl]furan-2-carboxamide;

N-[6[[[(1,1-dimethylethoxy)carbonyl]amino]methyl]-5-methyl-4-oxo-4H-3,1-benzoxazin-2-yl]-3,5-diiodo-O-methyl-L-tyrosine, methyl ester;

methyl αS-[6-[[[(1,1-dimethylethoxy)carbonyl]amino]methyl]-5-methyl-4-oxo-4H-3,1-benzoxazin-2-yl]amino]thiazole-4-propanoate;

$N^2$-[6[[[(1,1-dimethylethoxy)carbonyl]amino]methyl]-5-methyl-4-oxo-4H-3,1-benzoxazin-2-yl]-L-asparagine, methyl ester;

1,1-dimethylethyl[[5-methyl-2-[[3-methylsulfonyl)-1S-[(1-pyrrolidinyl)carbonyl]propyl]amino]-4-oxo-4H-3,1-benzoxazin-6-yl]methyl]carbamate;

1,1-dimethylethyl[[2-[[1S-[3,5-diiodo-4-methoxy phenyl)methyl]-2-[[2-(dimethylamino)ethyl]methyl amino]-2-oxoethyl]amino]-5-methyl-4-oxo-4H-3,1-benzoxazin-6-yl]methyl]carbamate;

1,1-dimethylethyl[[2-[[2-[[2-(dimethylamino)ethyl]methylamino]-1S-methyl-2-oxoethyl]amino]-5-methyl-4-oxo-4H-3,1-benzoxazin-6-yl]methyl]carbamate;

1,1-dimethylethyl[[2-[[1S-[[2-(dimethylamino)ethyl]methylamino]carbonyl]-3-(methylsulfonyl)propyl]amino]-5-methyl-4-oxo-4H-3,1-benzoxazin-6-yl]methyl]carbamate;

1,1-dimethylethyl[[5-methyl-2-[[1S-methyl-2-[methyl[2-(1-piperidiny)ethyl]amino]-2-oxoethyl]-amino]-4-oxo-4H-3,1-benzoxazin-6-yl]methyl]carbamate;

1,1-dimethylethyl[[5-methyl-2-[[1S-[[methyl-[2-(4-morpholinyl)ethyl]amino]carbonyl]-3-(methylsulfonyl)propyl]amino]-4-oxo-4H-3,1-benzoxazin-6-yl]methyl]carbamate;

1,1-dimethylethyl[[5-methyl-2-[[1S-methyl-2-(4-methyl-1-piperazinyl)ethyl]amino]-2-oxoethyl]amino]-4-oxo-4H-3,1-benzoxazin-6-yl]methyl]carbamate;

$N^1$-[2-(dimethylamino)ethyl]-$N^2$-[[5-methyl-2-[[1S-methyl-2-oxo-2-(1-pyrrolidinyl)ethyl]amino]-4-oxo-4H-3,1-benzoxazin-6-yl]methyl]urea;

2-(dimethylamino)-N-[[5-methyl-2-[[1S-methyl-2-oxo-2-(1-pyrrodinyl)ethyl]amino]-4-oxo-4H-3,1-benzoxazin-6-yl]methyl]acetamide;

N-[[5-methyl-2-[[3-(methylsulfonyl)-1S-(1-pyrrolidinyl)carbonyl]propyl]amino]-4-oxo-4H-3,1-benzoxazin-6-yl]methyl]morpholine-4-acetamide;

N-(5-methyl-4-oxo-4H-3,1-benzoxazin-2-yl)-L-alanine, tert-butyl ester;

N-(5-methyl-4-oxo-4H-3,1-benzoxazin-2-yl)-D-alanine, 1,1-dimethyl ester;

N-(5-methyl-4-oxo-4H-3,1-benzoxazin-2-yl)-L-alanine, methyl ester

N-(5-methyl-4-oxo-4H-3,1-benzoxazin-2-yl)-D-alanine, methyl ester;

N-5(5-methyl-4-oxo-4H-3,1-benzoxazin-2-yl)-L-valine, methyl ester;

N-(5-methyl-4-oxo-4H-3,1-benzoxazin-2-yl)-L-leucine, methyl ester;

N-(5-methyl-4-oxo-4H-3,1-benzoxazin-2-yl)-L-norleucine, methyl ester;

N-(5-methyl-4-oxo-4H-3,1-benzoxazin-2-yl)-L-isoleucine, methyl ester;

N-(5-methyl-4-oxo-4H-3,1-benzoxazin-2-yl)-L-methionine, methyl ester;

$N^{\alpha}$-(5-methyl-4-oxo-4H-3,1-benzoxazin-2-yl)-$N^{\epsilon}$-[(phenylmethoxy)carbonyl]-L-lysine, 1,1-dimethylethyl ester;

N-(5-methyl-4-oxo-4H-3,1-benzoxazin-2-yl)-L-phenylalanine, 1,1-dimethylethyl ester;

N-(5-methyl-4-oxo-4H-3,1-benzoxazin-2-yl)-L-phenylalanine, methyl ester

N-(5-methyl-4-oxo-4H-3,1-benzoxazin-2-yl)-L-tyrosine, 1,1-dimethylethyl ester;

N-(5-methyl-4-oxo-4H-3,1-benzoxazin-2-yl)-L-tryptophan, methyl ester;

N-(5-methyl-4-oxo-4H-3,1-benzoxazin-2-yl)-L-tryptophan, 1,1-dimethylethyl ester;

N-(5-methyl-4-oxo-4H-3,1-benzoxazin-2-yl)-L-phenylglycine, 1,1-dimethylethyl ester;

2-[[2-methoxy-(1S)-(1-phenylmethyl)ethyl]amino]-5-methyl-4H-3,1-benzoxazin-4-one;

3,5-diiodo-N-(5-methyl-4-oxo-4H-3,1-benzoxazin-2-yl)-L-tyrosine, methyl ester;

N-(5-methyl-4-oxo-4H-3,1-benzoxazin-2-yl)-O-methyl-L-tyrosine, methyl ester;

N-(6-bromo-5-methyl-4-oxo-4H-3,1-benzoxazin-2-yl)-L-alanine, 1,1-dimethylethyl ester;

N-(6-bromo-5-methyl-4-oxo-4H-3,1-benzoxazin-2-yl)-D-alanine, 1,1-dimethylethyl ester;

N-[6-[[(1,1-dimethylethoxy)carbonyl]amino]-5-methyl-4-oxo-4H-3,1-benzoxazin-2-yl]-L-alanine, 1,1-dimethylethyl ester;

N-[6-[[(1,1-dimethylethoxy)carbonyl]amino]-5-methyl-4-oxo-4H-3,1-benzoxazin-2-yl]-L-phenylalanine, methyl ester;

N-[6-[[(1,1-dimethylethoxy)carbonyl]amino]-5-methyl-4-oxo-4H-3,1-benzoxazin-2-yl]-O-(phenylmethyl)-L-serine, methyl ester;

N-[6-[[(1,1-dimethylethoxy)carbonyl]amino]-5-methyl-4-oxo-4H-3,1-benzoxazin-2yy]-O-methyl-L-tyrosine, methyl ester;

N-[6-[[(1,1-dimethylethoxy)carbonyl]amino]-5-methyl-4-oxo-4H-3,1-benzoxazin-2-yl]-O-methyl-L-tyrosine, dimethylamide;

N-[6-[[(1,1-dimethylethoxy)carbonyl]amino]-5-methyl-4-oxo-4H-3,1-benzoxazin-2-yl]-L-thiazol-4-yl-alanine, methyl ester;

N-[6-[[(1,1-dimethylethoxy)carbonyl]amino]-5-methyl-4-oxo-4H-3,1-benzoxazin-2-yl]-L-aspartic acid, alpha-methyl ester beta-dimethylamide;

N-[6-[[(1,1-dimethylethoxy)carbonyl]amino]-5-methyl-4-oxo-4H-3,1-benzoxazin-2-yl]-L-alanine, pyrrolidineamide;

N-[6-[[(1,1-dimethylethoxy)carbonyl]amino]-5-methyl-4-oxo-4H-3,1-benzoxazin-2-yl]-O-methyl-L-tyrosine, pyrrolidineamide;

N-[6-[[(1,1-dimethylethoxy)carbonyl]amino]-5-methyl-4-oxo-4H-3,1-benzoxazin-2-yl]-O-methyl-L-tyrosine, morpholineamide;

N-[6[[(1,1-dimethylethoxy)carbonyl]amino]-5-methyl-4-oxo-4H-3,1-benzoxazin-2-yl]-O-methyl-L-tyrosine, N-methylpiperazineamide;

N-[6-[[(1,1-dimethylethoxy)carbonyl]amino]-5-methyl-4-oxo-4H-3,1-benzoxazin-2-yl]-O-methyl-L-tyrosine, N-methyl-N-[2-(1-morpholinyl)ethyl]amide;

N-[6-[[(1,1-dimethylethoxy)carbonyl]amino]-5-methyl-4-oxo-4H-3,1-benzoxazin-2-yl]-O-methyl-L-tyrosine, N-methyl-N-[2-(1-piperidinyl)ethyl]amide;

N-[6-[[(1,1-dimethylethoxy)carbonyl]amino]-5-methyl-4-oxo-4H-3,1-benzoxazin-2-yl]-L-tryptophan, dimethylamide;

N-[6-[[(1,1-dimethylethoxy)carbonyl]amino]-5-methyl-4-oxo-4H-3,1-benzoxazin-2-yl]-O-methyl-L-threonine, methyl ester;

N-[6-[[(1,1-dimethylethoxy)carbonyl]amino]-5-methyl-4-oxo-4H-3,1-benzoxazin-2-yl]-O-methyl-L-serine, methyl ester;

N-[6-[[(1,1-dimethylethoxy)carbonyl]amino]-5-methyl-4-oxo-4H-3,1-benzoxazin-2-yl]-L-phenylglycine, 1,1-dimethylethyl ester;

N-[6-[[(1,1-dimethylethoxy)carbonyl]amino]-5-methyl-4-oxo-4H-3,1-benzoxazin-2-yl]-3,5-diiodo-O-methyl-L-tyrosine, methyl ester;

N-[6-[[(1,1-dimethylethoxy)carbonyl]amino]-5-methyl-4-oxo-4H-3,1-benzoxazin-2-yl]-4-iodo-L-phenylalanine, methyl ester;

N-[6-[[(1,1-dimethylethoxy)carbonyl]amino]-5-methyl-4-oxo-4H-3,1-benzoxazin-2-yl]-L-methionine sulfone, methyl ester;

N-[6-[[(1,1-dimethylethoxy)carbonyl]amino]-5-methyl-4-oxo-4H-3,1-benzoxazin-2-yl]-L-beta-naphthylalanine, methyl ester;

N-[6-[[(1,1-dimethylethoxy)carbonyl]amino]-5-methyl-4-oxo-4H-3,1-benzoxazin-2-yl]-2-aminoisobutyric acid, methyl ester;

N-[6-[[(1,1-dimethylethoxy)carbonyl]amino]-5-methyl-4-oxo-4H-3,1-benzoxazin-2-yl]-1-cyclopropanecarboxylic acid, methyl ester;

N-[6-[[(1,1-dimethylethoxy)carbonyl]amino]-5-methyl-4-oxo-4H-3,1-benzoxazin-2-yl]-[1-(4-cyanophenyl)]-3S-aminopyrrolidin-2-one;

N-[6-[[(1,1-dimethylethoxy)carbonyl]amino]-5-methyl-4-oxo-4H-3,1-benzoxazin-2-yl]-L-alanine, N-methyl-N-allylamide;

N-[6-[[(1,1-dimethylethoxy)carbonyl]amino]-5-methyl-4-oxo-4H-3,1-benzoxazin-2-yl]-L-alanine, N-methyl-N-phenylmethylamide;

N-[6[[(1,1-dimethylethoxy)carbonyl]amino]-5-methyl-4-oxo-4H-3,1-benzoxazin-2-yl]-L-alanine, phenyl methyl ester;

N-[6-[[(1,1-dimethylethoxy)carbonyl]amino]-5-methyl-4-oxo-4H-3,1-benzoxazin-2-yl]-3,5-diiodo-L-tyrosine, methyl ester;

N-[6-[[[(1,1-dimethylethoxy)carbonyl]amino]methyl]-5-methyl-4-oxo-4H-3,1-benzoxazin-2-yl]-L-alanine, dimethylamide;

N-[6-[[[(1,1-dimethylethoxy)carbonyl]amino]methyl]-5-methyl-4-oxo-4H-3,1-benzoxazin-2-yl]-L-alanine, morpholineamide;

N-[6-[[[(1,1-dimethylethoxy)carbonyl]amino]methyl]-5-methyl-4-oxo-4H-3,1-benzoxazin-2-yl]-O-methyl-L-tyrosine, pyrrolidineamide;

N-[6-[[[(1,1-dimethylethoxy)carbonyl]amino]methyl]-5-methyl-4-oxo-4H-3,1-benzoxazin-2-yl]-O-methyl-L-tyrosine, morpholineamide;

N-[6-[[[(1,1-dimethylethoxy)carbonyl]amino]methyl]-5-methyl-4-oxo-4H-3,1-benzoxazin-2-yl]-O-methyl-L-tyrosine, dimethylamide;

N-[6-[[[(1,1-dimethylethoxy)carbonyl]amino]methyl]-5-methyl-4-oxo-4H-3,1-benzoxazin-2-yl]-L-alanine, methyl ester;

N-[6-amino-5-methyl-4-oxo-4H-3,1-benzoxazin-2-yl]-L-alanine, methyl ester;

N-[6-amino-5-methyl-4-oxo-4H-3,1-benzoxazin-2-yl]-1-phenylalanine, methyl ester;

N-[6-aminomethyl-5-methyl-4-oxo-4H-3,1-benzoxazin-2-yl]-O-methyl-L-tyrosine, pyrrolidineamide;

N-[6-[[[[dimethylaminomethyl]carbonyl]amino]methyl]-5-methyl-4-oxo-4H-3,1-benzoxazin-2-yl]-O-methyl-L-tyrosine, pyrrolidineamide;

N-[6-[[[[(1-pyrrolidinyl)methyl]carbonyl]amino]methyl]-5-methyl-4-oxo-4H-3,1-benzoxazin-2-yl]-O-methyl-L-tyrosine, pyrrolidineamide;

N-[[6-(dimethylaminomethyl)carbonyl]amino]-5-methyl-4-oxo-4H-3,1-benzoxazin-2-yl]-L-alanine, methyl ester;

5-methyl-N-6-[[(2-pyridyl)carbonyl]amino]-4-oxo-4H-3,1-benzoxazin-2-yl]-L-alanine, methyl ester;

N-[6-[[(5-isoxazolyl)carbonyl]amino]-5-methyl-4-oxo-4H-3,1-benzoxazin-2-yl]-L-alanine, methyl ester;

N-[6-[[(methoxymethyl)carbonyl]amino]-5-methyl-4-oxo-4H-3,1-benzoxazin-2-yl]-L-alanine, methyl ester;

N-[6-[[(methoxymethyl)carbonyl]amino]-5-methyl-4-oxo-4H-3,1-benzoxazin-2-yl]-L-phenylalanine, methyl ester;

N-[6-[[(2-carboxyethyl)carbonyl]amino]-5-methyl-4-oxo-4H-3,1-benzoxazin-2-yl]-L-phenylalanine, methyl ester;

N-[6-[[(cyclobutyl)carbonyl]amino]-5-methyl-4-oxo-4H-3,1-benzoxazin-2-yl]-L-phenylalanine, methyl ester;

N-[N-[[(2-furanyl)carbonyl]amino]-5-methyl-4-oxo-4H-3,1-benzoxazin-2-yl]-L-phenylalanine, methyl ester;

N-[6-[[(2-thienylmethyl)carbonyl]amino]-5-methyl-4-oxo-4H-3,1-benzoxazin-2-yl]-L-phenylalanine, methyl ester;

N-[6-[[(2-thienylmethyl)carbonyl]amino]-5-methyl-4-oxo-4H-3,1-benzoxazin-2-yl]-L-phenylalanine, morpholineamide;

N-[6-[[(2-thienylmethyl)carbonyl]amino]-5-methyl-4-oxo-4H-3,1-benzoxazin-2-yl]-L-phenylalanine, pyrrolidineamide;

N-[6-[[[2-(2-thienyl)ethyl]amino]carbonyl]amino]-5-methyl-4-oxo-4H-3,1-benzoxazin-2-yl]-L-phenylalanine, methyl ester;

N-[6-[[[2-(2-thienyl)ethyl]amino]carbonyl]amino]-5-methyl-4-oxo-4H-3,1-benzoxazin-2-yl]-L-alanine, methyl ester;

N-[6[[(1-morpholinyl)carbonyl]amino]-5-methyl-4-oxo-4H-3,1-benzoxazin-2-yl]-L-alanine, methyl ester;

N-[6-[benzenesulfonyl]amino]-5-methyl-4-oxo-4H-3,1-benzoxazin-2-yl]-L-phenylalanine, methyl ester;

N-[6-[benzenesulfonyl]amino]-5-methyl-4-oxo-4H-3,1-benzoxazin-2-yl]-L-alanine, methyl ester; and N-[6-[[(1,1-dimethylethoxy)carbonyl]amino]-5-methyl-4-oxo-4H-3,1-benzoxazin-2-yl]-L-alanine.

The term "hydrido" denotes a single hydrogen atom (H). This hydrido radical may be attached, for example, to an oxygen atom to form a hydroxyl radical or two hydrido radicals may be attached to a carbon atom to form a methylene (—CH$_2$—) radical. Where used, either alone or within other terms such as "haloalkyl", "alkylsulfonyl", "alkoxyalkyl", "hydroxyalkyl" and "aralkyl" the term "alkyl" embraces linear or branched radicals having one to about twenty carbon atoms or, preferably, one to about twelve carbon atoms. More preferred alkyl radicals are "lower alkyl" radicals having one to about ten carbon atoms. Most preferred are lower alkyl radicals having one to about six carbon atoms. Examples of such radicals include methyl, ethyl, n-propyl, isopropyl, n-butyl, isobutyl, sec-butyl, tert-butyl, pentyl, iso-amyl, hexyl and the like. The term "alkenyl" embraces linear or branched radicals having at least one carbon-carbon double bond of two to about twenty carbon atoms or, preferably, two to about twelve carbon atoms, provided that the double bond does not occur at the point of attachment of the radical. More preferred alkenyl radicals are "lower alkenyl" radicals having two to about six carbon atoms. Examples of such radicals include ethenyl, n-propenyl, butenyl, and the like. The term "halo" means halogens such as fluorine, chlorine, bromine or iodine. The term "haloalkyl" embraces radicals wherein any one or more of the alkyl carbon atoms is substituted with halo as defined above. Specifically embraced are monohaloalkyl, dihaloalkyl and polyhaloalkyl radicals A monohaloalkyl radical, for one example, may have either an iodo, bromo, chloro or fluoro atom within the radical. Dihalo and polyhaloalkyl radicals may have two or more of the same halo atoms or a combination of different halo radicals. "Lower haloalkyl" embraces radicals having 1–6 carbon atoms. Examples of haloalkyl radicals include fluoromethyl, difluoromethyl, trifluoromethyl, chloromethyl, dichloromethyl, trichloromethyl, trichloromethyl, pentafluoroethyl, heptafluoropropyl, difluorochloromethyl, dichlorofluoromethyl, difluoroethyl, difluoropropyl, dichloroethyl and dichloropropyl. The term "hydroxyalkyl" embraces linear or branched alkyl radicals having one to about ten carbon atoms any one of which may be substituted with one or more hydroxyl radicals. More preferred hydroxyalkyl radicals are "lower hydroxyalkyl" radicals having one to six carbon atoms and one or more hydroxyl radicals. Examples of such radicals include hydroxymethyl, hydroxyethyl, hydroxypropyl, hydroxybutyl and hydroxyhexyl. The terms "alkoxy" and "alkoxyalkyl" embrace linear or branched oxy-containing radicals each having alkyl portions of one to about ten carbon atoms. More preferred alkoxy radicals are "lower alkoxy" radicals having one to six carbon atoms. Examples of such radicals include methoxy, ethoxy, propoxy, butoxy and tert-butoxy. The term "alkoxyalkyl" also embraces alkyl radicals having two or more alkoxy radicals attached to the alkyl radical, that is, to form monoalkoxyalkyl and dialkoxyalkyl radicals. More preferred alkoxyalkyl radicals are "lower alkoxyalkyl" radicals having one to six carbon atoms and one or two alkoxy radicals. Examples of such radicals include methoxymethyl, methoxyethyl, ethoxyethyl, methoxybutyl and methoxypropyl. The "alkoxy" or "alkoxyalkyl" radicals may be further substituted with one or more halo atoms, such as fluoro, chloro or bromo, to provide "haloalkoxy" or haloalkoxyalkyl radicals. More preferred haloalkoxy radicals are "lower haloalkoxy" radicals having one to six carbon atoms and one or more halo radicals. Examples of such radicals include fluoromethoxy, chloromethoxy, trifluoromethoxy, trifluoroethoxy, fluoroethoxy and fluoropropoxy. The term "aryl", alone or in combination, means a carbocyclic aromatic system containing one, two or three rings wherein such rings may be attached together in a pendent manner or may be fused The term "aryl" embraces aromatic radicals such as phenyl, naphthyl, tetrahydronaphthyl, indane and biphenyl. Aryl moieties may also be substituted at a substitutable position with one or more substituents selected independently from alkyl, aralkyl, alkoxyalkyl, alkylaminoalkyl, carboxyalkyl, alkoxycarbonylalkyl, aminocarbonylalkyl, alkoxy, aralkoxy, alkylaminoalkoxy, aminocarboxy, alkylaminocarboxy, aralkylaminocarboxy, amino, halo, nitro, alkylamino, alkylcarbonylamino, arylcarbonylamino, alkoxycarbonylamino, aralkoxycarbonylamino, aminocarbonylamino, alkylaminocarbonylamino, alkylsulfonylamino, arylsulfonylamino, acyl, cyano, carboxy, aminocarbonyl, alkoxycarbonyl and aralkoxycarbonyl. The terms "heterocyclo" or "heterocyclic" embrace saturated, partially saturated and unsaturated heteroatom-containing ring-shaped radicals, where the heteroatoms may be selected from nitrogen, sulfur and oxygen. Examples of saturated heterocyclic radicals include saturated 5 to 7-membered heteromonocyclic group containing 1 to 4 nitrogen atoms [e.g. pyrrolidinyl, imidazolidinyl, piperidinyl, piperazinyl, tropanyl, homotropanyl, etc.]; saturated 5 to 7-membered heteromonocyclic group containing 1 to 2 oxygen atoms and 1 to 3 nitrogen atoms [e.g. morpholinyl, etc.]; saturated 5 to 7-membered heteromonocyclic group containing 1 to 2 sulfur atoms and 1 to 3 nitrogen atoms [e.g., thiazolidinyl, etc.]. Examples of partially saturated heterocyclic radicals include dihydrothiophene, dihydropyran, oxazolinyl, dihydrofuran and dihydrothiazole. Examples of unsaturated heterocyclic radicals, also termed "heteroaryl" radicals include unsaturated 5 to 7 membered heteromonocyclic group containing 1 to 4 nitrogen atoms, for example, pyrrolyl, pyrrolinyl, imidazolyl, pyrazolyl, pyridyl, pyrimidyl, azepinyl, pyrazinyl, pyridazinyl, triazolyl [e.g., 4H-1,2,4-triazolyl, 1H-1,2,3-triazolyl, 2H-1,2,3-triazolyl, etc.] tetrazolyl [e.g. 1H-tetrazolyl, 2H-tetrazolyl, etc.], etc.; unsaturated condensed heterocyclic group containing 1 to 5 nitrogen atoms, for example, indolyl, isoindolyl, indolizinyl, benzimidazolyl, quinolyl, isoquinolyl, indazolyl, benzotriazolyl, tetrazolopyridazinyl [e.g., tetrazolo [1,5-b] pyridazinyl, etc.], etc.; unsaturated 3 to 6-membered heteromonocyclic group containing an oxygen atom, for example, pyranyl, furyl, etc.; unsaturated 5 to 7-membered heteromonocyclic group containing a sulfur atom, for example, thienyl, etc.; unsaturated 5 to 7-membered heteromonocyclic group containing 1 to 2 oxygen atoms and 1 to 3 nitrogen atoms, for example, oxazolyl, isoxazolyl, oxadiazolyl [e.g., 1,2,4-oxadiazolyl, 1,3,4-oxadiazolyl, 1,2,5-oxadiazolyl, etc.] etc.; unsaturated condensed heterocyclic group containing 1 to 2 oxygen atoms and 1 to 3 nitrogen atoms [e.g. benzoxazolyl, benzoxadiazolyl, etc.]; unsaturated 5 to 7-membered heteromonocyclic group containing 1 to 2 sulfur atoms and 1 to 3 nitrogen atoms, for example, thiazolyl, thiadiazolyl [e.g., 1,2,4-thiadiazolyl, 1,3,4-thiadiazolyl, 1,2,5-thiadiazolyl, etc.] etc.; unsaturated condensed heterocyclic group containing 1 to 2 sulfur atoms and 1 to 3 nitrogen atoms [e.g., benzothiazolyl, benzothiadiazolyl, etc.] and the like. The term also embraces radicals where heterocyclic radicals are fused with aryl radicals. Examples of such fused bicyclic radicals include benzofuryl, benzothienyl, and the like. Said "heterocyclo" radicals may also be substituted at a substitutable position with one or more substituents selected independently from alkyl, aralkyl, alkoxyalkyl, alkylaminoalkyl, carboxyalkyl, alkoxycarbonylalkyl, aminocarbonylalkyl, alkoxy, aralkoxy, alkylaminoalkoxy, aminocarboxy, alkylaminocarboxy, aralkylaminocarboxy, amino, halo, nitro, alkylamino, alkylcarbonylamino, arylcarbonylamino, alkoxycarbonylamino, aralkoxycarbonylamino, aminocarbonylamino, alkylaminocarbonylamino, alkylsulfonylamino, arylsulfonylamino, acyl, cyano, carboxy, aminocarbonyl, alkoxycarbonyl and aralkoxycarbonyl. More preferred heteroaryl radicals include five to six membered heteroaryl radicals. The term "cycloalkyl" embraces radicals having three to ten carbon atoms. More preferred cycloalkyl radicals are "lower cycloalkyl" radicals having three to seven carbon atoms. Examples include radicals such as cyclopropyl, cyclobutyl, cyclopentyl, cyclohexyl and cycloheptyl. The term "cycloalkylalkyl" embraces cycloalkyl radicals as defined above attached to alkyl radicals of one to ten carbon atoms. More preferred cycloalkylalkyl radicals are "lower cycloalkylalkyl" radicals having alkyl radicals of one to six carbon atoms. Examples include radicals such as cyclopropylpropyl, cyclobutylethyl, cyclopentylmethyl, and cyclohexylmethyl. The term "mercaptoalkyl" embraces radicals containing a free —SH group attached to an linear or branched alkyl radical, as defined above. Examples of such mercaptoalkyl radicals are mercatomethyl, mercaptopropyl and mercaptohexyl. The term "alkylthio" embraces radicals containing a linear or branched alkyl radical, of one to about ten carbon atoms attached to a divalent sulfur atom More preferred alkylthio radicals are "lower alkylthio" radicals having alkyl radicals of one to six carbon atoms. Examples of such lower alkylthio radicals are methylthio, ethylthio, propylthio, butylthio and hexylthio. The term "alkylthioalkyl" embraces alkylthio radicals attached to an alkyl radical. More preferred alkylthioalkyl radicals are "lower alkylthioalkyl" radicals having alkyl radicals of one to six carbon atoms and an alkylthio radical as described above. Examples of such radicals include methylthiomethyl. The term "alkylsulfinyl" embraces radicals containing a linear or branched alkyl radical, of one to ten carbon atoms, attached to a divalent —S(=O)— radical. More preferred alkylsulfinyl radicals are "lower alkylsulfinyl" radicals having one to six carbon atoms. Examples of such lower alkylsulfinyl radicals include methylsulfinyl, ethylsulfinyl, butylsulfinyl and hexylsulfinyl. The term "sulfonyl", whether used alone or linked to other terms such as alkylsulfonyl, denotes respectively divalent radicals —SO$_2$—. "Alkylsulfonyl" embraces alkyl radicals attached to a sulfonyl radical, where alkyl is defined as above. More preferred alkylsulfonyl radicals are "lower alkylsulfonyl" radicals having one to six carbon atoms. Examples of such lower alkylsulfonyl radicals include methylsulfonyl, ethylsulfonyl and propylsulfonyl. The "alkylsulfonyl" radicals may be further substituted with one or more halo atoms, such as fluoro, chloro or bromo, to provide "haloalkylsulfonyl" radicals. More preferred haloalkylsulfonyl radicals are "lower haloalkylsulfonyl" radicals having one or more halo atoms attached to lower alkylsulfonyl radicals as described above. Examples of such lower haloalkylsulfonyl radicals include fluoromethylsulfonyl, trifluoromethylsulfonyl and chloromethylsulfonyl. The term "arylsulfonyl" embraces aryl radicals as defined above, attached to a sulfonyl radical. Examples of such radicals include phenylsulfonyl. The terms "sulfamyl", "aminosulfonyl" and "sulfonamidyl" denotes NH$_2$O$_2$S—. The term "acyl" denotes a radical provided by the residue after removal of hydroxyl from an organic acid. Examples of such acyl radicals include formyl, alkanoyl and aroyl radicals. The term "alkylsulfinylalkyl" embraces radicals containing an alkylsulfinyl radical, as described above, attached to an alkyl radical More preferred alkylsulfinylalkyl radicals are "lower alkylsulfinylalkyl" radicals having one to six carbon atoms. Examples of such lower alkylsulfinylalkyl radicals include methylsulfinylethyl, ethylsulfinylmethyl, butylsulfinylethyl and methylsulfinylmethyl. "Alkylsulfonylalkyl" embraces alkylsulfonyl radicals attached to an alkyl radical, where alkyl and alkylsulfonyl are defined above. More preferred alkylsulfonylalkyl radicals are "lower alkylsulfonylalkyl" radicals having one to six carbon atoms. Examples of such lower alkylsulfonylalkyl radicals include methylsulfonylmethyl, ethylsulfonylethyl and methylsulfonylethyl. The terms "carboxy" or "carboxyl"; whether used alone or with other terms, such as "carboxyalkyl", denotes —CO$_2$H. The term "carbonyl", whether used alone or with other terms, such as "alkoxycarbonyl", denotes —(C=O)—. The term "alkoxycarbonyl" means a radical containing an alkoxy radical, as defined above, attached via an oxygen atom to a carbonyl radical. Preferably, "lower alkoxycarbonyl" embraces alkoxy radicals having one to six carbon atoms. Examples of such "lower alkoxycarbonyl" ester radicals include substituted or unsubstituted methoxycarbonyl, ethoxycarbonyl, propoxycarbonyl, butoxycarbonyl and hexyloxycarbonyl. The term "aralkyl" embraces aryl-substituted alkyl radicals. Preferable aralkyl radicals are "lower aralkyl" radicals having aryl radicals attached to alkyl radicals having one to six carbon atoms. Examples of such radicals include benzyl, diphenylmethyl, triphenylmethyl, phenylethyl and diphenylethyl. The aryl in said aralkyl may be additionally substituted as described above. The terms benzyl and phenylmethyl are interchangeable. The term "alkylcarbonyl" includes radicals having alkyl radicals as defined above, attached to a carbonyl radical. More preferred alkylcarbonyl radicals are "lower alkylcarbonyl" radicals having one to six carbon atoms. Examples of such radicals include methylcarbonyl and ethylcarbonyl. The term "alkoxycarbonylalkyl" embraces radicals having "alkoxycarbonyl", as defined above substituted to an alkyl radical. More preferred alkoxycarbonylalkyl radicals are "lower alkoxycarbonylalkyl" having lower alkoxycarbonyl radicals as defined above attached to one to six carbon atoms. Examples of such lower alkoxycarbonylalkyl radicals include methoxycarbonylmethyl. The term "haloalkylcarbonyl" embraces radicals having a haloalkyl radical as described above attached to a carbonyl radical. More preferred radicals are "lower haloalkylcarbonyl" radicals where lower haloalkyl radicals, as described above are attached to a carbonyl radical. The term "carboxyalkyl" embraces radicals having a carboxy radical as defined above, attached to an alkyl radical. The alkanoyl radicals may be substituted or unsubstituted, such as formyl, acetyl, propionyl, butyryl, isobutyryl, valeryl, isovaleryl, pivaloyl, hexanoyl, trifluoroacetyl or the like, in which the preferable one is formyl, acetyl, propionyl or trifluoroacetyl. The term "heterocycloalkyl" embraces heterocyclic-substituted alkyl radicals. More preferred heterocycloalkyl radicals are "lower heterocycloalkyl" radicals having five to six membered heterocyclo radicals attached to lower alkyl radicals having one to six carbon atoms. Examples of such radicals include pyrrolidinylmethyl, piperidinylmethyl, morpholinylmethyl, piperazinylmethyl, oxazolylmethyl, oxazolylethyl, oxazolinylmethyl, oxazolinylethyl, indolylethyl, indolylmethyl, pyridylmethyl, quinolylmethyl, thienylmethyl, furylethyl and quinolylethyl. The heterocyclic in said heterocycloalkyl may be additionally substituted as described above. The term "aryloxy" embraces aryl radicals, as defined above, attached to an oxygen atom. The aryl in said aryloxy may be additionally substituted as described above. Examples of such radicals include phenoxy. The term "aralkoxy" embraces oxy-containing aralkyl radicals attached through an oxygen atom to other radicals. The term "aralkoxyalkyl" embraces alkyl radicals having one or more aralkoxy radicals attached to the alkyl radical, that is, to form monoaralkyloxyalkyl and diaralkyloxyalkyl radicals. The "aralkoxy" or "aralkoxyalkyl" radicals may be further substituted on the aryl ring portion of the radical. More preferred aralkoxyalkyl radicals are "lower aralkoxyalkyl" having an alkoxy attached to one to six carbon atoms. Examples of lower aralkoxyalkyl radicals include benzyloxymethyl. The term "aminoalkyl" embraces alkyl radicals substituted with amino radicals. More preferred aminoalkyl radicals are "lower aminoalkyl" having one to six carbon atoms. Examples include aminomethyl, aminoethyl and aminobutyl. The term "guanidinoalkyl" denotes a guanidino radical [—C=NH$_2$(NH$_2$)$_2$] attached to an alkyl radical as defined above. More preferred alkylamino radicals are "lower alkylamino" radicals having one or two alkyl radicals of one to six carbon atoms, attached to a nitrogen atom. The term "alkylamino" denotes amino groups which have been substituted with one or two alkyl radicals. More preferred alkylamino radicals are "lower alkylamino" having alkyl radicals of one to six carbon atoms attached to the nitrogen atom of an amine. Suitable "lower alkylamino" may be mono or dialkylamino such as N-methylamino, N-ethylamino, N,N-dimethylamino, N,N-diethylamino or the like. The term "alkylaminoalkyl" denotes alkylamino groups, as defined above, attached to an alkyl radical. More preferred alkylaminoalkyl radicals are "lower alkylaminoalkyl" having one to six carbon atoms attached to a lower aminoalkyl radical as described above. Suitable "lower alkylaminoalkyl" may be mono or dialkylaminoalkyl radicals such as N-methylaminomethyl, N-ethylaminomethyl, N,N-dimethylaminomethyl, N,N-dimethylaminoethyl N,N-dimethylaminopropyl or the like. The term "dialkylaminoalkyl" also includes radicals where the bridging alkyl moiety is optionally substituted with alkylsulfonyl, alkoxy, aralkoxy, heterocyclo, and aryl. The term "alkylaminoalkoxy" denotes alkylamino groups, as defined above, attached to an alkoxy radical. Suitable "alkylaminoalkoxy" may be mono or dialkylaminoalkoxy radicals such as N-methylaminomethoxy, N-ethylaminomethoxy, N,N-dimethylaminomethoxy, N,N-dimethylaminoethoxy N,N-dimethylaminopropoxy or the like. The term "alkylaminocarbonyll" embraces alkylamino radicals, as described above, to a carbonyl radical. More preferred alkylaminocarbonyl radicals are "lower alkylaminocarbonyll" having lower alkylamino radicals, as described above, attached to a carbonyl radical. Examples of such radicals include N-methylaminocarbonyl and N,N-dimethylcarbonyl. The term "arylamino" denotes amino groups which have been substituted with one or two aryl radicals, such as N-phenylamino. The "arylamino" radicals may be further substituted on the aryl ring portion of the radical. The terms "N-arylaminoalkyl" and "N-aryl-N-alkyl-aminoalkyl" denote amino groups which have been substituted with one aryl radical or one aryl and one alkyl radical, respectively, and having the amino group attached to an alkyl radical. More preferred arylaminoalkyl radicals are "lower arylaminoalkyl" having the arylamino radical attached to one to six carbon atoms. Examples of such radicals include N-phenylaminomethyl and N-phenyl-N-methylaminomethyl. The term "aminocarbonyl" denotes an amide group of the formula —C(=O)NH$_2$. The term "aminocarbonylalkyl" denotes an aminocarbonyl group attached to an alkyl radical. More preferred are "lower aminocarbonylalkyl" having lower aminocarbonyl radicals as described above attached to alkyl of one to six carbon atoms. The term "alkylaminocarbonylalkyl" denotes an aminocarbonyl group which has been substituted with one or two alkyl radicals and attached to an alkyl radical. More preferred are "lower alkylaminocarbonylalkyl" having lower alkylaminocarbonyl radicals as described above attached to alkyl radicals of one to six carbon atoms. The term "aryloxyalkyl" embraces alkyl radicals having one or more aryloxy radicals, aryl radicals attached to a divalent oxygen atom, attached to the alkyl radical, that is, to form monoaryloxyalkyl and diaryloxyalkyl radicals. The more preferred aryloxyalkyl radicals are "lower aryloxyalkyl" radicals having aryloxy radicals attached to one to six carbon atoms. Examples include phenoxymethyl. "Amino acid residue" means any of the naturally occurring alpha-, beta- and gamma-amino carboxylic acids, including their D and L optical isomers and racemic mixtures thereof, synthetic amino acids, and derivatives of these natural and synthetic amino acids. The amino acid residue is bonded through a nitrogen of the amino acid. The naturally occurring amino acids which can be incorporated in the present invention include, but are not limited to, alanine, arginine, asparagine, aspartic acid, cysteine, cystine, glutamic acid, glutamine, glycine, histidine, isoleucine, leucine, lysine, methionine, ornithine, phenylalanine, proline, serine, threonine, thyroxin, tryptophan, tyrosine, valine, β-alanine, and γ-aminobutyric acid. Derivatives of amino acids which can be incorporated in the present invention include, but are not limited to amino acids having protected and modified carboxylic acids, including acid esters and amides, protected amines, and substituted phenyl rings, including but not limited to alkyl, alkoxy and halo substituted tyrosine and phenylalanine.

The present invention comprises a pharmaceutical composition comprising a therapeutically-effective amount of a compound of Formula I in association with at least one pharmaceutically-acceptable carrier, adjuvant or diluent.

The present invention also comprises a method of therapeutic and prophylactic treatment of viral infections, particularly herpetoviridae infection, in a subject, the method comprising administering to the subject having such herpes infection a therapeutically-effective amount of a compound of Formula I.

Also included in the family of compounds of Formula I are the stereoisomers and tautomers thereof. Compounds of the present invention can possess one or more asymmetric carbon atoms and are thus capable of existing in the form of optical isomers as well as in the form of racemic or nonracemic mixtures thereof. Accordingly, some of the compounds of this invention may be present in racemic mixtures which are also included in this invention. The optical isomers can be obtained by resolution of the racemic mixtures according to conventional processes, for example by formation of diastereoisomeric salts by treatment with an optically active acid or base. Examples of appropriate acids are tartaric, diacetyltartaric, dibenzoyltartaric, ditoluoyltartaric and camphorsulfonic acid and then separation of the mixture of diastereoisomers by crystallization followed by liberation of the optically active bases from these salts. A different process for separation of optical isomers involves the use of a chiral chromatography column optimally chosen to maximize the separation of the enantiomers. Still another available method involves synthesis of covalent diastereoisomeric molecules by reacting an amine functionality of precursors to compounds of Formula I with an optically pure acid in an activated form or an optically pure isocyanate. Alternatively, diastereomeric derivatives can be prepared by reacting a carboxyl functionality of precursors to compounds of Formula I with an optically pure amine base. The synthesized diastereoisomers can be separated by conventional means such as chromatography, distillation, crystallization or sublimation, and then hydrolyzed to deliver the enantiomerically pure compound. The optically active compounds of Formula I can likewise be obtained by utilizing optically active starting materials. These isomers may be in the form of a free acid, a free base, an ester or a salt.

Also included in the family of compounds of Formula I are the pharmaceutically-acceptable salts thereof. The term "pharmaceutically-acceptable salts" embraces salts commonly used to form alkali metal salts and to form addition salts of free acids or free bases. The nature of the salt is not critical, provided that it is pharmaceutically-acceptable. Suitable pharmaceutically-acceptable acid addition salts of compounds of Formula I may be prepared from an inorganic acid or from an organic acid. Examples of such inorganic acids are hydrochloric, hydrobromic, hydroiodic, nitric, carbonic, sulfuric and phosphoric acid. Appropriate organic acids may be selected from aliphatic, cycloaliphatic, aromatic, araliphatic, heterocyclic, carboxylic and sulfonic classes of organic acids, example of which are formic, acetic, propionic, succinic, glycolic, gluconic, lactic, malic, tartaric, citric, ascorbic, glucuronic, maleic, fumaric, pyruvic, aspartic, glutamic, benzoic, anthranilic, mesylic, salicylic, p-hydroxybenzoic, phenylacetic, mandelic, embonic (pamoic), methanesulfonic, ethylsulfonic, benzenesulfonic, pantothenic, toluenesulfonic, 2-hydroxyethanesulfonic, sulfanilic, stearic, cyclohexylaminosulfonic, algenic, β-hydroxybutyric, salicyclic, galactaric and galacturonic acid. Suitable pharmaceutically-acceptable base addition salts of compounds of Formula I include metallic salts made from aluminum, calcium, lithium, magnesium, potassium, sodium and zinc or organic salts made from N,N'-dibenzylethylenediamine, choline, chloroprocaine, diethanolamine, ethylenediamine, meglumine (N-methylglucamine) and procaine. All of these salts may be prepared by conventional means from the corresponding compound of Formula I by reacting, for example, the appropriate acid or base with the compound of Formula I.

GENERAL SYNTHETIC PROCEDURES

The compounds of the invention can be synthesized from commercially available 2-aminobenzoic acids, according to the following procedures of Schemes I–XIII, wherein the $R^1$–$R^{32}$ substituents are as defined for Formula I–II, above, except where further noted.

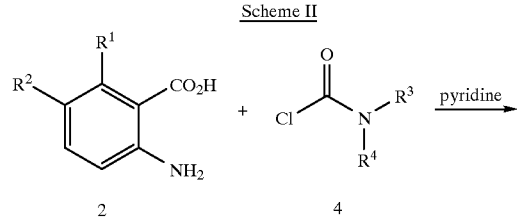

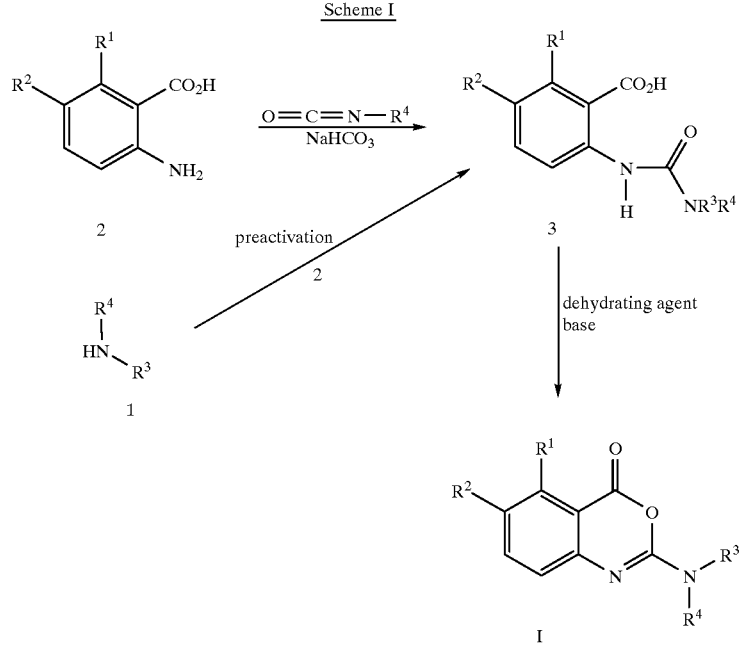

Scheme I illustrates the two step synthesis of compounds of Formula I which are 2-(substituted amino)-4H-3,1-benzoxazin-4-one derivatives. In the first step, condensation of the 2-aminobenzoic acid 2 with an isocyanate in the presence of base, such as bicarbonate, affords the ureidobenzoic acid 3 (where $R^3$ is hydrido). In step 2, cyclization of the ureidobenzoic acid 3 with an appropriate dehydrating agent, such as 1-(3-dimethylaminopropyl)-3-ethylcarbodiimide hydrochloride (EDC) or dicyclohexylcarbodiimide (DCC), and a base, such as triethylamine), affords the desired 4H-3,1-benzoxazin-4-ones I.

Alternatively, a primary or secondary amine 1 or amine salts, including but not limited to amino acid esters and amides, can be preactivated such as with N,N'-carbonyldiimidazole (CDI) in pyridine, or with triphosgene and a base, such as triethylamine. Addition of the 2-aminobenzoic acid 2 affords the ureidobenzoic acid 3 which can be cyclized as described above.

-continued

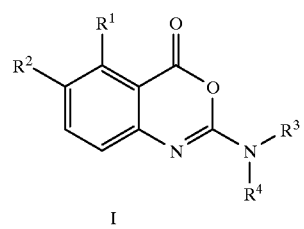

N,N-disubstituted benzoxazinones of Formula I are also synthesized according to Scheme II. Treatment of 2-aminobenzoic acid 2 with an excess (about 3–4 equivalents) of an appropriately substituted carbamoyl halide in base, such as pyridine, affords the desired compound of Formula I.

Scheme III

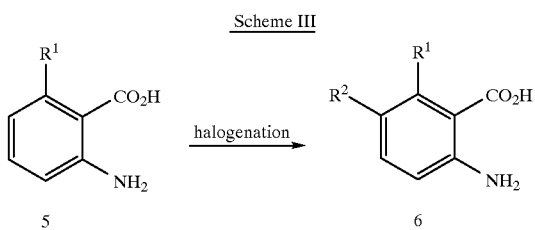

The synthesis of a 5,6-disubstituted 2-aminobenzoic acids 6, where $R^1$ is methyl, is described in Scheme III. 2-Amino-6-methylbenzoic acid 5 readily undergoes regioselective halogenation (e.g. with $Cl_2$, $Br_2$, ICl) at the 5 position affording the 2-amino-5-halobenzoic acids 6. Further manipulation as outlined in Schemes I and II leads to compounds of Formula I ($R^2$=Cl, Br, I).

carbonylating reagent (e.g. CDI) to form a benzoxazindione 7. The benzoxazindione 7 undergoes regioselective nitration to form 6-nitro-benzoxazindione 8. Hydrogenation of nitro compound 8, such as with hydrogen with platinum or palladium hydroxide on carbon as catalyst, affords the aminobenzoxazindione 9. Treatment of the aminobenzoxazindione 9 with a suitable protecting group reagent (e.g. $Boc_2O$, CBZ-Cl), followed by base hydrolysis leads to the 5,6-disubstituted 2-aminobenzoic acid 10, where $R^a$ is selected from alkyl, aralkyl, alkylaminoalkyl, heterocycloalkyl, aryl, heterocyclo, alkylamino, aralkylamino, heterocycloalkylamino, alkylaminoalkylamino, alkoxy, aralkoxy, heterocycloalkoxy, and alkylaminoalkoxy. Alternatively, in place of the acyl radical ($R^aCO$—), alkylsulfonyl or arylsulfonyl radicals may be incorporated. Alternatively, aminobenzoxazindiones 9 may be acylated or sulfonylated with a variety of readily available acids, acid chlorides, isocyanates, haloformates, or sulfonyl halides to afford Scheme IV

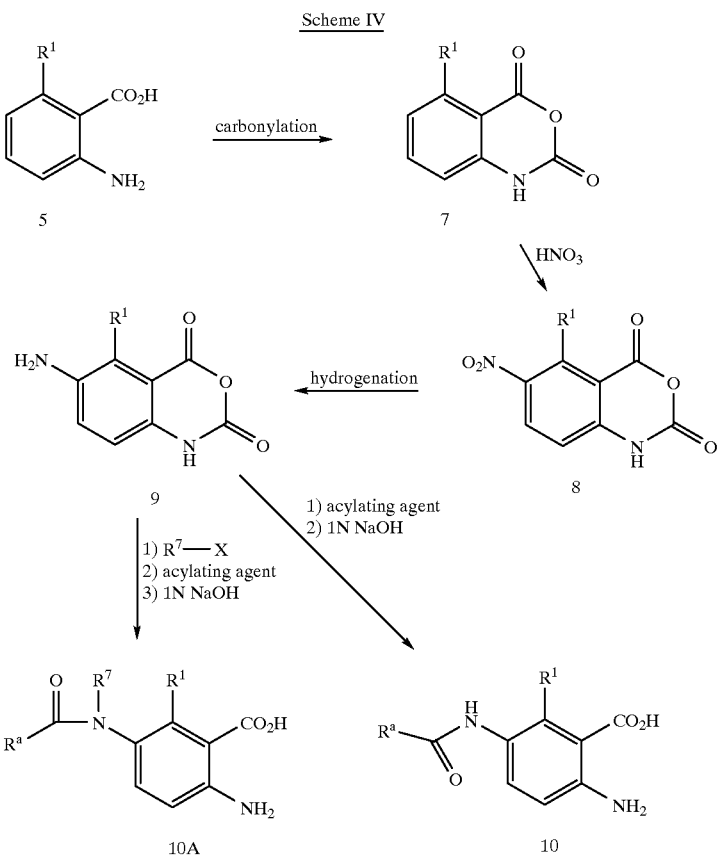

Scheme IV describes the four step preparation of acylamino substituted aminobenzoic acids 10 and 10A, where acylamino radicals include tert-butyloxycarbonylamino (BOC-amino). An aminobenzoic acid 5 is treated with a compounds of structure 10. Alternatively, aminobenzoxazindiones 9 may be monoalkylated (where X is halides or sulfonate/bases) under controlled conditions prior to protection and base hydrolysis to afford compound 10A.

Scheme V

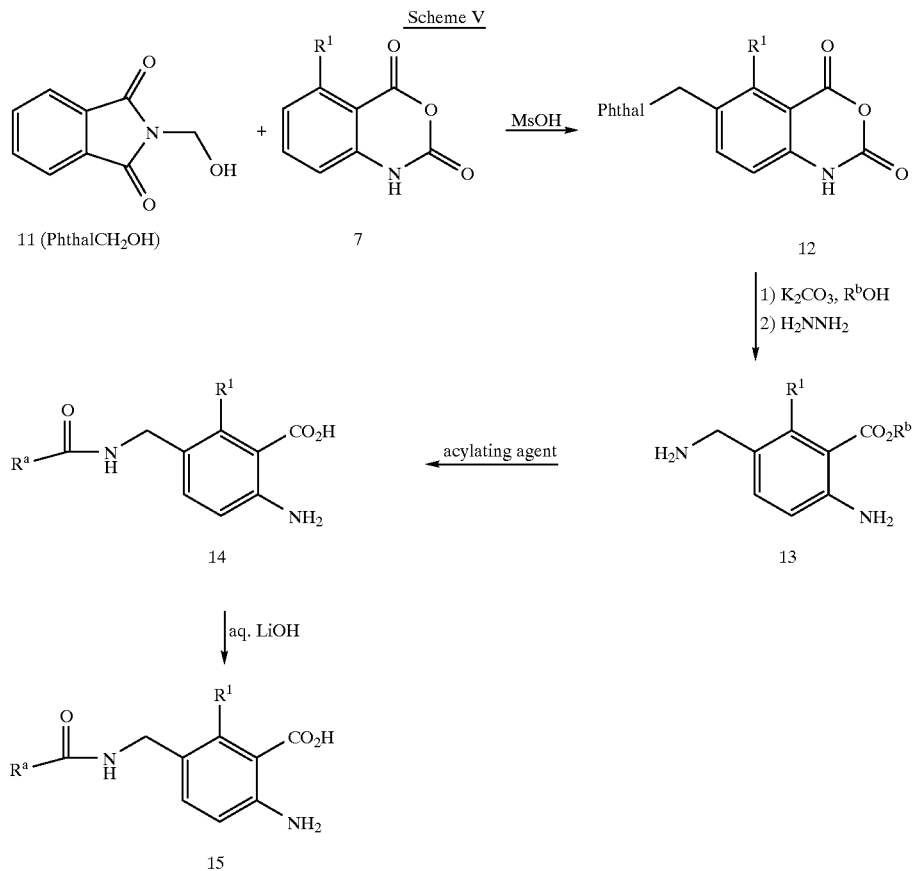

Synthetic Scheme V shows the preparation of a key aminobenzoic acid intermediate 15 for the synthesis of 6-R$^{28}$CONHCH$_2$-substituted benzoxazinones of Formula I. Electrophilic amidoalkylation of benzoxazindiones 7 with N-hydroxymethylphthalimide 11 [H. Zaugg, *Synthesis*, 85–110 (1984)] in methanesulfonic acid affords the phthalimide 12. Base-catalyzed alcoholysis, preferably with methanol or allyl alcohol, of phthalimidyl benzoxazinones 12, followed by removal of the phthalimide protecting group by hydrazinolysis affords the aminomethyl benzoic acid methyl ester 13 (where R$^b$ is alkyl such as methyl, or alkenyl such as allyl). Selective reaction of the primary aminoalkyl 13 with a suitable acylating reagent (e.g. acid chlorides, isocyanates, haloformates, Boc$_2$O, sulfonyl halides) affords variously substituted anthanilic esters 14. Base hydrolysis (e.g. sodium hydroxide or lithium hydroxide) of the methyl ester 14 affords the 5,6-disubstituted anthanilic acid 15.

Scheme VI

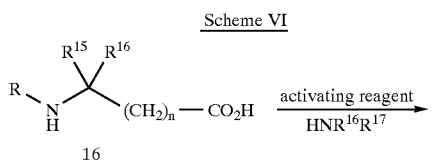

-continued

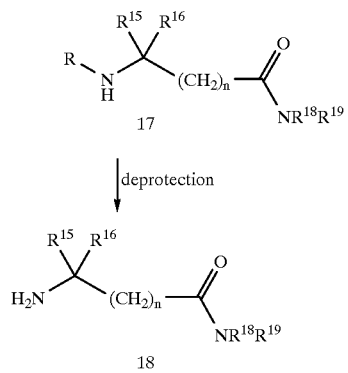

When —NR$_3$R$_4$ of Formula I represents an amino acid amide residue, such intermediates can be prepared by conventional means as outlined in Scheme VI. Generally the protected amino acid 16 (where R is a protecting group such as Boc, CBZ, FMOC and the like) can be activated with a suitable reagent such as N,N'-disuccinimoylcarbonate (DSC), then treated with an appropriate primary or secondary amine to give the protected amide 17. Removal of the protecting group can be accomplished by either acid treatment (e.g. HCl of TFA), hydrogenolysis or base, depending on the selected protecting group, to give the free amine or amine hydrochloride 18.

When —NR$_3$R$_4$ of Formula I represents β-aminoamide residue, such intermediates 17 (where n=1) can be prepared according to methods described by R. Garland et al in European Patent Publication 513,810.

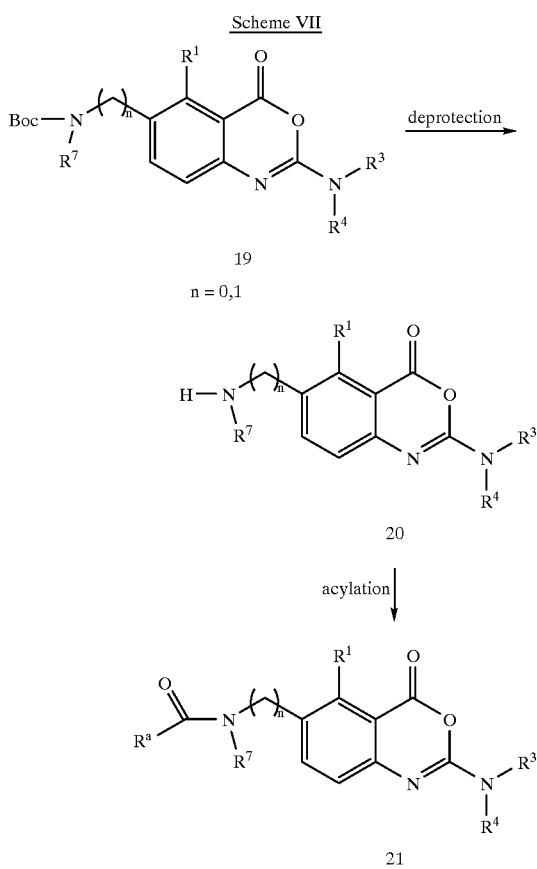

Compounds of Formula I having a Boc-protected amino or aminoalkyl residue at position 6 can be further derivatized as illustrated in Scheme VII. Deprotection of the amine by removal of the Boc protecting group with acid (e.g. HCl or TFA) liberates the free amine 20. This intermediate can be acylated or converted to a urea or carbamate or sulfonamide, using conventional reagents such as acid chlorides, sulfonyl chlorides, carboxylic acids in the presence of an activating reagent such as EDC, isocyanates, amines in the presence of a carbonylating reagent such as CDI or triphosgene, alkylchloroformates or aralkylchloroformates, resulting in further compounds 21 of Formula I where $R^a$ is as described above in Scheme IV.

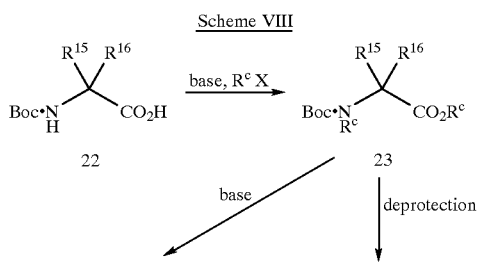

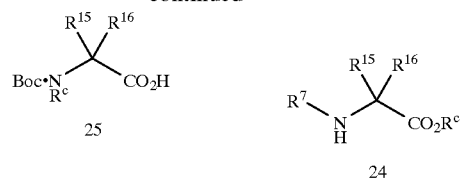

When —$NR^3R^4$ of Formula I represents an N-alkylated amino acid residue, such intermediates can be prepared by conventional means as outlined in Scheme VIII. A Boc-amino acid 22 can be deprotonated with about 2 equivalents of a suitable base [e.g. lithium hexamethyldisilazide (LiHMDS)] then quenched with an excess of a suitable electrophile (e.g. an alkyl halide such as methyl iodide) to give the N-alkylated methyl ester 23 (where $R^c=R^7$ or $R^{17}$). Removal of the Boc protecting group with acid (e.g. TFA) gives the free amine 24. Alternatively, the ester 23 can be hydrolyzed to the Boc-protected free acid 25, then converted to a variety of amides as described in Scheme VI.

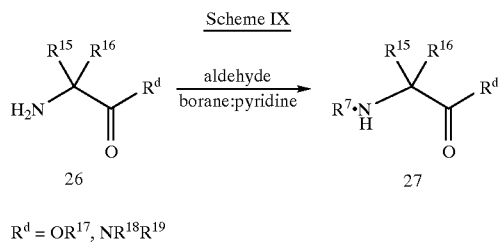

$R^d = OR^{17}, NR^{18}R^{19}$

An alternative general route to forming alkylated amino acid esters or amides 27 is outlined in Scheme IX. Reductive amination of amino acid esters or amides 26 with an aldehyde, in the presence of borane:pyridine complex, would afford the desired N-alkylated amino acid ester or amide 27.

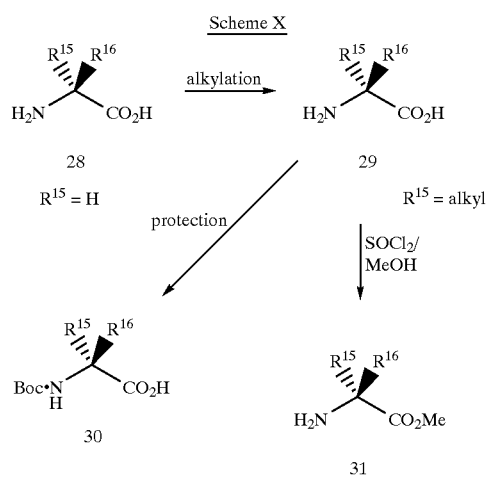

When —$NR^3R^4$ of Formula I represents a chiral α-methyl amino acid residue, such amino acids can be prepared from chiral amino acids 28 by the method of Seebach [A. Beck, and D. Seebach, *chimia*, 42, 142–144 (1988)] as illustrated in Scheme X. The chiral α-methyl amino acid 29 can be protected, such as with Boc, affording compounds 30 and functionalized as described in Scheme VI or esterified, such as with SOCl$_2$/methanol to amino acid esters 31.

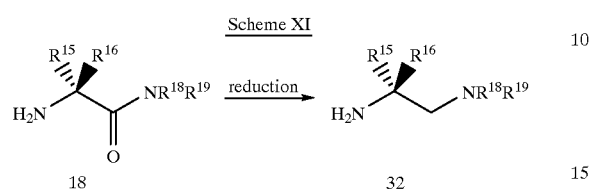

Scheme XI

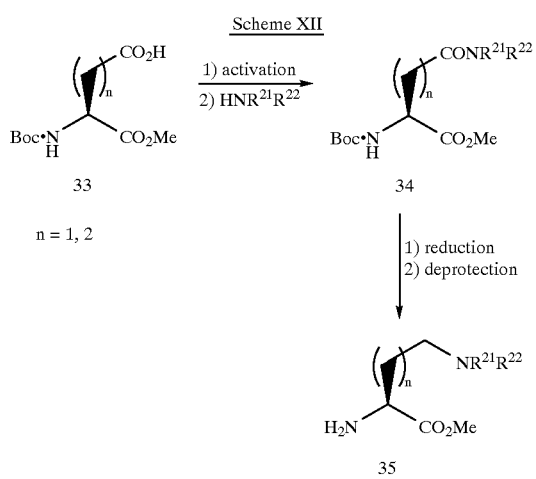

Scheme XII

When —NR$^3$R$^4$ of Formula I represents a chiral ethylenediamine residue 32, such compounds can be synthesized according to Scheme XI. Treatment of amino acid derivative 18 (where n is 0) with a reducing agent such as lithium aluminum hydride (LAH) affords the ethylenediamine analogs 32. These compounds can be further elaborated as described in Scheme I.

When —NR$^3$R$^4$ of Formula I represents chiral diamine residues, such diamines 35 can be synthesized according to Scheme XII. Activation of the free carboxylic acid of selectively protected aspartic or glutamic acid derivatives 33 with a suitable reagent (e.g. DSC) followed by condensation with a secondary amine, affords the amides 34. Selective reduction of the amide 34 with reagents such as borane (BH$_3$) and removal of the protecting group, such as with acid for the BOC group, affords the chiral diamine 35.

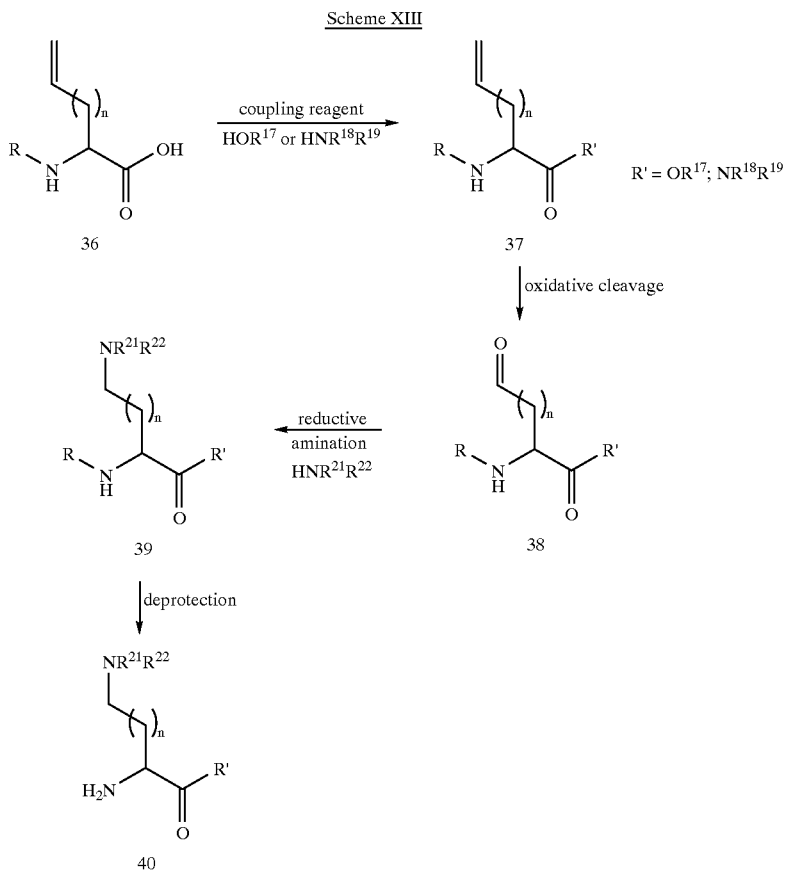

Synthetic Scheme XIII shows an alternative method for forming diamines 40. Suitably protected allyl and homoallylglycines 36 can be converted to their corresponding esters or amides 37. Oxidative cleavage (e.g. ozonolysis) of the olefin 37 to aldehyde 38, followed by reductive amination (e.g. NaCNBH$_3$ or NaBH(OAc)$_3$) affords the amine 39. Deprotection (e.g. acid treatment or hydrogenolysis) affords the diamine 40.

The following examples contain detailed descriptions of the methods of preparation of compounds of Formula I–II. These detailed descriptions fall within the scope, and serve to exemplify, the above described General Synthetic Procedures which form part of the invention. These detailed descriptions are presented for illustrative purposes only and are not intended as a restriction on the scope of the invention. All parts are by weight and temperatures are in Degrees centigrade unless otherwise indicated.

The following abbreviations are used:
EtOAc—ethyl acetate
HCl—hydrochloric acid
DMSO—dimethylsulfoxide
d$_6$-DMSO—deuterated dimethylsulfoxide
CDCl$_3$—deuterated chloroform
CHCl$_3$—chloroform
CD$_3$OD—deuterated methanol
Et$_2$O—diethyl ether
MgSO$_4$—magnesium sulfate
H$_2$SO$_4$—sulfuric acid
NaHCO$_3$—sodium bicarbonate
KHSO$_4$—potassium hydrogen sulfate
NMM—N-methylmorpholine
DMF—dimethylformamide
DMAP—4-dimethylaminopyridine
CDI—carbonyldiimidazole
NaOH—sodium hydroxide
KOH—potassium hydroxide
LiOH—lithium hydroxide
Pd(OH)$_2$/C—palladium hydroxide on carbon
Pd/C—palladium on carbon
EDC—1-(3-dimethylaminopropyl)-3-ethylcarbodiimide.HCl
BOC—tert-Butyloxycarbonyl
TLC—thin layer chromatography
MeOH—methanol
KI—potassium iodide
CH$_2$Cl$_2$—methylene chloride

PREPARATION I

A. Preparation of 2-[[(ethylamino)carbonyl]amino]-6-methylbenzoic acid and related compounds To an ice cooled solution of 2-amino-6-methylbenzoic acid (500 mg, 3.3 mmol) and sodium bicarbonate (277 mg, 3.3 mmol) in 9 mL of dioxane/water (2:1) was added ethyl isocyanate (281 mg, 3.96 mmol). The reaction was slowly warmed to room temperature while stirring overnight. The reaction mixture was diluted with water and extracted with EtOAc. The aqueous fraction was acidified with 2N HCl and extracted with EtOAc. The organic fraction was dried (MgSO$_4$), filtered, and evaporated under reduced pressure affording 272 mg of 2-[[(ethylamino)carbonyl]amino]-6-methylbenzoic acid used directly in the next reaction: $^1$H-NMR (300 MHz, d$_6$-DMSO) δ 1.02 (t, J=7 Hz, 3H), 2.32 (s, 3H), 3.03 (m, 2H), 6.67 (d, J=8 Hz, 1H), 6.87 (br. t, 1H, exchangeable), 6.99 (t, J=8 Hz, 1H), 7.79 (d. J=8 Hz, 1H), 9.46 (br. s, 1H, exchangeable).

Proceeding in a like manner but replacing ethyl isocyanate with other appropriately substituted isocyanates, the following compounds were prepared:

2-[[[(1-methylethyl)amino]carbonyl]amino]-6-methylbenzoic acid, $^1$H-NMR (300 MHz, d$_6$-DMSO) δ 1.04 (d, J=7 Hz, 6H), 2.31 (s, 3H), 3.70 (sept, J=7 Hz, 1H), 6.71 (d, J=8 Hz, 1H), 6.88 (br. d, J=7 Hz, 1H, exchangeable), 7.05 (t, J=8 Hz, 1H), 7.83 (d, J=8 Hz, 1H), 8.85 (br. s, 1H, exchangeable).

2-methyl-6-[[[(1S)-(phenethyl)amino]carbonyl]amino] benzoic acid, $^1$H-NMR (300 MHz, d$_6$-DMSO) δ 1.36 (d, J=7 Hz, 3H), 2.32 (s, 3H), 4.80 (pent, J=7 Hz, 1H), 6.84 (d, J=8 Hz, 1H), 7.18 (t, J=8 Hz, 1H), 7.20–7.37 (m, 5H), 7.55 (d, J=7 Hz, 1H, exchangeable), 7.75 (d, J=8 Hz, 1H), 8.23 (s, 1H, exchangeable).

2-methyl-6-[[[(1S)-(phenethyl)amino]carbonyl]amino] benzoic acid, $^1$H-NMR (300 MHz, d$_6$-DMSO) δ 1.36 (d, J=7 Hz, 3H), 2.32 (s, 3H), 4.80 (pent, J=7 Hz, 1H), 6.84 (d, J=8 Hz, 1H), 7.18 (t, J=8 Hz, 1H), 7.20–7.37 (m, 5H), 7.55 (d, J=7 Hz, 1H, exchangeable), 7.75 (d, J=8 Hz, 1H), 8.22 (s, 1H, exchangeable).

2-methyl-6-[[(phenylamino)carbonyl]amino]benzoic acid, $^1$H-NMR (300 MHz, CDCl$_3$/CD$_3$OD) δ 2.47 (s, 3H), 6.94 (d, J=8 Hz, 1H), 7.06 (d, J=8 Hz, 1H), 7.25–7.37 (m, 3H), 7.43 (d, J=8 Hz, 2H), 7.91 (d, J=8 Hz, 1H).

2-[[[(3-chlorophenyl)amino]carbonyl]amino]-6-methylbenzoic acid, $^1$H-NMR (300 MHz, d$_6$-DMSO) δ 2.37 (s, 3H), 6.97 (d, J=8 Hz, 1H), 7.01 (dt, J=8 Hz, 3 Hz, 1H), 7.23–7.35 (m, 3H), 7.69–7.76 (m, 2H), 8.57 (s, 1H, exchangeable), 9.64 (s, 1H, exchangeable).

2-[[[(2,6-dichlorophenyl)amino]carbonyl]amino]-6-methylbenzoic acid, $^1$H-NMR (300 MHz, d$_6$-DMSO) δ 2.36 (s, 3H), 6.93 (d, J=8 Hz,1H), 7.26 (t, J=8 Hz, 1H), 7.42 (t, J=8 Hz, 1H), 7.53 (d, J=8 Hz, 2H), 7.83 (d, J=8 Hz, 1H), 8.77 (s, 1H, exchangeable), 9.13 (s, 1H, exchangeable).

2-methyl-6-[[[(2-nitrophenyl)amino]carbonyl]amino] benzoic acid, $^1$H-NMR (300 MHz, d$_6$-DMSO) δ 2.34 (s, 3H), 7.02 (d, J=8 Hz, 1H), 7.23 (t, J=8 Hz, 1H), 7.29 (t, J=8 Hz, 1H), 7.52 (d, J=8 Hz, 1H), 7.68 (t, J=8 Hz, 1H), 8.03 (t, J=8 Hz, 2H), 9.28 (s, 1H, exchangeable), 9.81 (s, 1H, exchangeable).

2-methyl-6-[[[(4-nitrophenyl)amino]carbonyl]amino] benzoic acid, $^1$H-NMR (300 MHz, d$_6$-DMSO) δ 2.37 (s, 3H), 7.00 (d, J=8 Hz, 1H), 7.32 (t, J=8 Hz, 1H), 7.65–7.76 (m, 3H), 8.20 (d, J=8 Hz, 2H), 8.75 (s, 1H, exchangeable), 10.15 (s, 1H, exchangeable).

PREPARATION II

A. Preparation of 2-[3-(2,6-dichlorophenyl)ureido]-5-iodobenzoic acid and related compounds To an ice cooled solution of 2-amino-5-iodobenzoic acid (540 mg, 2.03 mmol) and sodium bicarbonate (170 mg, 2.03 mmol) in 9 mL of dioxane/water (2:1) was added 2,6-dichlorophenylisocyanate (468 mg, 2.44 mmol). The reaction was slowly warmed to room temperature while stirring overnight. The reaction mixture was acidified with 2N HCl and extracted with EtOAc. The product, which partially precipitated from the organic layer, was filtered and washed with EtOAc (173 mg). The filtrate was dried (MgSO$_4$) and evaporated under reduced pressure. Trituration of the residue with Et$_2$O afforded an additional 543 mg of 2-[3-(2,6-dichlorophenyl)ureido]-5-iodobenzoic acid: $^1$H-NMR (300 MHz, d$_6$-DMSO) δ 7.37 (t, J=8 Hz, 1H), 7.58 (d, J=8 Hz, 2H), 7.84 (dd, J=8 Hz, 4 Hz, 1H), 8.19 (d, J=4 Hz, 1H), 8.28 (d, J=8 Hz, 1H), 9.60 (s, 1H, exchangeable), 10.50 (s, 1H, exchangeable).

Proceeding in a like manner but replacing 2,6-dichlorophenylisocyanate with other appropriately substituted isocyanates, the following compounds were prepared:

5-iodo-2-[[[(1R)-(phenylethyl)amino]carbonyl]amino] benzoic acid, $^1$H-NMR (300 MHz, d$_6$-DMSO) δ 1.36 (d, J=7 Hz, 3H), 4.80 (pent, J=7 Hz, 1H), 7.20–7.37 (m, 5H), 7.84 (dd, J=8 Hz, 4 Hz, 1H), 8.05 (d, J=7 Hz, 1H, exchangeable), 8.19 (d, J=4 Hz, 1H), 8.28 (d, J=8 Hz, 1H), 10.15 (s, 1H, exchangeable).

5-iodo-2-[[[(1S)-(phenylethyl)amino]carbonyl]amino] benzoic acid, $^1$H-NMR (300 MHz, d$_6$-DMSO) δ 1.36 (d, J=7 Hz, 3H), 4.80 (pent, J=7 Hz, 1H), 7.20–7.37 (m, 5H), 7.84 (dd, J=8 Hz, 4 Hz, 1H), 8.05 (d, J=7 Hz, 1H, exchangeable), 8.19 (d, J=4 Hz, 1H), 8.28 (d, J=8 Hz, 1H), 10.15 (s, 1H, exchangeable).

PREPARATION III

Preparation of 5-chloro-2-[[[(1R) (phenylethyl) amino]carbonyl]amino]benzoic acid To an ice cooled solution of 2-amino-5-chlorobenzoic acid (250 mg, 1.46 mmol) and sodium bicarbonate (122 mg, 1.46 mmol) in 9 mL of dioxane/water (2:1) was added (1R)-1-phenylethylisocyanate (257 mg, 1.75 mmol). The reaction was slowly warmed to room temperature while stirring overnight. The reaction mixture was filtered to remove a precipitate, then the filtrate was acidified with 2N HCl. The precipitate was filtered, washed with water and dried affording 270 mg of 5-chloro-2-[[[(1R)-(phenylethyl) amino]carbonyl]amino]benzoic acid used directly in the next reaction: $^1$H-NMR (300 MHz, d$_6$-DMSO) δ 1.38 (d, J=7 Hz, 3H), 4.83 (pent, J=7 Hz, 1H), 7.20–7.38 (m, 5H), 7.52 (dd, J=8 Hz, 4 Hz, 1H), 7.85 (d, J=4 Hz, 1H), 8.10 (d, J=7 Hz, 1H, exchangeable), 8.41 (d, J=8 Hz, 1H), 10.10 (s, 1H, exchangeable).

PREPARATION IV

Preparation of 5-methyl-2-[[[(1R)(phenylethyl) amino]carbonyl]amino]benzoic acid and related compounds To an ice cooled solution of 2-amino-5-methylbenzoic acid (590 mg, 3.78 mmol) and sodium bicarbonate (317 mg, 3.78 mmol) in 9 mL of dioxane/water (2:1) was added (1R)-1-phenylethylisocyanate (667 mg, 4.54 mmol). The reaction was slowly warmed to room temperature while stirring overnight. The reaction mixture was diluted with water and extracted with EtOAc. The aqueous fraction was acidified with 2N HCl and extracted with EtOAc. The organic fraction was dried (MgSO$_4$), filtered, and evaporated under reduced pressure affording 1.20 g of 5-methyl-2-[[[(1R)-(phenylethyl)amino]carbonyl]amino]benzoic acid used directly in the next reaction: $^1$H-NMR (300 MHz, d$_6$-DMSO) δ 1.38 (d, J=7 Hz, 3H), 2.25 (s, 3H), 4.83 (pent, J=8 Hz, 1H), 7.15–7.45 (m, 6H), 7.71 (d, J=3 Hz, 1H), 7.90 (d, J=7 Hz, 1H, exchangeable), 8.25 (d, J=8 Hz, 1H), 10.00 (s, 1H, exchangeable).

Proceeding in a like manner but replacing (1R)-1-phenylethylisocyanate with other appropriately substituted isocyanates, the following compound was prepared:

5-methyl-2-[[[(1S)-(phenylethyl)amino]carbonyl] amino]-benzoic acid, $^1$H-NMR (300 MHz, d$_6$-DMSO) δ 1.38 (d, J=7 Hz, 3H), 2.25 (s, 3H), 4.83 (pent, J=8 Hz, 1H), 7.15–7.45 (m, 6H), 7.71 (d, J=3 Hz, 1H), 7.90 (d, J=7 Hz, 1H, exchangeable), 8.25 (d, J=8 Hz, 1H), 10.00 (s, 1H, exchangeable).

PREPARATION V

Preparation of 2-methyl-6-[[[[(1R)-(4-bromophenyl) ethyl]amino]carbonyl]amino]benzoic acid To an ice cooled solution of 1,1'-carbonyldiimidazole (CDI) (425 mg, 4.62 mmol) in 5 mL of pyridine was added (1R)-1-(4-bromophenyl)ethylamine (0.50 g, 2.50 mmol). After stirring at 0° C. for 30 minutes, 2-amino-6-methylbenzoic acid (377 mg, 2.50 mmol) was added followed by 25 mg of DMAP. The reaction was slowly warmed to room temperature while stirring overnight. The reaction mixture was poured into 2N HCl and extracted with EtOAc. The organic fraction was dried (MgSO$_4$), filtered and evaporated under reduced pressure affording 450 mg of 2-methyl-6-[[[[(1R)-(4 bromophenyl)ethyl]amino]carbonyl]amino] benzoic acid used directly in the next reaction: $^1$H-NMR (300 MHz, CDCl$_3$) δ 1.37 (d, J=7 Hz, 3H), 2.39 (s, 3H), 4.83 (q, J=7 Hz, 1H), 6.93 (d, J=8 Hz, 1H), 7.07 (d, J=8 Hz, 2H), 7.20–7.33 (m, 3H), 7.58 (d, J=8 Hz, 1H) 8.70 (br. s, 1H, exchangeable).

PREPARATION VI

Preparation of 6-amino-3-bromo-2-methylbenzoic acid

To an ice cooled solution of 2-amino-6-methylbenzoic acid (25.0 g, 165 mmol) in 350 mL of dioxane was added bromine (9.37 mL, 182 mmol). After stirring for 1 hour, the reaction mixture was diluted with Et$_2$O (350 mL) and the crude hydrobromide salt was filtered and washed with Et$_2$O and dried. The material was dissolve in 1 L of water adjusted to pH 11 with 3N KOH, treated with decolorizing carbon and filtered through a bed of Celite®. The filtrate was adjusted to pH 3.2 and the resulting precipitate was filtered, washed with water and dried affording 20.0 g of the bromobenzoic acid: $^1$H-NMR (300 MHz, d$_6$-DMSO) δ 2.34 (s, 3H), 6.58 (d, J=8 Hz, 1H), 7.28 (d, J=8 Hz, 1H).

PREPARATION VII

Preparation of 6-amino-3-[[(1,1-dimethylethoxy) carbonyl]amino]-2-methylbenzoic acid A. Preparation of 5-methyl-2H-3,1-benzoxazin-2,4(1H)-dione To a suspension of CDI (49.35 g, 305 mmol) in 100 mL of dioxane was added at room temperature a solution of the anthanilic acid (20 g, 132 mmol) in 100 mL of dioxane over 30 minutes. The reaction was stirred at ambient temperature until the mild exotherm subsided. The reaction mixture was filtered through a bed of silica gel (dioxane), concentrated then diluted with about 200 mL of water. The resulting precipitate was filtered, washed with water and dried affording 20.3 g (87%) of 5-methyl-2H-3,1-benzoxazin-2,4(1H)-dione.

B. Preparation of 5-methyl-6-nitro-4H-3,1-benzoxazin-2,4-dione

To a solution of 5-methyl-4H-3,1-benzoxazin-2,4-dione (20 g, 113 mmol) in 150 mL of concentrated H$_2$SO$_4$, cooled to −15° C., was added 7.83 g of 90% w/w HNO$_3$ (in 30 mL of conc. H$_2$SO$_4$) dropwise at such a rate to keep the internal temperature below 5° C. After the addition was complete, the reaction was stirred at 0° C. for an additional 20 minutes then quenched by pouring the reaction mixture over crushed ice. Following further dilution with water, the resulting precipitate was filtered, washed with water, resuspended in water then filtered and washed again with water affording 15.1 g (60%) of 5-methyl-6-nitro-4H-3,1-benzoxazin-2,4-dione, after drying: Anal. Calc'd. for C$_9$H$_6$N$_2$O$_5$: C, 48.66; H, 2.72; N, 12.61. Found: C, 48.19; H, 2.54; N, 12.51.

C. Preparation of 1,1-dimethylethyl (1,4-dihydro-5-methyl-2,4-dioxo-2H-3,1-benzoxazin-6-yl)carbamate A mixture of the product of step B (13.5 g, 60.8 mmol), di-tert-butyldicarbonate (6.53 g, 30 mmol) and 20% Pd(OH)

$_2$/C (2.5 g) in 200 mL of DMF was stirred under 5 psi of hydrogen for 20 hours. The catalyst was filtered and the filtrate was evaporated under reduced pressure. The resulting yellow solid was triturated with Et$_2$O, filtered, washed with Et$_2$O and dried affording 10.2 g (87%) of 6-amino-5-methyl-4H-3,1-benzoxazin 2,4-dione. This material (9.0 g, 46.8 mmol) was redissolved in 100 mL of DMF and 15.35 g (70 mmol) of di-tert-butyldicarbonate was added followed by a catalytic amount of DMAP was added. The reaction mixture was stirred at room temperature under nitrogen overnight (ca. 30 hours). The reaction mixture was diluted with 200 mL of ½ saturated NaCl, filtered, washed with water then with hexane and dried affording 11.1 g (81%) of 1,1-dimethylethyl (1,4-dihydro-5-methyl-2,4-dioxo-2H-3,1-benzoxazin-6-yl)carbamate: Anal. Calc'd. for $C_{14}H_{16}N_2O_5$: C, 57.53; H, 5.52; N, 9.58. Found: C, 57.47; H, 5.80; N, 9.59.

D. Preparation of 2-amino-5-[[(1,1-dimethylethoxy]carbonyl]amino]-6-methylbenzoic acid.

To a suspension of the product of step C ((10.5 g, 36.0 mmol) in 15 mL of acetone was added 107 mL of 1N NaOH. After stirring at room temperature for 1 hour, the solution was acidified to pH 3 by the careful addition of 2N HCl. The mixture was extracted (2×) with EtOAc, dried (MgSO$_4$), and concentrated under reduced pressure affording 8.35 g (87%) of 2-amino-5-[[(1,1-dimethylethoxy]carbonyl]amino]-6-methylbenzoic acid: Anal. Calc'd. for $C_{13}H_{18}N_2O_4$: C, 58.64; H, 6.81; N, 10.52. Found: C, 58.26; H, 6.72; N, 10,42.

PREPARATION VIII

Preparation of 6-amino-3-[[[(1,1-dimethylethoxy)carbonyl]amino]methyl]-2-methylbenzoic acid A. Preparation of 5-methyl-6-phthalimidomethyl-2H-3,1-benzoxazin-2,4(1H)-dione and 5-methyl-8-phthalimidomethyl-2H-3,1-benzoxazin-2,4(1H)-dione.

To a solution of 5-methyl-4H-3,1-benzoxazin-2,4-dione (Preparation VIIA) (19.7 g, 111 mmol) in methanesulfonic acid (150 mL) was added N-(hydroxymethyl)phthalimide (20.3 g, 111 mmol). The reaction mixture was heated to 50° C. and stirred for 3 hours. After cooling to room temperature, the reaction mixture was diluted with 2000 mL of Et$_2$O. After stirring for an additional 1 hour, the precipitate was filtered, washed with Et$_2$O and dried affording 30.7 g of crude phthalamide. $^1$H NMR showed a 3:2 mixture of the 6- and 8-substituted regioisomers respectively. The crude material was used directly in the next reaction where the two regeoisomers were separated.

B. Preparation of 6-amino-3-phthalimidomethyl-2-methylbenzoic acid, methyl ester (B-1) and 6-amino-5-phthalimidomethyl-2 methylbenzoic acid, methyl ester (B-2).

To a slurry of the product of step A (30.7 g, 91.3 mmol) in 1300 mL of anhydrous methanol was added a catalytic amount of NaHCO$_3$ (ca. 1.0 g). After stirring the slurry at reflux for 3 hours, the mixture was concentrated to near dryness then partitioned between EtOAc and water. The aqueous layer was extracted (3×) with EtOAc, combined, dried (MgSO$_4$), filtered and concentrated under reduced pressure Silica gel TLC chromatography revealed the two regioisomeric products [50% EtOAc/50% hexanes; Rf of B-2=0.6; Rf of B-1=0.4]. Silica gel chromatography of the crude product (gradient elution, 30% EtOAc/hexanes to 80% EtOAc/hexanes) afforded 2.6 g of (B-2) and 14.6 g of (B-1).

$^1$H NMR of 6-amino-3-phthalimidomethyl-2-methylbenzoic acid, methyl ester (300 MHz, CDCl$_3$) δ 2.46 (s, 3H), 3.89 (s, 3H), 4.59 (br. s, 2H) 4.79 (s, 2H), 6.50 (d, J=8 Hz, 1H), 7.25 (d, J=8 Hz, 1H), 7.70 (m, 2H), 7.83 (m, 2H).

$^1$H NMR of 6-amino-5-phthalimidomethyl-2-methylbenzoic acid, methyl ester (300 MHz, CDCl$_3$) δ 2.36 (s, 3H), 3.85 (s, 3H), 4.72 (s, 2H), 5.87 (br. s, 2H), 6.49 (d, J=8 Hz, 1H), 7.43 (d, J=8 Hz, 1H), 7.67 (m, 2H), 7.79 (m, 2H).

C. Preparation of 6-amino-3-aminomethyl-2-methylbenzoic acid, methyl ester.

To a solution of the product of step B-1 (14.6 g, 45.3 mmol) in 500 mL of 1:1 EtOH/CH$_2$Cl$_2$ was added hydrazine hydrate (7.26 mL, 149.3 mmol). After stirring at room temperature for 16 hours, the reaction mixture was concentrated to dryness. The residue was stirred with 150 mL of 1N HCl for 1 hour then filtered to remove the precipitate. The filtrate was basified to pH=14 with 3N KOH (saturated with NaCl) and extracted with 4×200 mL of CHCl$_3$. The organic fractions were combined, dried (MgSO$_4$), filtered and concentrated under reduced pressure affording 6.2 g (70%) of 6-amino-3-aminomethyl-2-methylbenzoic acid, methyl ester: $^1$H NMR (300 MHz, CDCl$_3$) δ 2.30 (s, 3H), 3.68 (s, 2H), 3.87 (s, 3H), 4.64 (br. s, 2H), 6.48 (d, J=8 Hz, 1H), 7.08 (d, J=8 Hz, 1H).

D. Preparation of 6-amino-3-[[[(1,1 dimethylethoxy)carbonyl]amino]methyl]-2-methylbenzoic acid.

To a solution of the product of step C (6.2 g, 31.8 mmol) in 150 mL of 1:1 dioxane/water was added LiOH monohydrate (4.0 g, 95.5 mmol). After refluxing for two hours, the mixture was cooled to room temperature and treated with di-tert-butyldicarbonate (7.70 g, 35 mmol). After stirring at room temperature overnight, the mixture was acidified to pH=3.0 with 1 N HCl (ca. 120 mL) and extracted 3× with EtOAc. The organic fractions were combined, dried (MgSO$_4$), filtered and concentrated under reduced pressure affording 6.15 g (69%) of compound: $^1$H NMR (300 MHz, CDCl$_3$) δ 1.46 (s, 9H), 2.43 (s, 3H), 4.23 (br. s, 2H), 4.65 (br. s, 1H), 6.53 (d, J=8 Hz, 1H), 7.03 (br. s, 2H), 7.12 (d, J=8 Hz, 1H).

PREPARATION IX

Preparation of 2-[[[[(1R)-(4-iodophenyl)ethyl]amino]carbonyl]amino]-6 methyl-benzoic acid A. Preparation of 2-methyl-6-[[[[(1R)-(4 nitrophenyl) ethyl]amino]carbonyl]amino]benzoic acid.

To an ice cooled, stirred suspension of CDI (840 mg, 5.19 mmol) in 7 mL of pyridine was added (1R)-(4-nitrophenyl)ethylamine hydrochloride (1.00 g, 4.94 mmol). After stirring at 0° C. for 30 minutes, 2-amino-6 methylbenzoic acid (746 mg, 4.94 mmol) was added. The ice bath was removed and the reaction mixture was stirred at 75–80° C. for 1.5 hours After cooling to room temperature, the reaction mixture was acidified to pH 1–2 with 2N HCl and extracted with EtOAc. The organic fraction was dried (MgSO$_4$), filtered and concentrated under reduced pressure. Crystallization of the oily product from EtOAc/Et$_2$O afforded 960 mg of material: $^1$H NMR (300 MHz, CDCl$_3$/CD$_3$OD) δ 1.49 (d, J=7 Hz, 3H), 2.47 (s, 3H), 5.01 (m, 1H), 6.90 (d, J=8 Hz, 1H), 7.26 (t, J=8 Hz, 1H), 7.53 (d, J=8 Hz, 2H), 7.84 (d, J=8 Hz, 1H), 8.19 (d, J=8 Hz, 2H)

B. Preparation of 2-[[[[(1R)-(4-aminophenyl)ethyl]amino]carbonyl]amino]-6-methyl-benzoic acid.

A mixture of the product of step A (950 mg, 2.77 mmol) and 5% Pd/C (100 mg) in 20 mL of MeOH was stirred under a balloon of hydrogen for 3 hours. The catalyst was removed by filtration and the filtrate was concentrated under reduced pressure. Trituration of the residue with EtOAc/Et$_2$O afforded 800 mg of 2-[[[[(1R)-(4-aminophenyl)ethyl]amino]carbonyl]amino]-6-methyl-benzoic acid: $^1$H NMR (300 MHz, CDCl$_3$/CD$_3$OD) δ 1.43 (d, J=7 Hz, 3H), 2.43 (s, 3H), 4.82 (m, 1H), 6.67 (d, J=8 Hz, 2H), 6.88 (d, J=8 Hz, 1H), 7.13 (d, J=8 Hz, 2H), 7.24 (t, J=8 Hz, 1H), 7.79 (d, J=8 Hz, 1H).

C. Preparation of 2-[[[[(1R)-(4-iodophenyl)ethyl]amino]carbonyl]amino]-6-methyl-benzoic acid.

To an ice cooled, stirred solution of the product of step B (750 mg, 2.40 mmol) in 12 mL of 1N HCl was added sodium nitrite (174 mg, 2.52 mmol) (in 3 mL of water). After stirring at 0° C. for 10 minutes, the cloudy mixture was filtered through a glass wool plug and placed back in the ice bath. To this solution was added KI (418 mg, 2.52 mmol) (in 3 mL of water). The ice bath was removed, the reaction mixture was stirred at ambient temperature for 30 minutes, then warmed on a steam bath for 10 minutes. The reaction mixture was diluted with water and extracted with EtOAc. The organic fraction was washed sequentially with water, 5% sodium sulfite then dried (MgSO$_4$), filtered and evaporated under reduced pressure affording 750 mg of crude 2-[[[[(1R)-(4-iodophenyl)ethyl]amino]carbonyl]amino]-6-methyl-benzoic acid: 1H-NMR (300 MHz, CDCl$_3$/CD$_3$OD) δ 1.44 (d, J=7 Hz, 3H), 2.44 (s, 3H), 4.38 (m, 1H)m 6.90 (d, J=8 Hz, 1H), 7.10 (d, J=8 Hz, 2H), 7.26 (t, J=8 Hz, 1H), 7.64 (d, J=8 Hz, 2H), 7.83 (d, J=8 Hz, 1H).

Example 1

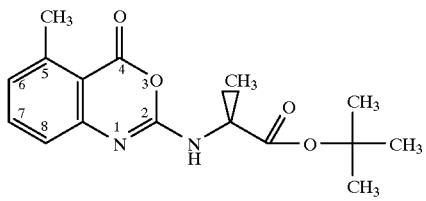

N-(5-Methyl-4-oxo-4H-3,1-benzoxazin-2-yl)-L-alanine, tert-butyl ester

To an ice cooled suspension of CDI (0.53 g, 3.27 mmol) in 5 mL of pyridine was added L-alanine t-butyl ester hydrochloride (0.57 g, 3.13 mmol). After stirring at 0° C. for 30 minutes, 2-amino-6-methylbenzoic acid (0.43 g, 2.85 mmol) was added. The ice bath was removed and the reaction was stirred at 65° C. for 2 hours. The reaction mixture was diluted with EtOAc and washed with 1N HCl, dried (MgSO$_4$), filtered and evaporated under reduced pressure. The crude product (0.30 g) was dissolved in 5 mL of CH$_2$Cl$_2$. Triethylamine (0.15 g, 1.47 mmol) and EDC (0.28 g, 1.47 mmol) were added sequentially After stirring at room temperature for 2 hours the reaction mixture was diluted with EtOAc and washed with 1N HCl, dried (MgSO$_4$), filtered and evaporated under reduced pressure. Silica gel chromatography of the residue (1:1 EtOAc/hexane) afforded 113 mg of N-(5-methyl-4-oxo-4H-3,1-benzoxazin-2-yl)-L-alanine, t-butyl ester: Anal. Calc'd. for C$_{16}$H$_{20}$N$_2$O$_4$: C, 63.14; H, 6.62; N, 9.21. Found: C, 62.90; H, 6.97; N, 9.11. $^1$H-NMR (300 MHz, CDCl$_3$) δ 1.49 (s, 9H), 1.50 (d, J=7 Hz, 3H), 2.70 (s, 3H), 4.48 (pent, J=7 Hz, 1H), 5.68 (br. s, 1H, exchangeable), 6.95 (d, J=8 Hz, 1H), 6.99 (d, J=8 Hz, 1H), 7.45 (t, J=8 Hz, 1H).

Proceeding in a like manner but replacing L-alanine t-butyl ester hydrochloride with other appropriately substituted amines or amine hydrochlorides, the following compounds were prepared:

(1a) N-(5-Methyl-4-oxo-4H-3,1-benzoxazin-2-yl)-D-alanine, 1,1 dimethylethyl ester: Anal. Calc'd. for C$_{16}$H$_{20}$N$_2$O$_4$: C, 63.14; H, 6.62; N, 9.21. Found: C, 62.99; H, 6.77; N. 9.10.

(1b) N-(5-Methyl-4-oxo-4H-3,1-benzoxazin-2-yl)-L-alanine, methyl ester: Anal. Calc'd. for C$_{13}$H$_{14}$N$_2$O$_4$: C, 59.53; H, 5.38; N, 10.68 Found: C, 59.60; H, 5.71; N, 10.89.

(1c) N-(5-Methyl-4-oxo-4H-3,1-benzoxazin-2-yl)-D-alanine, methyl ester: Anal. Calc'd. for C$_{13}$H$_{14}$N$_2$O$_4$: C, 59.53; H, 5.38; N, 10.68. Found: C, 59.32; H, 5.47; N, 10.31.

(1d) N-(5-Methyl-4-oxo-4H-3,1-benzoxazin-2-yl)-L-valine, methyl ester: Anal. Calc'd. for C$_{15}$H$_{18}$N$_2$O$_4$: C, 62.05; H, 6.25; N, 9.65. Found: C, 61.89; H, 6.26; N, 9.67.

(1e) N-(5-Methyl-4-oxo-4H-3,1-benzoxazin-2-yl)-L-leucine, methyl ester: $^1$H-NMR (300 MHz, CDCl$_3$) δ 0.99 (m, 6H), 1.60–1.75 (m, 3H), 2.71 (s, 3H), 3.77 (s, 3H), 4.67 (m, 1H), 5.25 (br. d, J=7 Hz, 1H, exchangeable), 6.98 (d, J=8 Hz, 1H), 7.00 (d, J=8 Hz, 1H), 7.46 (t, J=8 Hz, 1H).

(1f) N-(5-Methyl-4-oxo-4H-3,1-benzoxazin-2-yl)-L-norleucine, methyl ester: Anal. Calc'd. for C$_{16}$H$_{20}$N$_2$O$_4$: C, 63.14; H, 6.62; N, 9.21. Found: C, 62.82; H, 6.50; N, 9.11.

(1g) N-(5-Methyl-4-oxo-4H-3,1-benzoxazin-2-yl)-L-isoleucine, methyl ester: Anal. Calc'd. for C$_{16}$H$_{20}$N$_2$O$_4$: C, 63.14; H, 6.62; N, 9.21. Found: C, 62.91; H, 6.63; N, 9.05.

(1h) N-(5-Methyl-4-oxo-4H-3,1-benzoxazin-2-yl)-L-methionine, methyl ester: Anal. Calc'd. for C$_{15}$H$_{18}$N$_2$O$_4$S: C, 55.88; H, 5.63; N, 8.69. Found: C, 56.05; H, 5.69; N, 8.55.

(1i) N$^\alpha$-(5-Methyl-4-oxo-4H-3,1-benzoxazin-2-yl)-N$^\epsilon$-[(phenylmethoxy)carbonyl]-L-lysine, 1,1-dimethylethyl ester: $^1$H-NMR (300 MHz, CDCl$_3$) δ 1.40–1.63 (m, 13H), 1.75–1.95 (m, 2H), 2.65 (s, 3H), 3.18 (m, 3H), 4.42 (m, 1H), 5.08 (s, 2H), 5.47 (br. t, J=7 Hz, 1H, exchangeable), 6.25 (br. d, J=7 Hz, 1H, exchangeable), 6.88 (d, J=8 Hz, 1H), 7.05 (d, J=8 Hz, 1H), 7.20–7.35 (m, 5H), 7.39 (t, J=8 Hz, 1H).

(1j) N-(5-Methyl-4-oxo-4H-3,1-benzoxazin-2-yl)-L-phenylalanine, 1,1-dimethylethyl ester: $^1$H-NMR (300 MHz, CDCl$_3$) δ 1.40 (s, 9H), 2.65 (s, 3H), 3.17 (m, 2H), 4.74 (m, 1H), 5.75 (br. d, J=7 Hz, 1H, exchangeable), 6.90 (d, J=8 Hz, 1H), 7.08 (d, J=8 Hz, 1H), 7.15–7.30 (m, 5H), 7.40 (t, J=8 Hz, 1H).

(1k) N-(5-Methyl-4-oxo-4H-3,1-benzoxazin-2-yl)-L-phenylalanine, methyl ester: Anal. Calc'd. for C$_{19}$H$_{18}$N$_2$O$_4$: C, 67.44; H, 5.36; N, 8.28. Found: C, 67.20; H, 5.57; N, 8.05.

(1l) N-(5-Methyl-4-oxo-4H-3,1-benzoxazin-2-yl)-L-tyrosine, 1,1-dimethylethyl ester: $^1$H-NMR (300 MHz, CDCl$_3$) δ 1.43 (s, 9H), 2.69 (s, 3H), 3.10 (m, 2H), 4.68 (m, 1H), 6.72 (d, J=8 Hz, 2H), 6.93–7.03 (m, 3H), 7.10 (d, J=8 Hz, 1H), 7.45 (t, J=8 Hz, 1H).

(1m) N-(5-Methyl-4-oxo-4H-3,1-benzoxazin-2-yl)-L-tryptophan, methyl ester: $^1$H-NMR (300 MHz, CDCl$_3$) δ 2.67 (s, 3H), 3.40 (m, 2H), 3.70 (s, 3H), 4.93 (m, 1H), 5.47 (br. d, J=7 Hz, 1H, exchangeable), 6.90–7.20 (m, 5H), 7.30 (d, J=8 Hz, 1H), 7.43 (t, J=8 Hz, 1H), 7.55 (d, J=8 Hz, 1H), 8.44 (s, 1H, exchangeable).

(1n) N-(5-Methyl-4-oxo-4H-3,1-benzoxazin-2-yl)-L-tryptophan, 1,1-dimethylethyl ester: $^1$H-NMR (300 MHz, CDCl$_3$) δ 1.38 (s, 9H), 2.63 (s, 3H), 3.33 (m, 2H), 4.78 (m, 1H), 5.68 (br. d, J=7 Hz, 1H, exchangeable), 6.85–7.15 (m, 5H), 7.26 (d, J=8 Hz, 1H), 7.37 (t, J=8 Hz, 1H), 7.60 (d, J=8 Hz, 1H), 8.65 (s, 1H, exchangeable).

(1o) N-(5-Methyl-4-oxo-4H-3,1-benzoxazin-2-yl)-L-phenylglycine, 1,1-dimethylethyl ester: $^1$H-NMR (300 MHz, CDCl$_3$) δ 1.42 (s, 9H), 2.62 (s, 3H), 5.50 (d, J=7 Hz,1H), 6.38 (br. s 1H, exchangeable), 6.86 (d, J=8 Hz, 1H), 7.02 (d, J=8 Hz, 1H), 7.25–7.38 (m, 4H), 7.47 (d, J=8 Hz, 2H).

(1p) 2-[[2-Methoxy-(1S)-(1-phenylmethyl)ethyl]amino]-5-methyl-4H-3,1-benzoxazin-4-one: Anal. Calc'd. for $C_{19}H_{20}N_2O_3$: C, 70.35; H, 6.22; N, 8.64. Found: C, 70.00; H, 6.28; N, 8.54.

(1q) 3,5-Diiodo-N-(5-methyl-(3,5-diiodo)2-yl)-L-tyrosine, methyl ester: $^1$H-NMR (300 MHz, CDCl$_3$) δ 2.72 (s, 3H), 3.09 (m, 2H), 3.79 (s, 3H), 4.86 (t, J=7 Hz, 1H), 5.50 (br. s, 1H, exchangeable), 7.01 (d, J=8 Hz, 1H), 7.13 (d, J=8 Hz, 1H), 7.49 (t, J=8 Hz, 1H), 7.52 (s, 2H).

(1r) N-(5-Methyl-4-oxo-4H-3,1-benzoxazin-2-yl)-O-methyl-L-tyrosine, methyl ester: $^1$H-NMR (300 MHz, CDCl$_3$) δ 2.66 (s, 3H), 3.15 (m, 2H), 3.73 (s, 3H), 3.74 (s, 3H), 4.85 (br. m, 1H), 5.68 (br. s, 1H, exchangeable), 6.80 (d, J=8 Hz, 2H), 6.92 (d, J=8 Hz, 1H), 7.07 (m, 3H), 7.42 (t, J=8 Hz, 1H).

Proceeding in a like manner but replacing 2-amino-6-methylbenzoic acid with 2-amino-6-methoxybenzoic acid [c.f. S. Gould and R. Eisenberg, *J. Org. Chem.*, 56, 6666–6671 (1991)] and replacing L-alanine tert-butyl ester hydrochloride with other appropriate amines or amine hydrochlorides, the following compounds are prepared:

(1s) 5-Methoxy-2-[[(1R)-1-phenylethyl]amino]-4H-3,1-benzoxazin-4-one; and (1t) N-[5-Methoxy-4-oxo-4H-3,1-benzoxazin-2-yl]-O-methyl-L-tyrosine, N-methyl-N-phenylmethylamide.

Example 2

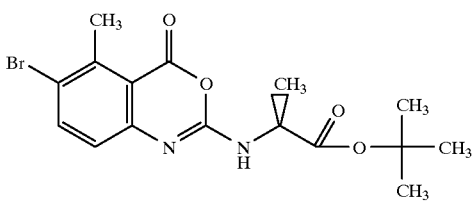

N-(6-Bromo-5-methyl-4-oxo-4H-3,1-benzoxazin-2-yl)-L-alanine 1,1-dimethylethyl ester To an ice cooled suspension of CDI (0.309 g, 1.91 mmol) in 2 mL of pyridine was added L-alanine tert-butyl ester hydrochloride (0.317 g, 1.74 mmol). After stirring at 0° C. for 30 minutes, 2-amino-5-bromo-6-methylbenzoic acid (0.494 g, 1.60 mmol) and 25 mg of DMAP was added. The ice bath was removed and the reaction was stirred at 65° C. for 2.5 hours. The reaction mixture was cooled to room temperature and diluted with 2 mL of DMF and 2 mL of CH$_2$Cl$_2$. Triethylamine (0.257 g, 2.54 mmol) and EDC (0.457 g, 2.38 mmol) were added sequentially. After stirring at room temperature for 2 hours, the reaction mixture was diluted with EtOAc and washed with 1N HCl, dried (MgSO$_4$), filtered and evaporated under reduced pressure. Silica gel chromatography of the residue (1:1 EtOAc/hexane) afforded 49 mg of product: $^1$H-NMR (300 MHz, CDCl$_3$) δ 1.49 (s, 9H), 1.50 (d, J=7 Hz, 3H), 2.83 (s, 3H), 4.47 (q, J=7 Hz, 1H), 5.60 (br. s, 1H, exchangeable), 6.97 (d, J=9 Hz, 1H), 7.73 (d, J=9 Hz, 1H).

Proceeding in a like manner but replacing L-alanine tert-butyl ester hydrochloride with other appropriately substituted amines or amine hydrochlorides, the following compounds were prepared:

(2a) N-(6-Bromo-5-methyl-4-oxo-4H-3,1-benzoxazin-2-yl)-D-alanine, 1,1-dimethylethyl ester: $^1$H-NMR (300 MHz, CDCl$_3$) δ 1.49 (s, 9H), 1.50 (d, J=7 Hz, 3H), 2.83 (s, 3H), 4.47 (q, J=7 Hz, 1H), 5.60 (br. s, 1H, exchangeable), 6.97 (d, J=9 Hz, 1H), 7.73 (d, J=9 Hz, 1H).

(2b) 6-Bromo-5-methyl-2-[[(1R)-1-phenylethyl]amino]-4H-3,1-benzoxazin-4-one: Anal. Calc'd. for $C_{17}H_{15}N_2O_2Br$: C, 56.84; H, 4.21; N, 7.80. Found: C, 56.49; H, 4.08; N, 7.70.

Example 3

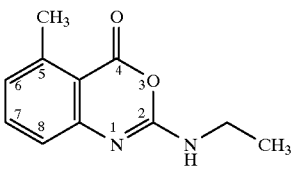

2-Ethylamino-5-methyl-4H-3,1-benzoxazin-4-one

To a stirred solution of 2-(3-ethylureido)-6-methylbenzoic acid (250 mg, 1.125 mmol) and triethylamine (170 mg, 1.69 mmol) in 10 mL CH$_2$Cl$_2$ at room temperature was added EDC (501 mg, 1.69 mmol). After stirring at room temperature for 3 hours, the reaction mixture was diluted with EtOAc and washed sequentially with 1N HCl and sat'd. NaHCO$_3$. The organic fraction was dried (MgSO$_4$), filtered and evaporated under reduced pressure. Silica gel chromatography of the residue (1:1 EtOAc/hexane) afforded 127 mg of product: Anal. Calc'd. for $C_{11}H_{12}N_2O_2.0.25 H_2O$: C, 63.30; H, 6.04; N, 13.42. Found: C, 63.32; H, 5.92; N, 13.10. $^1$H-NMR (300 MHz, d$_6$-DMSO) δ 1.14 (t, J=7 Hz, 3H), 2.60 (s, 3H), 3.27 (pent, J=7 Hz, 2H), 6.95 (d, J=8 Hz, 1H), 7.02 (d, J=8 Hz, 1H), 7.50 (t, J=8 Hz, 1H), 7.90 (br. t, J=7 Hz, 1H, exchangeable).

Proceeding in a like manner but replacing 2-(3-ethylureido)-6-methylbenzoic acid with other appropriately substituted benzoic acid listed in Preparations I, II, III, IV and V, the following compounds were prepared:

(3a) 2-[1-Methylethyl]amino-5-methyl-4H-3,1-benzoxazin-4-one: Anal. Calc'd. for $C_{12}H_{14}N_2O_2$: C, 66.04; H, 6.46; N, 12.84. Found: C, 65.88; H, 6.34; N, 12.71.

(3b) 5-Methyl-2-[[(1S)-1-phenylethyl]amino]-4H-3,1-benzoxazin-4-one: Anal. Calc'd. for $C_{17}H_{16}N_2O_2$: C, 72.84; H, 5.75; N, 9.99. Found: C, 72.74; H, 5.80; N, 9.94.

(3c) 5-Methyl-2-[[(1R)-1-phenylethyl]amino]-4H-3,1-benzoxazin-4-one: Anal. Calc'd. for $C_{17}H_{16}N_2O_2$: C, 72.84; H, 5.75; N, 9.99. Found: C, 72.51; H, 5.88; N, 9.97.

(3d) 5-Methyl-2-phenylamino-4H-3,1-benzoxazin-4-one: Anal. Calc'd. for $C_{15}H_{12}N_2O_2.0.1H_2O$: C, 70.91; H, 4.84; N, 11.03. Found: C, 70.86; H, 4.92; N, 10.68.

(3e) 2-[(3-Chlorophenyl)amino]-5-methyl-4H-3,1-benzoxazin-4-one: Anal. Calc'd. for $C_{15}H_{11}N_2O_2Cl$: C, 62.84; H, 3.87; N, 9.77; Cl, 12.36. Found: C, 62.60; H, 3.79; N, 9.59; Cl, 12.11.

(3f) 2-[(2,6-Dichlorophenyl)amino]-5-methyl-4H-3,1-benzoxazin-4-one: Anal. Calc'd. for $C_{15}H_{10}N_2O_2Cl_2$: C, 56.10; H, 3.14; N, 8.73; Cl, 22.08. Found: C, 55.79; H, 3.38; N, 8.63; Cl, 21.97.

(3g) 5-Methyl-2-[(2-nitrophenyl)amino]-4H-3,1-benzoxazin-4-one: Anal. Calc'd. for $C_{15}H_{11}N_3O_4.0.33H_2O$: C, 59.40; H, 3.88; N, 13.86. Found: C, 59.33; H, 3.78; N, 13.83.

(3h) 5-Methyl-2-[(4-nitrophenyl)amino]-4H-3,1-benzoxazin-4-one: Anal. Calc'd. for $C_{15}H_{11}N_3O_4.0.4H_2O$: C, 59.17; H, 3.91; N, 13.80. Found: C, 59.19; H, 3.791; N,13.83.

(3i) 6-Iodo-2-[[(1R)-1-phenylethyl]amino]-4H-3,1-benzoxazin-4-one: Anal. Calc'd. for $C_{16}H_{13}N_2O_2I$: C, 49.00; H, 3.34; N, 7.14. Found: C, 48.82; H, 3.31; N, 7.04.

(3j) 2-[(2,6-Dichlorophenyl)amino]-6-iodo-H-3,1-benzoxazin-4-one: Anal. Calc'd. for $C_{14}H_7N_2O_2Cl_2I$: C, 56.10; H, 3.14; N, 8.73; Cl, 22.08. Found: C, 55.79; H, 3.38; N, 8.63; Cl, 21.97.

(3k) 2-[[(1S)-1-phenylethyl]amino]-6-iodo-4H-3,1-benzoxazin-4-one: Anal. Calc'd. for $C_{16}H_{13}N_2O_2I$: C, 38.83; H,1.63; N, 6.47; Cl, 16.37. Found: C, 39.03; H,1.65; N, 6.36; Cl, 16.27.

(3l) 6-Chloro-2-[[(1R)-1-phenylethyl]amino]-4H-3,1-benzoxazin-4-one: Anal. Calc'd. for $C_{16}H_{13}N_2O_2Cl.0.1 H_2O$: C, 63.39; H, 4.35; N, 9.21. Found: C, 63.52; H, 4.40; N, 9.26.

(3m) 6-Methyl-2-[[(1R)-1-phenylethyl]amino]-4H-3,1-benzoxazin-4-one: Anal. Calc'd. for $C_{17}H_{16}N_2O_2$: C, 72.84; H, 5.75; N, 9.99. Found: C, 72.83; H, 5.98; N, 9.94.

(3n) 6-Methyl-2-[[(1S)-1-phenylethyl]amino]-4H-3,1-benzoxazin-4-one: Anal. Calc'd. for $C_{17}H_{16}N_2O_2$: C, 72.84; H,5.75; N, 9.99. Found: C, 72.69; H,5.91; N, 9.96.

(3o) 2-[[(1R)-1-(4-bromophenyl)ethyl]amino]-5-methyl-4H-3,1-benzoxazin-4-one: Anal. Calc'd. for $C_{17}H_{15}N_2O_2Br$: C, 56.84; H, 4.21; N, 7.80. Found: C, 56.71; H, 4.23; N, 7.67.

Example 4

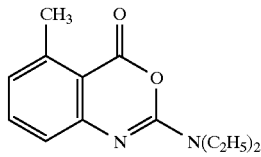

2-(N,N-Diethyl)amino-5-methyl-4H-3,1-benzoxazin-4-one

To an ice cooled solution of 2-amino-6-methylbenzoic acid (100 mg, 3.30 mmol) in 10 mL of pyridine was added N,N-diethylcarbamoyl chloride (1.79 g, 13.2 mmol). The ice bath was removed and the reaction stirred at room temperature for 2 hours. The reaction mixture was partially concentrated under a stream of nitrogen then diluted with water. The resulting precipitate was filtered, washed with water and dried. Silica gel chromatography (1:1 EtOAc/hexane) afforded 233 mg of product. Anal. Calc'd. for $C_{13}H_{16}N_2O_2$: C, 67.22; H, 6.94; N, 12.06. Found: C, 66.84; H, 7.17; N, 12.08.

Proceeding in a like manner but replacing N,N-diethylcarbamoyl chloride with other appropriately substituted carbamoyl chlorides, the following compound was prepared:

(4a) 5-Methyl-2-[methyl(phenylmethyl)amino]-4H-3,1-benzoxazin-4-one: Anal. Calc'd. for $C_{17}H_{16}N_2O_2$: C, 72.84; H, 5.75; N, 9.99. Found: C, 72.26; H, 5.65; N, 9.66. $^1$H-NMR (300 MHz, CDCl$_3$) δ 2.71 (s, 3H), 3.08 (s, 3H), 4.73, (s, 2H), 6.90 (d, J=8 Hz, 1H), 7.10 (d, J=8 Hz, 1H), 7.25–7.38 (m, 5H), 7.43 (t, J=8 Hz, 1H).

(4b) 5-Methyl-2-[methyl(2-pyridylmethyl)amino]-4H-3,1-benzoxazin-4-one: $^1$H-NMR (300 MHz, CDCl$_3$) δ 2.70 (s, 3H), 3.20 (s, 3H), 4.87 (s, 2H), 6.91 (d, J=8 Hz, 1H), 7.10 (d, J=7 Hz, 1H), 7.19 (dd, J=5, 8 Hz, 1H), 7.32 (d, J=8 Hz, 1H), 7.42 (t, J=8 Hz, 1H), 7.67 (dt, J=2, 8 Hz, 1H), 8.57 (d, J=5 Hz, 1H).

Example 5

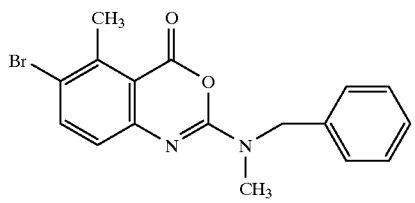

6-Bromo-5-methyl-2-[methyl(phenylmethyl)amino]-4H-3,1-benzoxazin-4-one

The title compound was prepared in a manner similar to example 4a, substituting 2-amino-6-methylbenzoic acid with 2-amino-5-bromo-6-methylbenzoic acid: $^1$H-NMR (300 MHz, CDCl$_3$) δ 2.85 (s, 3H), 3.09 (s, 3H), 4.74, (s, 2H), 6.99 (d, J=8 Hz, 1H), 7.25–7.40 (m, 5H), 7.71 (d, J=8 Hz, 1H).

Example 6

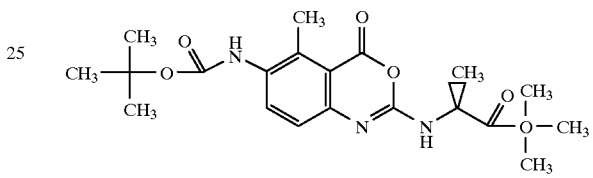

N-[6-[[(1,1-Dimethylethoxy)carbonyl]amino]-5-methyl-4-oxo-4H-3,1-benzoxazin-2-yl]-L-alanine, 1,1-dimethylethyl ester To an ice cooled suspension of CDI (128 mg, 0.789 mmol) in 2 mL of pyridine was added L-alanine t-butyl ester hydrochloride (136 mg, 0.752 mmol). After stirring for 30 minutes, 2-amino-5-[[[(1,1-dimethylethyl)oxy]carbonyl]amino]-6-methylbenzoic acid (200 mg, 0.752 mmol) was added. The ice bath was removed and the reaction mixture stirred at 75° C. for 2.5 hours. The reaction mixture was partitioned between EtOAc and 1N HCl, dried (MgSO$_4$) filtered and evaporated under reduced pressure. To a solution of the crude product and triethylamine (85 mg, 0.846 mmol) in 5 mL of CH$_2$Cl$_2$ was added EDC (162 mg, 0.846 mmol). After stirring at room temperature for 2 hours, the reaction mixture was applied directly to a silica gel column and the product was eluted with 30% EtOAc/hexane affording 180 mg of product: $^1$H-NMR (300 MHz, CDCl$_3$) δ 1.45–1.55 (m, 20H), 2.66 (s, 3H), 4.47, (pent, J=7 Hz, 1H), 5.35 (br. d, J=7 Hz, 1H, exchangeable), 6.27 (br. s, 1H, exchangeable), 7.11 (d, J=8 Hz, 1H), 7.88 (br. d, J=8 Hz, 1H).

Proceeding in a like manner but replacing L-alanine t-butyl ester hydrochloride with other appropriately substituted amines or amine hydrochlorides, the following compound was prepared:

(6a) N-[6-[[(1,1-Dimethylethoxy)carbonyl]amino]-5-methyl-4-oxo-4H-3,1-benzoxazin-2-yl]-L-phenylalanine, methyl ester: $^1$H-NMR (300 MHz, CDCl$_3$) δ 1.50 (s, 9H), 2.62 (s, 3H), 3.23 (m, 2H), 3.74 (s, 3H), 4.49, (q, J=7 Hz, 1H), 5.47 (br. s, 1H, exchangeable), 6.43 (br. s, 1H, exchangeable), 7.08 (d, J=8 Hz, 1H), 7.13–7.33 (m, 5H), 7.83 (br. d, J=8 Hz, 1H).

(6b) N-[6-[[(1,1-Dimethylethoxy)carbonyl]amino]-5-methyl-4-oxo-4H-3,1-benzoxazin-2-yl]-O-(phenylmethyl)-L-serine, methyl ester: $^1$H-NMR (300 MHz, CDCl$_3$) δ 1.52

(s, 9H), 2.63 (s, 3H), 3.78 (s, 3H), 3.84 (m, 1H), 3.96 (m, 1H), 4.55 (m, 2H), 4.76 (m, 1H), 5.73 (br. s 1H, exchangeable), 6.32 (br. s, 1H, exchangeable), 7.08 (d, J=8 Hz, 1H), 7.25–7.37 (m, 5H), 7.86 (br. d, J=8 Hz, 1H).

(6c) N-[6-[[(1,1-Dimethylethoxy)carbonyl]amino]-5-methyl-4-oxo-4H-3,1-benzoxazin-2-yl]-O-methyl-L-tyrosine, methyl ester: $^1$H-NMR (300 MHz, CDCl$_3$) δ 1.51 (s, 9H), 2.60 (s, 3H), 3.07–3.25 (m, 2H), 3.76 (s, 6H), 4.84 (m, 1H), 5.50 (br. s, 1H, exchangeable), 6.48 (s, 1H, exchangeable), 6.82 (d, J=8 Hz, 2H), 7.03–7.10 (m, 3H), 7.80 (br. d, J=8 Hz, 1H).

(6d) N-[6-[[(1,1-Dimethylethoxy)carbonyl]amino]-5-methyl-4-oxo-4H-3,1-benzoxazin-2-yl]-O-methyl-L-tyrosine, dimethylamide. $^1$H-NMR (300 MHz, CDCl$_3$) δ 1.51 (s, 9H), 2.43 (s, 3H), 2.90 (s, 3H), 2.98 (s, 3H), 3.11 (d, J=7 Hz, 2H), 3.78 (s, 3H), 5.08 (m, 1H), 6.62 (s, 1H, exchangeable), 6.83 (d, J=8 Hz, 2H), 6.93 (d, J=8 Hz, 1H), 7.19 (d, J=8 Hz, 2H), 7.60 (d, J=8 Hz, 1H).

(6e) N-[6-[[(1,1-Dimethylethoxy)carbonyl]amino]-5-methyl-4-oxo-4H-3,1-benzoxazin-2-yl]-L-thiazol-4-yl-alanine, methyl ester: $^1$H-NMR (300 MHz, CDCl$_3$) δ 1.51 (s, 9H), 2.57 (s, 3H), 3.42–3.62 (m, 2H), 3.73 (s, 3H), 5.06 (m, 1H), 6.53 (s, 1H, exchangeable), 6.78 (br. d, J=7 Hz, 1H, exchangeable), 7.04 (d, J=8 Hz, 1H), 7.09 (d, J=2 Hz, 1H), 7.73 (br. d, J=8 Hz, 1H), 8.71 (d, J=2 Hz, 1H).

(6f) N-[6-[[(1,1-Dimethylethoxy)carbonyl]amino]-5-methyl-4-oxo-4H-3,1-benzoxazin-2-yl]-L-aspartic acid, alpha-methyl ester beta dimethylamide: $^1$H-NMR (300 MHz, CDCl$_3$) δ 1.52 (s, 9H), 2.60 (s, 3H) 2.95 (s, 3H), 3.02 (s, 3H), 3.23 (m, 1H), 3.76 (s, 3H), 4.93 (m, 1H), 6.25 (br. d, J=7 Hz, 1H, exchangeable), 6.48 (s, 1H, exchangeable), 7.08 (d, J=8 Hz, 1H), 7.83 (br. d, J=8 Hz, 1H).

(6g) N-[6-[[(1,1-Dimethylethoxy)carbonyl]amino]-5-methyl-4-oxo-4H-3,1-benzoxazin-2-yl]-L-alanine, pyrrolidineamide: $^1$H-NMR (300 MHz, CDCl$_3$) δ 1.46 (d, J=7 Hz, 3H) 1.52 (s, 9H), 1.85–2.05 (m, 4H), 2.62 (s, 3H), 3.40–3.65 (m, 4H), 4.71 (m, 1H), 6.05 (br. d, J=7 Hz, 1H, exchangeable), 6.32 (s, 1H, exchangeable), 7.06 (d, J=8 Hz, 1H), 7.84 (br. d, J=8 Hz, 1H).

(6h) N-[6-[[(1,1-Dimethylethoxy)carbonyl]amino]-5-methyl-4-oxo-4H-3,1-benzoxazin-2-yl]-O-methyl-L-tyrosine, pyrrolidineamide: $^1$H-NMR (300 MHz, CDCl$_3$) δ 1.53 (s, 9H), 1.55–1.90 (m, 4H), 2.62 (s, 3H), 2.99–3.15 (m, 2H), 3.30–3.55 (m, 4H), 3.78 (s, 3H), 4.83 (m, 1H), 5.83 (br. d, J=7 Hz, 1H, exchangeable), 6.27 (s, 1H, exchangeable), 6.83 (d, J=8 Hz, 2H), 7.07 (d, J=8 Hz, 1H), 7.17 (d, J=8 Hz, 2H), 7.85 (d, J=8 Hz, 1H).

(6i) N-[6-[[(1,1-Dimethylethoxy)carbonyl]amino]-5-methyl-4-oxo-4H-3,1-benzoxazin-2-yl]-O-methyl-L-tyrosine, morpholineamide: $^1$H-NMR (300 MHz, CDCl$_3$) δ 1.53 (s, 9H), 2.55 (s, 3H), 3.00–3.15 (m, 2H), 3.45–3.70 (m, 8H), 3.79 (s, 3H), 5.04 (m, 1H), 6.17 (br. s,1H, exchangeable), 6.37 (s, 1H, exchangeable), 6.85 (d, J=8 Hz, 2H), 7.03 (d, J=8 Hz, 1H), 7.18 (d, J=8 Hz, 2H), 7.80 (d, J=8 Hz, 1H).

(6j) N-[6-[[(1,1-Dimethylethoxy)carbonyl]amino]-5-methyl-4-oxo-4H-3,1-benzoxazin-2-yl]-O-methyl-L-tyrosine, N-methylpiperazineamide: $^1$H-NMR (300 MHz, CDCl$_3$) δ 1.52 (s, 9H), 2.26 (s, 3H), 2.31 (m, 4H), 2.64 (s, 3H), 2.98–3.15 (m, 2H), 3.42–3.52 (m, 2H), 3.65–3.75 (m, 2H), 3.78 (s, 3H), 5.06 (m, 1H), 5.71 (br. s, 1H, exchangeable), 6.24 (s, 1H, exchangeable), 6.72 (d, J=8 Hz, 2H), 7.08–7.14 (m, 3H), 7.90 (br. d, J=8 Hz, 1H).

(6k) N-[6-[[(1,1-Dimethylethoxy)carbonyl]amino]-5-methyl-4-oxo-4H-3,1-benzoxazin-2-yl]-O-methyl-L-tyrosine, N-methyl-N-[2-(1 morpholinyl)ethyl]amide: Anal. calc'd. for C$_{31}$H$_{41}$N$_5$O$_7$.0.75H$_2$O: C, 61.12; H, 7.03; N, 11.53. Found: C, 61.13; H, 6.93; N, 11.14.

(6l) N-[6-[[(1,1-Dimethylethoxy)carbonyl]amino]-5-methyl-4-oxo-4H-3,1-benzoxazin-2-yl]-O-methyl-L-tyrosine, N-methyl-N-[2-(1-piperidinyl)ethyl]amide: Anal. calc'd. for C$_{32}$H$_{43}$N$_5$O$_6$.0.75H$_2$O: C, 63.29; H, 7.39; N, 11.53. Found: C, 63.35; H, 7.60; N, 11.17.

(6m) 6-[[(1,1-Dimethylethoxy)carbonyl]amino]-5-methyl-2-[[(1S)-phenylethyl]amino]-4H-3,1-benzoxazin-4-one: $^1$H-NMR (300 MHz, CDCl$_3$) δ 1.50 (s, 9H), 1.57 (d, J=7 Hz, 3H), 2.49 (s, 3H), 5.10 (m, 1H), 5.98 (br. s, 1H, exchangeable), 6.59 (br. s, 1H, exchangeable), 7.02 (d, J=8 Hz, 1H), 7.20–7.40 (m, 5H), 7.72 (br. d, J=8 Hz, 1H).

(6n) 6-[[(1,1-Dimethylethoxy)carbonyl]amino]-5-methyl-2-[[(1R)-phenylethyl]amino]-4H-3,1-benzoxazin-4-one: $^1$H-NMR (300 MHz, CDCl$_3$) δ 1.50 (s, 9H), 1.57 (d, J=7 Hz, 3H), 2.49 (s, 3H), 5.10 (m, 1H), 5.98 (br. s, 1H, exchangeable), 6.59 (br. s, 1H, exchangeable), 7.02 (d, J=8 Hz, 1H), 7.20–7.40 (m, 5H), 7.72 (br. d, J=8 Hz, 1H).

(6o) N-[6-[[(1,1-Dimethylethoxy)carbonyl]amino]-5-methyl-4-oxo-4H-3,1-benzoxazin-2-yl]-L-tryptophan, dimethylamide: $^1$H-NMR (300 MHz, CDCl$_3$) δ 1.52 (s, 9H), 2.50 (s, 3H), 2.71 (s, 3H), 2.87 (s, 3H), 3.20–3.40 (m, 2H), 5.20 (m, 1H), 6.46 (m, 2H), 7.00 (br. m, 1H), 7.04 (s, 1H), 7.14 (m, 2H), 7.33 (d, J=8 Hz, 1H), 7.62–7.74 (m, 2H), 8.58 (br. s, 1H).

(6p) N-[6-[[(1,1-Dimethylethoxy)carbonyl]amino]-5-methyl-4-oxo-4H-3,1-benzoxazin-2-yl]-O-methyl-L-threonine, methyl ester: $^1$H-NMR (300 MHz, CDCl$_3$) δ 1.28 (d, J=7 Hz, 3H), 1.52 (s, 9H), 2.65 (s, 3H), 3.33 (s, 3H), 3.69 (s, 3H), 4.03 (m, 1H), 4.60 (br. m, 1H), 5.50 (br. s, 1H, exchangeable), 6.32 (br. s, 1H, exchangeable), 7.08 (d, J=8 Hz, 1H), 7.87 (br. d, J=8 Hz, 1H).

(6q) N-[6-[[(1,1-Dimethylethoxy)carbonyl]amino]-5-methyl-4-oxo-4H-3,1-benzoxazin-2-yl]-O-methyl-L-serine, methyl ester: $^1$H-NMR (300 MHz, CDCl$_3$) δ 1.52 (s, 9H), 2.62 (s, 3H), 3.39 (s, 3H), 3.75 3.84 (m, 4H), 3.91 (m, 1H), 4.76 (m, 1H), 5.75 (br. d, J=7 Hz, 1H, exchangeable), 6.35 (br. s, 1H, exchangeable), 7.08 (d, J=8 Hz, 1H), 7.84 (br. d, J=8 Hz, 1H).

(6r) N-[6-[[(1,1-Dimethylethoxy)carbonyl]amino]-5-methyl-4-oxo-4H-3,1-benzoxazin-2-yl]-L-phenylglycine, 1,1-dimethylethyl ester: $^1$H-NMR (300 MHz, CDCl$_3$) δ 1.41 (s, 9H), 1.51 (s, 9H), 2.64 (s, 3H), 5.45(d, J=7 Hz, 1H), 5.80 (br. s, 1H, exchangeable), 6.22 (s, 1H, exchangeable), 7.10 (d, J=8 Hz, 1H), 7.31–7.47 (m, 5H), 7.88 (br. d, J=8 Hz, 1H).

(6s) N-[6-[[(1,1-Dimethylethoxy)carbonyl]amino]-5-methyl-4-oxo-4H-3,1-benzoxazin-2-yl]-3,5-diiodo-O-methyl-L-tyrosine, methyl ester: $^1$H-NMR (300 MHz, CDCl$_3$) δ 1.52 (s, 9H), 2.60 (s, 3H), 3.02 (m, 1H), 3.14 (m, 1H), 3.78 (s, 3H), 3.80 (s, 3H), 4.85 (m, 1H), 5.71 (br. s, 1H, exchangeable), 6.43 (br.s, 1H, exchangeable), 7.09 (d, J=8 Hz, 1H), 7.61 (s, 2H), 7.84 (br. d, J=8 Hz, 1H).

(6t) N-[6-[[(1,1-Dimethylethoxy)carbonyl]amino]-5-methyl-4-oxo-4H-3,1-benzoxazin-2-yl]-4-iodo-L-phenylalanine, methyl ester: $^1$H-NMR (300 MHz, CDCl$_3$) δ 1.52 (s, 9H), 2.59 (s, 3H), 3.10 (m, 1H), 3.22 (m, 1H), 3.76 (s, 3H), 4.87 (br. m, 1H), 5.70 (br. s, 1H, exchangeable), 6.53 (br. s, 1H, exchangeable), 6.92 (d, J=8 Hz, 2H), 7.05 (d, J=8 Hz, 1H), 7.60 (d, J=8 Hz, 2H), 7.70 (br. d, J=8 Hz, 1H).

(6u) N-[6-[[(1,1-Dimethylethoxy)carbonyl]amino]-5-methyl-4-oxo-4H-3,1-benzoxazin-2-yl]-L-methionine sulfone, methyl ester: $^1$H-NMR (300 MHz, CDCl$_3$) δ 1.53 (s, 9H), 2.36 (m, 1H), 2.56–2.69 (m, 4H), 2.96 (s, 3H), 3.10–3.35 (m, 2H), 3.84 (s, 3H), 4.80 (m, 1H), 5.70 (br. d, J=7 Hz, 1H, exchangeable), 6.33 (br. s, 1H, exchangeable), 7.08 (d, J=8 Hz, 1H), 7.88 (d, J=8 Hz, 1H).

(6v) N-[6-[[(1,1-Dimethylethoxy)carbonyl]amino]-5-methyl-4-oxo-4H-3,1-benzoxazin-2-yl]-L-beta-naphthylalanine, methyl ester: $^1$H-NMR (300 MHz, CDCl$_3$) δ 1.50 (s, 9H), 2.55 (s, 3H), 3.33 (m, 2H), 3.72 (s, 3H), 4.96 (m, 1H), 5.70 (br. s, 1H, exchangeable), 6.47 (br. s, 1H, exchangeable), 7.05 (d, J=8 Hz, 1H), 7.26 (d, J=8 Hz, 1H), 7.41 (m, 2H), 7.58 (s, 1H), 7.70–7.82 (m, 4H).

(6w) N-[6-[[(1,1-Dimethylethoxy)carbonyl]amino]-5-methyl-4-oxo-4H-3,1-benzoxazin-2-yl]-2-aminoisobutyric acid, methyl ester: $^1$H-NMR (300 MHz, CDCl$_3$) δ 1.52 (s, 9H), 1.68 (s, 6H), 2.63 (s, 3H), 3.73 (s, 3H), 5.75 (br. s, 1H, exchangeable), 6.42 (br. s, 1H, exchangeable), 7.08 (m, 1H), 7.82 (br., 1H).

(6x) N-[6-[[(1,1-Dimethylethoxy)carbonyl]amino]-5-methyl-4-oxo-4H-3,1-benzoxazin-2-yl]-1-cyclopropanecarboxylic acid, methyl ester: $^1$H-NMR (300 MHz, CDCl$_3$) δ 1.20 (m, 2H), 1.48 (s, 9H), 1.52 (s, 2H), 2.58 (s, 3H), 3.62 (s, 3H), 7.03 (d, J=8 Hz, 1H), 7.59 (br. s, 1H), 7.65 (br. d, J=8 Hz, 1H), 7.86 (br. s, 1H).

(6y) N-[6-[[(1,1-Dimethylethoxy)carbonyl]amino]-5-methyl-4-oxo-4H-3,1-benzoxazin-2-yl]-[1-(4-cyanophenyl)]-3S-aminopyrrolidin-2-one: [c.f. U.S. patent, Ser. No. 08/041,433 for the preparation of 1-(4-cyanophenyl)-3(S)-aminopyrrollidin-2-one.] $^1$H-NMR (300 MHz, CDCl$_3$) δ 1.253 (s, 9H), 2.20 (m, 1H), 2.52 (s, 3H), 2.93 (m, 1H), 4.90 (m, 2H), 4.84 (br. t, J=8 Hz, 1H), 6.54 (br. s, 2H), 6.95 (d, J=8 Hz, 1H), 7.64 (d, J=8 Hz, 2H), 7.68 (d, J=8 Hz, 1H), 7.80 (d, J=8 Hz, 2H).

(6z) N-[6-[[(1,1-Dimethylethoxy)carbonyl]amino]-5-methyl-4-oxo-4H-3,1-benzoxazin-2-yl]-L-alanine, N-methyl-N-allylamide: HRMS calc'd. for C$_{21}$H$_{28}$N$_4$O$_5$: 416.2060. Found: 416.2046.

(6aa) N-[6-[[(1,1-Dimethylethoxy)carbonyl]amino]-5-methyl-4-oxo-4H-3,1-benzoxazin-2-yl]-L-alanine, N-methyl-N-phenylmethylamide: Anal. calc'd. for C$_{25}$H$_{30}$N$_4$O$_5$: C, 64.36; H, 6.48; N, 12.01. Found: C, 64.05; H, 6.47; N, 11.79.

(6bb) N-[6-[[(1,1-Dimethylethoxy)carbonyl]amino]-5-methyl-4-oxo-4H-3,1-benzoxazin-2-yl]-L-alanine, phenylmethyl ester: Anal. calc'd. for C$_{24}$H$_{27}$N$_3$O$_6$: C, 63.56; H, 6.00; N, 9.27. Found: C, 63.58; H, 6.29; N, 9.00.

In a similar manner, the following compounds of Formula I are prepared:

(6cc) N-[6-[[[(1,1-Dimethylethyl)oxy]carbonyl]amino]-5-methyl-4-oxo- 4H-3,1-benzoxazin-2-yl]-L-(3,5-diiodo) tyrosine, methyl ester.

Example 7

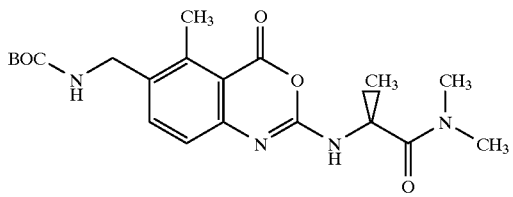

N-[6-[[[(1,1-Dimethylethoxy) carbonyl]amino]methyl]-5 methyl-4-oxo-4H-3,1-benzoxazin-2-yl]-L-alanine, dimethylamide To an ice cooled solution of triphosgene (124 mg, 0.42 mmol) in 15 mL of CH$_2$Cl$_2$ was added slowly a solution of L-alanine dimethylamide hydrochloride (190 mg, 1.25 mmol) and triethylamine (528 uL, 3.75 mmol) in 10 mL of CH$_2$Cl$_2$. After stirring at 0° C. for 30 minutes, the product of preparation VIII, step D (350 mg, 1.25 mmol) was added. After stirring at room temperature for 6 hours, EDC (367 mg, 1.88 mmol) and triethylamine (264 uL, 1.88 mmol) were added sequentially. After stirring at room temperature overnight, the reaction mixture was diluted with CH$_2$Cl$_2$ and washed with sat'd NaHCO$_3$, dried (MgSO$_4$), filtered and concentrated under reduced pressure. Silica gel chromatography (gradient elution 30% EtOAc/hexanes to 100% EtOAc) afforded 93 mg of product: $^1$H-NMR (300 MHz, CDCl$_3$) δ 1.44 (d, J=7 Hz, 3H), 1.46 (S, 9H), 2.68 (s, 3H), 3.02 (s, 3H), 3.17 (s, 3H), 4.33 (br. d, J=7 Hz, 2H), 4.78 (m, 1H), 4.90 (br. t, J=7 Hz, 1H, exchangeable), 6.07 (br. d, J=7 Hz, 1H, exchangeable), 7.05 (d, J=8 Hz, 1H), 7.49 (d, J=8 Hz, 1H).

Proceeding in a like manner but replacing L-alanine dimethylamide hydrochloride with other appropriately substituted amines or amine hydrochlorides, the following compounds were prepared:

(7a) N-[6-[[[(1,1-Dimethylethoxy)carbonyl]amino] methyl]-5-methyl-4-oxo-4H-3,1-benzoxazin-2-yl]-L-alanine, morpholineamide: $^1$H-NMR (300 MHz, CDCl$_3$) δ 1.46 (d, J=7 Hz, 3H), 1.46 (s, 9H), 2.65 (s, 3H), 3.53–3.83 (m, 8H), 4.32 (d, J=7 Hz, 2H), 4.84–4.95 (m, 2H), 6.24 (br. d, J=7 Hz, 1H), 7.01 (d, J=9 Hz, 1H), 7.49 (d, J=9 Hz, 1H).

(7b) N-[6-[[[(1,1-Dimethylethoxy)carbonyl]amino] methyl]-5-methyl-4-oxo 4H-3,1-benzoxazin-2-yl]-O-methyl-L-tyrosine, pyrrolidineamide: $^1$H-NMR (300 MHz, CDCl$_3$) δ 1.47 (s, 9H), 1.64–1.92 (m, 4H), 2.58 (s, 3H), 2.77 (m, 1H), 3.08 (m, 2H), 3.30–3.60 (m, 2H), 3.69 (m, 1H), 3.78 (s, 3H), 4.28 (br. d, J=7 Hz, 2H), 4.82 (m, 1H), 5.00 (br. s, 1H), 6.44 (br. s, 1H), 6.83 (d, J=8 Hz, 2H), 6.98 (d, J=9 Hz, 1H), 7.19 (d, J=8 Hz, 2H), 7.45 (d, J=9 Hz, 1H).

(7c) N-[6-[[[(1,1-Dimethylethoxy)carbonyl]amino] methyl]-5-methyl-4-oxo-4H-3,1-benzoxazin-2-yl]-O-methyl-L-tyrosine, morpholineamide $^1$H-NMR (300 MHz, CDCl$_3$) δ 1.47 (s, 9H), 2.58 (s, 3H), 3.00–3.18 (m, 4H), 3.45–3.70 (m, 6H), 3.79 (s, 3H), 4.29 (br. d, J=7 Hz, 2H), 4.92–5.10 (m, 2H), 6.43 (br. s, 1H), 6.85 (d, J=8 Hz, 2H), 7.00 (d, J=9 Hz, 1H), 7.18 (d, J=8 Hz, 2H), 7.48 (d, J=9 Hz, 1H).

(7d) N-[6-[[[(1,1-Dimethylethoxy)carbonyl]amino] methyl]-5-methyl-4-oxo 4H-3,1-benzoxazin-2-yl]-O-methyl-L-tyrosine, dimethylamide: $^1$H-NMR (300 MHz, CDCl$_3$) δ 1.47 (s, 9H), 2.58 (s, 3H), 2.83 (s, 3H), 2.93 (s, 3H), 3.00–3.15 (m, 2H), 3.78 (s, 3H), 4.29 (br. d, J=7 Hz, 2H), 4 95–5.13 (m, 2H), 6.35 (br. 1H), 6.82 (d, J=8 Hz, 2H), 7.00 (d, J=9 Hz, 1H), 7.16 (d, J=8 Hz, 2H), 7.45 (d, J=9 Hz, 1H).

(7e) N-[6-[[[(1,1-Dimethylethoxy)carbonyl]amino] methyl]-5-methyl-4-oxo 4H-3,1-benzoxazin-2-yl]-L-alanine, methyl ester: $^1$H-NMR (300 MHz, CDCl$_3$) δ 1.46 (s, 9H), 1.53 (d, J=7 Hz, 3H), 2.58 (s, 3H), 3.79 (s, 3H), 4.33 (br. d, J=7 Hz, 2H), 4.63 (m, 1H), 4.90 (br. s, 1H), 5.75 br. s, 1H), 7.05 (d, J=9 Hz, 1H), 7.49 (d, J=9 Hz, 1H).

(7f) 6-[[[(1,1-Dimethylethoxy)carbonyl]amino]methyl]-5-methyl-2-[[(1S)-phenylethyl]amino]-4H-3,1-benzoxazin-4-one: $^1$H-NMR (300 MHz, CDCl$_3$) δ 1.45 (s, 9H), 1.60 (d, J=7 Hz, 3H), 2.70 (s, 3H), 4.33 (br. d, J=7 Hz, 2H), 4.67 (m, 1H), 5.14 (m, 2H), 7.07 (d, J=9 Hz, 1H), 7.25–7.43 (m, 5H), 7.50 (d, J=9 Hz,

Example 8

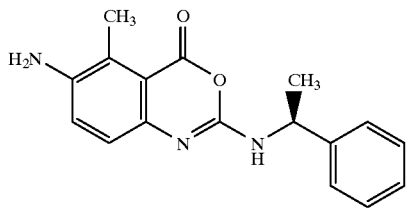

6-Amino-5-methyl-2-[[(1R)-phenylethyl]amino]-4H-3,1-benzoxazin-4-one, dihydrochloride The title compound was prepared from 6-[[(1,1-dimethylethoxy)carbonyl]amino]-5-methyl-2-[[(1R)-phenylethyl]amino]-4H-3,1-benzoxazin-4-one (6n) (1.1 g, 2.78 mmol) in 20 mL of EtOAc by bubbling in dry HCl at 0° C. for 5 minutes. After an additional 20 minutes, the precipitate was filtered, washed with Et$_2$O and dried affording 841 mg (91%) of product: $^1$H-NMR (300 MHz, d$_6$-DMSO) δ 1.17 (d, J=7 Hz, 3H), 2.30 (s, 3H), 4.79 (m, 1H), 7.20–7.38 (m, 5H), 7.40 (d, J=8 Hz, 1H), 7.60 (br. d, J=7 Hz, 1H), 7.80 (d, J=8 Hz, 1H), 8.06 (s, 1H), 10.0–10.5 (br. 2H).

Proceeding in a like manner but replacing (6n) with other appropriately substituted compounds of Example 6–6cc and Example 7–7f, the following compounds were prepared:

(8a) 6-Amino-5-methyl-2-[[(1S)-phenylethyl]amino]-4H-3,1-benzoxazin-4-one, dihydrochloride: $^1$H-NMR (300 MHz, d$_6$-DMSO) δ 1.17 (d, J=7 Hz, 3H), 2.30 (s, 3H), 4.79 (m, 1H), 7.20–7.38 (m, 5H), 7.40 (d, J=8 Hz, 1H), 7.60 (br. d, J=7 Hz, 1H), 7.80 (d, J=8 Hz, 1H), 8.06 (s, 1H), 10.0–10.5 (br. 2H).

(8b) N-[6-Amino-5-methyl-4-oxo-4H-3,1-benzoxazin-2-yl]-L-alanine, methyl ester, dihydrochloride: $^1$H-NMR (300 MHz, d$_6$-DMSO) δ 1.27 (d, J=7 Hz, 3H), 2.27 (s, 3H), 3.63 (s, 3H), 4.19 (m, 1H), 7.38 (d, J=8 Hz, 1H), 7.53 (br. d, J=8 Hz, 1H), 7.80 (d, J=8 Hz, 1H), 8.13 (s, 1H), 10.15 (br., 3H).

(8c) N-[6-amino-5-methyl-4-oxo-4H-3,1-benzoxazin-2-yl]-L-phenylalanine, methyl ester, dihydrochloride: Anal. calc'd. for C$_{19}$H$_{19}$N$_3$O$_4$.2HCl: C, 53.53; H, 4.97; N, 9.86. Found: C, 53.10; H, 4.90; N, 9.90.

(8d) N-[6-aminomethyl-5-methyl-4-oxo-4H-3,1-benzoxazin-2-yl]-O-methyl-L-tyrosine, pyrrolidineamide, dihydrochloride: $^1$H-NMR (300 MHz, d$_6$-DMSO) δ 1.60–1.84 (m, 4H), 2,28 (s, 3H), 2.65–2.87 (m, 2H), 3.00 (m, 1H), 3.15–3.23 (m, 2H), 3.47 (m, 1H), 3.72 (s, 3H), 3.97 (m, 2H), 4.53 (m, 1H), 6.84 (d, J=8 Hz, 2H), 7.13 (d, J=8 Hz, 2H), 7.32 (d, J=9 Hz, 1H), 7.55 (br. d, J=8 Hz, 1H), 7.73 (d, J=9 Hz, 1H), 8.05 (s, 1H), 8.25 (br. s, 3H).

(8e) 6-aminomethyl-5-methyl-2-[[(1S)-phenylethyl]amino]-4H-3,1 benzoxazin-4-one, dihydrochloride: $^1$H-NMR (300 MHz, d$_6$-DMSO) δ 1.36 (d, J=7 Hz, 3H), 2.28 (s, 3H), 3.96 (m, 2H), 4.78 (m, 1H), 7.20–7.35 (m, 6H), 7.57 (br. d, J=7 Hz, 1H), 7.75 (d, J=9 Hz, 1H), 7.94 (s, 1H), 8.31 (br. s, 3H).

Example 9

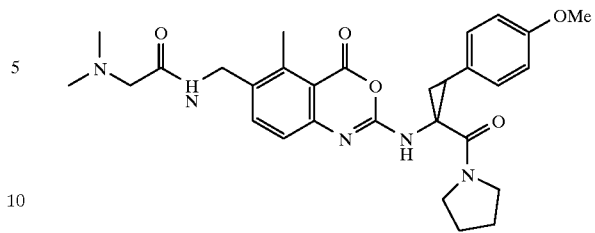

N-[6-[[[[Dimethylaminomethyl]carbonyl]amino]methyl]-5 methyl-4-oxo-4H-3,1-benzoxazin-2-yl]-O-methyl-L-tyrosine, pyrrolidineamide To a solution of N,N-dimethylglycine (21 mg, 0.20 mmol) in 3 mL of CH$_2$Cl$_2$ was added oxalyl chloride (18 uL, 0.20 mmol) and a catalytic amount of DMF. After stirring at room temperature for 1 hour, the solution was concentrated to dryness and redissolved in 3–5 mL of CH$_2$Cl$_2$. To the resulting solution was added the product of Example 8d (86 mg, 0.18 mol) and triethylamine (111 uL, 0.79 mmol), sequentially. After stirring at room temperature overnight, the reaction mixture was diluted with CH$_2$Cl$_2$, washed with sat'd NaHCO$_3$, dried (MgSO$_4$), filtered and concentrated under reduced pressure. Silica gel chromatography (THF) afforded 27 mg of product: $^1$H-NMR (300 MHz, CDCl$_3$) δ 1.65–1.90 (m, 4H), 2.27 (s, 6H), 2.68 (s, 3H), 2.77 (m, 1H), 2.99 (s, 2H), 3.00–3.14 (m, 2H), 3.30–3.55 (m, 2H), 3.61 (m, 1H), 3.78 (s, 3H), 4.48 (d, J=7 Hz, 2H), 4.83 (m, 1H), 6.10 (br. s, 1H), 6.83 (d, J=8 Hz, 2H), 7.04 (d, J=9 Hz, 1H), 7.17 (d, J=8 Hz, 2H), 7.33 (br. t, J=7 Hz, 1H), 7.50 (d, J=9 Hz, 1H).

Proceeding in a like manner but replacing the compound of Example 8d with other appropriately substituted compounds of Example 8, and/or other appropriately substituted carboxylic acids, the following compounds were prepared:

(9a) 6-[[[[Dimethylaminomethyl]carbonyl]amino]methyl]-5-methyl-2-[[(1S)-phenylethyl]amino]-4H-3,1-benzoxazin-4-one: $^1$H-NMR (300 MHz, CDCl$_3$) δ 1.59 (d, J=7 Hz, 3H), 2.26 (s, 6H), 2.66 (s, 3H), 2.99 (s, 2H), 4.45 (d, J=7 Hz, 2H), 5.13 (m, 1H), 5.95 (br. s, 1H), 7.03 (d, J=9 Hz, 1H), 7.21–7.42 (m, 5H), 7.44 (d, J=9 Hz, 1H).

(9b) N-[6-[[[[(1-Pyrrolidinyl)methyl]carbonyl]amino]methyl]-5-methyl-4 oxo-4H-3,1-benzoxazin-2-yl]-O-methyl-L-tyrosine, pyrrolidineamide: $^1$H-NMR (300 MHz, CDCl$_3$) δ 1.60–1.95 (m, 8H), 2.55–2.68 (m, 7H), 2.77 (m, 1H), 3.00–3.13 (m, 2H), 3.23 (s, 2H), 3.37 (m, 1H), 3.50 (m, 1H), 3.65 (m, 1H), 3.78 (s, 3H), 4.47 (d, J=7 Hz, 2H), 4.81 (m, 1H), 6.44 (br. s, 1H), 6.82 (d, J=8 Hz, 2H), 7.00 (d, J=9 Hz, 1H), 7.18 (d, J=8 Hz, 2H), 7.40 (br. t, J=7 Hz, 1H), 7.47 (d, J=9 Hz, 1H).

Example 10

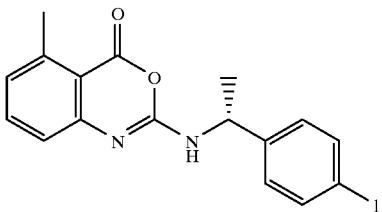

5-Methyl-2-[[(1R)-(4-iodophenyl)ethyl]amino]-4H-3,1 benzoxazin-4-one

The title compound was prepared from the product of Preparation IX, step C (750 mg, 1.77 mmol) in a manner similar to Example 3, affording 325 mg of product after silica gel chromatography (20% EtOAc/hexanes): $^1$H-NMR (300 MHz, CDCl$_3$) δ 1.58 (d, J=7 Hz, 3H), 2.70 (s, 3H), 5.02–5.20 (m, 2H), 6.95 (d, J=8 Hz, 1H), 7.08 (d, J=8 Hz, 1H), 7.15 (d, J=8 Hz, 2H), 7.45 (t, J=8 Hz, 1H), 7.68 (d, J=8 Hz, 2H).

Example 11

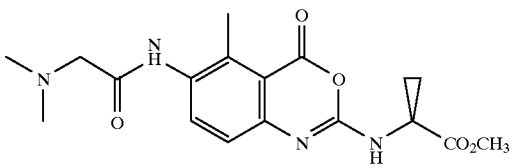

N-[[6-(Dimethylaminomethyl)carbonyl]amino]-5-methyl-4-oxo-4H-3,1-benzoxazin-2-yl]-L-alanine, methyl ester To a suspension of N,N-dimethylglycine (25.3 mg, 0.24 mmol) in 5 mL of CH$_2$Cl$_2$ was added oxalyl chloride (154 mg, 1.2 mmol) and a catalytic amount of DMF. After stirring at room temperature for 60 minutes, the solvent was removed and the residue was redissolved in 5 mL of CH$_2$Cl$_2$. To the solution was added sequentially, the compound Example 8b (70 mg, 0.22 mmol) and NMM (89 mg, 0.88 mmol). After stirring at room temperature for 3 hours, the reaction mixture was diluted with EtOAc and washed with sat'd NaHCO$_3$, dried (MgSO$_4$), filtered and concentrated under reduced pressure. Silica gel chromatography (3% MeOH/CH$_2$Cl$_2$) afforded 32 mg of product: $^1$H-NMR (300 MHz, CDCl$_3$) δ 1.52 (d, J=7 Hz, 3H), 2.45 (s, 6H), 2.67 (s, 3H), 3.15 (s, 2H), 3.80 (s, 3H), 4.63 (m, 1H), 5.47 (br. d, J=7 Hz, 1H), 7.15 (d, J=8 Hz, 1H), 8.13 (d, J=8 Hz, 1H), 9.23 (s, 1H).

Proceeding in a like manner but replacing the compound of Example 8b with other appropriately substituted compounds of Example 8, and/or other appropriately substituted carboxylic acids, acid chlorides or anhydrides, the following compounds were prepared:

(11a) 5-Methyl-N-[6-[[(2-pyridyl)carbonyl]amino]-4-oxo-4H-3,1-benzoxazin 2-yl]-L-alanine, methyl ester: $^1$H-NMR (300 MHz, CDCl$_3$) δ 1.58 (d, J=7 Hz, 3H), 2.82 (s, 3H), 3.83 (s, 3H), 4.68 (m, 1H), 5.45 (br. s, 1H), 7.24 (d, J=8 Hz, 1H), 7.54 (m, 1H), 7.95 (m, 1H), 8.30–8.40 (m, 2H), 8.67 (m, 1H), 10.10 (s, 1H).

(11b) N-[6-[[(5-Isoxazolyl)carbonyl]amino]-5-methyl-4-oxo-4H-3,1 benzoxazin-2-yl]-L-alanine, methyl ester: $^1$H-NMR (300 MHz, CDCl$_3$) δ 1.55 (d, J=7 Hz, 3H), 2.65 (s, 3H), 3.83 (s, 3H), 4.68 (m, 1H), 5.87 (br. d, J=7 Hz, 1H), 7.08 (d, J=2 Hz, 1H), 7.11 (d, J=8 Hz, 1H), 7.83 (d, J=8 Hz, 1H), 8.43 (d, J=2 Hz, 1H), 8.44 (s, 1H).

(11c) N-[6-[[(Methoxymethyl)carbonyl]amino]-5-methyl-4-oxo-4H-3,1-benzoxazin-2-yl]-L-phenylalanine, methyl ester: $^1$H-NMR (300 MHz, CDCl$_3$) δ 2.54 (s, 3H), 3.23 (m, 2H), 3.54 (s, 3H), 3.76 (s, 3H), 4.09 (s, 2H), 4.91 (m, 1H), 5.35 (br. d, J=7 Hz, 1H), 7.10–7.35 (m, 6H), 8.01 (d, J=8 Hz, 1H), 8.23 (s, 1H).

(11d) N-[6-[[(2-Carboxyethyl)carbonyl]amino]-5-methyl-4-oxo-4H-3,1-benzoxazin-2-yl]-L-phenylalanine, methyl ester: $^1$H-NMR (300 MHz, CDCl$_3$) δ 2.40–2.60 (m, 7H), 3.00 (m, 1H), 3.14 (m, 1H), 3.65 (s, 3H), 4.55 (m, 1H), 6.97 (d, J=8 Hz, 1H), 7.16–7.34 (m, 5H), 7.48 (d, J=8 Hz, 1H), 8.47 (d, J=8 Hz, exchangeable), 9.52 (s, 1H, exchangeable).

(11e) N-[6-[[(Cyclobutyl)carbonyl]amino]-5-methyl-4-oxo-4H-3,1-benzoxazin-2-yl]-L-phenylalanine, methyl ester: $^1$H-NMR (300 MHz, CDCl$_3$) δ 1.90–2.10 (m, 2H), 2.27 (m, 2H), 2.49 (m, 2H), 2.58 (s, 3H), 3.23 (m, 2H), 3.77 (s, 3H), 4.90 (m, 1H), 5.33 (br. s, 1H), 6.99 (s, 1H) 7.11 (d, J=8 Hz, 1H), 7.16 (m, 2H), 7.20–7.35 (m, 3H), 7.83 (d, J=8 Hz, 1H).

(11f) N-[6-[[(2-Furanyl)carbonyl]amino]-5-methyl-4-oxo-4H-3,1-benzoxazin-2-yl]-L-phenylalanine, methyl ester: $^1$H-NMR (300 MHz, CDCl$_3$) δ 2.70 (s, 3H), 3.24 (m, 2H), 3.78 (s, 3H), 4.92 (br. t, J=7 Hz, 1H), 6.59 (m, 1H), 7.15–7.35 (m, 7H), 7.55 (m, 1H), 8.00 (s, 1H), 8.04 (d, J=8 Hz, 1H).

(11g) N-[6-[[(2-Thienylmethyl)carbonyl]amino]-5-methyl-4-oxo-4H-3,1-benzoxazin-2-yl]-L-phenylalanine, methyl ester: $^1$H-NMR (300 MHz, CDCl$_3$) δ 2.40 (s, 3H), 3.21 (m, 2H), 3.76 (s, 3H), 3.98 (s, 2H), 4.88 (br. t, J=7 Hz, 1H), 5.40 (br. s, 1H), 7.05 (m, 3H), 7.14 (m, 2H), 7.20–7.34 (m, 4H), 7.40 (s, 1H), 7.79 (d, J=8 Hz, 1H).

(11h) N-[6-[[(2-Thienylmethyl)carbonyl]amino]-5-methyl-4-oxo-4H-3,1-benzoxazin-2-yl]-L-phenylalanine, morpholineamide: $^1$H-NMR (300 MHz, CDCl$_3$) δ 2.38 (s, 3H), 2.84–3.23 (m, 5H), 3.36–3.68 (m, 6H), 4.00 (s, 2H), 5.08 (m, 1H), 6.20 (br. s, 1H), 7.02–7.10 (m, 3H), 7.20 7.35 (m, 6H), 7.85 (d, J=8 Hz, 1H).

(11i) N-[6-[[(2-Thienylmethyl)carbonyl]amino]-5-methyl-4-oxo-4H-3,1-benzoxazin-2-yl]-L-phenylalanine, pyrrolidineamide: $^1$H-NMR (300 MHz, CDCl$_3$) δ 1.55–1.88 (m, 4H), 2.35 (s, 3H), 2.67 (m, 1H), 2.90 (br. d, J=5 Hz, 1H), 3.14 (m, 2H), 3.35 (m, 1H), 3.51 (m, 1H), 3.63 (m, 1H), 3.98 (s, 2H), 4.78–4.90 (m, 2H), 6.25 (br. s, 1H), 7.00 (d, J=8 Hz, 1H), 7.06 (m, 2H), 7.15–7.35 (m, 6H), 7.76 (d, J=8 Hz, 1H).

(11j) 5-Methyl-6-[[(1-morpholinylmethyl)carbonyl]amino]-2-[[(1S)-phenylethyl]-amino]-4H-3,1-benzoxazin-4-one: $^1$H-NMR (300 MHz, CDCl$_3$) δ 1.59 (d, J=7 Hz, 3H), 2.64 (s, 3H), 2.68 (m, 4H), 3.20 (s, 2H), 3.78 (m, 4H), 5.13 (m, 1H), 5.83 (br. d, J=7 Hz, 1H), 7.10 (d, J=8 Hz, 1H), 7.20–7.43 (m, 5H), 8.13 (d, J=8 Hz, 1H), 9.20 (s, 1H).

(11k) 6-[[(2-Furanyl)carbonyl]amino]-5-methyl-2-[[(1S)-phenylethyl]amino]-4H-3,1-benzoxazin-4-one: Anal. calc'd. for C$_{22}$H$_{19}$N$_3$O$_4$.0.1 H$_2$O: C, 67.54; H, 4.95; N, 10.74. Found: C, 67.25; H, 4.95; N, 10.74.

(11l) 5-Methyl-2-[[(1S)-phenylethyl]amino]-6-[[(1 pyrrolidinylmethyl)carbonyl]amino]-4H-3,1-benzoxazin-4-one: Anal. calc'd. for C$_{23}$H$_{26}$N$_4$O$_3$.0.1 H$_2$O: C, 67.66; H, 6.47; N, 13.72. Found: C, 67.49; H, 6.27; N, 13.47.

(11m) 5-Methyl-6-[[(dimethylaminomethyl)carbonyl]amino]-2-[[(1S)-phenylethyl]amino]-4H-3,1-benzoxazin-4- one: $^1$H-NMR (300 MHz, CDCl$_3$) δ 1.61 (d, J=7 Hz, 3H), 2.44 (s, 6H), 2.65 (s, 3H), 3.14 (s, 2H), 5.00 (br. d, J=7 Hz, 1H), 5.15 (m, 1H), 7.14 (d, J=8 Hz, 1H), 7.25–7.41 (m, 5H), 8.11 (d, J=8 Hz, 1H), 9.20 (br. s, 1H).

(11n) 5-Methyl-6-[[(3-dimethylaminopropyl)carbonyl]amino]-2-[[(1R)-phenylethyl]amino]-4H-3,1-benzoxazin-4-one: $^1$H-NMR (300 MHz, CDCl$_3$) δ 1.60 (d, J=7 Hz, 3H), 1.90 (pent., J=7 Hz, 2H), 2.27 (s, 6H), 2.45 (t, J=7 Hz, 2H), 2.53 (t, J=7 Hz, 2H), 2.61 (s, 3H), 5.13 (m, 2H), 7.10 (d, J=8 Hz, 1H), 7.22–7.40 (m, 5H), 7.79 (d, J=8 Hz, 1H), 9.03 (s, 1H).

Example 12

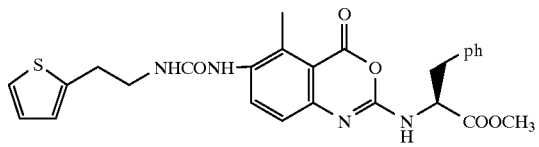

N-[6-[[[[2-(2-Thienyl)ethyl]amino]carbonyl]amino]-5-methyl-4-oxo-4H-3,1-benzoxazin-2-yl]-L-phenylalanine, methyl ester To an ice cooled, stirred solution of triphosgene (17 mg, 0.057 mmol) in 0.5 mL of CH$_2$Cl$_2$, was added slowly a solution of 2-(2-thienyl)ethylamine (20 mg, 0.157 mmol) and N,N,-diisopropyl-N-ethylamine (40 mg, 0.314 mmol) in 0.5 mL of CH$_2$Cl$_2$. After stirring at 0° C. for 30 minutes, the compound Example 8c (60 mg, 0.154 mmol) was added, followed by an additional 44 mg (0.341 mmol) of N,N,-diisopropyl-N-ethylamine. The ice bath was removed and the reaction was stirred at room temperature overnight. The reaction mixture was diluted with EtOAc, washed with 10% KHSO$_4$, sat'd. NaHCO$_3$, dried (MgSO$_4$), filtered and concentrated under reduced pressure. Silica gel chromatography (50% EtOAc/hexanes) afforded 10 mg of product: $^1$H-NMR (300 MHz, CDCl$_3$) δ 2.58 (s, 3H), 3.03 (t, J=7 Hz, 2H), 3.23 (m, 2H), 3.49 (q, J=7 Hz, 2H), 3.78 (s, 3H), 4.67 (br. t, J=7 Hz, 1H), 4.89 (m, 1H), 5.30 (br. s, 1H), 6.12 (s, 1H), 6.78 (m, 1H), 6.90 (m, 1H), 7.06 (d, J=8 Hz, 1H), 7.10–7.18 (m, 3H), 7.23–7.35 (m, 3H), 7.50 (d, J=8 Hz, 1H).

Proceeding in a like manner but replacing the compound of Example 8c with other appropriately substituted compounds of Example 8, and/or other appropriately substituted amines, isocyanates or carbamoyl chlorides, the following compounds were prepared:

(12a) N-[6-[[[[2-(2-thienyl)ethyl]amino]carbonyl]amino]-5-methyl-4-oxo 4H-3,1-benzoxazin-2-yl]-L-alanine, methyl ester: $^1$H-NMR (300 MHz, CDCl$_3$) δ 1.38 (d, J=7 Hz, 3H), 2.51 (s, 3H), 2.97 (t, J=7 Hz, 2H), 3.34 (q, J=7 Hz, 2H), 3.67 (s, 3H), 4.39 (m, 1H), 6.45 (br. t, J=7 Hz, 1H), 6.91 (m, 1H), 6.95–7.00 (m, 2H), 7.36 (m, 1H), 7.80 (d, J=8 Hz, 1H), 7.92 (s, 1H).

(12b) N-[6-[[(1-morpholinyl)carbonyl]amino]-5-methyl-4-oxo-4H-3,1 benzoxazin-2-yl]-L-alanine, methyl ester: $^{11}$H-NMR (300 MHz, CDCl$_3$) δ 1.53 (d, J=7 Hz, 3H), 2.62 (s, 3H), 3.50 (m, 4H), 3.77 (m, 4H), 3.80 (s, 3H), 4.64 (m, 1H), 5.40 (br. s, 1H), 6.17 (s, 1H), 7.10 (d, J=8 Hz, 1H), 7.69 (d, J=8 Hz, 1H).

(12c) 6-[[[[(1R)-phenylethyl]amino]carbonyl]amino]-5-methyl-2-[[(1R)-phenylethyl]amino]-4H-3,1-benzoxazin-4-one: 1H-NMR (300 MHz, CDCl$_3$/CD$_3$OD δ 1.44 (d, J=7 Hz, 3H), 1.58 (d, J=7 Hz, 3H), 2.54 (s, 3H), 4.93 (m, 1H), 5.08 (m, 1H), 5.97 (br. d, J=7 Hz, 1H), 7.07 (d, J=8 Hz, 1H), 7.19–7.45 (m, 10H), 7.71 (d, J=8 Hz, 1H).

Example 13

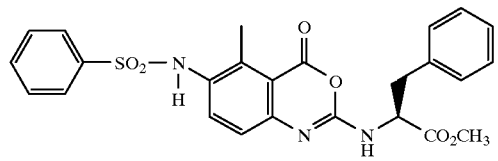

N-[6-[Benzenesulfonyl]amino]-5-methyl-4-oxo-4H-3,1 benzoxazin-2-yl]-L-phenylalanine, methyl ester To a solution of the product Example 8c (60 mg, 0.154 mmol) in CH$_2$Cl$_2$ (5 mL) was added benzenesulfonyl chloride (29 mg, 0.162 mmol), followed by N-methylmorpholine (36 mg, 0.354 mmol). The reaction mixture was stirred at room temperature overnight, diluted with EtOAc and washed successively with 10% KHSO$_4$ and sat'd NaHCO$_3$. The organic fraction was dried (MgSO$_4$), filtered and concentrated under reduced pressure. Silica gel chromatography (40% EtOAc/hexanes) afforded 16 mg of product: $^1$H-NMR (300 MHz, CDCl$_3$) δ 2.26 (s, 3H), 3.23 (m, 2H), 3.77 (s, 3H), 4.90 (m, 1H), 5.32 (br. s, 1H), 6.52 (s, 1H), 7.07 (d, J=8 Hz, 1H), 7.14 (m, 2H), 7.22 7.34 (m, 3H), 7.44 (t, J=8 Hz, 2H), 7.57 (m, 2H), 7.68 (d, J=8 Hz, 2H).

Proceeding in a like manner but replacing the compound of Example 8c with other appropriately substituted compounds of Example 8, and/or other appropriately substituted sulfonyl chlorides, the following compound was prepared:

(13a) N-[6-[Benzenesulfonyl]amino]-5-methyl-4-oxo-4H-3,1-benzoxazin-2yyl]-L-alanine, methyl ester: $^1$H-NMR (300 MHz, CDCl$_3$) δ 1.53 (d, J=7 Hz, 3H), 2.27 (s, 3H), 3.80 (s, 3H), 4.63 (m, 1H), 5.60 (br. s, 1H), 6.74 (br. s, 1H), 7.04 (d, J=8 Hz, 1H), 7.43 (t, J=8 Hz, 2H), 7.52 (d, J=8 Hz, 1H), 7.57 (m, 1H), 7.68 (d, J=8 Hz, 2H).

Example 14

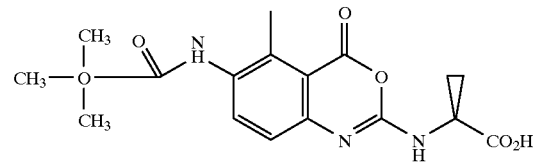

N-[6-[[(1,1-Dimethylethoxy)carbonyl]amino]-5-methyl 4-oxo-4H-3,1-benzoxazin-2-yl]-L-alanine A mixture of the product Example 6bb (200 mg, 0.441 mmol) and 22 mg of 10% Pd/C in EtOAc (5 mL) was stirred under a balloon of hydrogen for 2.5 hours. After removal of the catalyst, concentration of the filtrate under reduced pressure afforded 149 mg of product: $^1$H-NMR (300 MHz, d$_6$-DMSO) δ 1.49 (s, 9H), 1.55 (d, J=7 Hz, 3H), 2.62 (s, 3H), 4.57 (m, 1H), 6.98 (br. s, 1H), 7.06 (d, J=8 Hz, 1H), 7.69 (d, J=8 Hz, 1H), 7.79 (br. s, 1H).

BIOLOGICAL EVALUATION

The compounds of this invention exhibited antiviral activity as indicated by inhibition in vitro of herpesvirus protease and HCMV infectivity. The antiviral activity of the compounds of this invention illustrated in the Examples was determined by the following methods.

Enzymatic Assay for HCMV Protease (Assemblin) Inhibitors

Assemblin protease activity was determined using a chromogenic para-nitroanilide (pNA) substrate based on the hCMV maturation cleavage site, succinyl-AGVVNA-para-nitroanilide. Incubation of this substrate with assemblin resulted in cleavage of the alanyl para-nitroanilide amide bond, releasing free para-nitroaniline which could be determined by absorbance at 405 nm. Potential protease inhibitors were dissolved in DMSO and 10 µL were added to the wells of a 96-well plate (Dynatech, Immulon 1). Enzyme was diluted to 4.8 µg/mL in assay buffer (10 mM sodium phosphate, pH 7.4, 150 mM sodium acetate, 0.1% CHAPS, 20% glycerol) and 100 µL were added to each well. Following a 30 minute incubation at room temperature, 50 µL substrate (1 part 20 mM succinyl-AGVVNA-paranitroanilide (SEQID:1) in DMSO plus 9 parts assay buffer) were added, and periodic readings taken in a microplate reader at 405 nm relative to 650 nm. Activities were expressed as milliabsorbance unit (mAU) change per minute. Inhibitor potency was determined by comparison with incubations lacking inhibitor, which under these conditions gave an increase of 0.5–1 mAU/min. No increase was seen when enzyme was omitted. Results are included in Table 1.

Assay Components:

Recombinant HCMV protease:

HCMV protease was purified from $E.\ coli$ expressing a DNA construction encoding the protease domain of the $U_L 80$ open reading frame of human cytomegalovirus strain AD169. The construction also encoded six additional histidine residues at the amino terminus of the protease. These additional histidine residues provided an affinity ligand by which it was purified using nickel-nitriloacetic acid-agarose (Qiagen).

The purified protease was stored as a 1–3 mg/ml stock solution in 20 mM HEPES buffer, pH 7.4; containing 20% (v/v) glycerol. This stock was diluted with assay buffer to 4.8 µg/ml. A 100 µL aliquot of this solution was used in the enzyme reaction.

A specific substrate was synthesized based on the cleavage specificity of HCMV protease at the "maturation site" of the assembly protein (F. Liu and B. Roizman, $J.\ Virol.$, 65, 5149 (1991), and A. R. Welch, et al, $J.\ Virol.$, 65, 4091 (1991)). The assembly protein maturation site has the sequence . . . AGVVNA*SCRLATA . . . ; the substrate used was succinyl-AGVVNA-PNA (SEQID:1) which was prepared by standard peptide synthetic methods such as that described in Bodansky and Bodansky, "The Practice of Peptide Synthesis" (1984), and was stored as a stock solution at 20 mM in dimethyl sulfoxide. This was diluted 10-fold with assay buffer to give a concentration of 2 mM just before use. An aliquot of 50 µL was used in the reaction.

An assay Buffer (10 mM sodium phosphate buffer, pH 7.4; 150 mM sodium acetate; 0.1% CHAPS; and 20% (v/v) glycerol) was used to dilute stock solutions of enzyme and substrate.

Antiviral Assays

These complimentary assays tested the ability of a compound to inhibit the production of new virus and the toxicity of the compound to the host cells. It was important that both assays be performed simultaneously in order to compare the results directly since, toxicity may indirectly reduce viral yield.

Abbreviations:

DMEM—Dulbecco's Modified Eagle Medium; commercially available.

FBS—fetal bovine serum; commercially available and contains unknown factors necessary for growth of cells in culture.

PBS—phosphate buffered saline: 10 mM sodium phosphate buffer, pH 7.4, 120 mM sodium chloride, 2.7 mM potassium chloride.

Viral yield was estimated by measuring the amount of a viral antigen produced 4 days post infection with a monoclonal antibody to an abundant "immediate early" viral protein. An enzyme-linked (horseradish peroxidase) secondary antibody specific to the primary (mouse) antibody was used to measure the amount of viral antigen. Test compounds were diluted to 2-times the desired final concentration in DMEM+5% FBS. One hundred microliters of this solution was placed in each well of a 96-well plate. This was performed once for the antiviral 96-well plate and again for a cytotoxicity plate. Two controls were also included for both plates; a no drug control and a no virus control. Ganciclovir was routinely tested in antiviral and cytotoxicity plates as a reference standard because it has known antiviral activity for HCMV. All cells were prepared by harvesting human foreskin fibroblasts, with trypsin and re-suspending at a concentration of $5 \times 10^5$ cells per ml in DMEM. Infected cells were prepared by infecting these with HCMV (strain AD169) at a multiplicity of infection=0.2. One hundred microliters of uninfected cells ($5 \times 10^4$ cells) were added to the appropriate wells of the cytotoxicity plate. In a similar manner 100 µl of infected cells ($5 \times 10^4$ cells) were added to the appropriate wells of the antiviral plate. Additionally, uninfected cells not treated with test compound were included as controls on the antiviral plate. Plates were incubated for 96 hours at 37° C. in 5% $CO_2$ atmosphere and processed to measure the amount of viral antigen and toxicity. Results are included in Table 1.

Enzyme Linked ImmunoSorbant Assay (ELISA) for HCMV Antigens:

The following was performed on the antiviral plate only. Media was removed and cells were fixed with 1:1 acetone:methanol for 15 minutes at −20° C. Fixative was removed and cells were washed once with PBS containing 0.05% Tween20. In order to block nonspecific binding of antibodies, each well was incubated with PBS containing 3% (w/v) bovine serum albumin (BSA) for 1 hour at 22° C. The blocking solution was removed and the cells were washed once with PBS containing 0.05% Tween20 before incubating with 1:100 dilution of primary antibody in PBS containing 3% BSA for 2 hours at 22° C. The primary antibody was a monoclonal antibody (mouse source) specific to the immediate early nuclear antigen of HCMV and was commercially available (Dupont). The 1° antibody solution was removed and the plate was rinsed 5 times with PBS containing 1% (v/v) Triton X-100 (PBST) before incubating with secondary antibody diluted 1:1000 in PBS containing 3% BSA for 2 hours at 22° C. The secondary antibody (goat source) recognized the murine-specific determinants of the 1° antibody and was covalently linked to horseradish peroxidase (Sigma). The plate was rinsed 5 times with PBST and once with deionized water before adding 100 µl TMB substrate solution and incubating 30 minutes at 22° C. The reaction was stopped by adding 100 µL of phosphoric acid and the OD at 450 nm recorded. TMB (3,3',5,5' tetramethylbenzidine) was the substrate for the horseradish peroxidase linked to the 2° antibody. It was made from a commercially available kit (Kirkegaard & Perry Laboratories, Inc.). Antiviral activity was calculated by comparing the amount of viral antigen produced in drug treated wells with that produced in wells absent of drug. Results are included in Table 1.

Recombinant Human Cytomegalovirus Antiviral Assay

In this assay, HCMV replication was monitored by the production of $E.\ coli$ beta-galactosidase by the engineered virus RC256 [Spaete and Mocarski, *Proc.Nat.Acad.Sci.*, 84, 7213–7217 (1987)]. One antiviral assay and one cytotoxicity assay were done for each compound. Dilutions of test compounds and infection of cells in a 96-well plate was essentially as described above for the HCMV ELISA except for the following. Human foreskin fibroblasts at $3.5 \times 10^5$ cells per milliliter were infected in solution with RC256 at 0.05 pfu per cell. Compounds and cells were incubated 3 days and processed at 2 days post infection. For the beta galactosidase detection, the supernatant was aspirated from the antiviral assay plates and 50 μl Reporter Lysis Buffer (Promega, diluted to 1x with water) was added per well. The plates were incubated at room temperature at least 30 minutes and plates were frozen at −20° C. at this point for later processing. 50 μl of 2x assay buffer [120 mM $Na_2HPO_4$, 80 mM $NaH_2PO_4$, 2 mM $MgCl_2$, 100 mM 2-mercaptoethanol, 4.4 mM ONPG (Sigma)] was added per well and incubated at room temperature 30 to 45 minutes. The reaction was stopped with 100 μl 1M CAPS buffer, pH=11.0, per well and the optical density was read at 410 nanometers. Ganciclovir was used as a positive control and the EC50 was determined as described above for the HCMV ELISA. Results are included in Table 1.

Chymotrypsin Assay

The chymotrypsin assay was modified from the method of Delmar et al [*Anal. Biochem.*, 99, 316–320 (1979)]. Bovine pancreas α-chymotrypsin (type II, Sigma) was dissolved in 0.001 N HCl at 1 mg/ml and further diluted 1/600 in assay buffer (0.1 M Tris, pH 7.8, containing 0.1 M $CaCl_2$) before use. 20 μl of test compound in DMSO (or DMSO alone), 100 μl of assay buffer and 30 μl of enzyme were added to 96 well plates, mixed and pre-incubated for 30 minutes at ambient temperature. Reaction was initiated by addition of 50 μl of 0.2 mM N-succinyl-Ala-Ala-Pro-Phe-p-nitroanilide (Sigma; 2 mM in DMSO diluted 1/10 in assay buffer before use). The increase in absorbance at 405 nm was monitored for 10 minutes with a Biotek EL340 plate reader. Results are incuded in Table 1.

Human Leukocyte Elastase Assay

Human leukocyte elastase (HLE) (gift of R. Senior, Washington University) was dissolved in saline at 1 mg/ml and further diluted 1/20 in assay buffer (0.2 M Tris, pH 8.0) before use. 10 μl of test compound in DMSO (or DMSO alone), 100 μl of assay buffer and 50 μl of enzyme were added to 96 well plates, mixed and pre-incubated for 30 minutes at ambient temperature. Reaction was initiated by addition of 40 μl of 2.5 mM methoxysuccinyl-Ala-Ala-Pro-Val-p-nitroanilide (Sigma; 25 mM in DMSO diluted 1/10 in assay buffer before use). The increase in absorbance at 405 nm was monitored for 10 minutes with a Biotek EL340 plate reader. Results are shown in Table 3.

TABLE 1

| Example | Assemblin Protease | Antiviral Activity | Chymotrypsin | HLE |
|---|---|---|---|---|
| 1 | 2.9 | RC256 = 100/>100 | 57% @ 100 | 0.19 |
| 1a | 1.8 | | 3.4 | |
| 1b | 0.85 | Elisa = 72/>100 | 47% @ 10 | 1.5 |
| 1c | 2.0 | RC256 = >100/>100 | 7,7 | 0.87 |
| 1d | 0.68 | | 0.82 | |
| 1e | 1.0 | | 0.56 | |
| 1f | 0.41 | | 0.78 | |
| 1g | 1.2 | | 0.52 | |
| 1h | 0.46 | | 0.76 | 0.29 |
| 1i | 1.5 | RC256 = 9/20 | 3.3 | 0.15 |
| 1j | 0.74 | | 0.89 | |
| 1k | 0.2 | RC256 = >100/>100 | 0.49 | 0.13 |
| 1l | 2.2 | RC256 = 35/>100 | 2.7 | 0.49 |
| 1m | 0.2 | RC256 = 56/56 | 3.0 | 0.061 |
| 1n | 0.64 | | 27% @ 10 | |
| 1o | 1.4 | RC256 = 10/100 | 0.62 | 0.17 |
| 1p | 0.94 | RC256 = 38/>100 | 2.8 | 0.054 |
| 1q | 0.073 | RC256 = 33/70 | 0.64 | 0.063 |
| 1r | 0.21 | RC256 = 59/>100 | 1.6 | 0.071 |
| 2 | 0.71 | | 5.7 | |
| 2a | 1.8 | | 10.0 | 0.053 |
| 2b | 0.32 | | 0.022 | |
| 3 | | | | 0.17 |
| 3a | 4.0 | | 2.0 | 0.032 |
| 3b | 2.5 | Elisa = 27/>>100 | 0.18 | 0.042 |
| 3c | 0.92 | RC256 = 17/>100 Elisa = 22/>100 | 0.088 | 0.044 |
| 3d | | | 0.76 | 0.095 |
| 3f | | Elisa = >100/>100 | 1.4 | 0.06 |
| 3i | | | 0.05 | 43% @ 10 |
| 3k | | | 0.15 | 25.0 |
| 3l | 43% @ 10 | Elisa = 42/>100 | 0.22 | 43% @ 10 |
| 3n | 4.9 | | 1.3 | |
| 3o | 0.46 | | 0.14 | |
| 4 | 22 | | 2.4 | 0.13 |
| 4a | 10 | | 0.8 | |
| 4b | 16.0 | | 1.1 | |
| 5 | 3.1 | | 0.14 | |
| 6 | 2.4 | RC256 = >100/>100 | 63% @ 100 | 29% @ 100 |
| 6a | 0.82 | RC256 = 71/>100 | 20 | 0.91 or 41 check |
| 6b | 0.82 | | 53% @ 100 | |
| 6c | 0.52 | RC256 = 59/72 | 16% @ 100 | 29% @ 100 |
| 6d | 3.7 | RC256 = 45/70 | >>100 | 91.0 |
| 6e | 0.53 | Elisa = 58/>100 | 17% @ 100 | |
| 6f | 4.2 | | >>100 | |
| 6g | 1.5 | Elisa = 100/>100 | >>100 | |
| 6h | 2.3 | | >>10 | 99% @ 100 |
| 6i | 3.4 | RC256 = 48/75 | >>100 | |
| 6j | 4.9 | | >>100 | |
| 6k | 5.8 | | >>100 | |
| 6l | | | >>100 | |
| 6m | 2.2 | RC256 = 50/70 | 57% @ 100 | 82% @ 100 |
| 6n | 1.3 | RC256 = 10/62 | 42 | 40 |
| 6o | 1.3 | RC256 = 59/75 | >>100 | |
| 6q | 2.4 | | 21% @ 100 | |
| 6r | 3.0 | | 100 | |
| 6s | 0.25 | RC256 = 18/24 | 78 | 5.6 |
| 6t | 0.27 | RC256 = 17/18 | 65 | 14 |
| 6u | 0.77 | RC256 = 100/>100 | >>100 | 29% @ 100 |
| 6v | 0.28 | RC256 = 18/22 | 40 | 12 |
| 6w | 1.1 | RC256 = >100/>100 | 85% @ 100 | 7.4 |
| 6x | 5.3 | RC256 = >100/>100 | 45% @ 100 | 25% @ 10 |
| 6y | 1.2 | RC256 = 67/>100 | >>100 | 25% @ 10 |
| 6aa | 1.9 | Elisa = 75/>100 | >>100 | |
| 6bb | 4.7 | | >>100 | |
| 6cc | 0.41 | RC256 = 67/>100 | 68% @ 100 | 89% @ 100 |
| 7 | 0.81 | Elisa = 100/>100 | 4.6 | |
| 7a | 0.59 | Elisa = 100/>100 | 2.5 | |
| 7b | 0.58 | RC256 = 20/50 | >>10 | |

TABLE 1-continued

| Example | Assemblin Protease | Antiviral Activity | Chymotrypsin | HLE |
|---|---|---|---|---|
| 7c | 0.91 | RC256 = 16/48 | >>10 | |
| 7d | 1.1 | RC256 = 22/70 | >>10 | 48% @ 10 |
| 7e | 0.74 | Elisa = 100/>100 | 0.91 | |
| 7f | 0.69 | RC256 = 50/70 | 1.6 | |
| 9 | 1.1 | | 46% @ 100 | |
| 9a | 0.79 | | 14 | |
| 9b | 1.0 | | 65% @ 100 | |
| 10 | 0.23 | RC256 = 60/>100 | 0.61 | 0.086 |
| 11 | 1.4 | RC256 = >100/>100 | 47% @ 100 | 34% @ 100 |
| 11a | 0.31 | | 33 | 59% @ 100 |
| 11b | 0.83 | RC256 = >100/>100 | 64% @ 100 | 43% @ 100 |
| 11c | 0.64 | Elisa – 77/>100 | 4.9 | 83% @ 100 |
| 11d | 0.69 | RC256 = >100/>100 | 26% @ 100 | 76% @ 100 |
| 11e | 0.57 | RC256 = >100/>100 | 2.7 | 59% @ 100 |
| 11F | 0.50 | Elisa – 65/>100 | 2.5 | 58% @ 100 |
| 11g | 0.40 | RC256 = 10/>100 | 0.25 | 19 |
| 11h | 1.2 | | 1.0 | |
| 11i | 1.6 | | 1.7 | |
| 11j | 9.9 | Elisa – 150/>100 | 86% @ 100 | 30% @ 100 |
| 11k | 4.0 | RC256 = 65/>100 | 7.8 | 63% @ 100 |
| 11l | 17 | | 84% @ 100 | |
| 11m | 67% @ 1.0 | Elisa – 88/>100 | 8.3 | 37% @ 100 |
| 11n | | | 87% @ 100 20% @ 10 | |
| 12 | 0.59 | RC256 = 60/70 | 2.7 | >>10 |
| 12a | 0..91 | RC256 = >100/>100 | 7.1 | 55% @ 100 |
| 12b | 0.94 | | 34% @ 100 | |
| 12c | 2.1 | RC256 = 17/62 | 28% @ 10 | 4.0 |
| 13 | 0.93 | RC256 = 60/>100 | 6.0 | 1.3 |
| 13a | 0.71 | RC256 = 60/>100 | 2.0 | 2.7 |
| 14 | 9.4 | | >>100 | |

Also embraced within this invention is a class of pharmaceutical compositions comprising one or more compounds of Formula I in association with one or more non-toxic, pharmaceutically-acceptable carriers and/or diluents and/or adjuvants (collectively referred to herein as "carrier" materials) and, if desired, other active ingredients. The compounds of the present invention may be administered by any suitable route, preferably in the form of a pharmaceutical composition adapted to such a route, and in a dose effective for the treatment intended. The compounds and composition may, for example, be administered intravascularly, intraperitoneally, subcutaneously, intramuscularly or topically.

For oral administration, the pharmaceutical composition may be in the form of, for example, a tablet, capsule, suspension or liquid. The pharmaceutical composition is preferably made in the form of a dosage unit containing a particular amount of the active ingredient. Examples of such dosage units are tablets or capsules. The active ingredient may also be administered by injection as a composition wherein, for example, saline, dextrose or water may be used as a suitable carrier.

The amount of therapeutically active compound that is administered and the dosage regimen for treating a disease condition with the compounds and/or compositions of this invention depends on a variety of factors, including the age, weight, sex and medical condition of the subject, the severity of the disease, the route and frequency of administration, and the particular compound employed, and thus may vary widely. The pharmaceutical compositions may contain active ingredient in the range of about 0.1 to 2000 mg, preferably in the range of about 0.5 to 500 mg and most preferably between about 1 and 100 mg. A daily dose of about 0.01 to 100 mg/kg body weight, preferably between about 0.1 and about 50 mg/kg body weight and most preferably between about 1 to 20 mg/kg body weight, may be appropriate. The daily dose can be administered in one to four doses per day.

For therapeutic purposes, the compounds of this invention are ordinarily combined with one or more adjuvants appropriate to the indicated route of administration. If administered per os, the compounds may be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration. Such capsules or tablets may contain a controlled-release formulation as may be provided in a dispersion of active compound in hydroxypropylmethyl cellulose. Formulations for parenteral administration may be in the form of aqueous or non-aqueous isotonic sterile injection solutions or suspensions. These solutions and suspensions may be prepared from sterile powders or granules having one or more of the carriers or diluents mentioned for use in the formulations for oral administration. The compounds may be dissolved in water, polyethylene glycol, propylene glycol, ethanol, corn oil, cottonseed oil, peanut oil, sesame oil, benzyl alcohol, sodium chloride, and/or various buffers. Other adjuvants and modes of administration are well and widely known in the pharmaceutical art.

For infections of the eye or other external tissues, e.g., mouth and skin, the formulations are preferably applied as a topical ointment or cream containing the active ingredient (s) in a total amount of, for example, 0.075 to 30% w/w, preferably 0.2 to 20% w/w and most preferably 0.4 to 15% w/w. When formulated in an ointment, the active ingredients may be employed with either paraffinic or a water-miscible ointment base. Alternatively, the active ingredients may be formulated in a cream with an oil-in-water cream base. If desired, the aqueous phase of the cream base may include, for example at least 30% w/w of a polyhydric alcohol such as propylene glycol, butane-1,3-diol, mannitol, sorbitol, glycerol, polyethylene glycol and mixtures thereof. The topical formulation may desirably include a compound which enhances absorption or penetration of the active ingredient through the skin or other affected areas. Examples of such dermal penetration enhancers include dimethylsulfoxide and related analogs. The compounds of this invention can also be administered by a transdermal device. Preferably topical administration will be accomplished using a patch either of the reservoir and porous membrane type or of a solid matrix variety. In either case, the active agent is delivered continuously from the reservoir or microcapsules through a membrane into the active agent permeable adhesive, which is in contact with the skin or mucosa of the recipient. If the active agent is absorbed through the skin, a controlled and predetermined flow of the active agent is administered to the recipient. In the case of microcapsules, the encapsulating agent may also function as the membrane.

The oily phase of the emulsions of this invention may be constituted from known ingredients in a known manner.

While the phase may comprise merely an emulsifier, it may comprise a mixture of at least one emulsifier with a fat or an oil or with both a fat and an oil. Preferably, a hydrophilic emulsifier is included together with a lipophilic emulsifier which acts as a stabilizer. It is also preferred to include both an oil and a fat. Together, the emulsifier(s) with or without stabilizer(s) make-up the so-called emulsifying wax, and the wax together with the oil and fat make up the so-called emulsifying ointment base which forms the oily dispersed phase of the cream formulations. Emulsifiers and emulsion stabilizers suitable for use in the formulation of the present invention include Tween 60, Span 80, cetostearyl alcohol, myristyl alcohol, glyceryl monostearate, and sodium lauryl sulfate, among others The choice of suitable oils or fats for the formulation is based on achieving the desired cosmetic properties, since the solubility of the active compound in most oils likely to be used in pharmaceutical emulsion formulations is very low. Thus, the cream should preferably be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters may be used. These may be used alone or in combination depending on the properties required. Alternatively, high melting point lipids such as white soft paraffin and/or liquid paraffin or other mineral oils can be used.

Formulations suitable for topical administration to the eye also include eye drops wherein the active ingredients are dissolved or suspended in suitable carrier, especially an aqueous solvent for the active ingredients. The antiviral active ingredients are preferably present in such formulations in a concentration of 0.5 to 20%, advantageously 0.5 to 10% and particularly about 1.5% w/w.

Although this invention has been described with respect to specific embodiments, the details of these embodiments are not to be construed as limitations.

What is claimed is:

1. A compound of Formula I

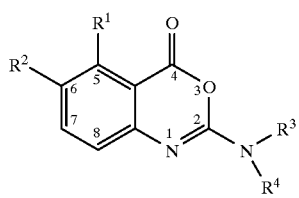

I wherein $R^1$ is an alkyl;
wherein $R^2$ is a substituent selected from alkyl,

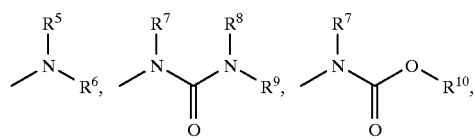

-continued

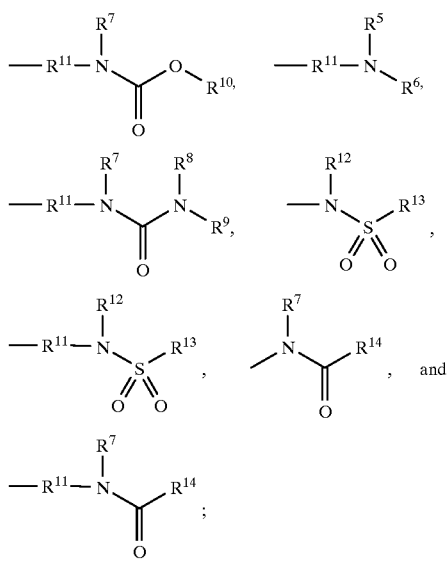

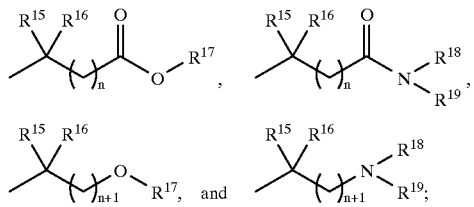

wherein $R^3$ is selected from hydrido, alkyl, alkylaminoalkyl, aralkyl, and heterocycloalkyl;
wherein $R^4$ is selected from hydrido, alkyl, cycloalkyl, cycloalkylalkyl, aryl, heterocyclo, aralkyl, heterocycloalkyl, wherein n is 0–6, inclusive;
wherein $R^5$ and $R^6$ are independently selected from hydrido, alkyl, cycloalkyl, cycloalkylalkyl, aryl, aralkyl, heterocyclo, heterocycloalkyl, alkylaminoalkyl, aralkylaminoalkyl, alkoxyalkyl, and aralkoxyalkyl;
wherein $R^7$, $R^{12}$ and $R^{23}$ are independently selected from hydrido, alkyl and aralkyl;
wherein $R^8$, $R^9$ and $R^{14}$ are independently selected from hydrido, alkyl, cycloalkyl, cycloalkylalkyl, haloalkyl, aminoalkyl, alkylaminoalkyl, carboxyalkyl, aminocarbonylalkyl, alkylaminocarbonylalkyl, hydroxyalkyl, alkoxyalkyl, aralkoxyalkyl, alkylsulfonylalkyl, alkylsulfinylalkyl, alkylthioalkyl, aryl, aralkyl, heterocyclo, and heterocycloalkyl;
wherein $R^{10}$ is selected from alkyl, haloalkyl, alkylaminoalkyl, carboxyalkyl, aminocarbonylalkyl, alkylaminocarbonylalkyl, aralkoxyalkyl, alkoxyalkyl, cycloalkyl, cycloalkylalkyl, alkylsulfonylalkyl, alkylsulfinylalkyl, alkylthioalkyl, aryl, aralkyl, heterocyclo, and heterocycloalkyl;
wherein $R^{11}$ is alkylene;
wherein $R^{13}$ is selected from amino, alkyl, alkylamino, alkylaminoalkyl and aryl;
wherein $R^{15}$ is selected from hydrido, alkyl, hydroxyalkyl, alkoxyalkyl, aralkoxyalkyl, alkylaminoalkyl and N-aryl-N-alkylaminoalkyl;

wherein R¹⁶ is selected from hydrido, alkyl, cycloalkyl, cycloalkylalkyl, haloalkyl, guanidinylalkyl, carboxyalkyl, hydroxyalkyl, alkoxyalkyl, aralkoxyalkyl, alkylthioalkyl, alkylsulfinylalkyl, alkylsulfonylalkyl, aryl, heterocyclo, aralkyl, heterocycloalkyl,

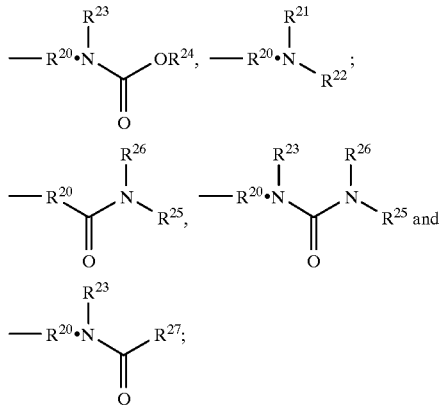

or wherein R¹⁵ and R¹⁶ together form cycloalkyl;

wherein R¹⁷ is selected from hydrido, alkyl, cycloalkyl and aralkyl;

wherein R¹⁸ and R¹⁹ are independently selected from hydrido, alkyl, alkenyl, cycloalkyl, cycloalkylalkyl, aryl, heterocyclo, aralkyl, heterocycloalkyl, and alkylaminoalkyl;

wherein R²⁰ is alkylene;

wherein R²¹, R²², R²⁵, and R²⁶ are independently selected from hydrido, alkyl, cycloalkyl, cycloalkylalkyl, aminoalkyl, alkylaminoalkyl, hydroxyalkyl, alkoxyalkyl, aralkoxyalkyl, aryl, heterocyclo, aralkyl, heterocycloalkyl;

wherein R²⁴ is selected from alkyl, cycloalkyl, cycloalkylalkyl, alkylaminoalkyl, aralkoxyalkyl, alkoxyalkyl, aryl, aralkyl, heterocyclo, and heterocycloalkyl; and wherein R²⁷ is selected from hydrido, alkyl, cycloalkyl, cycloalkylalkyl, alkylaminoalkyl, aminoalkyl, carboxyalkyl, aminocarbonylalkyl, hydroxyalkyl, aralkoxyalkyl, alkoxyalkyl, aryl, aralkyl, heterocyclo, and heterocycloalkyl;

provided R² is not methyl when R¹ is methyl and when R³ is benzyl or lower alkyl;

or a pharmaceutically-acceptable salt or tautomer thereof.

2. Compound of claim 1 wherein R¹ is a lower alkyl; wherein R² is a substituent selected from lower alkyl,

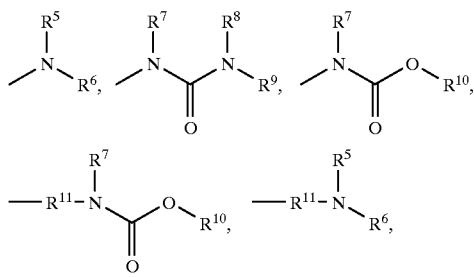

-continued

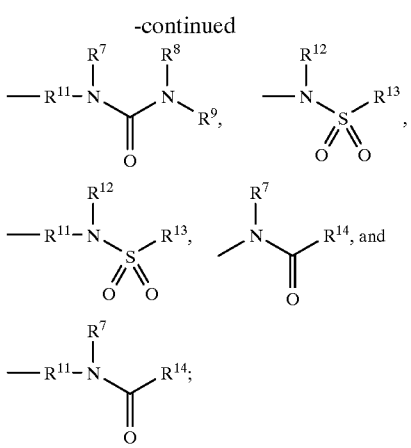

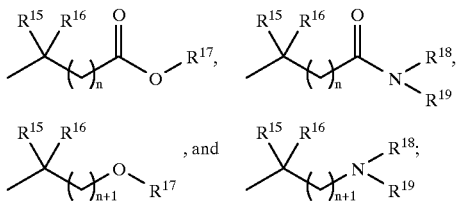

wherein R³ is selected from hydrido, lower alkyl, lower alkylaminoalkyl, lower aralkyl, and lower heterocycloalkyl; wherein R⁴ is selected from hydrido, lower alkyl, lower cycloalkyl, lower cycloalkylalkyl, aryl, heterocyclo, lower aralkyl, lower heterocycloalkyl, wherein n is 0–6, inclusive; wherein R⁵ and R⁶ are independently selected from hydrido, lower alkyl, lower cycloalkyl, lower cycloalkylalkyl, aryl, lower aralkyl, heterocyclo, lower heterocycloalkyl, lower alkylaminoalkyl, lower aralkylaminoalkyl, lower alkoxyalkyl, and lower aralkoxyalkyl; wherein R⁷, R¹² and R²³ are independently selected from hydrido, lower alkyl and lower aralkyl; wherein R⁸, R⁹ and R¹⁴ are independently selected from hydrido, lower alkyl, lower cycloalkyl, lower cycloalkylalkyl, lower haloalkyl, lower aminoalkyl, lower alkylaminoalkyl, lower carboxyalkyl, lower aminocarbonylalkyl, lower alkylaminocarbonylalkyl, lower hydroxyalkyl, lower alkoxyalkyl, lower aralkoxyalkyl, lower alkylsulfonylalkyl, lower alkylsulfinylalkyl, lower alkylthioalkyl, aryl, lower aralkyl, heterocyclo, and lower heterocycloalkyl; wherein R¹⁰ is selected from lower alkyl, lower haloalkyl, lower alkylaminoalkyl, lower carboxyalkyl, lower aminocarbonylalkyl, lower alkylaminocarbonylalkyl, lower aralkoxyalkyl, lower alkoxyalkyl, lower cycloalkyl, lower cycloalkylalkyl, lower alkylsulfonylalkyl, lower alkylsulfinylalkyl, lower alkylthioalkyl, aryl, lower aralkyl, heterocyclo, and lower heterocycloalkyl; wherein R¹¹ is lower alkylene; wherein R¹³ is selected from amino, lower alkyl, lower alkylamino, lower alkylaminoalkyl and aryl; wherein R¹⁵ is selected from hydrido, lower alkyl, lower hydroxyalkyl, lower alkoxyalkyl, lower aralkoxyalkyl, lower alkylaminoalkyl and lower N-aryl-N-alkylaminoalkyl; wherein R¹⁶ is selected from hydrido, lower alkyl, lower cycloalkyl, lower cycloalkylalkyl, lower haloalkyl, lower guanidinylalkyl, lower carboxyalkyl, lower hydroxyalkyl, lower alkoxyalkyl, lower aralkoxyalkyl, lower alkylthioalkyl, lower alkylsulfinylalkyl, lower alkylsulfonylalkyl, aryl, lower heterocyclo, lower aralkyl, lower heterocycloalkyl,

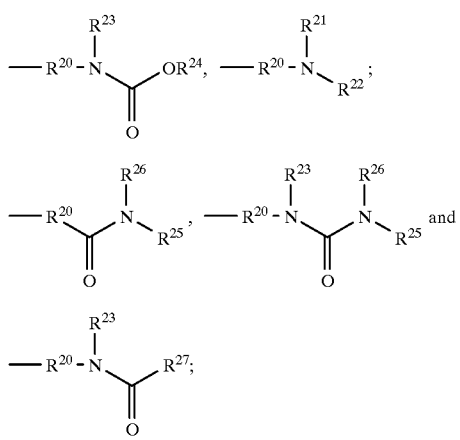

or wherein $R^{15}$ and $R^{16}$ together form cycloalkyl wherein $R^{17}$ is selected from hydrido, lower alkyl, lower cycloalkyl and lower aralkyl; wherein $R^{18}$ and $R^{19}$ are independently selected from hydrido, lower alkyl, lower alkenyl, lower cycloalkyl, lower cycloalkylalkyl, aryl, heterocyclo, lower aralkyl, lower heterocycloalkyl, and lower alkylaminoalkyl; wherein $R^{20}$ is lower alkylene; wherein $R^{21}$, $R^{22}$, $R^{25}$, and $R^{26}$ are independently selected from hydrido, lower alkyl, lower cycloalkyl, lower cycloalkylalkyl, lower aminoalkyl, lower alkylaminoalkyl, lower hydroxyalkyl, lower alkoxyalkyl, lower aralkoxyalkyl, aryl, heterocyclo, lower aralkyl, lower heterocycloalkyl; wherein $R^{24}$ is selected from lower alkyl, lower cycloalkyl, lower cycloalkylalkyl, lower alkylaminoalkyl, lower aralkoxyalkyl, lower alkoxyalkyl, aryl, lower aralkyl, heterocyclo, and lower heterocycloalkyl; and wherein $R^{27}$ is selected from hydrido, lower alkyl, lower cycloalkyl, lower cycloalkylalkyl, lower alkylaminoalkyl, lower aminoalkyl, lower carboxyalkyl, lower aminocarbonylalkyl, lower hydroxyalkyl, lower aralkoxyalkyl, lower alkoxyalkyl, aryl, lower aralkyl, heterocyclo, and lower heterocycloalkyl; or a pharmaceutically-acceptable salt or tautomer thereof.

3. Compound of claim 2 wherein $R^1$ is a lower alkyl; wherein $R^2$ is a substituent selected from lower alkyl,

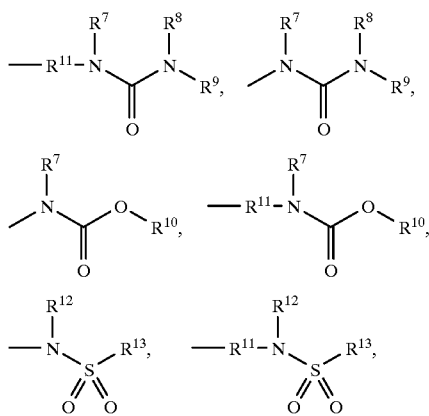

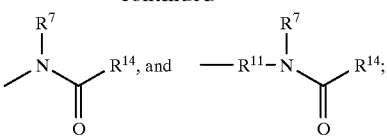

wherein $R^3$ is selected from hydrido, lower alkyl, lower alkylaminoalkyl, lower aralkyl, and lower heterocycloalkyl; wherein $R^4$ is selected from hydrido, lower alkyl, lower cycloalkyl, lower cycloalkylalkyl, aryl, heterocyclo, lower aralkyl, lower heterocycloalkyl,

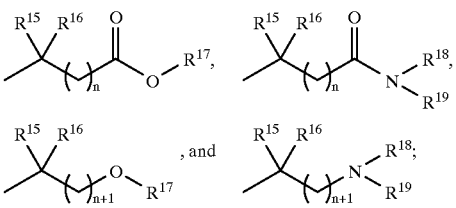

wherein n is 0–6, inclusive; wherein $R^5$ and $R^6$ are independently selected from hydrido, lower alkyl, lower cycloalkyl, lower cycloalkylalkyl, aryl, lower aralkyl, heterocyclo, lower heterocycloalkyl, lower alkylaminoalkyl, lower aralkylaminoalkyl, lower alkoxyalkyl, and lower aralkoxyalkyl; wherein $R^7$, $R^{12}$ and $R^{23}$ are independently selected from hydrido, lower alkyl and lower aralkyl; wherein $R^8$, $R^9$ and $R^{14}$ are independently selected from hydrido, lower alkyl, lower cycloalkyl, lower cycloalkylalkyl, lower haloalkyl, lower aminoalkyl, lower alkylaminoalkyl, lower carboxyalkyl, lower aminocarbonylalkyl, lower alkylaminocarbonylalkyl, lower hydroxyalkyl, lower alkoxyalkyl, lower aralkoxyalkyl, lower alkylsulfonylalkyl, lower alkylsulfinylalkyl, lower alkylthioalkyl, aryl, lower aralkyl, heterocyclo, and lower heterocycloalkyl; wherein $R^{10}$ is selected from lower alkyl, lower haloalkyl, lower alkylaminoalkyl, lower carboxyalkyl, lower aminocarbonylalkyl, alkylaminocarbonylalkyl, lower aralkoxyalkyl, lower alkoxyalkyl, lower cycloalkyl, lower cycloalkylalkyl, lower alkylsulfonylalkyl, lower alkylsulfinylalkyl, lower alkylthioalkyl, aryl, lower aralkyl, heterocyclo, and lower heterocycloalkyl; wherein $R^{11}$ is lower alkylene; wherein $R^{13}$ is selected from amino, lower alkyl, lower alkylamino, lower alkylaminoalkyl and aryl; wherein $R^{15}$ is selected from hydrido, and lower alkyl; wherein $R^{16}$ is selected from hydrido, lower alkyl, lower cycloalkyl, lower cycloalkylalkyl, lower haloalkyl, lower guanidinylalkyl, lower carboxyalkyl, lower hydroxyalkyl, lower alkoxyalkyl, lower aralkoxyalkyl, lower alkylthioalkyl, lower alkylsulfinylalkyl, lower alkylsulfonylalkyl, aryl, heterocyclo, lower aralkyl, lower heterocycloalkyl,

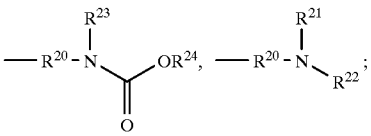

-continued

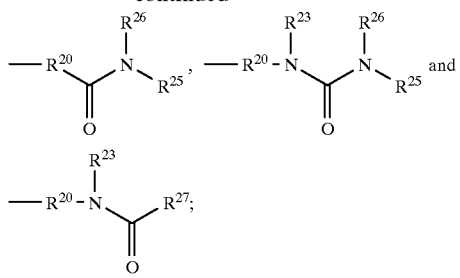

or wherein $R^{15}$ and $R^{16}$ together form lower cycloalkyl; wherein $R^{17}$ is selected from hydrido, lower alkyl, lower cycloalkyl and lower aralkyl; wherein $R^{18}$ and $R^{19}$ are independently selected from hydrido, lower alkyl, lower alkenyl, lower cycloalkyl, lower cycloalkylalkyl, aryl, heterocyclo, lower aralkyl, lower heterocycloalkyl, and lower alkylaminoalkyl; wherein $R^{20}$ is lower alkylene; wherein $R^{21}$, $R^{22}$, $R^{25}$, and $R^{26}$ are independently selected from hydrido, lower alkyl, lower cycloalkyl, lower cycloalkylalkyl, lower aminoalkyl, lower alkylaminoalkyl, lower hydroxyalkyl, lower alkoxyalkyl, lower aralkoxyalkyl, aryl, heterocyclo, lower aralkyl, lower heterocycloalkyl; wherein $R^{24}$ is selected from lower alkyl, lower cycloalkyl, lower cycloalkylalkyl, lower alkylaminoalkyl, lower aralkoxyalkyl, lower alkoxyalkyl, aryl, lower aralkyl, heterocyclo, and lower heterocycloalkyl; and wherein $R^{27}$ is selected from hydrido, lower alkyl, lower cycloalkyl, lower cycloalkylalkyl, lower alkylaminoalkyl, lower aminoalkyl, lower carboxyalkyl, lower aminocarbonylalkyl, lower hydroxyalkyl, lower aralkoxyalkyl, lower alkoxyalkyl, aryl, lower aralkyl, heterocyclo, and lower heterocycloalkyl; or a pharmaceutically-acceptable salt or tautomer thereof.

4. Compound of claim 3 wherein $R^1$ is a lower alkyl; wherein $R^2$ is a substituent selected from lower alkyl,

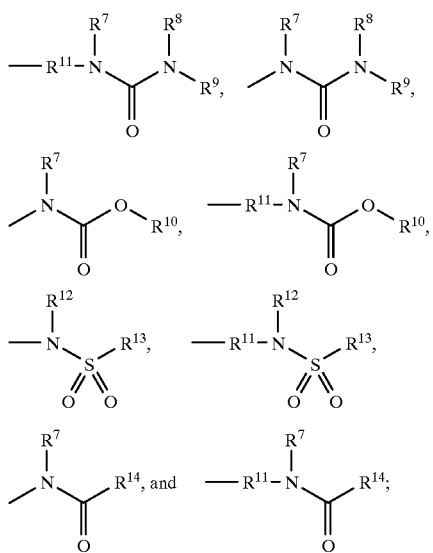

wherein $R^3$ is selected from hydrido, lower alkyl, and lower aralkyl; wherein $R^4$ is selected from

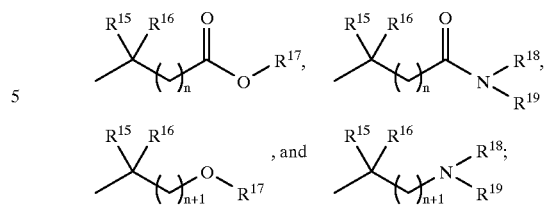

wherein n is 0–4; wherein $R^5$ and $R^6$ are independently selected from hydrido, lower alkyl, lower cycloalkyl, lower cycloalkylalkyl, aryl, lower aralkyl, heterocyclo, lower heterocycloalkyl, lower alkylaminoalkyl, lower aralkylaminoalkyl, lower alkoxyalkyl, and lower aralkoxyalkyl; wherein $R^7$, $R^{12}$ and $R^{23}$ are independently selected from hydrido, lower alkyl and lower aralkyl; wherein $R^8$, $R^9$ and $R^{14}$ are independently selected from hydrido, lower alkyl, lower cycloalkyl, lower cycloalkylalkyl, lower haloalkyl, lower aminoalkyl, lower alkylaminoalkyl, lower carboxyalkyl, lower aminocarbonylalkyl, lower alkylaminocarbonylalkyl, lower hydroxyalkyl, lower alkoxyalkyl, lower aralkoxyalkyl, lower alkylsulfonylalkyl, lower alkylsulfinylalkyl, lower alkylthioalkyl, aryl, lower aralkyl, heterocyclo, and lower heterocycloalkyl; wherein $R^{10}$ is selected from lower alkyl, lower haloalkyl, lower alkylaminoalkyl, lower carboxyalkyl, lower aminocarbonylalkyl, alkylaminocarbonylalkyl, lower aralkoxyalkyl, lower alkoxyalkyl, lower cycloalkyl, lower cycloalkylalkyl, lower alkylsulfonylalkyl, lower alkylsulfinylalkyl, lower alkylthioalkyl, aryl, lower aralkyl, heterocyclo, and lower heterocycloalkyl; wherein $R^{11}$ is lower alkylene; wherein $R^{13}$ is selected from amino, lower alkyl, lower alkylamino, lower alkylaminoalkyl and aryl; wherein $R^{15}$ is selected from hydrido, and lower alkyl; wherein $R^{16}$ is selected from hydrido, lower alkyl, lower cycloalkyl, lower cycloalkylalkyl, lower haloalkyl, lower guanidinylalkyl, lower carboxyalkyl, lower hydroxyalkyl, lower alkoxyalkyl, lower aralkoxyalkyl, lower alkylthioalkyl, lower alkylsulfinylalkyl, lower alkylsulfonylalkyl, aryl, heterocyclo, lower aralkyl, lower heterocycloalkyl,

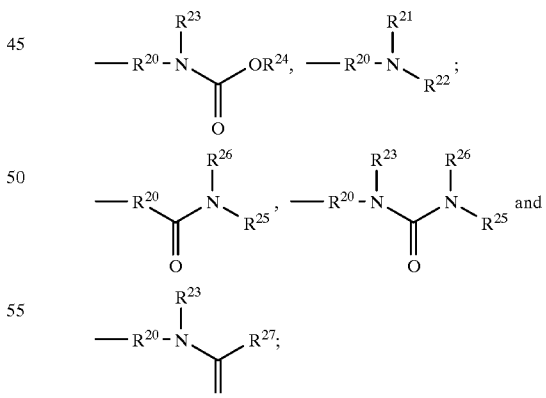

or wherein $R^{15}$ and $R^{16}$ together form lower cycloalkyl; wherein $R^{17}$ is selected from hydrido, lower alkyl, lower cycloalkyl and lower aralkyl; wherein $R^{18}$ and $R^{19}$ are independently selected from hydrido, lower alkyl, lower alkenyl, lower cycloalkyl, lower cycloalkylalkyl, aryl, heterocyclo, lower aralkyl, lower heterocycloalkyl, and lower alkylaminoalkyl; wherein $R^{20}$ is lower alkylene;

wherein $R^{21}$, $R^{22}$, $R^{25}$, and $R^{26}$ are independently selected from hydrido, lower alkyl, lower cycloalkyl, lower cycloalkylalkyl, lower aminoalkyl, lower alkylaminoalkyl, lower hydroxyalkyl, lower alkoxyalkyl, lower aralkoxyalkyl, aryl, heterocyclo, lower aralkyl, lower heterocycloalkyl; wherein $R^{24}$ is selected from lower alkyl, lower cycloalkyl, lower cycloalkylalkyl, lower alkylaminoalkyl, lower aralkoxyalkyl, lower alkoxyalkyl, aryl, lower aralkyl, heterocyclo, and lower heterocycloalkyl; and wherein $R^{27}$ is selected from hydrido, lower alkyl, lower cycloalkyl, lower cycloalkylalkyl, lower alkylaminoalkyl, lower aminoalkyl, lower carboxyalkyl, lower aminocarbonylalkyl, lower hydroxyalkyl, lower aralkoxyalkyl, lower alkoxyalkyl, aryl, lower aralkyl, heterocyclo, and lower heterocycloalkyl; or a pharmaceutically-acceptable salt or tautomer thereof.

5. Compound of claim 4 wherein $R^1$ is a substituent selected from methyl, ethyl, n-propyl, isopropyl, n-butyl, isobutyl, sec-butyl, and tert-butyl; wherein $R^2$ is a substituent selected from methyl, ethyl, n-propyl, isopropyl, n-butyl, isobutyl, sec-butyl, tert-butyl, pentyl, hexyl,

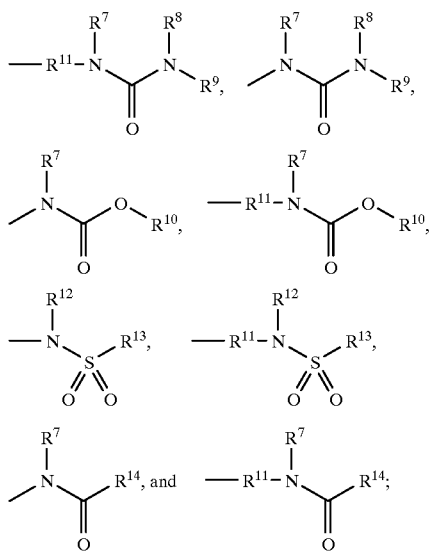

wherein $R^3$ is selected from hydrido, methyl, ethyl, n-propyl, isopropyl, n-butyl, isobutyl, sec-butyl, tert-butyl, pentyl, hexyl, benzyl, phenylethyl and diphenylmethyl; wherein $R^4$ is selected from

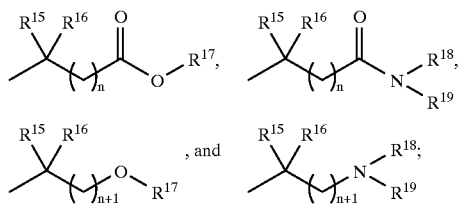

wherein n is 0–4, inclusive; wherein $R^5$ and $R^6$ are independently selected from hydrido, methyl, ethyl, n-propyl, isopropyl, n-butyl, isobutyl, sec-butyl, tert-butyl, pentyl, hexyl, cyclopropyl, cyclobutyl, cyclopentyl, cyclohexyl, cyclopropylmethyl, cyclobutylmethyl, phenyl, benzyl, furyl, thienyl, thiazolyl, pyrrolyl, furylmethyl, thienylethyl, thiazolylmethyl, pyrrolylmethyl, methylaminomethyl, N,N-dimethylaminomethyl, N,N-dimethylaminoethyl, N,N-dimethylaminohexyl, N,N-diethylaminobutyl, benzylaminomethyl, methoxymethyl, methoxyethyl, ethoxyethyl, methoxybutyl, methoxypropyl, and benzyloxymethyl; wherein $R^7$, $R^{12}$ and $R^{23}$ are independently selected from hydrido, methyl, ethyl, n-propyl, isopropyl, n-butyl, isobutyl, sec-butyl, tert-butyl, pentyl, hexyl, benzyl and phenylethyl; wherein $R^8$, $R^9$ and $R^{14}$ are independently selected from hydrido, methyl, ethyl, n-propyl, isopropyl, n-butyl, isobutyl, sec-butyl, tert-butyl, pentyl, hexyl, cyclopropyl, cyclobutyl, cyclopentyl, cyclohexyl, cyclopropylpropyl, cyclobutylethyl, cyclopentylmethyl, cyclohexylmethyl, fluoromethyl, difluoromethyl, trifluoromethyl, chloromethyl, dichloromethyl, trichloromethyl, trichloromethyl, pentafluoroethyl, heptafluoropropyl, difluorochloromethyl, dichlorofluoromethyl, difluoroethyl, difluoropropyl, dichloroethyl and dichloropropyl, methylamino, ethylamino, propylamino, N,N-dimethylaminomethyl, N,N-dimethylaminoethyl, N,N-dimethylaminopropyl, N,N-dimethylaminohexyl, N,N-diethylaminobutyl, N,N-diethylaminoethyl, N,N-diethylaminopropyl, carboxymethyl, carboxyethyl, carboxypropyl, aminocarbonylmethyl, N,N-dimethylaminocarbonylmethyl, hydroxymethyl, hydroxypropyl, methoxymethyl, methoxyethyl, ethoxyethyl, methoxybutyl, methoxypropyl, benzyloxymethyl, methylsulfonylmethyl, methylsulfinylmethyl, methylthiomethyl, phenyl optionally substituted at a substitutable position with one or more substituents selected independently from methyl, ethyl, n-propyl, isopropyl, n-butyl, isobutyl, sec-butyl, tert-butyl, pentyl, hexyl, methoxy, ethoxy, propoxy, isopropoxy, butoxy, tert-butoxy, amino, fluoro, chloro, bromo, iodo, N,N-dimethylaminomethyl, N,N-dimethylaminohexyl, N,N-diethylaminobutyl, N,N-dimethylaminoethyl, N,N-diethylaminoethyl, N,N-dimethylamino, and N,N-diethylamino, lower aralkyl selected from benzyl, naphthylmethyl, phenylethyl, and phenylisopropyl, wherein the phenyl ring is optionally substituted at a substitutable position with one or more substituents selected independently from methyl, ethyl, n-propyl, isopropyl, n-butyl, isobutyl, sec-butyl, tert-butyl, pentyl, hexyl, methoxy, ethoxy, propoxy, isopropoxy, butoxy, tert-butoxy, amino, fluoro, chloro, bromo, iodo, N,N-dimethylaminomethyl, N,N-dimethylaminohexyl, N,N-diethylaminobutyl, N,N-dimethylaminoethyl, N,N-diethylaminoethyl, N,N-dimethylamino, and N,N-diethylamino, heterocyclo selected from furyl, pyrrolyl, pyridyl, oxazolyl, pyrazolyl, isoxazolyl, thienyl, and thiazolyl, and lower heterocycloalkyl selected from thienylmethyl, morpholinylethyl, morpholinylmethyl, piperazinylethyl, piperdinylethyl, piperdinylmethyl, pyrrolidinylethyl, pyrrolidinylmethyl, pyrrolidinylpropyl, imidazolylethyl, oxazolylmethyl, thiazolylmethyl, furylmethyl, thienylethyl, and thiazolylmethyl, wherein the heterocyclo moiety may be substituted at a substitutable position with a radical selected from fluoro, chloro, bromo, iodo, methyl, ethyl, n-propyl, isopropyl, n-butyl, isobutyl, sec-butyl, tert-butyl, pentyl, and hexyl; wherein $R^{10}$ is selected from methyl, ethyl, n-propyl, isopropyl, n-butyl, isobutyl, sec-butyl, tert-butyl, pentyl, hexyl, fluoromethyl, difluoromethyl, trifluoromethyl, chloromethyl, dichloromethyl, trichloromethyl, trichloromethyl, pentafluoroethyl, heptafluoropropyl, difluorochloromethyl, dichlorofluoromethyl, difluoroethyl, difluoropropyl, dichloroethyl and dichloropropyl, N,N-dimethylaminomethyl, N,N-dimethylaminoethyl, N,N-dimethylaminopropyl, N,N-dimethylaminohexyl, N,N- diethylaminoethyl, N,N-diethylaminopropyl, N,N-diethylaminobutyl, carboxymethyl, carboxyethyl, carboxypropyl, aminocarbonylmethyl, N,N-dimethylaminocarbonylmethyl, benzyloxymethyl, methoxymethyl, methoxyethyl, ethoxyethyl, methoxybutyl, methoxypropyl, cyclopropyl, cyclobutyl, cyclopentyl, cyclohexyl, cyclopropylpropyl, cyclobutylethyl, cyclopentylmethyl, cyclohexylmethyl, methylsulfonylmethyl, methylsulfinylmethyl, methylthiomethyl, phenyl optionally substituted at a substitutable position with one or more substituents selected independently from methyl, ethyl, n-propyl, isopropyl, n-butyl, isobutyl, sec-butyl, tert-butyl, pentyl, hexyl, methoxy, ethoxy, propoxy, isopropoxy, butoxy, tert-butoxy, amino, fluoro, chloro, bromo, iodo, N,N-dimethylaminomethyl, N,N-dimethylaminohexyl, N,N-diethylaminobutyl, N,N-dimethylaminoethyl, N,N-diethylaminoethyl, N,N-dimethylamino, and N,N-diethylamino, lower aralkyl selected from benzyl, phenethyl, naphthylmethyl, wherein the aryl ring is optionally substituted at a substitutable position with one or more substituents selected independently from methyl, ethyl, n-propyl, isopropyl, n-butyl, isobutyl, sec-butyl, tert-butyl, pentyl, hexyl, methoxy, ethoxy, propoxy, isopropoxy, butoxy, tert-butoxy, amino, fluoro, chloro, bromo, iodo, N,N-dimethylaminomethyl, N,N-dimethylaminoethyl, N,N-dimethylaminohexyl, N,N-diethylaminoethyl, N,N-diethylaminobutyl, N,N-dimethylamino, N,N-dimethylamino, and N,N-diethylamino, heterocyclo selected from furyl, thienyl, and thiazolyl, and lower heterocycloalkyl selected from thienylmethyl, morpholinylethyl, morpholinylmethyl, piperazinylethyl, piperdinylethyl, piperdinylmethyl, pyrrolidinylethyl, pyrrolidinylmethyl, pyrrolidinylpropyl, imidazolylethyl, oxazolylmethyl, thiazolylmethyl, furylmethyl, thienylethyl, and thiazolylmethyl, wherein the heterocyclo moiety may be substituted at a substitutable position with a radical selected from fluoro, chloro, bromo, iodo, methyl, ethyl, n-propyl, isopropyl, n-butyl, isobutyl, sec-butyl, tert-butyl, pentyl, and hexyl; wherein $R^{11}$ is selected from methylene, ethylene, n-propylene, isopropylene, n-butylene, isobutylene, sec-butylene, pentylene, and hexylene; wherein $R^{13}$ is selected from phenyl, amino, methyl, ethyl, n-propyl, isopropyl, n-butyl, isobutyl, sec-butyl, tert-butyl, pentyl, hexyl N,N-dimethylaminomethyl, N,N-dimethylaminoethyl, N,N-dimethylaminohexyl, N,N-diethylaminoethyl, N,N-diethylaminobutyl, N,N-dimethylamino, N,N-dimethylamino, and N,N-diethylamino; wherein $R^{15}$ is selected from hydrido, methyl, ethyl, n-propyl, isopropyl, n-butyl, isobutyl, sec-butyl, tert-butyl, pentyl, and hexyl; wherein $R^{16}$ is selected from hydrido, methyl, ethyl, n-propyl, isopropyl, n-butyl, isobutyl, sec-butyl, tert-butyl, pentyl, hexyl, hydroxymethyl, hydroxyethyl, hydroxypropyl, hydroxybutyl, mercaptoethyl, methoxymethyl, methoxyethyl, ethoxyethyl, methoxybutyl, methoxypropyl, phenylmethoxymethyl, aminomethyl, aminohexyl, aminobutyl, N,N-dimethylaminomethyl, N,N-dimethylaminoethyl, N,N-dimethylaminopropyl, N,N-dimethylaminohexyl, N,N-diethylaminopropyl, N,N-diethylaminobutyl, mercaptomethyl, methylthioethyl, methylsulfonylethyl, phenyl optionally substituted at a substitutable position with one or more substituents independently selected from methyl, ethyl, n-propyl, isopropyl, n-butyl, isobutyl, sec-butyl, tert-butyl, pentyl, hexyl, hydroxy, methoxy, ethoxy, propoxy, isopropoxy, butoxy, tert-butoxy, fluoro, chloro, bromo, iodo, nitro, amino, N,N-dimethylaminomethyl, N,N-dimethylaminoethyl, N,N-dimethylaminopropyl, N,N-dimethylaminohexyl, N,N-diethylaminopropyl, N,N-diethylaminobutyl, methylamino, and hexylamino, heterocyclo selected from pyridyl, thienyl, morpholinyl, piperidinyl, indolyl, quinolinyl, pyrrolidinyl, furyl, oxazolyl, thiazolyl, imidazolyl, pyrazolyl, and isoxazolyl, optionally substituted at a substitutable position with one or more substituents independently selected from methyl, ethyl, n-propyl, isopropyl, n-butyl, isobutyl, sec-butyl, tert-butyl, pentyl, hexyl, methoxy, ethoxy, propoxy, butoxy, tert-butoxy, fluoro, chloro, bromo, iodo, amino, oxo, N,N-dimethylamino, and N,N-diethylamino, lower aralkyl selected from benzyl, phenethyl and naphthylmethyl, wherein the aryl ring is optionally substituted at a substitutable position with one or more substituents independently selected from methyl, ethyl, n-propyl, isopropyl, n-butyl, isobutyl, sec-butyl, tert-butyl, pentyl, hexyl, hydroxy, methoxy, ethoxy, propoxy, butoxy, tert-butoxy, fluoro, chloro, bromo, iodo, nitro, amino, methylamino, N,N-dimethylaminomethyl, N,N-dimethylaminoethyl, N,N-dimethylaminopropyl, N,N-dimethylaminohexyl, N,N-diethylaminopropyl, N,N-diethylaminobutyl, ethylamino, N,N-dimethylamino, N,N-dimethylamino, and N,N-diethylamino, lower heterocycloalkyl selected from pyrrolidinylethyl, furylmethyl, pyrrolidinylmethyl, piperazinylmethyl, piperazinylethyl, imidazolylmethyl, indolylmethyl, morpholinylmethyl, morpholinylethyl, quinolinylmethyl, thienylmethyl, thiazolylethyl and thiazolylmethyl, wherein the heterocyclo moiety may be substituted at a substitutable position with a radical selected from fluoro, chloro, bromo, iodo, methyl, ethyl, n-propyl, isopropyl, n-butyl, isobutyl, sec-butyl, tert-butyl, pentyl, and hexyl,

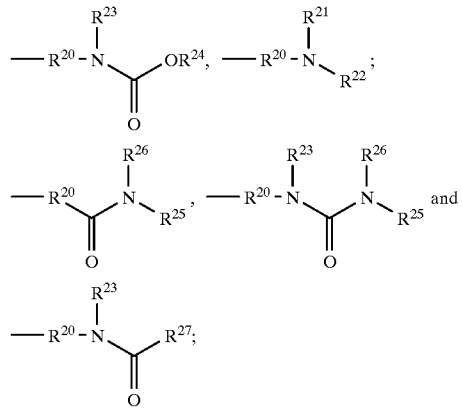

or wherein $R^{15}$ and $R^{16}$ together form a ring selected from cyclopropyl, cyclobutyl, cyclopentyl and cyclohexyl; wherein $R^{17}$ is selected from hydrido, methyl, ethyl, n-propyl, isopropyl, n-butyl, isobutyl, sec-butyl, tert-butyl, pentyl, hexyl, and benzyl; wherein $R^{18}$ and $R^{19}$ are independently selected from hydrido, methyl, ethyl, n-propyl, isopropyl, n-butyl, isobutyl, sec-butyl, tert-butyl, pentyl, hexyl, butenyl, propenyl, N,N-dimethylaminomethyl, N,N-dimethylaminoethyl, N,N-dimethylaminopropyl, N,N-dimethylaminohexyl, N,N-diethylaminopropyl, N,N-diethylaminobutyl, butenyl, phenyl, pyridyl, thienyl, morpholinyl, piperidinyl, indolyl, quinolinyl, pyrrolidinyl, furyl, oxazolyl, thiazolyl, imidazolyl, pyrazolyl, isoxazolyl, benzyl, phenethyl, lower heterocycloalkyl selected from furylmethyl, thienylmethyl, morpholinylethyl, piperazinylethyl, piperdinylethyl, pyrrolidinylethyl, pyrrolidinylpropyl, imidazolylethyl, oxazolylmethyl, and thiazolylmethyl, wherein the heterocyclo moiety may be substituted at a substitutable position with a radical selected from fluoro, chloro, bromo, iodo, methyl, ethyl, n-propyl, isopropyl, n-butyl, isobutyl, sec-butyl, tert-butyl, pentyl, hexyl, methylaminomethyl, methylaminohexyl, ethylaminobutyl, N,N-dimethylaminomethyl, N,N-dimethylaminoethyl, N,N-dimethylaminohexyl, and N,N-diethylaminobutyl; wherein $R^{20}$ is selected from methylene, ethylene, n-propylene, isopropylene, n-butylene, isobutylene, sec-butylene, pentylene, and hexylene; wherein $R^{21}$, $R^{22}$, $R^{25}$, and $R^{26}$ are independently selected from hydrido, methyl, ethyl, n-propyl, isopropyl, n-butyl, isobutyl, sec-butyl, tert-butyl, pentyl, hexyl, propenyl, butenyl, phenyl optionally substituted at a substitutable position with one or more substituents selected independently from methyl, ethyl, n-propyl, isopropyl, n-butyl, isobutyl, sec-butyl, tert-butyl, pentyl, hexyl, methoxy, ethoxy, propoxy, isopropoxy, butoxy, tert-butoxy, amino, fluoro, chloro, bromo, iodo, N,N-dimethylaminomethyl, N,N-dimethylaminohexyl, N,N-diethylaminobutyl, N,N-dimethylaminoethyl, N,N-diethylaminoethyl, N,N-dimethylamino, and N,N-diethylamino, pyridyl, thienyl, morpholinyl, piperidinyl, indolyl, quinolinyl, pyrrolidinyl, furyl, oxazolyl, thiazolyl, imidazolyl, pyrazolyl, and isoxazolyl, benzyl, phenethyl, lower heterocycloalkyl selected from furylmethyl, thienylmethyl, morpholinylethyl, piperazinylethyl, piperdinylethyl, pyrrolidinylethyl, pyrrolidinylpropyl, imidazolylethyl, oxazolylmethyl, and thiazolylmethyl, wherein the heterocyclo moiety may be substituted at a substitutable position with a radical selected from fluoro, chloro, bromo, iodo, methyl, ethyl, n-propyl, isopropyl, n-butyl, isobutyl, sec-butyl, tert-butyl, pentyl, hexyl, methylaminomethyl, methylaminohexyl, ethylaminobutyl, N,N-dimethylaminomethyl, N,N-dimethylaminoethyl, N,N-dimethylaminohexyl, and N,N-diethylaminobutyl; wherein $R^{24}$ is selected from methyl, ethyl, n-propyl, isopropyl, n-butyl, isobutyl, sec-butyl, tert-butyl, pentyl, hexyl, N,N-dimethylaminomethyl, N,N-dimethylaminoethyl, N,N-dimethylaminopropyl, N,N-dimethylaminohexyl, N,N-diethylaminopropyl, N,N-diethylaminobutyl, methoxymethyl, methoxyethyl, ethoxyethyl, methoxybutyl, methoxypropyl, benzyloxyethyl, benzyloxymethyl, cyclopropyl, cyclobutyl, cyclopentyl, cyclohexyl, cyclopropylmethyl, cyclobutylmethyl, cyclopentylethyl, cyclohexylpropyl, phenyl optionally substituted at a substitutable position with one or more substituents selected independently from methyl, ethyl, n-propyl, isopropyl, n-butyl, isobutyl, sec-butyl, tert-butyl, pentyl, hexyl, methoxy, ethoxy, propoxy, isopropoxy, butoxy, tert-butoxy, amino, fluoro, chloro, bromo, iodo, N,N-dimethylaminomethyl, N,N-dimethylaminohexyl, N,N-diethylaminobutyl, N,N-dimethylaminoethyl, N,N-diethylaminoethyl, N,N-dimethylamino, and N,N-diethylamino, heterocyclo selected from pyridyl, thienyl, morpholinyl, pyrimidyl, indolyl, isoquinolyl, quinolyl, tetrahydroquinolinyl, piperidinyl, pyrrolidinyl, furyl, oxazolyl, thiazolyl, imidazolyl, pyrazolyl, and isoxazolyl, wherein the heterocyclo is optionally substituted at a substitutable position with one or more substituents selected independently from lower alkyl, lower alkoxy, amino, halo, lower dialkylaminoalkyl, and lower dialkylamino, lower aralkyl selected from benzyl, phenethyl, and naphthylmethyl, wherein the aryl ring is optionally substituted at a substitutable position with one or more substituents selected independently from methyl, ethyl, n-propyl, isopropyl, n-butyl, isobutyl, sec-butyl, tert-butyl, pentyl, hexyl, methoxy, ethoxy, propoxy, butoxy, tert-butoxy, amino, fluoro, chloro, bromo, iodo, N,N-dimethylaminomethyl, N,N-dimethylaminoethyl, N,N-dimethylaminopropyl, N,N-dimethylaminohexyl, N,N-diethylaminopropyl, N,N-diethylaminobutyl, N,N-dimethylamino, and N,N-diethylamino, and lower heterocycloalkyl selected from furylmethyl, pyrrolidinylmethyl, quinolinylmethyl, piperazinylmethyl, imidazolylmethyl, indolylmethyl, morpholinylmethyl, thienylmethyl, and thiazolylmethyl, wherein the heterocyclo moiety may be substituted at a substitutable position with a radical selected from fluoro, chloro, bromo, iodo, methyl, ethyl, n-propyl, isopropyl, n-butyl, isobutyl, sec-butyl, tert-butyl, pentyl, and hexyl; and wherein $R^{27}$ is selected from hydrido, methyl, ethyl, n-propyl, isopropyl, n-butyl, isobutyl, sec-butyl, tert-butyl, pentyl, hexyl, trifluoromethyl, N,N-dimethylaminomethyl, N,N-dimethylaminoethyl, N,N-dimethylaminopropyl, N,N-dimethylaminohexyl, N,N-diethylaminopropyl, N,N-diethylaminobutyl, hydroxymethyl, hydroxyethyl, hydroxypropyl, hydroxybutyl, methoxymethyl, methoxyethyl, ethoxyethyl, methoxybutyl, methoxypropyl, phenylmethoxymethyl, benzyloxyethyl, aminomethyl, aminohexyl, aminobutyl, carboxyethyl, carboxypropyl, carboxymethyl, cyclopropyl, cyclobutyl, cyclopentyl, cyclohexyl, cyclopropylmethyl, cyclobutylmethyl, cyclopentylethyl, cyclohexylpropyl, phenyl optionally substituted at a substitutable position with one or more substituents selected independently from methyl, ethyl, n-propyl, isopropyl, n-butyl, isobutyl, sec-butyl, tert-butyl, pentyl, hexyl, methoxy, ethoxy, propoxy, isopropoxy, butoxy, tert-butoxy, amino, fluoro, chloro, bromo, iodo, N,N-dimethylaminomethyl, N,N-dimethylaminohexyl, N,N-diethylaminobutyl, N,N-dimethylaminoethyl, N,N-diethylaminoethyl, N,N-dimethylamino, and N,N-diethylamino, heterocyclo selected from pyridyl, thienyl, morpholinyl, pyrimidyl, indolyl, isoquinolyl, quinolyl, tetrahydroquinolinyl, piperidinyl, pyrrolidinyl, furyl, oxazolyl, thiazolyl, imidazolyl, pyrazolyl, and isoxazolyl, wherein the heterocyclo is optionally substituted at a substitutable position with one or more substituents selected independently from lower alkyl, lower alkoxy, amino, halo, lower dialkylaminoalkyl, and lower dialkylamino, lower aralkyl selected from benzyl, phenethyl, and naphthylmethyl, wherein the aryl ring is optionally substituted at a substitutable position with one or more substituents selected independently from methyl, ethyl, n-propyl, isopropyl, n-butyl, isobutyl, sec-butyl, tert-butyl, pentyl, hexyl, methoxy, ethoxy, propoxy, butoxy, tert-butoxy, amino, fluoro, chloro, bromo, iodo, N,N-dimethylaminomethyl, N,N-dimethylaminoethyl, N,N-dimethylaminopropyl, N,N-dimethylaminohexyl, N,N-diethylaminopropyl, N,N-diethylaminobutyl, N,N-dimethylamino, and N,N-diethylamino, and lower heterocycloalkyl selected from furylmethyl, pyrrolidinylmethyl, quinolinylmethyl, piperazinylmethyl, imidazolylmethyl, indolylmethyl, morpholinylmethyl, thienylmethyl, and thiazolylmethyl, wherein the heterocyclo moiety may be substituted at a substitutable position with a radical selected from fluoro, chloro, bromo, iodo, methyl, ethyl, n-propyl, isopropyl, n-butyl, isobutyl, sec-butyl, tert-butyl, pentyl, and hexyl; or a pharmaceutically-acceptable salt or tautomer thereof.

6. Compound of claim 5 selected from compounds and their pharmaceutically-acceptable salts, of the group consisting of 1,1-dimethylethyl[2-[[2-(3,5-diiodo-4-methoxy phenyl)-1S-[(dimethylamino)methyl]ethyl]amino]-5-methyl-4-oxo-4H-3,1-benzoxazin-6-yl]carbamate;

1,1-dimethylethyl[2-[[1S-[(dimethylamino)methyl]-3-(methylsulfonyl)propyl]amino]-5-methyl-4-oxo-4H-3,1-benzoxazin-6-yl]carbamate;

1,1-dimethylethyl[2-[[2-(dimethylamino)-1S-methylethyl]amino]-5-methyl-4-oxo-4H-3,1-benzoxazin-6-yl]carbamate;

1,1-dimethylethyl[[2-[[2-(dimethylamino)-1S-methylethyl]amino]-5-methyl-4-oxo-4H-3,1-benzoxazin-6-yl]methyl]carbamate;

N-[6-[[(1,1-dimethylethoxy)carbonyl]amino]-5-methyl-4-oxo-4H-3,1-benzoxazin-2-yl]-3,5-diiodo-L-tyrosine, methyl ester;

N-[6-[[(1,1-dimethylethoxy)carbonyl]amino]-5-methyl-4-oxo-4H-3,1-benzoxazin-2-yl-]-3,5-diiodo-O-methyl-L-tyrosine, methyl ester;

N-[6-[[(1,1-dimethylethoxy)carbonyl]amino]-5-methyl-4-oxo-4H-3,1-benzoxazin-2-yl-]-3,5-diiodo-N,0-dimethyl-L-tyrosine, methyl ester;

3,5-dibromo-N-[6-[[(1,1-dimethylethoxy)carbonyl]amino]-5-methyl-4-oxo-4H-3,1-benzoxazin-2-yl-]-O-methyl-L-tyrosine, methyl ester;

methyl αS-[[6-[[(1,1-dimethylethoxy)carbonyl]amino]-5-methyl-4-oxo-4H-3,1-benzoxazin-2-yl]amino]thiazole-4-propanoate;

methyl αS-[[6-[[(1,1-dimethylethoxy)carbonyl]amino]-5-methyl-4-oxo-4H-3,1-benzoxazin-2-yl]amino]oxazole-4-propanoate;

methyl 4-[(aminocarbonyl)amino]-2S-[[6-[[(1,1-dimethylethoxy)carbonyl]amino]-5-methyl-4-oxo-4H-3,1-benzoxazin-2-yl]amino]butanoate;

$N^2$-[6-[[(1,1-dimethylethoxy)carbonyl]amino]-5-methyl-4-oxo-4H-3,1-benzoxazin-2-yl]-L-asparagine, methyl ester;

$N^2$-[6-[[(1,1-dimethylethoxy)carbonyl]amino]-5-methyl-4-oxo-4H-3,1-benzoxazin-2-yl]-L-glutamine, methyl ester;

1,1-dimethylethyl[2-[[2-(diethylamino)-1S-[(4-hydroxy-3,5-diiodophenyl)methyl]-2-oxoethyl]amino]-5-methyl-4-oxo-4H-3,1-benzoxazin-6-yl]carbamate;

1,1-dimethylethyl[2-[[2-(diethylamino)-1S-methyl-2-oxoethyl]amino]-5-methyl-4-oxo-4H-3,1-benzoxazin-6-yl]carbamate;

1,1-dimethylethyl[2-[[2-(diethylamino)-1S-[(3,5-diiodo-4-methoxyphenyl)methyl]-2-oxoethyl]amino]-5-methyl-4-oxo-4H-3,1-benzoxazin-6-yl]carbamate;

1,1-dimethylethyl[2-[[1S[(3,5-diiodo-4-methoxy phenyl)methyl]-2-[(1-methylethyl)amino]-2-oxo ethyl]amino]-5-methyl-4-oxo-4H-3,1-benzoxazin-6-yl]carbamate;

1,1-dimethylethyl[2-[[1S-[(4-hydroxy-3,5-diiodo phenyl)methyl]-2-[[2-(dimethylamino)ethyl]methyl amino]-2-oxoethyl]amino]-5-methyl-4-oxo-4H-3,1-benzoxazin-6-yl]carbamate;

1,1-dimethylethyl[2-[[2-[[2-(dimethylamino)ethyl]methylamino]-1S-methyl-2-oxoethyl]amino]-5-methyl-4-oxo-4H-3,1-benzoxazin-6-yl]carbamate;

1,1-dimethylethyl[2-[[2-[[2-(dimethylamino)ethyl]methylamino]-1,1-dimethyl-2-oxoethyl]amino]-5-methyl-4-oxo-4H-3,1-benzoxazin-6-yl]carbamate;

1,1-dimethylethyl[2-[[1S[[[2-(dimethylamino)ethyl]methylamino]carbonyl]-3-(methylsulfonyl)propyl]amino]-5-methyl-4-oxo-4H-3,1-benzoxazin-6-yl]carbamate;

1,1-dimethylethyl[2-[[1S[(3,5-diiodo-4-methoxy phenyl)methyl]-2-[methyl[2-(1-piperidinyl)ethyl]amino]-2-oxoethyl]amino]-5-methyl-4-oxo-4H-3,1-benzoxazin-6-yl]carbamate;

1,1-dimethylethyl[2-[[1S-methyl-[2-(1-piperidinyl)ethyl]amino]-2-oxoethyl]amino]-5-methyl-4-oxo-4H-3,1-benzoxazin-6-yl]carbamate;

1,1-dimethylethyl[2-[[1S-[[methyl-[2-(1-piperidinyl)ethyl]amino]carbonyl]-3-(methylsulfonyl)propyl]amino]-5-methyl-4-oxo-4H-3,1-benzoxazin-6-yl]carbamate;

1,1-dimethylethyl[2-[[1S-[3,5-diiodo-4-methoxy phenyl)methyl]-2-[methyl[2-(4-morpholinyl)ethyl]amino]-2-oxoethyl]amino]-5-methyl-4-oxo-4H-3,1-benzoxazin-6-yl]carbamate;

1,1-dimethylethyl[2-[[1S-[[methyl-[2-(4-morpholinyl)ethyl]amino]carbonyl]-3-(methylsulfonyl)propyl]amino]-5-methyl-4-oxo-4H-3,1-benzoxazin-6-yl]carbamate;

1,1-dimethylethyl[5-methyl-2-[[1S-methyl-2-[methyl-[2-(4-methylpiperazin-1-yl)ethyl]amino]-2-oxoethyl]amino]-4-oxo-4H-3,1-benzoxazin-6-yl]carbamate;

1,1-dimethylethyl[5-methyl-2-[[1S-methyl-2-[methyl-[2-(4-methylpiperazin-1-yl)ethyl]amino]carbonyl]-3-(methylsulfonyl)propyl]amino]-4-oxo-4H-3,1-benzoxazin-6-yl]carbamate;

methyl αS-[[6-[[1,1-dimethylethoxy)carbonyl]amino]-5-methyl-4-oxo-4H-3,1-benzoxazin-2-yl]amino]morpholine-4-butanoate;

methyl αS-[[6-[[(1,1-dimethylethoxy)carbonyl]amino]-5-methyl-4-oxo-4H-3,1-benzoxazin-2-yl]amino]pyrrolidine-1-butanoate;

N-[2-(dimethylamino)ethyl]-αS-[[6-[[(ethylamino)carbonyl]amino]-5-methyl-4-oxo-4H-3,1-benzoxazin-2-yl]amino]-3,5-diiodo-4-methoxy-N-methylbenzenepropanamide;

N-[2-dimethylamino)ethyl]-αS-[[6-[[ethyl amino)carbonyl]amino]-5-methyl-4-oxo-4H-3,1-benzoxazin-2-yl]amino]-N-methylpropanamide;

N-[2-(dimethylamino)ethyl]-3,5-diiodo-4-methoxy-N-methyl-αS[[5-methyl-4-oxo-6-[(propylsulfonyl)amino]-4H-3,1-benzoxazin-2-yl]amino]-N-methylpropanamide;

N-[6-[[[(1,1-dimethylethoxy)carbonyl]amino]methyl]-5-methyl-4-oxo-4H-3,1-benzoxazin-2-yl]-3,5-diiodo-O-methyl-L-tyrosine, methyl ester;

methyl αS-[6-[[[(1,1-dimethylethoxy)carbonyl]amino]methyl]-5-methyl-4-oxo-4H-3,1-benzoxazin-2-yl]amino]thiazole-4-propanoate;

$N^2$-[6-[[[(1,1-dimethylethoxy)carbonyl]amino]methyl]-5-methyl-4-oxo-4H-3,1-benzoxazin-2-yl]-L-asparagine, methyl ester;

1,1-dimethylethyl[[2-[[1S-[3,5-diiodo-4-methoxy phenyl)methyl]-2-[[2-(dimethylamino)ethyl]methyl amino]-2-oxoethyl]amino]-5-methyl-4-oxo-4H-3,1-benzoxazin-6-yl]methyl]carbamate;

1,1-dimethylethyl[[2-[[2-[[2-(dimethylamino)ethyl]methylamino]-1S-methyl-2-oxoethyl]amino]-5-methyl-4-oxo-4H-3,1-benzoxazin-6-yl]methyl]carbamate;

1,1-dimethylethyl[[2-[[1S-[[2-(dimethylamino)ethyl]methylamino]carbonyl]-3-(methylsulfonyl)propyl]amino]-5-methyl-4-oxo-4H-3,1-benzoxazin-6-yl]methyl]carbamate;

1,1-dimethylethyl[[5-methyl-2-[[1S-methyl-2-[methyl[2-(1-piperidiny)ethyl]amino]-2-oxoethyl]-amino]-4-oxo-4H-3,1-benzoxazin-6-yl]methyl]carbamate;

1,1-dimethylethyl[[5-methyl-2-[[1S-[[methyl-[2-(4-morpholinyl)ethyl]amino]carbonyl]-3-(methylsulfonyl)propyl]amino]-4-oxo-4H-3,1-benzoxazin-6-yl]methyl]carbamate;

1,1-dimethylethyl[[5-methyl-2-[[1S-methyl-[2-(4-methyl-1-piperazinyl)ethyl]amino]-2-oxoethyl]amino]-4-oxo-4H-3,1-benzoxazin-6-yl]methyl]carbamate;

N-(6-bromo-5-methyl-4-oxo-4H-3,1-benzoxazin-2-yl)-L-alanine, 1,1-dimethylethyl ester;

N-(6-bromo-5-methyl-4-oxo-4H-3,1-benzoxazin-2-yl)-D-alanine, 1,1-dimethylethyl ester;

N-[6-[[(1,1-dimethylethoxy)carbonyl]amino]-5-methyl-4-oxo-4H-3,1-benzoxazin-2-yl]-L-alanine, 1,1-dimethylethyl ester;

N-[6-[[(1,1-dimethylethoxy)carbonyl]amino]-5-methyl-4-oxo-4H-3,1-benzoxazin-2-yl]-L-phenylalanine, methyl ester;

N-[6-[[(1,1-dimethylethoxy)carbonyl]amino]-5-methyl-4-oxo-4H-3,1-benzoxazin-2-yl]-O-(phenylmethyl)-L-serine, methyl ester;

N-[6-[[(1,1-dimethylethoxy)carbonyl]amino]-5-methyl-4-oxo-4H-3,1-benzoxazin-2yyl]-O-methyl-L-tyrosine, methyl ester;

N-[6-[[(1,1-dimethylethoxy)carbonyl]amino]-5-methyl-4-oxo-4H-3,1-benzoxazin-2-yl]-o-methyl-L-tyrosine, dimethylamide;

N-[6-[[(1,1-dimethylethoxy)carbonyl]amino]-5-methyl-4-oxo-4H-3,1-benzoxazin-2-yl]-L-thiazol-4-yl-alanine, methyl ester;

N-[6-[[(1,1-dimethylethoxy)carbonyl]amino]-5-methyl-4-oxo-4H-3,1-benzoxazin-2-yl]-L-aspartic acid, alpha-methyl ester beta-dimethylamide;

N-[6-[[(1,1-dimethylethoxy)carbonyl]amino]-5-methyl-4-oxo-4H-3,1-benzoxazin-2-yl]-O-methyl-L-tyrosine, N-methyl-N-[2-(1-morpholinyl)ethyl]amide;

N-[6-[[(1,1-dimethylethoxy)carbonyl]amino]-5-methyl-4-oxo-4H-3,1-benzoxazin-2-yl]-O-methyl-L-tyrosine, N-methyl-N-[2-(1-piperidinyl)ethyl]amide;

N-[6-[[(1,1-dimethylethoxy)carbonyl]amino]-5-methyl-4-oxo-4H-3,1-benzoxazin-2-yl]-L-tryptophan, dimethylamide;

N-[6-[[(1,1-dimethylethoxy)carbonyl]amino]-5-methyl-4-oxo-4H-3,1-benzoxazin-2-yl]-O-methyl-L-threonine, methyl ester;

N-[6-[[(1,1-dimethylethoxy)carbonyl]amino]-5-methyl-4-oxo-4H-3,1-benzoxazin-2-yl]-O-methyl-L-serine, methyl ester;

N-[6-[[(1,1-dimethylethoxy) carbonyl]amino]-5-methyl-4-oxo-4H-3,1-benzoxazin-2-yl]-L-phenylglycine, 1,1-dimethylethyl ester;

N-[6-[[(1,1-dimethylethoxy)carbonyl]amino]-5-methyl-4-oxo-4H-3,1-benzoxazin-2-yl]-3,5-diiodo-O-methyl-L-tyrosine, methyl ester;

N-[6-[[(1,1-dimethylethoxy)carbonyl]amino]-5-methyl-4-oxo-4H-3,1-benzoxazin-2-yl]-4-iodo-L-phenylalanine, methyl ester;

N-[6-[[(1,1-dimethylethoxy)carbonyl]amino]-5-methyl-4-oxo-4H-3,1-benzoxazin-2-yl]-L-methionine sulfone, methyl ester;

N-[6-[[(1,1-dimethylethoxy)carbonyl]amino]-5-methyl-4-oxo-4H-3,1-benzoxazin-2-yl]-L-beta-naphthylalanine, methyl ester;

N-[6-[[(1,1-dimethylethoxy)carbonyl]amino]-5-methyl-4-oxo-4H-3,1-benzoxazin-2-yl]-2-aminoisobutyric acid, methyl ester;

N-[6-[[(1,1-dimethylethoxy)carbonyl]amino]-5-methyl-4-oxo-4H-3,1-benzoxazin-2-yl]-1-cyclopropanecarboxylic acid, methyl ester;

N-[6-[[(1,1-dimethylethoxy)carbonyl]amino]-5-methyl-4-oxo-4H-3,1-benzoxazin-2-yl]-L-alanine, N-methyl-N-allylamide;

N-[6-[[(1,1-dimethylethoxy)carbonyl]amino]-5-methyl-4-oxo-4H-3,1-benzoxazin-2-yl]-L-alanine, N-methyl-N-phenylmethylamide;

N-[6[[(1,1-dimethylethoxy)carbonyl]amino]-5-methyl-4-oxo-4H-3,1-benzoxazin-2-yl]-L-alanine, phenyl methyl ester;

N-[6-[[(1,1-dimethylethoxy)carbonyl]amino]-5-methyl-4-oxo-4H-3,1-benzoxazin-2-yl]-3,5-diiodo-L-tyrosine, methyl ester;

N-[6-[[[(1,1-dimethylethoxy)carbonyl]amino]methyl]-5-methyl-4-oxo-4H-3,1-benzoxazin-2-yl]-L-alanine, dimethylamide;

N-[6-[[[(1,1-dimethylethoxy)carbonyl]amino]methyl]-5-methyl-4-oxo-4H-3,1-benzoxazin-2-yl]-O-methyl-L-tyrosine, dimethylamide;

N-[6-[[[(1,1-dimethylethoxy)carbonyl]amino]methyl]-5-methyl-4-oxo-4H-3,1-benzoxazin-2-yl]-L-alanine, methyl ester;

N-[6-amino-5-methyl-4-oxo-4H-3,1-benzoxazin-2-yl]-L-alanine, methyl ester;

N-[6-amino-5-methyl-4-oxo-4H-3,1-benzoxazin-2-yl]-1-phenylalanine, methyl ester;

N-[[6-(dimethylaminomethyl)carbonyl]amino]-5-methyl-4-oxo-4H-3,1-benzoxazin-2-yl]-L-alanine, methyl ester;

5-methyl-N-6-[[(2-pyridyl)carbonyl]amino]-4-oxo-4H-3,1-benzoxazin-2-yl]-L-alanine, methyl ester;

N-[6-[[(5-isoxazolyl)carbonyl]amino]-5-methyl-4-oxo-4H-3,1-benzoxazin-2-yl]-L-alanine, methyl ester;

N-[6-[[(methoxymethyl)carbonyl]amino]-5-methyl-4-oxo-4H-3,1-benzoxazin-2-yl]-L-alanine, methyl ester;

N-[6-[[(methoxymethyl)carbonyl]amino]-5-methyl-4-oxo-4H-3,1-benzoxazin-2-yl]-L-phenylalanine, methyl ester;

N-[6-[[(2-carboxyethyl)carbonyl]amino]-5-methyl-4-oxo-4H-3,1-benzoxazin-2-yl]-L-phenylalanine, methyl ester;

N-[6-[[(cyclobutyl)carbonyl]amino]-5-methyl-4-oxo-4H-3,1-benzoxazin-2-yl]-L-phenylalanine, methyl ester;

N-[6-[[(2-furanyl)carbonyl]amino]-5-methyl-4-oxo-4H-3,1-benzoxazin-2-yl]-L-phenylalanine, methyl ester;

N-[6-[[(2-thienylmethyl)carbonyl]amino]-5-methyl-4-oxo-4H-3,1-benzoxazin-2-yl]-L-phenylalanine, methyl ester;

N-[6-[[[[2-(2-thienyl)ethyl]amino]carbonyl]amino]-5-methyl-4-oxo-4H-3,1-benzoxazin-2-yl]-L-phenylalanine, methyl ester;

N-[6-[[[[2-(2-thienyl)ethyl]amino]carbonyl]amino]-5-methyl-4-oxo-4H-3,1-benzoxazin-2-yl]-L-alanine, methyl ester;

N-[6-[benzenesulfonyl]amino]-5-methyl-4-oxo-4H-3,1-benzoxazin-2-yl]-L-phenylalanine, methyl ester;

N-[6-[benzenesulfonyl]amino]-5-methyl-4-oxo-4H-3,1-benzoxazin-2-yl]-L-alanine, methyl ester; and N-[6-[[(1,1-dimethylethoxy)carbonyl]amino]-5-methyl-4-oxo-4H-3,1-benzoxazin-2-yl]-L-alanine.

7. Compound of claim 3 wherein $R^1$ is a lower alkyl; wherein $R^2$ is a substituent selected from lower alkyl,

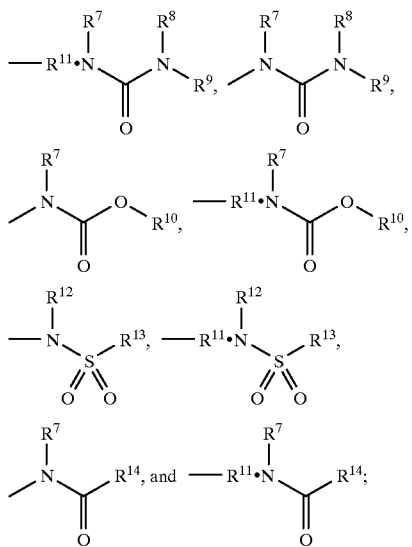

wherein $R^3$ is selected from hydrido, lower alkyl, and lower aralkyl; wherein $R^4$ is selected from hydrido, lower alkyl, lower cycloalkyl, lower cycloalkylalkyl, aryl, heterocyclo, lower aralkyl and lower heterocycloalkyl;

wherein n is 0–5, inclusive; wherein $R^5$ and $R^6$ are independently selected from hydrido, lower alkyl, lower cycloalkyl, lower cycloalkylalkyl, aryl, lower aralkyl, heterocyclo, lower heterocycloalkyl, lower alkylaminoalkyl, lower aralkylaminoalkyl, lower alkoxyalkyl, and lower aralkoxyalkyl;

wherein $R^7$, $R^{12}$ and $R^{23}$ are independently selected from hydrido, lower alkyl and lower aralkyl; wherein $R^8$, $R^9$ and $R^{14}$ are independently selected from hydrido, lower alkyl, lower cycloalkyl, lower cycloalkylalkyl, lower haloalkyl, lower aminoalkyl, lower alkylaminoalkyl, lower carboxyalkyl, lower aminocarbonylalkyl, lower alkylaminocarbonylalkyl, lower hydroxyalkyl, lower alkoxyalkyl, lower aralkoxyalkyl, lower alkylsulfonylalkyl, lower alkylsulfinylalkyl, lower alkylthioalkyl, aryl, lower aralkyl, heterocyclo, and lower heterocycloalkyl; wherein $R^{10}$ is selected from lower alkyl, lower haloalkyl, lower alkylaminoalkyl, lower carboxyalkyl, lower aminocarbonylalkyl, alkylaminocarbonylalkyl, lower aralkoxyalkyl, lower alkoxyalkyl, lower cycloalkyl, lower cycloalkylalkyl, lower alkylsulfonylalkyl, lower alkylsulfinylalkyl, lower alkylthioalkyl, aryl, lower aralkyl, heterocyclo, and lower heterocycloalkyl; wherein $R^{11}$ is lower alkylene; and wherein $R^{13}$ is selected from amino, lower alkyl, lower alkylamino, lower alkylaminoalkyl and aryl; or a pharmaceutically-acceptable salt or tautomer thereof.

8. Compound of claim 7 wherein $R^1$ is a substituent selected from methyl, ethyl, n-propyl, isopropyl, n-butyl, isobutyl, sec-butyl, and tert-butyl; wherein $R^2$ is a substituent selected from methyl, ethyl, n-propyl, isopropyl, n-butyl, isobutyl, sec-butyl, tert-butyl, pentyl, hexyl,

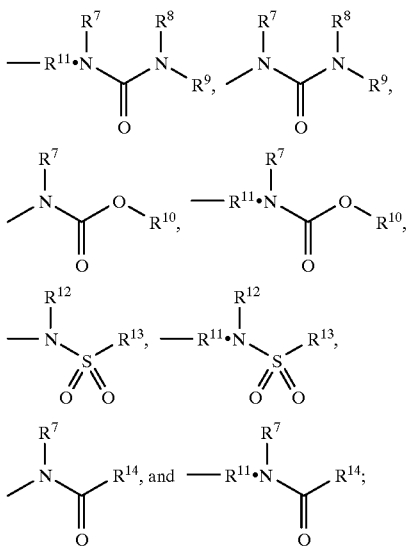

wherein $R^3$ is selected from hydrido, methyl, ethyl, n-propyl, isopropyl, n-butyl, isobutyl, sec-butyl, tert-butyl, pentyl, hexyl, benzyl, phenylethyl and diphenylmethyl; wherein $R^4$ is selected from hydrido, methyl, ethyl, n-propyl, isopropyl, n-butyl, isobutyl, sec-butyl, tert-butyl, pentyl, hexyl, cyclopropyl, cyclobutyl, cyclopentyl, cyclohexyl, cyclopropylmethyl, cyclobutylmethyl, cyclopentylethyl, cyclohexylpropyl, phenyl optionally substituted at a substitutable position with one or more substituents selected independently from fluoro, chloro, iodo, bromo, nitro, methyl, ethyl, n-propyl, isopropyl, n-butyl, isobutyl, sec-butyl, tert-butyl, pentyl, hexyl, lower alkoxy, N,N-dimethylaminoethyl, N,N-dimethylaminohexyl, N,N-diethylaminobutyl, N,N-dimethylaminoethoxy, N,N-dimethylaminohexyloxy, and N,N-diethylaminobutoxy, lower aralkyl selected from benzyl, naphthylmethyl, phenylethyl, and phenylisopropyl, wherein the phenyl ring is optionally substituted at a substitutable position with one or more substituents selected independently from methyl, ethyl, n-propyl, isopropyl, n-butyl, isobutyl, sec-butyl, tert-butyl, pentyl, hexyl, methoxy, ethoxy, propoxy, isopropoxy, butoxy, tert-butoxy, amino, fluoro, chloro, bromo, iodo, N,N-dimethylaminomethyl, N,N-dimethylaminohexyl, N,N-diethylaminobutyl, N,N-dimethylaminoethyl, N,N-diethylaminoethyl, N,N-dimethylamino, and N,N-diethylamino, heterocyclo selected from methylpiperidinyl, methylazabicyclooctanyl, morpholinyl, pyrrolidinyl, and piperazinyl, phenylmethyl, phenylethyl, and lower heterocycloalkyl selected from pyridylmethyl, furylmethyl, thienylmethyl, and thiazolylmethyl, where the heterocyclic rings are optionally substituted at a substitutable position with one or more substituents selected independently from fluoro, chloro, iodo, bromo, nitro, methyl, ethyl, n-propyl, isopropyl, n-butyl, isobutyl, sec-butyl, tert-butyl, pentyl, hexyl, lower alkoxy, N,N-dimethylaminoethyl, N,N-dimethylaminohexyl, N,N-diethylaminobutyl, N,N-dimethylaminoethoxy, N,N-dimethylaminoethoxy, N,N-dimethylaminohexyloxy, and N,N-diethylaminobutoxy; wherein n is 0–4, inclusive; wherein $R^5$ and $R^6$ are independently selected from hydrido, methyl, ethyl, n-propyl, isopropyl, n-butyl, isobutyl, sec-butyl, tert-butyl, pentyl, hexyl, cyclopropyl, cyclobutyl, cyclopentyl, cyclohexyl, cyclopropylmethyl, cyclobutylmethyl, phenyl, benzyl, furyl, thienyl, thiazolyl, pyrrolyl, furylmethyl, thienylethyl, thiazolylmethyl, pyrrolylmethyl, methylaminomethyl, N,N-dimethylaminomethyl, N,N-dimethylaminoethyl, N,N-dimethylaminohexyl, N,N-diethylaminobutyl, benzylaminomethyl, methoxymethyl, methoxyethyl, ethoxyethyl, methoxybutyl, methoxypropyl, and benzyloxymethyl; wherein $R^7$, $R^{12}$ and $R^{23}$ are independently selected from hydrido, methyl, ethyl, n-propyl, isopropyl, n-butyl, isobutyl, sec-butyl, tert-butyl, pentyl, hexyl, benzyl and phenylethyl; wherein $R^8$, $R^9$ and $R^{14}$ are independently selected from hydrido, methyl, ethyl, n-propyl, isopropyl, n-butyl, isobutyl, sec-butyl, tert-butyl, pentyl, hexyl, cyclopropyl, cyclobutyl, cyclopentyl, cyclohexyl, cyclopropylpropyl, cyclobutylethyl, cyclopentylmethyl, cyclohexylmethyl, fluoromethyl, difluoromethyl, trifluoromethyl, chloromethyl, dichloromethyl, trichloromethyl, trichloromethyl, pentafluoroethyl, heptafluoropropyl, difluorochloromethyl, dichlorofluoromethyl, difluoroethyl, difluoropropyl, dichloroethyl and dichloropropyl, methylamino, ethylamino, propylamino, N,N-dimethylaminomethyl, N,N-dimethylaminoethyl, N,N-dimethylaminopropyl, N,N-dimethylaminohexyl, N,N-diethylaminobutyl, N,N-diethylaminoethyl, N,N-diethylaminopropyl, carboxymethyl, carboxyethyl, carboxypropyl, aminocarbonylmethyl, N,N-dimethylaminocarbonylmethyl, hydroxymethyl, hydroxypropyl, methoxymethyl, methoxyethyl, ethoxyethyl, methoxybutyl, methoxypropyl, benzyloxymethyl, methylsulfonylmethyl, methylsulfinylmethyl, methylthiomethyl, phenyl optionally substituted at a substitutable position with one or more substituents selected independently from methyl, ethyl, n-propyl, isopropyl, n-butyl, isobutyl, sec-butyl, tert-butyl, pentyl, hexyl, methoxy, ethoxy, propoxy, isopropoxy, butoxy, tert-butoxy, amino, fluoro, chloro, bromo, iodo, N,N-dimethylaminomethyl, N,N-dimethylaminohexyl, N,N-diethylaminobutyl, N,N-dimethylaminoethyl, N,N-diethylaminoethyl, N,N-dimethylamino, and N,N-diethylamino, lower aralkyl selected from benzyl, naphthylmethyl, phenylethyl, and phenylisopropyl, wherein the phenyl ring is optionally substituted at a substitutable position with one or more substituents selected independently from methyl, ethyl, n-propyl, isopropyl, n-butyl, isobutyl, sec-butyl, tert-butyl, pentyl, hexyl, methoxy, ethoxy, propoxy, isopropoxy, butoxy, tert-butoxy, amino, fluoro, chloro, bromo, iodo, N,N-dimethylaminomethyl, N,N-dimethylaminohexyl, N,N-diethylaminobutyl, N,N-dimethylaminoethyl, N,N-diethylaminoethyl, N,N-dimethylamino, and N,N-diethylamino, heterocyclo selected from furyl, pyrrolyl, pyridyl, oxazolyl, pyrazolyl, isoxazolyl, thienyl, and thiazolyl, and lower heterocycloalkyl selected from thienylmethyl, morpholinylethyl, morpholinylmethyl, piperazinylethyl, piperdinylethyl, piperdinylmethyl, pyrrolidinylethyl, pyrrolidinylmethyl, pyrrolidinylpropyl, imidazolylethyl, oxazolylmethyl, thiazolylmethyl, furylmethyl, thienylethyl, and thiazolylmethyl, wherein the heterocyclo moiety may be substituted at a substitutable position with a radical selected from fluoro, chloro, bromo, iodo, methyl, ethyl, n-propyl, isopropyl, n-butyl, isobutyl, sec-butyl, tert-butyl, pentyl, and hexyl; wherein $R^{10}$ is selected from methyl, ethyl, n-propyl, isopropyl, n-butyl, isobutyl, sec-butyl, tert-butyl, pentyl, hexyl, fluoromethyl, difluoromethyl, trifluoromethyl, chloromethyl, dichloromethyl, trichloromethyl, trichloromethyl, pentafluoroethyl, heptafluoropropyl, difluorochloromethyl, dichlorofluoromethyl, difluoroethyl, difluoropropyl, dichloroethyl and dichloropropyl, N,N-dimethylaminomethyl, N,N-dimethylaminoethyl, N,N-dimethylaminopropyl, N,N-dimethylaminohexyl, N,N-diethylaminoethyl, N,N-diethylaminopropyl, N,N-diethylaminobutyl, carboxymethyl, carboxyethyl, carboxypropyl, aminocarbonylmethyl, N,N-dimethylaminocarbonylmethyl, benzyloxymethyl, methoxymethyl, methoxyethyl, ethoxyethyl, methoxybutyl, methoxypropyl, cyclopropyl, cyclobutyl, cyclopentyl, cyclohexyl, cyclopropylpropyl, cyclobutylethyl, cyclopentylmethyl, cyclohexylmethyl, methylsulfonylmethyl, methylsulfinylmethyl, methylthiomethyl, phenyl optionally substituted at a substitutable position with one or more substituents selected independently from methyl, ethyl, n-propyl, isopropyl, n-butyl, isobutyl, sec-butyl, tert-butyl, pentyl, hexyl, methoxy, ethoxy, propoxy, isopropoxy, butoxy, tert-butoxy, amino, fluoro, chloro, bromo, iodo, N,N-dimethylaminomethyl, N,N-dimethylaminohexyl, N,N-diethylaminobutyl, N,N-dimethylaminoethyl, N,N-diethylaminoethyl, N,N-dimethylamino, and N,N-diethylamino, lower aralkyl selected from benzyl, phenethyl, naphthylmethyl, wherein the aryl ring is optionally substituted at a substitutable position with one or more substituents selected independently from methyl, ethyl, n-propyl, isopropyl, n-butyl, isobutyl, sec-butyl, tert-butyl, pentyl, hexyl, methoxy, ethoxy, propoxy, isopropoxy, butoxy, tert-butoxy, amino, fluoro, chloro, bromo, iodo, N,N-dimethylaminomethyl, N,N-dimethylaminoethyl, N,N-dimethylaminohexyl, N,N-diethylaminoethyl, N,N-diethylaminobutyl, N,N-dimethylamino, N,N-dimethylamino, and N,N-diethylamino, heterocyclo selected from furyl, thienyl, and thiazolyl, and lower heterocycloalkyl selected from thienylmethyl, morpholinylethyl, morpholinylmethyl, piperazinylethyl, piperdinylethyl, piperdinylmethyl, pyrrolidinylethyl, pyrrolidinylmethyl, pyrrolidinylpropyl, imidazolylethyl, oxazolylmethyl, thiazolylmethyl, furylmethyl, thienylethyl, and thiazolylmethyl, wherein the heterocyclo moiety may be substituted at a substitutable position with a radical selected from fluoro, chloro, bromo, iodo, methyl, ethyl, n-propyl, isopropyl, n-butyl, isobutyl, sec-butyl, tert-butyl, pentyl, and hexyl; wherein $R^{11}$ is selected from methylene, ethylene, n-propylene, isopropylene, n-butylene, isobutylene, sec-butylene, pentylene, and hexylene; and wherein $R^{13}$ is selected from phenyl, amino, methyl, ethyl, n-propyl, isopropyl, n-butyl, isobutyl, sec-butyl, tert-butyl, pentyl, hexyl N,N-dimethylaminomethyl, N,N-dimethylaminoethyl, N,N-dimethylaminohexyl, N,N-diethylaminoethyl, N,N-diethylaminobutyl, N,N-dimethylamino, N,N-dimethylamino, and N,N-diethylamino; or a pharmaceutically-acceptable salt or tautomer thereof.

9. Compound of claim 8 selected from compounds and their pharmaceutically-acceptable salts, of the group consisting of 1,1-dimethylethyl[5-methyl-2-[(1-methylpiperidin-4-yl)amino]-4-oxo-4H-3,1-benzoxazin-6-yl]carbamate;

1,1-dimethylethyl[2-[[8-methyl-8-azabicyclo[3.2.1]octan-3-yl]amino]-5-methyl-4-oxo-4H-3,1-benzoxazin-6-yl]carbamate;

1,1-dimethylethyl[5-methyl-4-oxo-2-[(1S-phenyl ethyl)amino]-4H-3,1-benzoxazin-6-yl]carbamate;

1,1-dimethylethyl[5-methyl-4-oxo-2[[1S-(4-bromophenyl)ethyl]amino]-4H-3,1-benzoxazin-6-yl]carbamate;

1,1-dimethylethyl[5-methyl-4-oxo-2[[1S-(3-pyridinyl)ethyl]amino]-4H-3,1-benzoxazin-6-yl]carbamate;

1,1-dimethylethyl[2-[[1S-[2-[2-(dimethylamino)ethoxy]
pyridin-5-yl]ethyl]amino]-5-methyl-4-oxo-4H-3,1-
benzoxazin-6-yl]carbamate;

1,1-dimethylethyl[2-[[1S-4-[2-(dimethylamino)ethyl]
phenyl]ethyl]amino]-5-methyl-4-oxo-4H-3,1-
benzoxazin-6-yl]carbamate;

1,1-dimethylethyl N-methyl-[5-methyl-4-oxo-2-[(1S-
phenylethyl)amino]4H-3,1-benzoxazin-6-yl]
carbamate;

$N^1$-ethyl-$N^2$-[5-methyl-4-oxo-2-[(1S-phenylethyl)
amino]-4H-3,1-benzoxazin-6-yl]urea;

$N^1$-[2-(dimethylamino)ethyl]-$N^2$-(5-methyl-4-oxo-2-
[(1S-phenylethyl)amino]-4H-3,1-benzoxazin-6-yl]
urea;

$N^1$-[2-(dimethylamino)ethyl]-$N^2$-[[5-methyl-4-oxo-2-
[(1S-phenylethyl)amino]-4H-3,1-benzoxazin-6-yl]
methyl]urea;

2-(dimethylamino)-N-[5-methyl-4-oxo-2-[(1S-
phenylethyl)amino]-4H-3,1-benzoxazin-6-yl]
acetamide;

N-[5-methyl-4-oxo-2-[(1S-phenylethyl)amino]-4H-3,1-
benzoxazin-6-yl]pyrrolidine-1-acetamide;

N-methyl-N-[5-methyl-4-oxo-2-[(1S-phenylethyl)
amino]-4H-3,1-benzoxazin-6-yl]pyrrolidine-1-
acetamide;

N-[5-methyl-4-oxo-2-[(1S-phenylethyl)amino]-4H-3,1-
benzoxazin-6-yl]morpholine-4-acetamide;

4-methyl-N-[5-methyl-4-oxo-2-[(1S-phenylethyl)
amino]-4H-3,1-benzoxazin-6-yl]piperazine-1-
acetamide;

1-methyl-N-[5-methyl-4-oxo-2-[(1S-phenylethyl)
amino]-4H-3,1-benzoxazin-6-yl]pyrrolidine-2S-
carboxamide;

1,1-dimethylethyl[[5-methyl-4-oxo-2[(1S-phenyl ethyl)
amino]-4H-3,1-benzoxazin-6-yl]methyl]carbamate;

1,1-dimethylethyl[[5-methyl-4-oxo-2[[1S-(3-pyridinyl)
ethyl]amino]-4H-3,1-benzoxazin-6-yl]methyl]
carbamate;

1,1-dimethylethyl[[2-[[1S[4-[2-(dimethylamino)ethyl]
phenyl]ethyl]amino]-5-methyl-4-oxo-4H-3,1-
benzoxazin-6-yl]methyl]carbamate;

2-(dimethylamino)-N-[[5-methyl-4-oxo-2-[(1S-
phenylethyl)amino]-4H-3,1-benzoxazin-6-yl]methyl]
acetamide;

N-[[5-methyl-4-oxo-2-[(1S-phenylethyl)amino]-4H-3,1-
benzoxazin-6-yl]methyl]pyrrolidine-1-acetamide;

N-[[5-methyl-4-oxo-2-[(1S-phenylethyl)amino]-4H-3,1-
benzoxazin-6-yl]methyl]morpholine-4-acetamide;

4-methyl-N-[[5-methyl-4-oxo-2-[(1S-phenylethyl)
amino]-4H-3,1-benzoxazin-6-yl]methyl]piperazine-1-
acetamide;

1-methyl-N-[[5-methyl-4-oxo-2[(1S-phenylethyl)
amino]-4H-3,1-benzoxazin-6-yl]methyl]pyrrolidine-
2S-carboxamide;

6-[[(1,1-dimethylethoxy)carbonyl]amino]-5-methyl-2-
[[(1S)-phenylethyl]amino]-4H-3,1-benzoxazin-4-one;

6-[[(1,1-dimethylethoxy)carbonyl]amino]-5-methyl-2-
[[(1R)-phenylethyl]amino]-4H-3,1-benzoxazin-4-one;

6-[[[(1,1-dimethylethoxy)carbonyl]amino]methyl]-5-
methyl-2-[[(1S)-phenylethyl]amino]-4H-3,1-
benzoxazin-4-one;

6-[[[[dimethylaminomethyl]carbonyl]amino]methyl]-5-
methyl-2-[[(1S)-phenylethyl]amino]-4H-3,1-
benzoxazin-4-one;

5-methyl-6-[[(1-morpholinylmethyl)carbonyl]amino]-2-
[[(1S)-phenylethyl]amino]-4H-3,1-benzoxazin-4-one;

6-[[(2-furanyl)carbonyl]amino]-5-methyl-2-[[(1S)-
phenylethyl]amino]-4H-3,1-benzoxazin-4-one;

5-methyl-2[[(1S)-phenylethyl]amino]-6-[[(1-
pyrrolidinylmethyl)carbonyl]amino]-4H-3,1-
benzoxazin-4-one;

5-methyl-6-[[(dimethylaminomethyl)carbonyl]amino]-2-
[[(1S)-phenylethyl]amino]-4H-3,1-benzoxazin-4-one;

5-methyl-6-[[(3-dimethylaminopropyl)carbonyl]amino]-
2-[[(1R)-phenylethyl]amino]-4H-3,1-benzoxazin-4-
one; and 6-[[[[(1R)-phenylethyl]amino]carbonyl]amino]-5-
methyl-2-[[(1R)-phenylethyl]amino]-4H-3,1-
benzoxazin-4-one.

10. A compound of Formula II

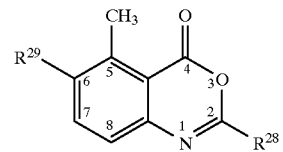

wherein $R^{28}$ is selected from (a) amino substituted with one or two radicals selected from alkyl, aralkyl, heterocycloalkyl, heterocyclo, and aryl, and (b) amino acid residues and amide or ester derivatives thereof;

wherein $R^{29}$ is selected from alkyl,

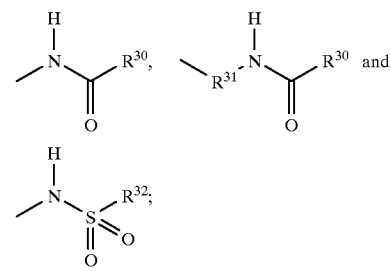

wherein $R^{30}$ is selected from alkyl, alkoxy, alkylamino, carboxyalkyl, alkoxyalkyl, alkylaminoalkyl, cycloalkyl, heterocyclo, heterocycloalkyl, heterocycloalkoxy, alkylaminoalkoxy, alkylaminoalkylamino, heterocycloalkylamino, and N-aralkylamino;

wherein $R^{31}$ is alkylene;

wherein $R^{32}$ is alkyl and aryl;

provided $R^{29}$ is not methyl when $R^{28}$ is amino substituted with benzyl or lower alkyl;

or a pharmaceutically-acceptable salt thereof.

11. Compound of claim 10 wherein $R^{28}$ is selected from (a) amino substituted with one or two radicals selected from lower alkyl, lower aralkyl, lower heterocycloalkyl, heterocyclo, and aryl, and (b) amino acid residues and amide or ester derivatives thereof; wherein $R^{29}$ is selected from lower alkyl,

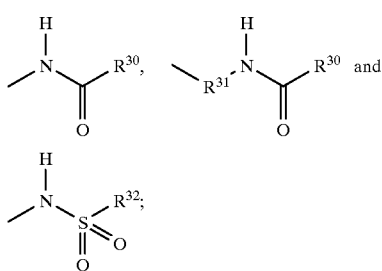

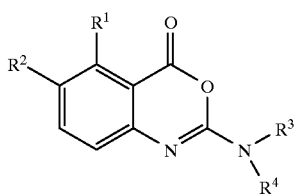

wherein $R^{30}$ is selected from lower alkyl, lower alkoxy, lower alkylamino, lower carboxyalkyl, lower alkoxyalkyl, lower alkylaminoalkyl, lower cycloalkyl, heterocyclo, lower heterocycloalkyl, lower heterocycloalkoxy, lower alkylaminoalkoxy, lower alkylaminoalkylamino, lower heterocycloalkylamino, and lower N-aralkylamino; wherein $R^{31}$ is lower alkylene; wherein $R^{32}$ is lower alkyl and aryl; or a pharmaceutically-acceptable salt thereof.

12. A pharmaceutical composition comprising a therapeutically-effective amount of a compound and a pharmaceutically-acceptable carrier or diluent, said compound selected from a compound as in any of claims 1–5, and 7–11.

13. A method of therapeutic treatment of herpes viral infection in a subject, said method comprising treating said subject with an effective amount of a compound of Formula I

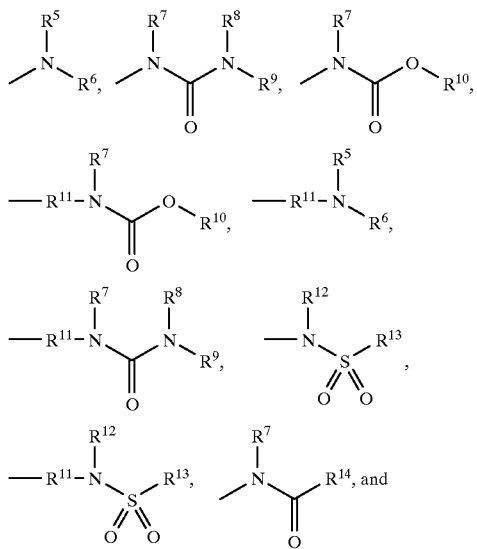

wherein $R^1$ is an alkyl;
wherein $R^2$ is a substituent selected from alkyl,

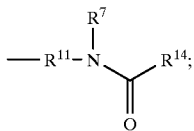

wherein $R^3$ is selected from hydrido, alkyl, alkylaminoalkyl, aralkyl, and heterocycloalkyl;
wherein $R^4$ is selected from hydrido, alkyl, cycloalkyl, cycloalkylalkyl, aryl, heterocyclo, aralkyl, heterocycloalkyl,

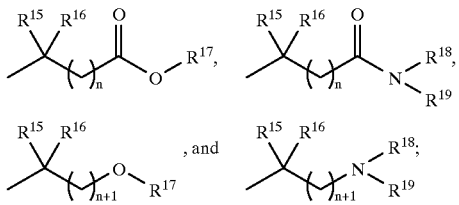

wherein n is 0–6, inclusive;
wherein $R^5$ and $R^6$ are independently selected from hydrido, alkyl, cycloalkyl, cycloalkylalkyl, aryl, aralkyl, heterocyclo, heterocycloalkyl, alkylaminoalkyl, aralkylaminoalkyl, alkoxyalkyl, and aralkoxyalkyl;
wherein $R^7$, $R^{12}$ and $R^{23}$ are independently selected from hydrido, alkyl and aralkyl;
wherein $R^8$, $R^9$ and $R^{14}$ are independently selected from hydrido, alkyl, cycloalkyl, cycloalkylalkyl, haloalkyl, aminoalkyl, alkylaminoalkyl, carboxyalkyl, aminocarbonylalkyl, alkylaminocarbonylalkyl, hydroxyalkyl, alkoxyalkyl, aralkoxyalkyl, alkylsulfonylalkyl, alkylsulfinylalkyl, alkylthioalkyl, aryl, aralkyl, heterocyclo, and heterocycloalkyl;
wherein $R^{10}$ is selected from alkyl, haloalkyl, alkylaminoalkyl, carboxyalkyl, aminocarbonylalkyl, alkylaminocarbonylalkyl, aralkoxyalkyl, alkoxyalkyl, cycloalkyl, cycloalkylalkyl, alkylsulfonylalkyl, alkylsulfinylalkyl, alkylthioalkyl, aryl, aralkyl, heterocyclo, and heterocycloalkyl;
wherein $R^{11}$ is alkylene;
wherein $R^{13}$ is selected from amino, alkyl, alkylamino, alkylaminoalkyl and aryl;
wherein $R^{15}$ is selected from hydrido, alkyl, hydroxyalkyl, alkoxyalkyl, aralkoxyalkyl, alkylaminoalkyl and N-aryl-N-alkylaminoalkyl;
wherein $R^{16}$ is selected from hydrido, alkyl, cycloalkyl, cycloalkylalkyl, haloalkyl, guanidinylalkyl, carboxyalkyl, hydroxyalkyl, alkoxyalkyl, aralkoxyalkyl, alkylthioalkyl, alkylsulfinylalkyl, alkylsulfonylalkyl, aryl, heterocyclo, aralkyl, heterocycloalkyl,

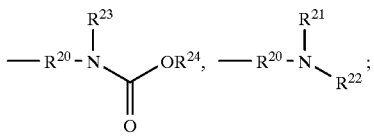

-continued

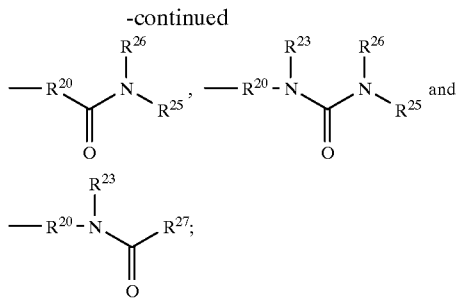

or wherein $R^{15}$ and $R^{16}$ together form cycloalkyl;
wherein $R^{17}$ is selected from hydrido, alkyl, cycloalkyl and aralkyl;
wherein $R^{18}$ and $R^{19}$ are independently selected from hydrido, alkyl, alkenyl, cycloalkyl, cycloalkylalkyl, aryl, heterocyclo, aralkyl, heterocycloalkyl, and alkylaminoalkyl;
wherein $R^{20}$ is alkylene;
wherein $R^{21}$, $R^{22}$, $R^{25}$, and $R^{26}$ are independently selected from hydrido, alkyl, cycloalkyl, cycloalkylalkyl, aminoalkyl, alkylaminoalkyl, hydroxyalkyl, alkoxyalkyl, aralkoxyalkyl, aryl, heterocyclo, aralkyl, heterocycloalkyl;
wherein $R^{24}$ is selected from alkyl, cycloalkyl, cycloalkylalkyl, alkylaminoalkyl, aralkoxyalkyl, alkoxyalkyl, aryl, aralkyl, heterocyclo, and heterocycloalkyl; and
wherein $R^{27}$ is selected from hydrido, alkyl, cycloalkyl, cycloalkylalkyl, alkylaminoalkyl, aminoalkyl, carboxyalkyl, aminocarbonylalkyl, hydroxyalkyl, aralkoxyalkyl, alkoxyalkyl, aryl, aralkyl, heterocyclo, and heterocycloalkyl;
or a pharmaceutically-acceptable salt or tautomer thereof.

14. The method of claim 13 wherein $R^1$ is a lower alkyl; wherein $R^2$ is a substituent selected from lower alkyl,

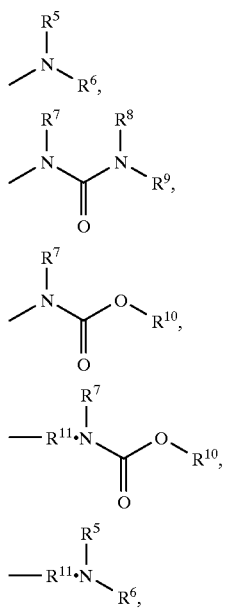

-continued

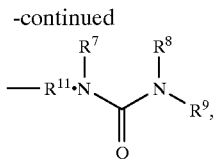

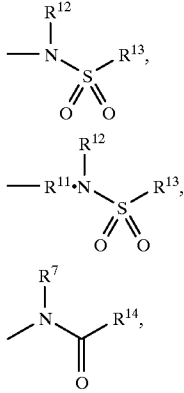

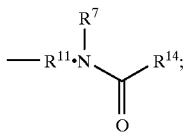

and

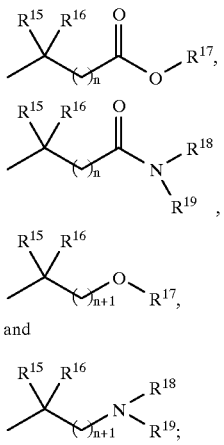

wherein $R^3$ is selected from hydrido, lower alkyl, lower alkylaminoalkyl, lower aralkyl, and lower heterocycloalkyl;
wherein $R^4$ is selected from hydrido, lower alkyl, lower cycloalkyl, lower cycloalkylalkyl, aryl, heterocyclo, lower aralkyl, lower heterocycloalkyl, wherein n is 0–6, inclusive; wherein $R^5$ and $R^6$ are independently selected from hydrido, lower alkyl, lower cycloalkyl, lower cycloalkylalkyl, aryl, lower aralkyl, heterocyclo, lower heterocycloalkyl, lower alkylaminoalkyl, lower aralkylaminoalkyl, lower alkoxyalkyl, and lower aralkoxyalkyl; wherein $R^7$, $R^{12}$ and $R^{23}$ are independently selected from hydrido, lower alkyl and lower aralkyl; wherein $R^8$, $R^9$ and $R^{14}$ are independently selected from hydrido, lower alkyl, lower cycloalkyl, lower cycloalkylalkyl, lower haloalkyl, lower aminoalkyl, lower alkylaminoalkyl, lower carboxyalkyl, lower aminocarbonylalkyl, lower alkylaminocarbonylalkyl, lower hydroxyalkyl, lower alkoxyalkyl, lower aralkoxyalkyl, lower alkylsulfonylalkyl, lower alkylsulfinylalkyl, lower alkylthioalkyl, aryl, lower aralkyl, heterocyclo, and lower heterocycloalkyl; wherein $R^{10}$ is selected from lower alkyl, lower haloalkyl, lower alkylaminoalkyl, lower carboxyalkyl, lower aminocarbonylalkyl, lower alkylaminocarbonylalkyl, lower aralkoxyalkyl, lower alkoxyalkyl, lower cycloalkyl, lower cycloalkylalkyl, lower alkylsulfonylalkyl, lower alkylsulfinylalkyl, lower alkylthioalkyl, aryl, lower aralkyl, heterocyclo, and lower heterocycloalkyl; wherein $R^{11}$ is lower alkylene; wherein $R^{13}$ is selected from amino, lower alkyl, lower alkylamino, lower alkylaminoalkyl and aryl; wherein $R^{15}$ is selected from hydrido, lower alkyl, lower hydroxyalkyl, lower alkoxyalkyl, lower aralkoxyalkyl, lower alkylaminoalkyl and lower N-aryl-N-alkylaminoalkyl; wherein $R^{16}$ is selected from hydrido, lower alkyl, lower cycloalkyl, lower cycloalkylalkyl, lower haloalkyl, lower guanidinylalkyl, lower carboxyalkyl, lower hydroxyalkyl, lower alkoxyalkyl, lower aralkoxyalkyl, lower alkylthioalkyl, lower alkylsulfinylalkyl, lower alkylsulfonylalkyl, aryl, lower heterocyclo, lower aralkyl, lower heterocycloalkyl,

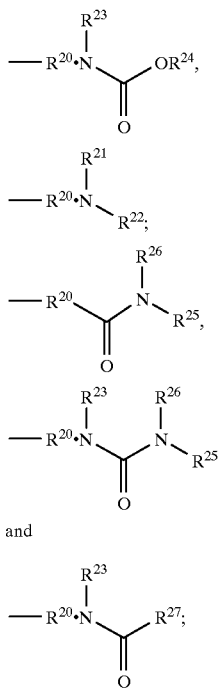

and or wherein $R^{15}$ and $R^{16}$ together form; wherein $R^{17}$ is selected from hydrido, lower alkyl, lower cycloalkyl and lower aralkyl; wherein $R^{18}$ and $R^{19}$ are independently selected from hydrido, lower alkyl, lower alkenyl, lower cycloalkyl, lower cycloalkylalkyl, aryl, heterocyclo, lower aralkyl, lower heterocycloalkyl, and lower alkylaminoalkyl, wherein $R^{20}$ is lower alkylene; wherein $R^{21}$, $R^{22}$, $R^{25}$, and $R^{26}$ are independently selected from hydrido, lower alkyl, lower cycloalkyl, lower cycloalkylalkyl, lower aminoalkyl, lower alkylaminoalkyl, lower hydroxyalkyl, lower alkoxyalkyl, lower aralkoxyalkyl, aryl, heterocyclo, lower aralkyl, lower heterocycloalkyl; wherein $R^{24}$ is selected from lower alkyl, lower cycloalkyl, lower cycloalkylalkyl, lower alkylaminoalkyl, lower aralkoxyalkyl, lower alkoxyalkyl, aryl, lower aralkyl, heterocyclo, and lower heterocycloalkyl; and wherein $R^{27}$ is selected from hydrido, lower alkyl, lower cycloalkyl, lower cycloalkylalkyl, lower alkylaminoalkyl, lower aminoalkyl, lower carboxyalkyl, lower aminocarbonylalkyl, lower hydroxyalkyl, lower aralkoxyalkyl, lower alkoxyalkyl, aryl, lower aralkyl, heterocyclo, and lower heterocycloalkyl; or a pharmaceutically-acceptable salt or tautomer thereof.

15. The method of claim 14 wherein $R^1$ is a lower alkyl; wherein $R^2$ is a substituent selected from lower alkyl,

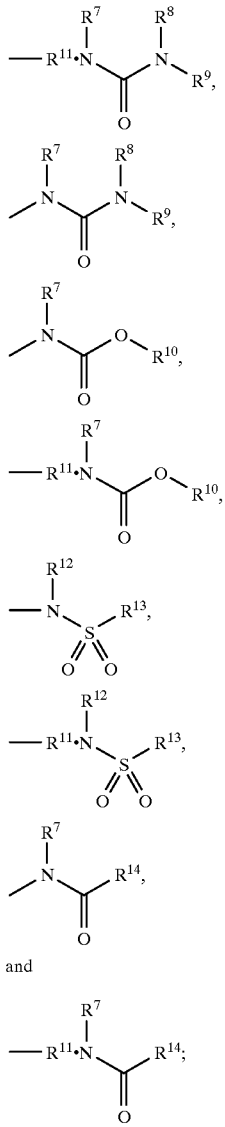

and wherein $R^3$ is selected from hydrido, lower alkyl, lower alkylaminoalkyl, lower aralkyl, and lower heterocycloalkyl; wherein $R^4$ is selected from hydrido, lower alkyl, lower cycloalkyl, lower cycloalkylalkyl, aryl, heterocyclo, lower aralkyl, lower heterocycloalkyl,

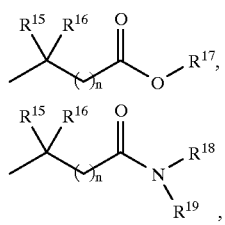

-continued

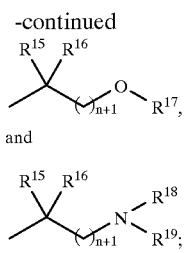

and

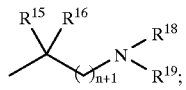

wherein n is 0–6, inclusive; wherein $R^5$ and $R^6$ are independently selected from hydrido, lower alkyl, lower cycloalkyl, lower cycloalkylalkyl, aryl, lower aralkyl, heterocyclo, lower heterocycloalkyl, lower alkylaminoalkyl, lower aralkylaminoalkyl, lower alkoxyalkyl, and lower aralkoxyalkyl; wherein $R^7$, $R^{12}$ and $R^{23}$ are independently selected from hydrido, lower alkyl and lower aralkyl; wherein $R^8$, $R^9$ and $R^{14}$ are independently selected from hydrido, lower alkyl, lower cycloalkyl, lower cycloalkylalkyl, lower haloalkyl, lower aminoalkyl, lower alkylaminoalkyl, lower carboxyalkyl, lower aminocarbonylalkyl, lower alkylaminocarbonylalkyl, lower hydroxyalkyl, lower alkoxyalkyl, lower aralkoxyalkyl, lower alkylsulfonylalkyl, lower alkylsulfinylalkyl, lower alkylthioalkyl, aryl, lower aralkyl, heterocyclo, and lower heterocycloalkyl; wherein Rlc is selected from lower alkyl, lower haloalkyl, lower alkylaminoalkyl, lower carboxyalkyl, lower aminocarbonylalkyl, alkylaminocarbonylalkyl, lower aralkoxyalkyl, lower alkoxyalkyl, lower cycloalkyl, lower cycloalkylalkyl, lower alkylsulfonylalkyl, lower alkylsulfinylalkyl, lower alkylthioalkyl, aryl, lower aralkyl, heterocyclo, and lower heterocycloalkyl; wherein $R^{11}$ is lower alkylene; wherein $R^{13}$ is selected from amino, lower alkyl, lower alkylamino, lower alkylaminoalkyl and aryl; wherein $R^{15}$ is selected from hydrido, and lower alkyl; wherein $R^{16}$ is selected from hydrido, lower alkyl, lower cycloalkyl, lower cycloalkylalkyl, lower haloalkyl, lower guanidinylalkyl, lower carboxyalkyl, lower hydroxyalkyl, lower alkoxyalkyl, lower aralkoxyalkyl, lower alkylthioalkyl, lower alkylsulfinylalkyl, lower alkylsulfonylalkyl, aryl, heterocyclo, lower aralkyl, lower heterocycloalkyl,

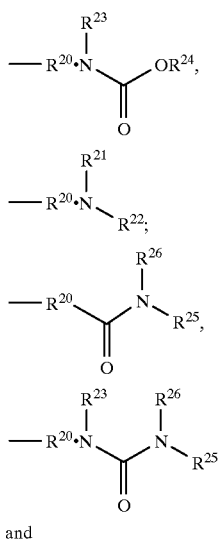

and

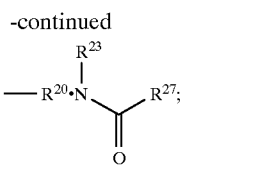

or wherein $R^{15}$ and $R^{16}$ together form lower cycloalkyl; wherein $R^{17}$ is selected from hydrido, lower alkyl, lower cycloalkyl and lower aralkyl; wherein $R^{18}$ and $R^{19}$ are independently selected from hydrido, lower alkyl, lower alkenyl, lower cycloalkyl, lower cycloalkylalkyl, aryl, heterocyclo, lower aralkyl, lower heterocycloalkyl, and lower alkylaminoalkyl; wherein $R^{20}$ is lower alkylene; wherein $R^{21}$, $R^{22}$, $R^{25}$, and $R^{26}$ are independently selected from hydrido, lower alkyl, lower cycloalkyl, lower cycloalkylalkyl, lower aminoalkyl, lower alkylaminoalkyl, lower hydroxyalkyl, lower alkoxyalkyl, lower aralkoxyalkyl, aryl, heterocyclo, lower aralkyl, lower heterocycloalkyl; wherein $R^{24}$ is selected from lower alkyl, lower cycloalkyl, lower cycloalkylalkyl, lower alkylaminoalkyl, lower aralkoxyalkyl, lower alkoxyalkyl, aryl, lower aralkyl, heterocyclo, and lower heterocycloalkyl; and wherein $R^{27}$ is selected from hydrido, lower alkyl, lower cycloalkyl, lower cycloalkylalkyl, lower alkylaminoalkyl, lower aminoalkyl, lower carboxyalkyl, lower aminocarbonylalkyl, lower hydroxyalkyl, lower aralkoxyalkyl, lower alkoxyalkyl, aryl, lower aralkyl, heterocyclo, and lower heterocycloalkyl; or a pharmaceutically-acceptable salt or tautomer thereof.

16. The method of claim 15 wherein $R^1$ is a lower alkyl; wherein $R^2$ is a substituent selected from lower alkyl,

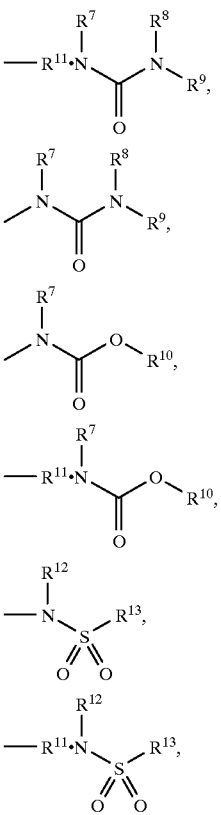

-continued

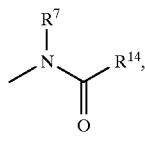

and

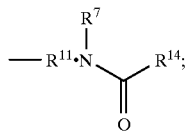

wherein R³ is selected from hydrido, lower alkyl, and lower aralkyl; wherein R⁴ is selected from

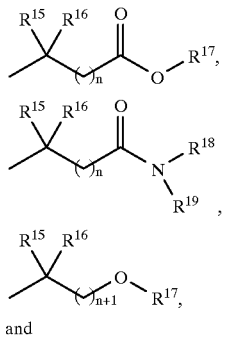

and

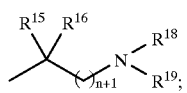

wherein n is 0–4; wherein $R^5$ and $R^6$ are independently selected from hydrido, lower alkyl, lower cycloalkyl, lower cycloalkylalkyl, aryl, lower aralkyl, heterocyclo, lower heterocycloalkyl, lower alkylaminoalkyl, lower aralkylaminoalkyl, lower alkoxyalkyl, and lower aralkoxyalkyl; wherein $R^7$, $R^{12}$ and $R^{23}$ are independently selected from hydrido, lower alkyl and lower aralkyl; wherein $R^8$, $R^9$ and $R^{14}$ are independently selected from hydrido, lower alkyl, lower cycloalkyl, lower cycloalkylalkyl, lower haloalkyl, lower aminoalkyl, lower alkylaminoalkyl, lower carboxyalkyl, lower aminocarbonylalkyl, lower alkylaminocarbonylalkyl, lower hydroxyalkyl, lower alkoxyalkyl, lower aralkoxyalkyl, lower alkylsulfonylalkyl, lower alkylsulfinylalkyl, lower alkylthioalkyl, aryl, lower aralkyl, heterocyclo, and lower heterocycloalkyl; wherein $R^{10}$ is selected from lower alkyl, lower haloalkyl, lower alkylaminoalkyl, lower carboxyalkyl, lower aminocarbonylalkyl, alkylaminocarbonylalkyl, lower aralkoxyalkyl, lower alkoxyalkyl, lower cycloalkyl, lower cycloalkylalkyl, lower alkylsulfonylalkyl, lower alkylsulfinylalkyl, lower alkylthioalkyl, aryl, lower aralkyl, heterocyclo, and lower heterocycloalkyl; wherein $R^{11}$ is lower alkylene; wherein $R^{13}$ is selected from amino, lower alkyl, lower alkylamino, lower alkylaminoalkyl and aryl; wherein $R^{15}$ is selected from hydrido, and lower alkyl; wherein $R^{16}$ is selected from hydrido, lower alkyl, lower cycloalkyl, lower cycloalkylalkyl, lower haloalkyl, lower guanidinylalkyl, lower carboxyalkyl, lower hydroxyalkyl, lower alkoxyalkyl, lower aralkoxyalkyl, lower alkylthioalkyl, lower alkylsulfinylalkyl, lower alkylsulfonylalkyl, aryl, heterocyclo, lower aralkyl, lower heterocycloalkyl,

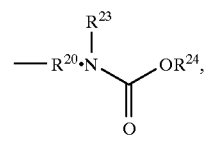

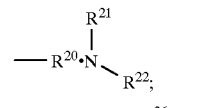

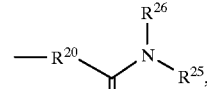

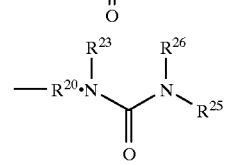

and

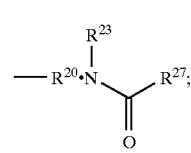

or wherein $R^{15}$ and $R^{16}$ together form lower cycloalkyl; wherein $R^{17}$ is selected from hydrido, lower alkyl, lower cycloalkyl and lower aralkyl; wherein $R^{18}$ and $R^{19}$ are independently selected from hydrido, lower alkyl, lower alkenyl, lower cycloalkyl, lower cycloalkylalkyl, aryl, heterocyclo, lower aralkyl, lower heterocycloalkyl, and lower alkylaminoalkyl; wherein $R^{20}$ is lower alkylene; wherein $R^{21}$, $R^{22}$, $R^{25}$, and $R^{26}$ are independently selected from hydrido, lower alkyl, lower cycloalkyl, lower cycloalkylalkyl, lower aminoalkyl, lower alkylaminoalkyl, lower hydroxyalkyl, lower alkoxyalkyl, lower aralkoxyalkyl, aryl, heterocyclo, lower aralkyl, lower heterocycloalkyl; wherein $R^{24}$ is selected from lower alkyl, lower cycloalkyl, lower cycloalkylalkyl, lower alkylaminoalkyl, lower aralkoxyalkyl, lower alkoxyalkyl, aryl, lower aralkyl, heterocyclo, and lower heterocycloalkyl; and wherein $R^{27}$ is selected from hydrido, lower alkyl, lower cycloalkyl, lower cycloalkylalkyl, lower alkylaminoalkyl, lower aminoalkyl, lower carboxyalkyl, lower aminocarbonylalkyl, lower hydroxyalkyl, lower aralkoxyalkyl, lower alkoxyalkyl, aryl, lower aralkyl, heterocyclo, and lower heterocycloalkyl; or a pharmaceutically-acceptable salt or tautomer thereof.

17. The method of claim 16 wherein R¹ is a substituent selected from methyl, ethyl, n-propyl, isopropyl, n-butyl, isobutyl, sec-butyl, and tert-butyl; wherein R² is a substituent selected from methyl, ethyl, n-propyl, isopropyl, n-butyl, isobutyl, sec-butyl, tert-butyl, pentyl, hexyl,

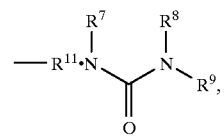

-continued

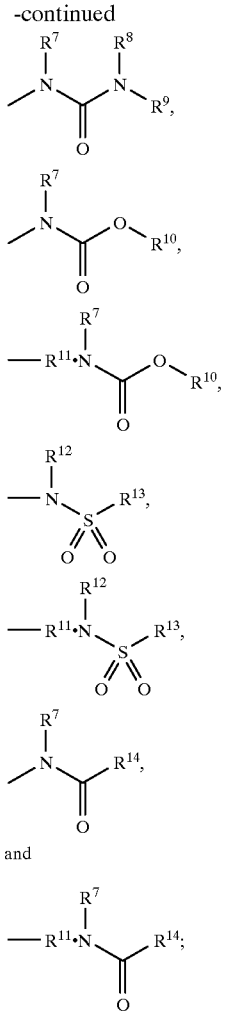

wherein R³ is selected from hydrido, methyl, ethyl, n-propyl, isopropyl, n-butyl, isobutyl, sec-butyl, tert-butyl, pentyl, hexyl, benzyl, phenylethyl and diphenylmethyl; wherein R⁴ is selected from

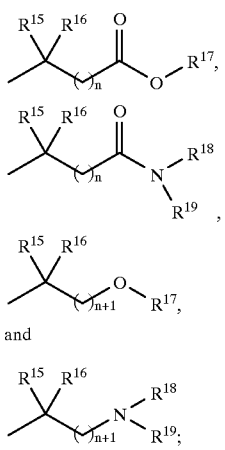

wherein n is 0–4, inclusive; wherein R⁵ and R⁶ are independently selected from hydrido, methyl, ethyl, n-propyl, isopropyl, n-butyl, isobutyl, sec-butyl, tert-butyl, pentyl, hexyl, cyclopropyl, cyclobutyl, cyclopentyl, cyclohexyl, cyclopropylmethyl, cyclobutylmethyl, phenyl, benzyl, furyl, thienyl, thiazolyl, pyrrolyl, furylmethyl, thienylethyl, thiazolylmethyl, pyrrolylmethyl, methylaminomethyl, N,N-dimethylaminomethyl, N,N-dimethylaminoethyl, N,N-dimethylaminohexyl, N,N-diethylaminobutyl, benzylaminomethyl, methoxymethyl, methoxyethyl, ethoxyethyl, methoxybutyl, methoxypropyl, and benzyloxymethyl; wherein R⁷, R¹² and R²³ are independently selected from hydrido, methyl, ethyl, n-propyl, isopropyl, n-butyl, isobutyl, sec-butyl, tert-butyl, pentyl, hexyl, benzyl and phenylethyl; wherein R⁸, R⁹ and R¹⁴ are independently selected from hydrido, methyl, ethyl, n-propyl, isopropyl, n-butyl, isobutyl, sec-butyl, tert-butyl, pentyl, hexyl, cyclopropyl, cyclobutyl, cyclopentyl, cyclohexyl, cyclopropylpropyl, cyclobutylethyl, cyclopentylmethyl, cyclohexylmethyl, fluoromethyl, difluoromethyl, trifluoromethyl, chloromethyl, dichloromethyl, trichloromethyl, trichloromethyl, pentafluoroethyl, heptafluoropropyl, difluorochloromethyl, dichlorofluoromethyl, difluoroethyl, difluoropropyl, dichloroethyl and dichloropropyl, methylamino, ethylamino, propylamino, N,N-dimethylaminomethyl, N,N-dimethylaminoethyl, N,N-dimethylaminopropyl, N,N-dimethylaminohexyl, N,N-diethylaminobutyl, N,N-diethylaminoethyl, N,N-diethylaminopropyl, carboxymethyl, carboxyethyl, carboxypropyl, aminocarbonylmethyl, N,N-dimethylaminocarbonylmethyl, hydroxymethyl, hydroxypropyl, methoxymethyl, methoxyethyl, ethoxyethyl, methoxybutyl, methoxypropyl, benzyloxymethyl, methylsulfonylmethyl, methylsulfinylmethyl, methylthiomethyl, phenyl optionally substituted at a substitutable position with one or more substituents selected independently from methyl, ethyl, n-propyl, isopropyl, n-butyl, isobutyl, sec-butyl, tert-butyl, pentyl, hexyl, methoxy, ethoxy, propoxy, isopropoxy, butoxy, tert-butoxy, amino, fluoro, chloro, bromo, iodo, N,N-dimethylaminomethyl, N,N-dimethylaminohexyl, N,N-diethylaminobutyl, N,N-dimethylaminoethyl, N,N-diethylaminoethyl, N,N-dimethylamino, and N,N-diethylamino, lower aralkyl selected from benzyl, naphthylmethyl, phenylethyl, and phenylisopropyl, wherein the phenyl ring is optionally substituted at a substitutable position with one or more substituents selected independently from methyl, ethyl, n-propyl, isopropyl, n-butyl, isobutyl, sec-butyl, tert-butyl, pentyl, hexyl, methoxy, ethoxy, propoxy, isopropoxy, butoxy, tert-butoxy, amino, fluoro, chloro, bromo, iodo, N,N-dimethylaminomethyl, N,N-dimethylaminohexyl, N N-diethylaminobutyl, N,N-dimethylaminoethyl, N,N-diethylaminoethyl, N,N-dimethylamino, and N,N-diethylamino, heterocyclo selected from furyl, pyrrolyl, pyridyl, oxazolyl, pyrazolyl, isoxazolyl, thienyl, and thiazolyl, and lower heterocycloalkyl selected from thienylmethyl, morpholinylethyl, morpholinylmethyl, piperazinylethyl, piperdinylethyl, piperdinylmethyl, pyrrolidinylethyl, pyrrolidinylmethyl, pyrrolidinylpropyl, imidazolylethyl, oxazolylmethyl, thiazolylmethyl, furylmethyl, thienylethyl, and thiazolylmethyl, wherein the heterocyclo moiety may be substituted at a substitutable position with a radical selected from fluoro, chloro, bromo, iodo, methyl, ethyl, n-propyl, isopropyl, n-butyl, isobutyl, sec-butyl, tert-butyl, pentyl, and hexyl; wherein R¹⁰ is selected from methyl, ethyl, n-propyl, isopropyl, n-butyl, isobutyl, sec-butyl, tert-butyl, pentyl, hexyl, fluoromethyl, difluoromethyl, trifluoromethyl, chloromethyl, dichloromethyl, trichloromethyl, trichloromethyl, pentafluoroethyl, heptafluoropropyl, difluorochloromethyl, dichlorofluoromethyl, difluoroethyl, difluoropropyl, dichloroethyl and dichloropropyl, N,N-dimethylaminomethyl, N,N-dimethylaminoethyl, N,N-dimethylaminopropyl, N,N-dimethylaminohexyl, N,N-diethylaminoethyl, N,N-diethylaminopropyl, N,N-diethylaminobutyl, carboxymethyl, carboxyethyl, carboxypropyl, aminocarbonylmethyl, N,N-dimethylaminocarbonylmethyl, benzyloxymethyl, methoxymethyl, methoxyethyl, ethoxyethyl, methoxybutyl, methoxypropyl, cyclopropyl, cyclobutyl, cyclopentyl, cyclohexyl, cyclopropylpropyl, cyclobutylethyl, cyclopentylmethyl, cyclohexylmethyl, methylsulfonylmethyl, methylsulfinylmethyl, methylthiomethyl, phenyl optionally substituted at a substitutable position with one or more substituents selected independently from methyl, ethyl, n-propyl, isopropyl, n-butyl, isobutyl, sec-butyl, tert-butyl, pentyl, hexyl, methoxy, ethoxy, propoxy, isopropoxy, butoxy, tert-butoxy, amino, fluoro, chloro, bromo, iodo, N,N-dimethylaminomethyl, N,N-dimethylaminohexyl, N,N-diethylaminobutyl, N,N-dimethylaminoethyl, N,N-diethylaminoethyl, N,N-dimethylamino, and N,N-diethylamino, lower aralkyl selected from benzyl, phenethyl, naphthylmethyl, wherein the aryl ring is optionally substituted at a substitutable position with one or more substituents selected independently from methyl, ethyl, n-propyl, isopropyl, n-butyl, isobutyl, sec-butyl, tert-butyl, pentyl, hexyl, methoxy, ethoxy, propoxy, isopropoxy, butoxy, tert-butoxy, amino, fluoro, chloro, bromo, iodo, N,N-dimethylaminomethyl, N,N-dimethylaminoethyl, N,N-dimethylaminohexyl, N,N-diethylaminoethyl, N,N-diethylaminobutyl, N,N-dimethylamino, N,N-dimethylamino, and N,N-diethylamino, heterocyclo selected from furyl, thienyl, and thiazolyl, and lower heterocycloalkyl selected from thienylmethyl, morpholinylethyl, morpholinylmethyl, piperazinylethyl, piperdinylethyl, piperdinylmethyl, pyrrolidinylethyl, pyrrolidinylmethyl, pyrrolidinylpropyl, imidazolylethyl, oxazolylmethyl, thiazolylmethyl, furylmethyl, thienylethyl, and thiazolylmethyl, wherein the heterocyclo moiety may be substituted at a substitutable position with a radical selected from fluoro, chloro, bromo, iodo, methyl, ethyl, n-propyl, isopropyl, n-butyl, isobutyl, sec-butyl, tert-butyl, pentyl, and hexyl; wherein $R^{11}$ is selected from methylene, ethylene, n-propylene, isopropylene, n-butylene, isobutylene, sec-butylene, pentylene, and hexylene; wherein $R^{13}$ is selected from phenyl, amino, methyl, ethyl, n-propyl, isopropyl, n-butyl, isobutyl, sec-butyl, tert-butyl, pentyl, hexyl N,N-dimethylaminomethyl, N,N-dimethylaminoethyl, N,N-dimethylaminohexyl, N,N-diethylaminoethyl, N,N-diethylaminobutyl, N,N-dimethylamino, N,N-dimethylamino, and N,N-diethylamino; wherein $R^{15}$ is selected from hydrido, methyl, ethyl, n-propyl, isopropyl, n-butyl, isobutyl, sec-butyl, tert-butyl, pentyl, and hexyl; wherein $R^{16}$ is selected from hydrido, methyl, ethyl, n-propyl, isopropyl, n-butyl, isobutyl, sec-butyl, tert-butyl, pentyl, hexyl, hydroxymethyl, hydroxyethyl, hydroxypropyl, hydroxybutyl, mercaptoethyl, methoxymethyl, methoxyethyl, ethoxyethyl, methoxybutyl, methoxypropyl, phenylmethoxymethyl, aminomethyl, aminohexyl, aminobutyl, N,N-dimethylaminomethyl, N,N-dimethylaminoethyl, N,N-dimethylaminopropyl, N,N-dimethylaminohexyl, N,N-diethylaminopropyl, N,N-diethylaminobutyl, mercaptomethyl, methylthioethyl, methylsulfonylethyl, phenyl optionally substituted at a substitutable position with one or more substituents independently selected from methyl, ethyl, n-propyl, isopropyl, n-butyl, isobutyl, sec-butyl, tert-butyl, pentyl, hexyl, hydroxy, methoxy, ethoxy, propoxy, isopropoxy, butoxy, tert-butoxy, fluoro, chloro, bromo, iodo, nitro, amino, N,N-dimethylaminomethyl, N,N-dimethylaminoethyl, N,N-dimethylaminopropyl, N,N-dimethylaminohexyl, N,N-diethylaminopropyl, N,N-diethylaminobutyl, methylamino, and hexylamino, heterocyclo selected from pyridyl, thienyl, morpholinyl, piperidinyl, indolyl, quinolinyl, pyrrolidinyl, furyl, oxazolyl, thiazolyl, imidazolyl, pyrazolyl, and isoxazolyl, optionally substituted at a substitutable position with one or more substituents independently selected from methyl, ethyl, n-propyl, isopropyl, n-butyl, isobutyl, sec-butyl, tert-butyl, pentyl, hexyl, methoxy, ethoxy, propoxy, butoxy, tert-butoxy, fluoro, chloro, bromo, iodo, amino, oxo, N,N-dimethylamino, and N,N-diethylamino, lower aralkyl selected from benzyl, phenethyl and naphthylmethyl, wherein the aryl ring is optionally substituted at a substitutable position with one or more substituents independently selected from methyl, ethyl, n-propyl, isopropyl, n-butyl, isobutyl, sec-butyl, tert-butyl, pentyl, hexyl, hydroxy, methoxy, ethoxy, propoxy, butoxy, tert-butoxy, fluoro, chloro, bromo, iodo, nitro, amino, methylamino, N,N-dimethylaminomethyl, N,N-dimethylaminoethyl, N,N-dimethylaminopropyl, N,N-dimethylaminohexyl, N,N-diethylaminopropyl, N,N-diethylaminobutyl, ethylamino, N,N-dimethylamino, N,N-dimethylamino, and N,N-diethylamino, lower heterocycloalkyl selected from pyrrolidinylethyl, furylmethyl, pyrrolidinylmethyl, piperazinylmethyl, piperazinylethyl, imidazolylmethyl, indolylmethyl, morpholinylmethyl, morpholinylethyl, quinolinylmethyl, thienylmethyl, thiazolylethyl and thiazolylmethyl, wherein the heterocyclo moiety may be substituted at a substitutable position with a radical selected from fluoro, chloro, bromo, iodo, methyl, ethyl, n-propyl, isopropyl, n-butyl, isobutyl, sec-butyl, tert-butyl, pentyl, and hexyl,

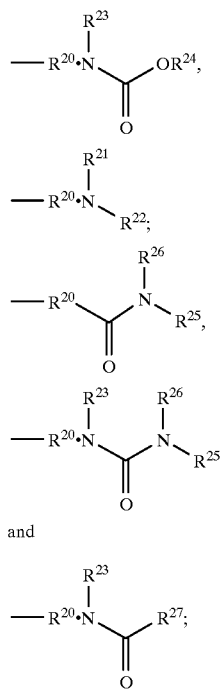

and or wherein $R^{15}$ and $R^{16}$ together form a ring selected from cyclopropyl, cyclobutyl, cyclopentyl and cyclohexyl;

wherein $R^{17}$ is selected from hydrido, methyl, ethyl, n-propyl, isopropyl, n-butyl, isobutyl, sec-butyl, tert-butyl, pentyl, hexyl, and benzyl;

wherein $R^{18}$ and $R^{19}$ are independently selected from hydrido, methyl, ethyl, n-propyl, isopropyl, n-butyl, isobutyl, sec-butyl, tert-butyl, pentyl, hexyl, butenyl, propenyl, N,N-dimethylaminomethyl, N,N-dimethylaminoethyl, N,N-dimethylaminopropyl, N,N-dimethylaminohexyl, N,N-diethylaminopropyl, N,N-diethylaminobutyl, butenyl, phenyl, pyridyl, thienyl, morpholinyl, piperidinyl, indolyl, quinolinyl, pyrrolidinyl, furyl, oxazolyl, thiazolyl, imidazolyl, pyrazolyl, isoxazolyl, benzyl, phenethyl, lower heterocycloalkyl selected from furylmethyl, thienylmethyl, morpholinylethyl, piperazinylethyl, piperdinylethyl, pyrrolidinylethyl, pyrrolidinylpropyl, imidazolylethyl, oxazolylmethyl, and thiazolylmethyl, wherein the heterocyclo moiety may be substituted at a substitutable position with a radical selected from fluoro, chloro, bromo, iodo, methyl, ethyl, n-propyl, isopropyl, n-butyl, isobutyl, sec-butyl, tert-butyl, pentyl, hexyl, methylaminomethyl, methylaminohexyl, ethylaminobutyl, N,N-dimethylaminomethyl, N,N-dimethylaminoethyl, N,N-dimethylaminohexyl, and N,N-diethylaminobutyl; wherein $R^{20}$ is selected from methylene, ethylene, n-propylene, isopropylene, n-butylene, isobutylene, sec-butylene, pentylene, and hexylene; wherein $R^{21}$, $R^{22}$, $R^{25}$, and $R^{26}$ are independently selected from hydrido, methyl, ethyl, n-propyl, isopropyl, n-butyl, isobutyl, sec-butyl, tert-butyl, pentyl, hexyl, propenyl, butenyl, phenyl optionally substituted at a substitutable position with one or more substituents selected independently from methyl, ethyl, n-propyl, isopropyl, n-butyl, isobutyl, sec-butyl, tert-butyl, pentyl, hexyl, methoxy, ethoxy, propoxy, isopropoxy, butoxy, tert-butoxy, amino, fluoro, chloro, bromo, iodo, N,N-dimethylaminomethyl, N,N-dimethylaminohexyl, N,N-diethylaminobutyl, N,N-dimethylaminoethyl, N,N-diethylaminoethyl, N,N-dimethylamino, and N,N-diethylamino, pyridyl, thienyl, morpholinyl, piperidinyl, indolyl, quinolinyl, pyrrolidinyl, furyl, oxazolyl, thiazolyl, imidazolyl, pyrazolyl, and isoxazolyl, benzyl, phenethyl, lower heterocycloalkyl selected from furylmethyl, thienylmethyl, morpholinylethyl, piperazinylethyl, piperdinylethyl, pyrrolidinylethyl, pyrrolidinylpropyl, imidazolylethyl, oxazolylmethyl, and thiazolylmethyl, wherein the heterocyclo moiety may be substituted at a substitutable position with a radical selected from fluoro, chloro, bromo, iodo, methyl, ethyl, n-propyl, isopropyl, n-butyl, isobutyl, sec-butyl, tert-butyl, pentyl, hexyl, methylaminomethyl, methylaminohexyl, ethylaminobutyl, N,N-dimethylaminomethyl, N,N-dimethylaminoethyl, N,N-dimethylaminohexyl, and N,N-diethylaminobutyl; wherein $R^{24}$ is selected from methyl, ethyl, n-propyl, isopropyl, n-butyl, isobutyl, sec-butyl, tert-butyl, pentyl, hexyl, N,N-dimethylaminomethyl, N,N-dimethylaminoethyl, N,N-dimethylaminopropyl, N,N-dimethylaminohexyl, N,N-diethylaminopropyl, N,N-diethylaminobutyl, methoxymethyl, methoxyethyl, ethoxyethyl, methoxybutyl, methoxypropyl, benzyloxyethyl, benzyloxymethyl, cyclopropyl, cyclobutyl, cyclopentyl, cyclohexyl, cyclopropylmethyl, cyclobutylmethyl, cyclopentylethyl, cyclohexylpropyl, phenyl optionally substituted at a substitutable position with one or more substituents selected independently from methyl, ethyl, n-propyl, isopropyl, n-butyl, isobutyl, sec-butyl, tert-butyl, pentyl, hexyl, methoxy, ethoxy, propoxy, isopropoxy, butoxy, tert-butoxy, amino, fluoro, chloro, bromo, iodo, N,N-dimethylaminomethyl, N,N-dimethylaminohexyl, N,N-diethylaminobutyl, N,N-dimethylaminoethyl, N,N-diethylaminoethyl, N,N-dimethylamino, and N,N-diethylamino, heterocyclo selected from pyridyl, thienyl, morpholinyl, pyrimidyl, indolyl, isoquinolyl, quinolyl, tetrahydroquinolinyl, piperidinyl, pyrrolidinyl, furyl, oxazolyl, thiazolyl, imidazolyl, pyrazolyl, and isoxazolyl, wherein the heterocyclo is optionally substituted at a substitutable position with one or more substituents selected independently from lower alkyl, lower alkoxy, amino, halo, lower dialkylaminoalkyl, and lower dialkylamino, lower aralkyl selected from benzyl, phenethyl, and naphthylmethyl, wherein the aryl ring is optionally substituted at a substitutable position with one or more substituents selected independently from methyl, ethyl, n-propyl, isopropyl, n-butyl, isobutyl, sec-butyl, tert-butyl, pentyl, hexyl, methoxy, ethoxy, propoxy, butoxy, tert-butoxy, amino, fluoro, chloro, bromo, iodo, N,N-dimethylaminomethyl, N,N-dimethylaminoethyl, N,N-dimethylaminopropyl N,N-dimethylaminohexyl, N,N-diethylaminopropyl, N,N-diethylaminobutyl, N,N-dimethylamino, and N,N-diethylamino, and lower heterocycloalkyl selected from furylmethyl, pyrrolidinylmethyl, quinolinylmethyl, piperazinylmethyl, imidazolylmethyl, indolylmethyl, morpholinylmethyl, thienylmethyl, and thiazolylmethyl, wherein the heterocyclo moiety may be substituted at a substitutable position with a radical selected from fluoro, chloro, bromo, iodo, methyl, ethyl, n-propyl, isopropyl, n-butyl, isobutyl, sec-butyl, tert-butyl, pentyl, and hexyl; and wherein $R^{27}$ is selected from hydrido, methyl, ethyl, n-propyl, isopropyl, n-butyl, isobutyl, sec-butyl, tert-butyl, pentyl, hexyl, trifluoromethyl, N,N-dimethylaminomethyl, N,N-dimethylaminoethyl, N,N-dimethylaminopropyl, N,N-dimethylaminohexyl, N,N-diethylaminopropyl, N,N-diethylaminobutyl, hydroxymethyl, hydroxyethyl, hydroxypropyl, hydroxybutyl, methoxymethyl, methoxyethyl, ethoxyethyl, methoxybutyl, methoxypropyl, phenylmethoxymethyl, benzyloxyethyl, aminomethyl, aminohexyl, aminobutyl, carboxyethyl, carboxypropyl, carboxymethyl, cyclopropyl, cyclobutyl, cyclopentyl, cyclohexyl, cyclopropylmethyl, cyclobutylmethyl, cyclopentylethyl, cyclohexylpropyl, phenyl optionally substituted at a substitutable position with one or more substituents selected independently from methyl, ethyl, n-propyl, isopropyl, n-butyl, isobutyl, sec-butyl, tert-butyl, pentyl, hexyl, methoxy, ethoxy, propoxy, isopropoxy, butoxy, tert-butoxy, amino, fluoro, chloro, bromo, iodo, N,N-dimethylaminomethyl, N,N-dimethylaminohexyl, N,N-diethylaminobutyl, N,N-dimethylaminoethyl, N,N-diethylaminoethyl, N,N-dimethylamino, and N,N-diethylamino, heterocyclo selected from pyridyl, thienyl, morpholinyl, pyrimidyl, indolyl, isoquinolyl, quinolyl, tetrahydroquinolinyl, piperidinyl, pyrrolidinyl, furyl, oxazolyl, thiazolyl, imidazolyl, pyrazolyl, and isoxazolyl, wherein the heterocyclo is optionally substituted at a substitutable position with one or more substituents selected independently from lower alkyl, lower alkoxy, amino, halo, lower dialkylaminoalkyl, and lower dialkylamino, lower aralkyl selected from benzyl, phenethyl, and naphthylmethyl, wherein the aryl ring is optionally substituted at a substitutable position with one or more substituents selected independently from methyl, ethyl, n-propyl, isopropyl, n-butyl, isobutyl, sec-butyl, tert-butyl, pentyl, hexyl, methoxy, ethoxy, propoxy, butoxy, tert-butoxy, amino, fluoro, chloro, bromo, iodo, N,N-dimethylaminomethyl, N,N-dimethylaminoethyl, N,N-dimethylaminopropyl, N,N-dimethylaminohexyl, N,N-diethylaminopropyl, N,N-diethylaminobutyl, N,N-dimethylamino, and N,N-diethylamino, and lower heterocycloalkyl selected from furylmethyl, pyrrolidinylmethyl, quinolinylmethyl, piperazinylmethyl, imidazolylmethyl, indolylmethyl, morpholinylmethyl, thienylmethyl, and thiazolylmethyl, wherein the heterocyclo moiety may be substituted at a substitutable position with a radical selected from fluoro, chloro, bromo, iodo, methyl, ethyl, n-propyl, isopropyl, n-butyl, isobutyl, sec-butyl, tert-butyl, pentyl, and hexyl; or a pharmaceutically-acceptable salt or tautomer thereof.

18. The method of claim 17 wherein the compound is selected from compounds and their pharmaceutically-acceptable salts, of the group consisting of 1,1-dimethylethyl[2-[[2-(3,5-diiodo-4-methoxy phenyl)-1S-[(dimethylamino)methyl]ethyl]amino]-5-methyl-4-oxo-4H-3,1-benzoxazin-6-yl]carbamate;

1,1-dimethylethyl[2-[[1S-[(dimethylamino)methyl]-3-(methylsulfonyl)propyl]amino]-5-methyl-4-oxo-4H-3,1-benzoxazin-6-yl]carbamate;

1,1-dimethylethyl[2-[[2-(dimethylamino)-1S-methylethyl]amino]-5-methyl-4-oxo-4H-3,1-benzoxazin-6-yl]carbamate;

1,1-dimethylethyl[[2-[[2-(dimethylamino)-1S-methylethyl]amino]-5-methyl-4-oxo-4H-3,1-benzoxazin-6-yl]methyl]carbamate;

N-[6-[[(1,1-dimethylethoxy)carbonyl]amino]-5-methyl-4-oxo-4H-3,1-benzoxazin-2-yl]-3,5-diiodo-L-tyrosine, methyl ester;

N-[6-[[(1,1-dimethylethoxy)carbonyl]amino]-5-methyl-4-oxo-4H-3,1-benzoxazin-2-yl-]-3,5-diiodo-O-methyl-L-tyrosine, methyl ester;

N-[6-[[(1,1-dimethylethoxy)carbonyl]amino]-5-methyl-4-oxo-4H-3,1-benzoxazin-2-yl-]-3,5-diiodo-N,O-dimethyl-L-tyrosine, methyl ester;

3,5-dibromo-N-[6-[[(1,1-dimethylethoxy)carbonyl]amino]-5-methyl-4-oxo-4H-3,1-benzoxazin-2-yl-]-O-methyl-L-tyrosine, methyl ester;

methyl αS-[[6-[[(1,1-dimethylethoxy)carbonyl]amino]-5-methyl-4-oxo-4H-3,1-benzoxazin-2-yl]amino] thiazole-4-propanoate;

methyl αS-[[6-[[(1,1-dimethylethoxy)carbonyl]amino]-5-methyl-4-oxo-4H-3,1-benzoxazin-2-yl]amino] oxazole-4-propanoate;

methyl 4-[(aminocarbonyl)amino]-2S-[[6-[[(1,1-dimethylethoxy)carbonyl]amino]-5-methyl-4-oxo-4H-3,1-benzoxazin-2-yl]amino]butanoate;

N²-[6-[[(1,1-dimethylethoxy)carbonyl]amino]-5-methyl-4-oxo-4H-3,1-benzoxazin-2-yl]-L-asparagine, methyl ester;

N²-[6-[[(1,1-dimethylethoxy)carbonyl]amino]-5-methyl-4-oxo-4H-3,1-benzoxazin-2-yl]-L-glutamine, methyl ester;

1,1-dimethylethyl[2-[[2-(diethylamino)-1S-[(4-hydroxy-3,5-diiodophenyl)methyl]-2-oxoethyl]amino]-5-methyl-4-oxo-4H-3,1-benzoxazin-6-yl]carbamate;

1,1-dimethylethyl[2-[[2-(diethylamino)-1S-methyl-2-oxoethyl]amino]-5-methyl-4-oxo-4H-3,1-benzoxazin-6-yl]carbamate;

1,1-dimethylethyl[2-[[2-(diethylamino)-1S-[(3,5-diiodo-4-methoxyphenyl)methyl]-2-oxoethyl]amino]-5-methyl-4-oxo-4H-3,1-benzoxazin-6-yl]carbamate;

1,1-dimethylethyl[2-[[1S[(3,5-diiodo-4-methoxy phenyl) methyl]-2-[(1-methylethyl)amino]-2-oxo ethyl] amino]-5-methyl-4-oxo-4H-3,1-benzoxazin-6-yl] carbamate;

1,1-dimethylethyl[2-[[1S-[(4-hydroxy-3,5-diiodo phenyl) methyl]-2-[[2-(dimethylamino)ethyl]methyl amino]-2-oxoethyl]amino]-5-methyl-4-oxo-4H-3,1-benzoxazin-6-yl]carbamate;

1,1-dimethylethyl[2-[[2-[[2-(dimethylamino)ethyl] methylamino]-1S-methyl-2-oxoethyl]amino]-5-methyl-4-oxo-4H-3,1-benzoxazin-6-yl]carbamate;

1,1-dimethylethyl[2-[[2-[[2-(dimethylamino)ethyl] methylamino]-1,1-dimethyl-2-oxoethyl]amino]-5-methyl-4-oxo-4H-3,1-benzoxazin-6-yl]carbamate;

1,1-dimethylethyl[2-[[1S[[[2-(dimethylamino)ethyl] methylamino]carbonyl]-3-(methylsulfonyl)propyl] amino]-5-methyl-4-oxo-4H-3,1-benzoxazin-6-yl] carbamate;

1,1-dimethylethyl[2-[[1S[(3,5-diiodo-4-methoxy phenyl) methyl]-2-[methyl[2-(1-piperidinyl)ethyl]amino]-2-oxoethyl]amino]-5-methyl-4-oxo-4H-3,1-benzoxazin-6-yl]carbamate;

1,1-dimethylethyl[2-[[1S-methyl-[2-(1-piperidinyl)ethyl] amino]-2-oxoethyl]amino]-5-methyl-4-oxo-4H-3,1-benzoxazin-6-yl]carbamate;

1,1-dimethylethyl[2-[[1S-[[methyl-[2-(1-piperidinyl) ethyl]amino]carbonyl]-3-(methylsulfonyl)propyl] amino]-5-methyl-4-oxo-4H-3,1-benzoxazin-6-yl] carbamate;

1,1-dimethylethyl[2-[[1S-[3,5-diiodo-4-methoxy phenyl) methyl]-2-[methyl[2-(4-morpholinyl)ethyl]amino]-2-oxoethyl]amino]-5-methyl-4-oxo-4H-3,1-benzoxazin-6-yl]carbamate;

1,1-dimethylethyl[2-[[1S-[[methyl-[2-(4-morpholinyl) ethyl]amino]carbonyl]-3-(methylsulfonyl)propyl] amino]-5-methyl-4-oxo-4H-3,1-benzoxazin-6-yl] carbamate;

1,1-dimethylethyl[5-methyl-2-[[1S-methyl-2-[methyl-[2-(4-methylpiperazin-1-yl)ethyl]amino]-2-oxoethyl] amino]-4-oxo-4H-3,1-benzoxazin-6-yl]carbamate;

1,1-dimethylethyl[5-methyl-2-[[1S-methyl-2-[methyl-[2-(4-methylpiperazin-1-yl)ethyl]amino]carbonyl]-3-(methylsulfonyl)propyl]amino]-4-oxo-4H-3,1-benzoxazin-6-yl]carbamate;

methyl αS-[[6-[[1,1-dimethylethoxy)carbonyl]amino]-5-methyl-4-oxo-4H-3,1-benzoxazin-2-yl]amino] morpholine-4-butanoate;

methyl αS-[[6-[[(1,1-dimethylethoxy)carbonyl]amino]-5-methyl-4-oxo-4H-3,1-benzoxazin-2-yl]amino] pyrrolidine-1-butanoate;

N-[2-(dimethylamino)ethyl]-αS-[[6-[[(ethylamino) carbonyl]amino]-5-methyl-4-oxo-4H-3,1-benzoxazin-2-yl]amino]-3,5-diiodo-4-methoxy-N-methylbenzenepropanamide;

N-[2-dimethylamino)ethyl]-αS-[[6-[[ethyl amino) carbonyl]amino]-5-methyl-4-oxo-4H-3,1-benzoxazin-2-yl]amino]-N-methylpropanamide;

N-[2-(dimethylamino)ethyl]-3,5-diiodo-4-methoxy-N-methyl-αS[[5-methyl-4-oxo-6-[(propylsulfonyl)

amino]-4H-3,1-benzoxazin-2-yl]amino]-N-methylpropanamide;

N-[6-[[[(1,1-dimethylethoxy)carbonyl]amino]methyl]-5-methyl-4-oxo-4H-3,1-benzoxazin-2-yl]-3,5-diiodo-O-methyl-L-tyrosine, methyl ester;

methyl αS-[6-[[[(1,1-dimethylethoxy)carbonyl]amino]methyl]-5-methyl-4-oxo-4H-3,1-benzoxazin-2-yl]amino]thiazole-4-propanoate;

$N^2$-[6-[[[(1,1-dimethylethoxy)carbonyl]amino]methyl]-5-methyl-4-oxo-4H-3,1-benzoxazin-2-yl]-L-asparagine, methyl ester;

1,1-dimethylethyl[[2-[[1S-[3,5-diiodo-4-methoxy phenyl)methyl]-2-[[2-(dimethylamino)ethyl]methyl amino]-2-oxoethyl]amino]-5-methyl-4-oxo-4H-3,1-benzoxazin-6-yl]methyl]carbamate;

1,1-dimethylethyl[[2-[[2-[[2-(dimethylamino)ethyl]methylamino]-1S-methyl-2-oxoethyl]amino]-5-methyl-4-oxo-4H-3,1-benzoxazin-6-yl]methyl]carbamate;

1,1-dimethylethyl[[2-[[1S-[[2-(dimethylamino)ethyl]methylamino]carbonyl]-3-(methylsulfonyl)propyl]amino]-5-methyl-4-oxo-4H-3,1-benzoxazin-6-yl]methyl]carbamate;

1,1-dimethylethyl[[5-methyl-2-[[1S-methyl-2-[methyl[2-(1-piperidinyl)ethyl]amino]-2-oxoethyl]-amino]-4-oxo-4H-3,1-benzoxazin-6-yl]methyl]carbamate;

1,1-dimethylethyl[[5-methyl-2-[[1S-[[methyl-[2-(4-morpholinyl)ethyl]amino]carbonyl]-3-(methyl sulfonyl)propyl]amino]-4-oxo-4H-3,1-benzoxazin-6-yl]methyl]carbamate;

1,1-dimethylethyl[[5-methyl-2-[[1S-methyl-[2-(4-methyl-1-piperazinyl)ethyl]amino]-2-oxoethyl]amino]-4-oxo-4H-3,1-benzoxazin-6-yl]methyl]carbamate;

N-(6-bromo-5-methyl-4-oxo-4H-3,1-benzoxazin-2-yl)-L-alanine, 1,1-dimethylethyl ester;

N-(6-bromo-5-methyl-4-oxo-4H-3,1-benzoxazin-2-yl)-D-alanine, 1,1-dimethylethyl ester;

N-[6-[[(1,1-dimethylethoxy)carbonyl]amino]-5-methyl-4-oxo-4H-3,1-benzoxazin-2-yl]-L-alanine, 1,1-dimethylethyl ester;

N-[6-[[(1,1-dimethylethoxy)carbonyl]amino]-5-methyl-4-oxo-4H-3,1-benzoxazin-2-yl]-L-phenylalanine, methyl ester;

N-[6-[[(1,1-dimethylethoxy)carbonyl]amino]-5-methyl-4-oxo-4H-3,1-benzoxazin-2-yl]-O-(phenylmethyl)-L-serine, methyl ester;

N-[6-[[(1,1-dimethylethoxy)carbonyl]amino]-5-methyl-4-oxo-4H-3,1-benzoxazin-2yyl]-O-methyl-L-tyrosine, methyl ester;

N-[6-[[(1,1-dimethylethoxy)carbonyl]amino]-5-methyl-4-oxo-4H-3,1-benzoxazin-2-yl]-O-methyl-L-tyrosine, dimethylamide;

N-[6-[[(1,1-dimethylethoxy)carbonyl]amino]-5-methyl-4-oxo-4H-3,1-benzoxazin-2-yl]-L-thiazol-4-yl-alanine, methyl ester;

N-[6-[[(1,1-dimethylethoxy)carbonyl]amino]-5-methyl-4-oxo-4H-3,1-benzoxazin-2-yl]-L-aspartic acid, alpha-methyl ester beta-dimethylamide;

N-[6-[[(1,1-dimethylethoxy)carbonyl]amino]-5-methyl-4-oxo-4H-3,1-benzoxazin-2-yl]-O-methyl-L-tyrosine, N-methyl-N-[2-(1-morpholinyl)ethyl]amide;

N-[6-[[(1,1-dimethylethoxy)carbonyl]amino]-5-methyl-4-oxo-4H-3,1-benzoxazin-2-yl]-O-methyl-L-tyrosine, N-methyl-N-[2-(1-piperidinyl)ethyl]amide;

N-[6-[[(1,1-dimethylethoxy)carbonyl]amino]-5-methyl-4-oxo-4H-3,1-benzoxazin-2-yl]-L-tryptophan, dimethylamide;

N-[6-[[(1,1-dimethylethoxy)carbonyl]amino]-5-methyl-4-oxo-4H-3,1-benzoxazin-2-yl]-O-methyl-L-threonine, methyl ester;

N-[6-[[(1,1-dimethylethoxy)carbonyl]amino]-5-methyl-4-oxo-4H-3,1-benzoxazin-2-yl]-O-methyl-L-serine, methyl ester;

N-[6-[[(1,1-dimethylethoxy) carbonyl]amino]-5-methyl-4-oxo-4H-3,1-benzoxazin-2-yl]-L-phenylglycine, 1,1-dimethylethyl ester;

N-[6-[[(1,1-dimethylethoxy)carbonyl]amino]-5-methyl-4-oxo-4H-3,1-benzoxazin-2-yl]-3,5-diiodo-O-methyl-L-tyrosine, methyl ester;

N-[6-[[(1,1-dimethylethoxy)carbonyl]amino]-5-methyl-4-oxo-4H-3,1-benzoxazin-2-yl]-4-iodo-L-phenylalanine, methyl ester;

N-[6-[[(1,1-dimethylethoxy)carbonyl]amino]-5-methyl-4-oxo-4H-3,1-benzoxazin-2-yl]-L-methionine sulfone, methyl ester;

N-[6-[[(1,1-dimethylethoxy)carbonyl]amino]-5-methyl-4-oxo-4H-3,1-benzoxazin-2-yl]-L-beta-naphthylalanine, methyl ester;

N-[6-[[(1,1-dimethylethoxy)carbonyl]amino]-5-methyl-4-oxo-4H-3,1-benzoxazin-2-yl]-2-aminoisobutyric acid, methyl ester;

N-[6-[[(1,1-dimethylethoxy)carbonyl]amino]-5-methyl-4-oxo-4H-3,1-benzoxazin-2-yl]-1-cyclopropanecarboxylic acid, methyl ester;

N-[6-[[(1,1-dimethylethoxy)carbonyl]amino]-5-methyl-4-oxo-4H-3,1-benzoxazin-2-yl]-L-alanine, N-methyl-N-allylamide;

N-[6-[[(1,1-dimethylethoxy)carbonyl]amino]-5-methyl-4-oxo-4H-3,1-benzoxazin-2-yl]-L-alanine, N-methyl-N-phenylmethylamide;

N-[6[[(1,1-dimethylethoxy)carbonyl]amino]-5-methyl-4-oxo-4H-3,1-benzoxazin-2-yl]-L-alanine, phenyl methyl ester;

N-[6-[[(1,1-dimethylethoxy)carbonyl]amino]-5-methyl-4-oxo-4H-3,1-benzoxazin-2-yl]-3,5-diiodo-L-tyrosine, methyl ester;

N-[6-[[[(1,1-dimethylethoxy)carbonyl]amino]methyl]-5-methyl-4-oxo-4H-3,1-benzoxazin-2-yl]-L-alanine, dimethylamide;

N-[6-[[[(1,1-dimethylethoxy)carbonyl]amino]methyl]-5-methyl-4-oxo-4H-3,1-benzoxazin-2-yl]-O-methyl-L-tyrosine, dimethylamide;

N-[6-[[[(1,1-dimethylethoxy)carbonyl]amino]methyl]-5-methyl-4-oxo-4H-3,1-benzoxazin-2-yl]-L-alanine, methyl ester;

N-[6-amino-5-methyl-4-oxo-4H-3,1-benzoxazin-2-yl]-L-alanine, methyl ester;

N-[6-amino-5-methyl-4-oxo-4H-3,1-benzoxazin-2-yl]-1-phenylalanine, methyl ester;

N-[[6-(dimethylaminomethyl)carbonyl]amino]-5-methyl-4-oxo-4H-3,1-benzoxazin-2-yl]-L-alanine, methyl ester;

5-methyl-N-6-[[(2-pyridyl)carbonyl]amino]-4-oxo-4H,1-benzoxazin-2-yl]-L-alanine, methyl ester;

N-[6-[[(5-isoxazolyl)carbonyl]amino]-5-methyl-4-oxo-4H-3,1-benzoxazin-2-yl]-L-alanine, methyl ester;

N-[6-[[(methoxymethyl)carbonyl]amino]-5-methyl-4-oxo-4H-3,1-benzoxazin-2-yl]-L-alanine, methyl ester;

N-[6-[[(methoxymethyl)carbonyl]amino]-5-methyl-4-oxo-4H-3,1-benzoxazin-2-yl]-L-phenylalanine, methyl ester;

N-[6-[[(2-carboxyethyl)carbonyl]amino]-5-methyl-4-oxo-4H-3,1-benzoxazin-2-yl]-L-phenylalanine, methyl ester;

N-[6-[[(cyclobutyl)carbonyl]amino]-5-methyl-4-oxo-4H-3,1-benzoxazin-2-yl]-L-phenylalanine, methyl ester;

N-[6-[[(2-furanyl)carbonyl]amino]-5-methyl-4-oxo-4H-3,1-benzoxazin-2-yl]-L-phenylalanine, methyl ester;

N-[6-[[(2-thienylmethyl)carbonyl]amino]-5-methyl-4-oxo-4H-3,1-benzoxazin-2-yl]-L-phenylalanine, methyl ester;

N-[6-[[[[2-(2-thienyl)ethyl]amino]carbonyl]amino]-5-methyl-4-oxo-4H-3,1-benzoxazin-2-yl]-L-phenylalanine, methyl ester;

N-[6-[[[[2-(2-thienyl)ethyl]amino]carbonyl]amino]-5-methyl-4-oxo-4H-3,1-benzoxazin-2-yl]-L-alanine, methyl ester;

N-[6-[benzenesulfonyl]amino]-5-methyl-4-oxo-4H-3,1-benzoxazin-2-yl]-L-phenylalanine, methyl ester;

N-[6-[benzenesulfonyl]amino]-5-methyl-4-oxo-4H-3,1-benzoxazin-2-yl]-L-alanine, methyl ester; and N-[6-[[(1,1-dimethylethoxy)carbonyl]amino]-5-methyl-4-oxo-4H-3,1-benzoxazin-2-yl]-L-alanine.

19. The method of claim 15 wherein $R^1$ is a; wherein $R^2$ is a substituent selected from lower alkyl,

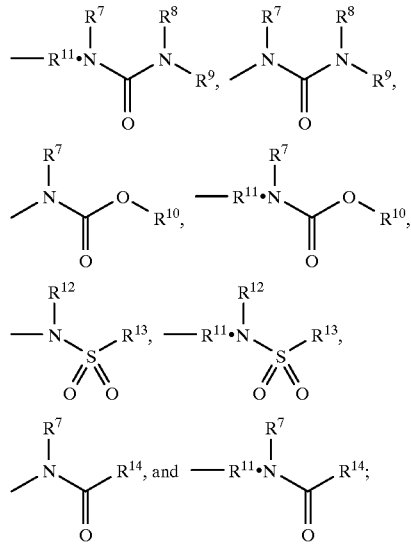

wherein $R^3$ is selected from hydrido, lower alkyl, and lower aralkyl; wherein $R^4$ is selected from hydrido, lower alkyl, lower cycloalkyl, lower cycloalkylalkyl, aryl, heterocyclo, lower aralkyl and lower heterocycloalkyl; wherein n is 0–5, inclusive; wherein $R^5$ and $R^6$ are independently selected from hydrido, lower alkyl, lower cycloalkyl, lower cycloalkylalkyl, aryl, lower aralkyl, heterocyclo, lower heterocycloalkyl, lower alkylaminoalkyl, lower aralkylaminoalkyl, lower alkoxyalkyl, and lower aralkoxyalkyl; wherein $R^7$, $R^{12}$ and $R^{23}$ are independently selected from hydrido, lower alkyl and lower aralkyl; wherein $R^8$, $R^9$ and $R^{14}$ are independently selected from hydrido, lower alkyl, lower cycloalkyl, lower cycloalkylalkyl, lower haloalkyl, lower aminoalkyl, lower alkylaminoalkyl, lower carboxyalkyl, lower aminocarbonylalkyl, lower alkylaminocarbonylalkyl, lower hydroxyalkyl, lower alkoxyalkyl, lower aralkoxyalkyl, lower alkylsulfonylalkyl, lower alkylsulfinylalkyl, lower alkylthioalkyl, aryl, lower aralkyl, heterocyclo, and lower heterocycloalkyl; wherein $R^{10}$ is selected from lower alkyl, lower haloalkyl, lower alkylaminoalkyl, lower carboxyalkyl, lower aminocarbonylalkyl, alkylaminocarbonylalkyl, lower aralkoxyalkyl, lower alkoxyalkyl, lower cycloalkyl, lower cycloalkylalkyl, lower alkylsulfonylalkyl, lower alkylsulfinylalkyl, lower alkylthioalkyl, aryl, lower aralkyl, heterocyclo, and lower heterocycloalkyl;

wherein $R^{11}$ is lower alkylene; and wherein $R^{13}$ is selected from amino, lower alkyl, lower alkylamino, lower alkylaminoalkyl and aryl; or a pharmaceutically-acceptable salt or tautomer thereof.

20. The method of claim 19 wherein $R^1$ is a substituent selected from methyl, ethyl, n-propyl, isopropyl, n-butyl, isobutyl, sec-butyl, and tert-butyl; wherein $R^2$ is a substituent selected from methyl, ethyl, n-propyl, isopropyl, n-butyl, isobutyl, sec-butyl, tert-butyl, pentyl, hexyl,

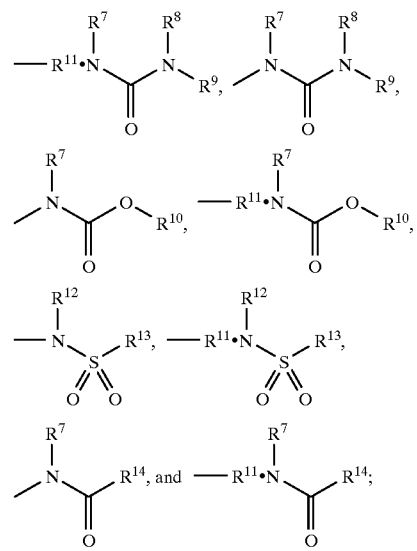

wherein $R^3$ is selected from hydrido, methyl, ethyl, n-propyl, isopropyl, n-butyl, isobutyl, sec-butyl, tert-butyl, pentyl, hexyl, benzyl, phenylethyl and diphenylmethyl; wherein $R^4$ is selected from hydrido, methyl, ethyl, n-propyl, isopropyl, n-butyl, isobutyl, sec-butyl, tert-butyl, pentyl, hexyl, cyclopropyl, cyclobutyl, cyclopentyl, cyclohexyl, cyclopropylmethyl, cyclobutylmethyl, cyclopentylethyl, cyclohexylpropyl, phenyl optionally substituted at a substitutable position with one or more substituents selected independently from fluoro, chloro, iodo, bromo, nitro, methyl, ethyl, n-propyl, isopropyl, n-butyl, isobutyl, sec-butyl, tert-butyl, pentyl, hexyl, lower alkoxy, N,N-dimethylaminoethyld, N,N-dimethylaminohexyl, N,N-diethylaminobutyl, N,N-dimethylaminoethoxy, N,N-dimethylaminohexyloxy, and N,N-diethylaminobutoxy, lower aralkyl selected from benzyl, naphthylmethyl, phenylethyl, and phenylisopropyl, wherein the phenyl ring is optionally substituted at a substitutable position with one or more substituents selected independently from methyl, ethyl, n-propyl, isopropyl, n-butyl, isobutyl, sec-butyl, tert-butyl, pentyl, hexyl, methoxy, ethoxy, propoxy, isopropoxy, butoxy, tert-butoxy, amino, fluoro, chloro, bromo, iodo, N,N-dimethylaminomethyl, N,N-dimethylaminohexyl, N,N-diethylaminobutyl, N,N-dimethylaminoethyl, N,N- diethylaminoethyl, N,N-dimethylamino, and N,N-diethylamino, heterocyclo selected from methylpiperidinyl, methylazabicyclooctanyl, morpholinyl, pyrrolidinyl, and piperazinyl, phenylmethyl, phenylethyl, and lower heterocycloalkyl selected from pyridylmethyl, furylmethyl, thienylmethyl, and thiazolylmethyl, where the heterocyclic rings are optionally substituted at a substitutable position with one or more substituents selected independently from fluoro, chloro, iodo, bromo, nitro, methyl, ethyl, n-propyl, isopropyl, n-butyl, isobutyl, sec-butyl, tert-butyl, pentyl, hexyl, lower alkoxy, N,N-dimethylaminoethyl, N,N-dimethylaminohexyl, N,N-diethylaminobutyl, N,N-dimethylaminoethoxy, N,N-dimethylaminohexyloxy, and N,N-diethylaminobutoxy; wherein n is 0–4, inclusive; wherein $R^5$ and $R^6$ are independently selected from hydrido, methyl, ethyl, n-propyl, isopropyl, n-butyl, isobutyl, sec-butyl, tert-butyl, pentyl, hexyl, cyclopropyl, cyclobutyl, cyclopentyl, cyclohexyl, cyclopropylmethyl, cyclobutylmethyl, phenyl, benzyl, furyl, thienyl, thiazolyl, pyrrolyl, furylmethyl, thienylethyl, thiazolylmethyl, pyrrolylmethyl, methylaminomethyl, N,N-dimethylaminomethyl, N,N-dimethylaminoethyl, N,N-dimethylaminohexyl, N,N-diethylaminobutyl, benzylaminomethyl, methoxymethyl, methoxyethyl, ethoxyethyl, methoxybutyl, methoxypropyl, and benzyloxymethyl; wherein $R^7$, $R^{12}$ and $R^{23}$ are independently selected from hydrido, methyl, ethyl, n-propyl, isopropyl, n-butyl, isobutyl, sec-butyl, tert-butyl, pentyl, hexyl, benzyl and phenylethyl; wherein $R^8$, $R^9$ and $R^{14}$ are independently selected from hydrido, methyl, ethyl, n-propyl, isopropyl, n-butyl, isobutyl, sec-butyl, tert-butyl, pentyl, hexyl, cyclopropyl, cyclobutyl, cyclopentyl, cyclohexyl, cyclopropylpropyl, cyclobutylethyl, cyclopentylmethyl, cyclohexylmethyl, fluoromethyl, difluoromethyl, trifluoromethyl, chloromethyl, dichloromethyl, trichloromethyl, trichloromethyl, pentafluoroethyl, heptafluoropropyl, difluorochloromethyl, dichlorofluoromethyl, difluoroethyl, difluoropropyl, dichloroethyl and dichloropropyl, methylamino, ethylamino, propylamino, N,N-dimethylaminomethyl, N,N-dimethylaminoethyl, N,N-dimethylaminopropyl, N,N-dimethylaminohexyl, N,N-diethylaminobutyl, N,N-diethylaminoethyl, N,N-diethylaminopropyl, carboxymethyl, carboxyethyl, carboxypropyl, aminocarbonylmethyl, N,N-dimethylaminocarbonylmethyl, hydroxymethyl, hydroxypropyl, methoxymethyl, methoxyethyl, ethoxyethyl, methoxybutyl, methoxypropyl, benzyloxymethyl, methylsulfonylmethyl, methylsulfinylmethyl, methylthiomethyl, phenyl optionally substituted at a substitutable position with one or more substituents selected independently from methyl, ethyl, n-propyl, isopropyl, n-butyl, isobutyl, sec-butyl, tert-butyl, pentyl, hexyl, methoxy, ethoxy, propoxy, isopropoxy, butoxy, tert-butoxy, amino, fluoro, chloro, bromo, iodo, N,N-dimethylaminomethyl, N,N-dimethylaminohexyl, N,N-diethylaminobutyl, N,N-dimethylaminoethyl, N,N-diethylaminoethyl, N,N-dimethylamino, and N,N-diethylamino, lower aralkyl selected from benzyl, naphthylmethyl, phenylethyl, and phenylisopropyl, wherein the phenyl ring is optionally substituted at a substitutable position with one or more substituents selected independently from methyl, ethyl, n-propyl, isopropyl, n-butyl, isobutyl, sec-butyl, tert-butyl, pentyl, hexyl, methoxy, ethoxy, propoxy, isopropoxy, butoxy, tert-butoxy, amino, fluoro, chloro, bromo, iodo, N,N-dimethylaminomethyl, N,N-dimethylaminohexyl, N,N-diethylaminobutyl, N,N-dimethylaminoethyl, N,N-diethylaminoethyl, N,N-dimethylamino, and N,N-diethylamino, heterocyclo selected from furyl, pyrrolyl, pyridyl, oxazolyl, pyrazolyl, isoxazolyl, thienyl, and thiazolyl, and lower heterocycloalkyl selected from thienylmethyl, morpholinylethyl, morpholinylmethyl, piperazinylethyl, piperdinylethyl, piperdinylmethyl, pyrrolidinylethyl, pyrrolidinylmethyl, pyrrolidinylpropyl, imidazolylethyl, oxazolylmethyl, thiazolylmethyl, furylmethyl, thienylethyl, and thiazolylmethyl, wherein the heterocyclo moiety may be substituted at a substitutable position with a radical selected from fluoro, chloro, bromo, iodo, methyl, ethyl, n-propyl, isopropyl, n-butyl, isobutyl, sec-butyl, tert-butyl, pentyl, and hexyl; wherein $R^{10}$ is selected from methyl, ethyl, n-propyl, isopropyl, n-butyl, isobutyl, sec-butyl, tert-butyl, pentyl, hexyl, fluoromethyl, difluoromethyl, trifluoromethyl, chloromethyl, dichloromethyl, trichloromethyl, trichloromethyl, pentafluoroethyl, heptafluoropropyl, difluorochloromethyl, dichlorofluoromethyl, difluoroethyl, difluoropropyl, dichloroethyl and dichloropropyl, N,N-dimethylaminomethyl, N,N-dimethylaminoethyl, N,N-dimethylaminopropyl, N,N-dimethylaminohexyl, N,N-diethylaminoethyl, N,N-diethylaminopropyl, N,N-diethylaminobutyl, carboxymethyl, carboxyethyl, carboxypropyl, aminocarbonylmethyl, N,N-dimethylaminocarbonylmethyl, benzyloxymethyl, methoxymethyl, methoxyethyl, ethoxyethyl, methoxybutyl, methoxypropyl, cyclopropyl, cyclobutyl, cyclopentyl, cyclohexyl, cyclopropylpropyl, cyclobutylethyl, cyclopentylmethyl, cyclohexylmethyl, methylsulfonylmethyl, methylsulfinylmethyl, methylthiomethyl, phenyl optionally substituted at a substitutable position with one or more substituents selected independently from methyl, ethyl, n-propyl, isopropyl, n-butyl, isobutyl, sec-butyl, tert-butyl, pentyl, hexyl, methoxy, ethoxy, propoxy, isopropoxy, butoxy, tert-butoxy, amino, fluoro, chloro, bromo, iodo, N,N-dimethylaminomethyl, N,N-dimethylaminohexyl, N,N-diethylaminobutyl, N,N-dimethylaminoethyl, N,N-diethylaminoethyl, N,N-dimethylamino, and N,N-diethylamino, lower aralkyl selected from benzyl, phenethyl, naphthylmethyl, wherein the aryl ring is optionally substituted at a substitutable position with one or more substituents selected independently from methyl, ethyl, n-propyl, isopropyl, n-butyl, isobutyl, sec-butyl, tert-butyl, pentyl, hexyl, methoxy, ethoxy, propoxy, isopropoxy, butoxy, tert-butoxy, amino, fluoro, chloro, bromo, iodo, N,N-dimethylaminomethyl, N,N-dimethylaminoethyl, N,N-dimethylaminohexyl, N,N-diethylaminoethyl, N,N-diethylaminobutyl, N,N-dimethylamino, N,N-dimethylamino, and N,N-diethylamino, heterocyclo selected from furyl, thienyl, and thiazolyl, and lower heterocycloalkyl selected from thienylmethyl, morpholinylethyl, morpholinylmethyl, piperazinylethyl, piperdinylethyl, piperdinylmethyl, pyrrolidinylethyl, pyrrolidinylmethyl, pyrrolidinylpropyl, imidazolylethyl, oxazolylmethyl, thiazolylmethyl, furylmethyl, thienylethyl, and thiazolylmethyl, wherein the heterocyclo moiety may be substituted at a substitutable position with a radical selected from fluoro, chloro, bromo, iodo, methyl, ethyl, n-propyl, isopropyl, n-butyl, isobutyl, sec-butyl, tert-butyl, pentyl, and hexyl; wherein $R^{11}$ is selected from methylene, ethylene, n-propylene, isopropylene, n-butylene, isobutylene, sec-butylene, pentylene, and hexylene; and wherein $R^{13}$ is selected from phenyl, amino, methyl, ethyl, n-propyl, isopropyl, n-butyl, isobutyl, sec-butyl, tert-butyl, pentyl, hexyl N,N-dimethylaminomethyl, N,N-dimethylaminoethyl, N,N-dimethylaminohexyl, N,N- diethylaminoethyl, N,N-diethylaminobutyl, N,N-dimethylamino, N,N-dimethylamino, and N,N-diethylamino; or a pharmaceutically-acceptable salt or tautomer thereof.

21. The method of claim 20 selected from compounds and their pharmaceutically-acceptable salts, of the group consisting of 1,1-dimethylethyl[5-methyl-2-[(1-methylpiperidin-4-yl)amino]-4-oxo-4H-3,1-benzoxazin-6-yl]carbamate;

1,1-dimethylethyl[2-[[8-methyl-8-azabicyclo[3.2.1]octan-3-yl]amino]-5-methyl-4-oxo-4H-3,1-benzoxazin-6-yl]carbamate;

1,1-dimethylethyl[5-methyl-4-oxo-2-[(1S-phenyl ethyl)amino]-4H-3,1-benzoxazin-6-yl]carbamate;

1,1-dimethylethyl[5-methyl-4-oxo-2[[1S-(4-bromophenyl)ethyl]amino]-4H-3,1-benzoxazin-6-yl]carbamate;

1,1-dimethylethyl[5-methyl-4-oxo-2[[1S-(3-pyridinyl)ethyl]amino]-4H-3,1-benzoxazin-6-yl]carbamate;

1,1-dimethylethyl[2-[[1S-[2-[2-(dimethylamino)ethoxy]pyridin-5-yl]ethyl]amino]-5-methyl-4-oxo-4H-3,1-benzoxazin-6-yl]carbamate;

1,1-dimethylethyl[2-[[1S-4-[2-(dimethylamino)ethyl]phenyl]ethyl]amino]-5-methyl-4-oxo-4H-3,1-benzoxazin-6-yl]carbamate;

1,1-dimethylethyl N-methyl-[5-methyl-4-oxo-2-[(1S-phenylethyl)amino]4H-3,1-benzoxazin-6-yl]carbamate;

$N^1$-ethyl-$N^2$-[5-methyl-4-oxo-2-[(1S-phenylethyl)amino]-4H-3,1-benzoxazin-6-yl]urea;

$N^1$-[2-(dimethylamino)ethyl]-$N^2$-(5-methyl-4-oxo-2-[(1S-phenylethyl)amino]-4H-3,1-benzoxazin-6-yl]urea;

$N^1$-[2-(dimethylamino)ethyl]-$N^2$-[[5-methyl-4-oxo-2-[(1S-phenylethyl)amino]-4H-3,1-benzoxazin-6-yl]methyl]urea;

2-(dimethylamino)-N-[5-methyl-4-oxo-2-[(1S-phenylethyl)amino]-4H-3,1-benzoxazin-6-yl]acetamide;

N-[5-methyl-4-oxo-2-[(1S-phenylethyl)amino]-4H-3,1-benzoxazin-6-yl]pyrrolidine-1-acetamide;

N-methyl-N-[5-methyl-4-oxo-2-[(1S-phenylethyl)amino]-4H-3,1-benzoxazin-6-yl]pyrrolidine-1-acetamide;

N-[5-methyl-4-oxo-2-[(1S-phenylethyl)amino]-4H-3,1-benzoxazin-6-yl]morpholine-4-acetamide;

4-methyl-N-[5-methyl-4-oxo-2-[(1S-phenylethyl)amino]-4H-3,1-benzoxazin-6-yl]piperazine-1-acetamide;

1-methyl-N-[5-methyl-4-oxo-2-[(1S-phenylethyl)amino]-4H-3,1-benzoxazin-6-yl]pyrrolidine-2S-carboxamide;

1,1-dimethylethyl[[5-methyl-4-oxo-2[(1S-phenyl ethyl)amino]-4H-3,1-benzoxazin-6-yl]methyl]carbamate;

1,1-dimethylethyl[[5-methyl-4-oxo-2[[1S-(3-pyridinyl)ethyl]amino]-4H-3,1-benzoxazin-6-yl]methyl]carbamate;

1,1-dimethylethyl[[2-[[1S[4-[2-(dimethylamino)ethyl]phenyl]ethyl]amino]-5-methyl-4-oxo-4H-3,1-benzoxazin-6-yl]methyl]carbamate;

2-(dimethylamino)-N-[[5-methyl-4-oxo-2-1(1S-phenylethyl)amino]-4H-3,1-benzoxazin-6-yl]methyl]acetamide;

N-[[5-methyl-4-oxo-2-[(1S-phenylethyl)amino]-4H-3,1-benzoxazin-6-yl]methyl]pyrrolidine-1-acetamide;

N-[[5-methyl-4-oxo-2-[(1S-phenylethyl)amino]-4H-3,1-benzoxazin-6-yl]methyl]morpholine-4-acetamide;

4-methyl-N-[[5-methyl-4-oxo-2-[(1S-phenylethyl)amino]-4H-3,1-benzoxazin-6-yl]methyl]piperazine-1-acetamide;

1-methyl-N-[[5-methyl-4-oxo-2[(1S-phenylethyl)amino]-4H-3,1-benzoxazin-6-yl]methyl]pyrrolidine-2S-carboxamide;

6-[[(1,1-dimethylethoxy)carbonyl]amino]-5-methyl-2-[[(1S)-phenylethyl]amino]-4H-3,1-benzoxazin-4-one;

6-[[(1,1-dimethylethoxy)carbonyl]amino]-5-methyl-2-[[(1R)-phenylethyl]amino]-4H-3,1-benzoxazin-4-one;

6-[[[(1,1-dimethylethoxy)carbonyl]amino]methyl]-5-methyl-2-[[(1S)-phenylethyl]amino]-4H-3,1-benzoxazin-4-one;

6-[[[[dimethylaminomethyl]carbonyl]amino]methyl]-5-methyl-2-[[(1S)-phenylethyl]amino]-4H-3,1-benzoxazin-4-one;

5-methyl-6-[[(1-morpholinylmethyl)carbonyl]amino]-2-[[(1S)-phenylethyl]amino]-4H-3,1-benzoxazin-4-one;

6-[[(2-furanyl)carbonyl]amino]-5-methyl-2-[[(1S)-phenylethyl]amino]-4H-3,1-benzoxazin-4-one;

5-methyl-2[[(1S)-phenylethyl]amino]-6-[[(1-pyrrolidinylmethyl)carbonyl]amino]-4H-3,1-benzoxazin-4-one;

5-methyl-6-[[(dimethylaminomethyl)carbonyl]amino]-2-[[(1S)-phenylethyl]amino]-4H-3,1-benzoxazin-4-one;

5-methyl-6-[[(3-dimethylaminopropyl)carbonyl]amino]-2-[[(1R)-phenylethyl]amino]-4H-3,1-benzoxazin-4-one; and 6-[[[[(1R)-phenylethyl]amino]carbonyl]amino]-5-methyl-2-[[(1R)-phenylethyl]amino]-4H-3,1-benzoxazin-4-one.

22. A method of treating herpes viral infection in a subject, said method comprising treating said subject with an effective amount of a compound of Formula II

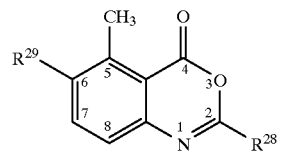

II wherein $R^{28}$ is selected from (a) amino substituted with one or two radicals selected from alkyl, aralkyl, heterocycoalkyl, heterocyclo, and aryl, and (b) amino acid residues and amide or ester derivatives thereof;

wherein $R^{29}$ is selected from alkyl,

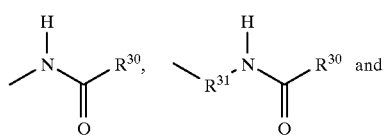

-continued

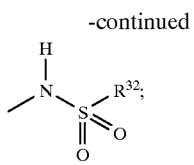

wherein $R^{30}$ is selected from alkyl, alkoxy, alkylamino, carboxyalkyl, alkoxyalkyl, alkylaminoalkyl, cycloalkyl, heterocyclo, heterocycloalkyl, heterocycloalkoxy, alkylaminoalkoxy, alkylaminoalkylamino, heterocycloalkylamino, and N-aralkylamino;

wherein $R^{31}$ is alkylene;

wherein $R^{32}$ is alkyl and aryl;

or a pharmaceutically-acceptable salt thereof.

23. The method of claim 22 wherein $R^{28}$ is selected from (a) amino substituted with one or two radicals selected from lower alkyl, lower aralkyl, lower heterocycoalkyl, heterocyclo, and aryl, and (b) amino acid residues and amide or ester derivatives thereof; wherein $R^{29}$ is selected from lower alkyl,

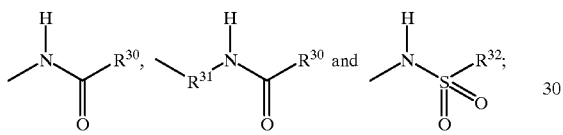

wherein $R^{30}$ is selected from lower alkyl, lower alkoxy, lower alkylamino, lower carboxyalkyl, lower alkoxyalkyl, lower alkylaminoalkyl, lower cycloalkyl, heterocyclo, lower heterocycloalkyl, lower heterocycloalkoxy, lower alkylaminoalkoxy, lower alkylaminoalkylamino, lower heterocycloalkylamino, and lower N-aralkylamino; wherein $R^{31}$ is lower alkylene; wherein $R^{32}$ is lower alkyl and aryl; or a pharmaceutically-acceptable salt thereof.

24. A method of inhibiting a herpes viral protease in a subject infected with a herpes virus having said protease, said method comprising treating said subject with an effective amount of a compound of Formula I

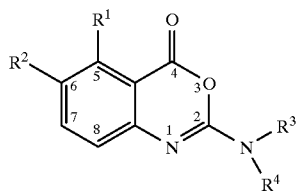

I wherein $R^1$ is an alkyl;

wherein $R^2$ is a substituent selected from alkyl,

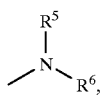

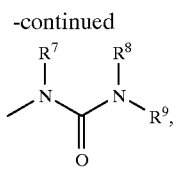

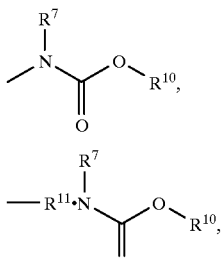

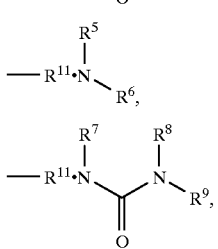

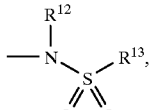

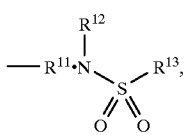

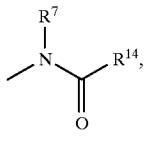

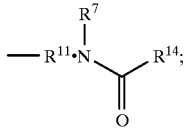

and

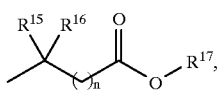

wherein $R^3$ is selected from hydrido, alkyl, alkylaminoalkyl, aralkyl, and heterocycloalkyl;

wherein $R^4$ is selected from hydrido, alkyl, cycloalkyl, cycloalkylalkyl, aryl, heterocyclo, aralkyl, heterocycloalkyl,

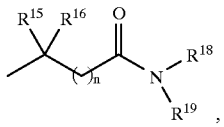

-continued

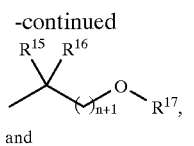
and

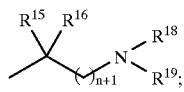

wherein n is 0–6, inclusive;

wherein $R^5$ and $R^6$ are independently selected from hydrido, alkyl, cycloalkyl, cycloalkylalkyl, aryl, aralkyl, heterocyclo, heterocycloalkyl, alkylaminoalkyl, aralkylaminoalkyl, alkoxyalkyl, and aralkoxyalkyl;

wherein $R^7$, $R^{12}$ and $R^{23}$ are independently selected from hydrido, alkyl and aralkyl;

wherein $R^8$, $R^9$ and $R^{14}$ are independently selected from hydrido, alkyl, cycloalkyl, cycloalkylalkyl, haloalkyl, aminoalkyl, alkylaminoalkyl, carboxyalkyl, aminocarbonylalkyl, alkylaminocarbonylalkyl, hydroxyalkyl, alkoxyalkyl, aralkoxyalkyl, alkylsulfonylalkyl, alkylsulfinylalkyl, alkylthioalkyl, aryl, aralkyl, heterocyclo, and heterocycloalkyl;

wherein $R^{10}$ is selected from alkyl, haloalkyl, alkylaminoalkyl, carboxyalkyl, aminocarbonylalkyl, alkylaminocarbonylalkyl, aralkoxyalkyl, alkoxyalkyl, cycloalkyl, cycloalkylalkyl, alkylsulfonylalkyl, alkylsulfinylalkyl, alkylthioalkyl, aryl, aralkyl, heterocyclo, and heterocycloalkyl;

wherein $R^{11}$ is alkylene;

wherein $R^{13}$ is selected from amino, alkyl, alkylamino, alkylaminoalkyl and aryl;

wherein $R^{15}$ is selected from hydrido, alkyl, hydroxyalkyl, alkoxyalkyl, aralkoxyalkyl, alkylaminoalkyl and N-aryl-N-alkylaminoalkyl;

wherein $R^{16}$ is selected from hydrido, alkyl, cycloalkyl, cycloalkylalkyl, haloalkyl, guanidinylalkyl, carboxyalkyl, hydroxyalkyl, alkoxyalkyl, aralkoxyalkyl, alkylthioalkyl, alkylsulfinylalkyl, alkylsulfonylalkyl, aryl, heterocyclo, aralkyl, heterocycloalkyl,

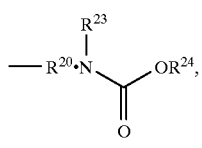

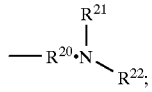

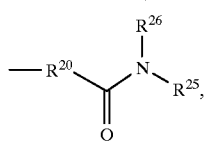

-continued

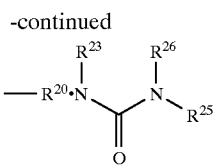
and

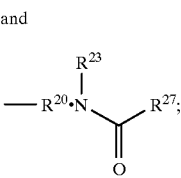

or wherein $R^{15}$ and $R^{16}$ together form cycloalkyl;

wherein $R^{17}$ is selected from hydrido, alkyl, cycloalkyl and aralkyl;

wherein $R^{18}$ and $R^{19}$ are independently selected from hydrido, alkyl, alkenyl, cycloalkyl, cycloalkylalkyl, aryl, heterocyclo, aralkyl, heterocycloalkyl, and alkylaminoalkyl;

wherein $R^{20}$ is alkylene;

wherein $R^{21}$, $R^{22}$, $R^{25}$, and $R^{26}$ are independently selected from hydrido, alkyl, cycloalkyl, cycloalkylalkyl, aminoalkyl, alkylaminoalkyl, hydroxyalkyl, alkoxyalkyl, aryl, heterocyclo, aralkyl, heterocycloalkyl;

wherein $R^{24}$ is selected from alkyl, cycloalkyl, cycloalkylalkyl, alkylaminoalkyl, aralkoxyalkyl, alkoxyalkyl, aryl, aralkyl, heterocyclo, and heterocycloalkyl; and wherein $R^{27}$ is selected from hydrido, alkyl, cycloalkyl, cycloalkylalkyl, alkylaminoalkyl, aminoalkyl, carboxyalkyl, aminocarbonylalkyl, hydroxyalkyl, aralkoxyalkyl, alkoxyalkyl, aryl, aralkyl, heterocyclo, and heterocycloalkyl;

or a pharmaceutically-acceptable salt or tautomer thereof.

25. The method of claim 24 wherein $R^1$ is a lower alkyl; wherein $R^2$ is a substituent selected from lower alkyl,

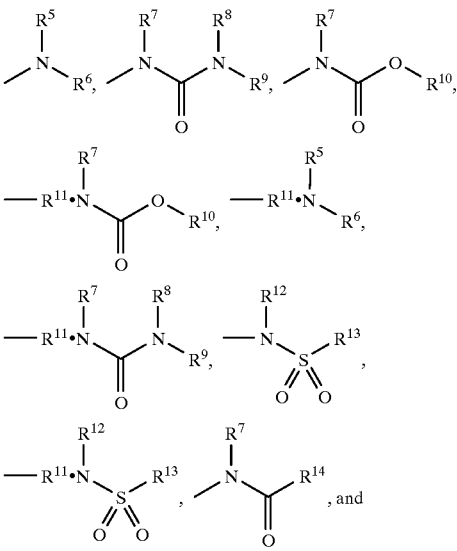

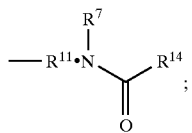

wherein R³ is selected from hydrido, lower alkyl, lower alkylaminoalkyl, lower aralkyl, and lower heterocycloalkyl; wherein R⁴ is selected from hydrido, lower alkyl, lower cycloalkyl, lower cycloalkylalkyl, aryl, heterocyclo, lower aralkyl, lower heterocycloalkyl,

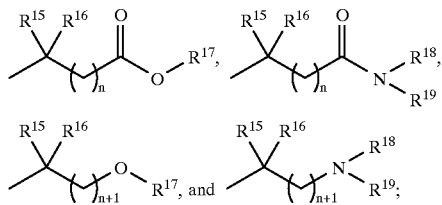

wherein n is 0–6, inclusive; wherein R⁵ and R⁶ are independently selected from hydrido, lower alkyl, lower cycloalkyl, lower cycloalkylalkyl, aryl, lower aralkyl, heterocyclo, lower heterocycloalkyl, lower alkylaminoalkyl, lower aralkylaminoalkyl, lower alkoxyalkyl, and lower aralkoxyalkyl; wherein R⁷, R¹² and R²³ are independently selected from hydrido, lower alkyl and lower aralkyl; wherein R⁸, R⁹ and R¹⁴ are independently selected from hydrido, lower alkyl, lower cycloalkyl, lower cycloalkylalkyl, lower haloalkyl, lower aminoalkyl, lower alkylaminoalkyl, lower carboxyalkyl, lower aminocarbonylalkyl, lower alkylaminocarbonylalkyl, lower hydroxyalkyl, lower alkoxyalkyl, lower aralkoxyalkyl, lower alkylsulfonylalkyl, lower alkylsulfinylalkyl, lower alkylthioalkyl, aryl, lower aralkyl, heterocyclo, and lower heterocycloalkyl; wherein R¹⁰ is selected from lower alkyl, lower haloalkyl, lower alkylaminoalkyl, lower carboxyalkyl, lower aminocarbonylalkyl, lower alkylaminocarbonylalkyl, lower aralkoxyalkyl, lower alkoxyalkyl, lower cycloalkyl, lower cycloalkylalkyl, lower alkylsulfonylalkyl, lower alkylsulfinylalkyl, lower alkylthioalkyl, aryl, lower aralkyl, heterocyclo, and lower heterocycloalkyl; wherein R¹¹ is lower alkylene; wherein R¹³ is selected from amino, lower alkyl, lower alkylamino, lower alkylaminoalkyl and aryl; wherein R¹⁵ is selected from hydrido, lower alkyl, lower hydroxyalkyl, lower alkoxyalkyl, lower aralkoxyalkyl, lower alkylaminoalkyl and lower N-aryl-N-alkylaminoalkyl; wherein R¹⁶ is selected from hydrido, lower alkyl, lower cycloalkyl, lower cycloalkylalkyl, lower haloalkyl, lower guanidinylalkyl, lower carboxyalkyl, lower hydroxyalkyl, lower alkoxyalkyl, lower aralkoxyalkyl, lower alkylthioalkyl, lower alkylsulfinylalkyl, lower alkylsulfonylalkyl, aryl, lower heterocyclo, lower aralkyl, lower heterocycloalkyl,

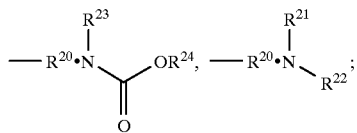

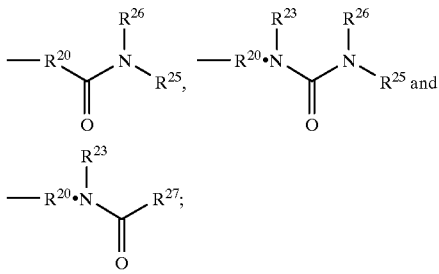

or wherein R¹⁵ and R¹⁶ together form cycloalkyl; wherein R¹⁷ is selected from hydrido, lower alkyl, lower cycloalkyl and lower aralkyl; wherein R¹⁸ and R¹⁹ are independently selected from hydrido, lower alkyl, lower alkenyl, lower cycloalkyl, lower cycloalkylalkyl, aryl, heterocyclo, lower aralkyl, lower heterocycloalkyl, and lower alkylaminoalkyl; wherein R²⁰ is lower alkylene; wherein R²¹, R²², R²⁵, and R²⁶ are independently selected from hydrido, lower alkyl, lower cycloalkyl, lower cycloalkylalkyl, lower aminoalkyl, lower alkylaminoalkyl, lower hydroxyalkyl, lower alkoxyalkyl, lower, aryl, heterocyclo, lower aralkyl, lower heterocycloalkyl; wherein R²⁴ is selected from lower alkyl, lower cycloalkyl, lower cycloalkylalkyl, lower alkylaminoalkyl, lower aralkoxyalkyl, lower alkoxyalkyl, aryl, lower aralkyl, heterocyclo, and lower heterocycloalkyl; and wherein R²⁷ is selected from hydrido, lower alkyl, lower cycloalkyl, lower cycloalkylalkyl, lower alkylaminoalkyl, lower aminoalkyl, lower carboxyalkyl, lower aminocarbonylalkyl, lower hydroxyalkyl, lower aralkoxyalkyl, lower alkoxyalkyl, aryl, lower aralkyl, heterocyclo, and lower heterocycloalkyl; or a pharmaceutically-acceptable salt or tautomer thereof.

26. The method of claim 25 wherein R¹ is a lower alkyl; wherein R² is a substituent selected from lower alkyl,

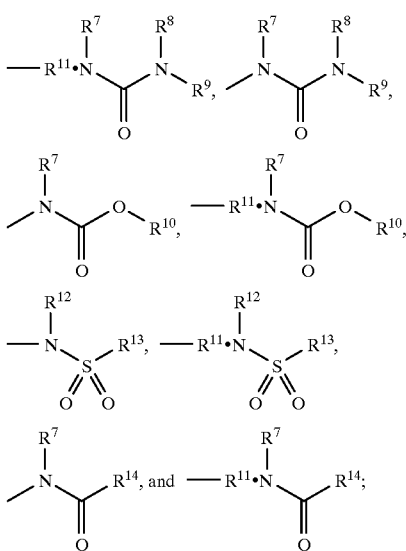

wherein R³ is selected from hydrido, lower alkyl, lower alkylaminoalkyl, lower aralkyl, and lower heterocycloalkyl; wherein R⁴ is selected from hydrido, lower alkyl, lower cycloalkyl, lower cycloalkylalkyl, aryl, heterocyclo, lower aralkyl, lower heterocycloalkyl,

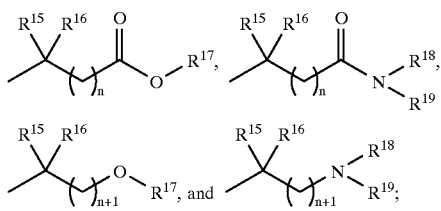

wherein n is 0–6, inclusive; wherein $R^5$ and $R^6$ are independently selected from hydrido, lower alkyl, lower cycloalkyl, lower cycloalkylalkyl, aryl, lower aralkyl, heterocyclo, lower heterocycloalkyl, lower alkylaminoalkyl, lower aralkylaminoalkyl, lower alkoxyalkyl, and lower aralkoxyalkyl; wherein $R^7$, $R^{12}$ and $R^{23}$ are independently selected from hydrido, lower alkyl and lower aralkyl; wherein $R^8$, $R^9$ and $R^{14}$ are independently selected from hydrido, lower alkyl, lower cycloalkyl, lower cycloalkylalkyl, lower haloalkyl, lower aminoalkyl, lower alkylaminoalkyl, lower carboxyalkyl, lower aminocarbonylalkyl, lower alkylaminocarbonylalkyl, lower hydroxyalkyl, lower alkoxyalkyl, lower aralkoxyalkyl, lower alkylsulfonylalkyl, lower alkylsulfinylalkyl, lower alkylthioalkyl, aryl, lower aralkyl, heterocyclo, and lower heterocycloalkyl; wherein $R^{10}$ is selected from lower alkyl, lower haloalkyl, lower alkylaminoalkyl, lower carboxyalkyl, lower aminocarbonylalkyl, alkylaminocarbonylalkyl, lower aralkoxyalkyl, lower alkoxyalkyl, lower cycloalkyl, lower cycloalkylalkyl, lower alkylsulfonylalkyl, lower alkylsulfinylalkyl, lower alkylthioalkyl, aryl, lower aralkyl, heterocyclo, and lower heterocycloalkyl; wherein $R^{11}$ is lower alkylene; wherein $R^{13}$ is selected from amino, lower alkyl, lower alkylamino, lower alkylaminoalkyl and aryl; wherein $R^{15}$ is selected from hydrido, and lower alkyl; wherein $R^{16}$ is selected from hydrido, lower alkyl, lower cycloalkyl, lower cycloalkylalkyl, lower haloalkyl, lower guanidinylalkyl, lower carboxyalkyl, lower hydroxyalkyl, lower alkoxyalkyl, lower aralkoxyalkyl, lower alkylthioalkyl, lower alkylsulfinylalkyl, lower alkylsulfonylalkyl, aryl, heterocyclo, lower aralkyl, lower heterocycloalkyl,

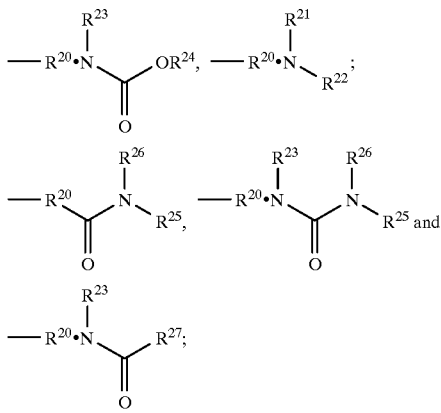

or wherein $R^{15}$ and $R^{16}$ together form lower cycloalkyl; wherein $R^{17}$ is selected from hydrido, lower alkyl, lower cycloalkyl and lower aralkyl; wherein $R^{18}$ and $R^{19}$ are independently selected from hydrido, lower alkyl, lower alkenyl, lower cycloalkyl, lower cycloalkylalkyl, aryl, heterocyclo, lower aralkyl, lower heterocycloalkyl, and lower alkylaminoalkyl; wherein $R^{20}$ is lower alkylene;

wherein $R^{21}$, $R^{22}$, $R^{25}$, and $R^{26}$ are independently selected from hydrido, lower alkyl, lower cycloalkyl, lower cycloalkylalkyl, lower aminoalkyl, lower alkylaminoalkyl, lower hydroxyalkyl, lower alkoxyalkyl, lower, aryl, heterocyclo, lower aralkyl, lower heterocycloalkyl; wherein $R^{24}$ is selected from lower alkyl, lower cycloalkyl, lower cycloalkylalkyl, lower alkylaminoalkyl, lower aralkoxyalkyl, lower alkoxyalkyl, aryl, lower aralkyl, heterocyclo, and lower heterocycloalkyl; and wherein $R^{27}$ is selected from hydrido, lower alkyl, lower cycloalkyl, lower cycloalkylalkyl, lower alkylaminoalkyl, lower aminoalkyl, lower carboxyalkyl, lower aminocarbonylalkyl, lower hydroxyalkyl, lower aralkoxyalkyl, lower alkoxyalkyl, aryl, lower aralkyl, heterocyclo, and lower heterocycloalkyl; or a pharmaceutically-acceptable salt or tautomer thereof.

27. Method of claim 24 wherein the viral protease is selected from a CMV protease, an HSV-1 protease and a HSV-2 protease.

28. Method of claim 24 wherein the viral protease is a CMV protease, encoded by $U_L 80$.

29. The method of claim 26 wherein the compound is selected from compounds and their pharmaceutically-acceptable salts, of the group consisting of 1,1-dimethylethyl[2-[[2-(3,5-diiodo-4-methoxy phenyl)-1S-[(dimethylamino)methyl]ethyl]amino]-5-methyl-4-oxo-4H-3,1-benzoxazin-6-yl]carbamate;

1,1-dimethylethyl[2-[[1S-[(dimethylamino)methyl]-3-(methylsulfonyl)propyl]amino]-5-methyl-4-oxo-4H-3,1-benzoxazin-6-yl]carbamate;

1,1-dimethylethyl[2-[[2-(dimethylamino)-1S-methylethyl]amino]-5-methyl-4-oxo-4H-3,1-benzoxazin-6-yl]carbamate;

1,1-dimethylethyl[[2-[[2-(dimethylamino)-1S-methylethyl]amino]-5-methyl-4-oxo-4H-3,1-benzoxazin-6-yl]methyl]carbamate;

N-[6-[[(1,1-dimethylethoxy)carbonyl]amino]-5-methyl-4-oxo-4H-3,1-benzoxazin-2-yl]-3,5-diiodo-L-tyrosine, methyl ester;

N-[6-[[(1,1-dimethylethoxy)carbonyl]amino]-5-methyl-4-oxo-4H-3,1-benzoxazin-2-yl-]-3,5-diiodo-O-methyl-L-tyrosine, methyl ester;

N-[6-[[(1,1-dimethylethoxy)carbonyl]amino]-5-methyl-4-oxo-4H-3,1-benzoxazin-2-yl-]-3,5-diiodo-N,0-dimethyl-L-tyrosine, methyl ester;

3,5-dibromo-N-[6-[[(1,1-dimethylethoxy)carbonyl]amino]-5-methyl-4-oxo-4H-3,1-benzoxazin-2-yl-]-O-methyl-L-tyrosine, methyl ester;

methyl αS-[[6-[[(1,1-dimethylethoxy)carbonyl]amino]-5-methyl-4-oxo-4H-3,1-benzoxazin-2-yl]amino]thiazole-4-propanoate;

methyl αS-[[6-[[(1,1-dimethylethoxy)carbonyl]amino]-5-methyl-4-oxo-4H-3,1-benzoxazin-2-yl]amino]oxazole-4-propanoate;

methyl 4-[(aminocarbonyl)amino]-2S-[[6-[[(1,1-dimethylethoxy)carbonyl]amino]-5-methyl-4-oxo-4H-3,1-benzoxazin-2-yl]amino]butanoate;

$N^2$-[6-[[(1,1-dimethylethoxy)carbonyl]amino]-5-methyl-4-oxo-4H-3,1-benzoxazin-2-yl]-L-asparagine, methyl ester;

$N^2$-[6-[[(1,1-dimethylethoxy)carbonyl]amino]-5-methyl-4-oxo-4H-3,1-benzoxazin-2-yl]-L-glutamine, methyl ester;

1,1-dimethylethyl[2-[[2-(diethylamino)-1S-[(4-hydroxy-3,5-diiodophenyl)methyl]-2-oxoethyl]amino]-5-methyl-4-oxo-4H-3,1-benzoxazin-6-yl]carbamate;

1,1-dimethylethyl[2-[[2-(diethylamino)-1S-methyl-2-oxoethyl]amino]-5-methyl-4-oxo-4H-3,1-benzoxazin-6-yl]carbamate;

1,1-dimethylethyl[2-[[2-(diethylamino)-1S-[(3,5-diiodo-4-methoxyphenyl)methyl]-2-oxoethyl]amino]-5-methyl-4-oxo-4H-3,1-benzoxazin-6-yl]carbamate;

1,1-dimethylethyl[2-[[1S[(3,5-diiodo-4-methoxy phenyl)methyl]-2-[(1-methylethyl)amino]-2-oxo ethyl]amino]-5-methyl-4-oxo-4H-3,1-benzoxazin-6-yl]carbamate;

1,1-dimethylethyl[2-[[1S-[(4-hydroxy-3,5-diiodo phenyl)methyl]-2-[[2-(dimethylamino)ethyl]methyl aminol-2-oxoethyl]amino]-5-methyl-4-oxo-4H-3,1-benzoxazin-6-yl]carbamate;

1,1-dimethylethyl[2-[[2-[[2-(dimethylamino)ethyl]methylamino]-1S-methyl-2-oxoethyl]amino]-5-methyl-4-oxo-4H-3,1-benzoxazin-6-yl]carbamate;

1,1-dimethylethyl[2-[[2-[[2-(dimethylamino)ethyl]methylamino]-1,1-dimethyl-2-oxoethyl]amino]-5-methyl-4-oxo-4H-3,1-benzoxazin-6-yl]carbamate;

1,1-dimethylethyl[2-[[1S[[[2-(dimethylamino)ethyl]methylamino]carbonyl]-3-(methylsulfonyl)propyl]amino]-5-methyl-4-oxo-4H-3,1-benzoxazin-6-yl]carbamate;

1,1-dimethylethyl[2-[[1S[(3,5-diiodo-4-methoxy phenyl)methyl]-2-[methyl[2-(1-piperidinyl)ethyl]amino]-2-oxoethyl]amino]-5-methyl-4-oxo-4H-3,1-benzoxazin-6-yl]carbamate;

1,1-dimethylethyl[2-[[1S-methyl-2-(1-piperidinyl)ethyl]amino]-2-oxoethyl]amino]-5-methyl-4-oxo-4H-3,1-benzoxazin-6-yl]carbamate;

1,1-dimethylethyl[2-[[1S-[[methyl-[2-(1-piperidinyl)ethyl]amino]carbonyl]-3-(methylsulfonyl)propyl]amino]-5-methyl-4-oxo-4H-3,1-benzoxazin-6-yl]carbamate;

1,1-dimethylethyl[2-[[1S-[3,5-diiodo-4-methoxy phenyl)methyl]-2-[methyl[2-(4-morpholinyl)ethyl]amino]-2-oxoethyl]amino]-5-methyl-4-oxo-4H-3,1-benzoxazin-6-yl]carbamate;

1,1-dimethylethyl[2-[[1S-[[methyl-[2-(4-morpholinyl)ethyl]amino]carbonyl]-3-(methylsulfonyl)propyl]amino]-5-methyl-4-oxo-4H-3,1-benzoxazin-6-yl]carbamate;

1,1-dimethylethyl[5-methyl-2-[[1S-methyl-2-[methyl-[2-(4-methylpiperazin-1-yl)ethyl]amino]-2-oxoethyl]amino]-4-oxo-4H-3,1-benzoxazin-6-yl]carbamate;

1,1-dimethylethyl[5-methyl-2-[[1S-methyl-2-[methyl-[2-(4-methylpiperazin-1-yl)ethyl]amino]carbonyl]-3-(methylsulfonyl)propyl]amino]-4-oxo-4H-3,1-benzoxazin-6-yl]carbamate;

methyl αS-[[6-[[1,1-dimethylethoxy)carbonyl]amino]-5-methyl-4-oxo-4H-3,1-benzoxazin-2-yl]amino]morpholine-4-butanoate;

methyl αS-[[6-[[(1,1-dimethylethoxy)carbonyl]amino]-5-methyl-4-oxo-4H-3,1-benzoxazin-2-yl]amino]pyrrolidine-1-butanoate;

N-[2-(dimethylamino)ethyl]-αS-[[6-[[(ethylamino)carbonyl]amino]-5-methyl-4-oxo-4H-3,1-benzoxazin-2-yl]amino]-3,5-diiodo-4-methoxy-N-methylbenzenepropanamide;

N-[2-dimethylamino)ethyl]-αS-[[6-[[ethyl amino)carbonyl]amino-5-methyl-4-oxo-4H-3,1-benzoxazin-2-yl]amino]-N-methylpropanamide;

N-[2-(dimethylamino)ethyl]-3,5-diiodo-4-methoxy-N-methyl-αS[[5-methyl-4-oxo-6-[(propylsulfonyl)amino]-4H-3,1-benzoxazin-2-yl]amino]-N-methylpropanamide;

N-[6-[[[(1,1-dimethylethoxy)carbonyl]amino]methyl]-5-methyl-4-oxo-4H-3,1-benzoxazin-2-yl]-3,5-diiodo-O-methyl-L-tyrosine, methyl ester;

methyl αS-[6-[[[(1,1-dimethylethoxy)carbonyl]amino]methyl]-5-methyl-4-oxo-4H-3,1-benzoxazin-2-yl]amino]thiazole-4-propanoate;

$N^2$-[6-[[[(1,1-dimethylethoxy)carbonyl]amino]methyl]-5-methyl-4-oxo-4H-3,1-benzoxazin-2-yl]-L-asparagine, methyl ester;

1,1-dimethylethyl[[2-[[1S-[3,5-diiodo-4-methoxy phenyl)methyl]-2-[[2-(dimethylamino)ethyl]methyl amino]-2-oxoethyl]amino]-5-methyl-4-oxo-4H-3,1-benzoxazin-6-yl]methyl]carbamate;

1,1-dimethylethyl[[2-[[2-[[2-(dimethylamino)ethyl]methylamino]-1S-methyl-2-oxoethyl]amino]-5-methyl-4-oxo-4H-3,1-benzoxazin-6-yl]methyl]carbamate;

1,1-dimethylethyl[[2-[[1S-[[2-(dimethylamino)ethyl]methylamino]carbonyl]-3-(methylsulfonyl)propyl]amino]-5-methyl-4-oxo-4H-3,1-benzoxazin-6-yl]methyl]carbamate;

1,1-dimethylethyl[[5-methyl-2-[[1S-methyl-2-[methyl[2-(1-piperidiny)ethyl]amino]-2-oxoethyl]-amino]-4-oxo-4H-3,1-benzoxazin-6-yl]methyl]carbamate;

1,1-dimethylethyl[[5-methyl-2-[[1S-[[methyl-[2-(4-morpholinyl)ethyl]amino]carbonyl]-3-(methyl sulfonyl)propyl]amino]-4-oxo-4H-3,1-benzoxazin-6-yl]methyl]carbamate;

1,1-dimethylethyl[[5-methyl-2-[[1S-methyl-[2-(4-methyl-1-piperazinyl)ethyl]amino]-2-oxoethyl]amino]-4-oxo-4H-3,1-benzoxazin-6-yl]methyl]carbamate;

N-(6-bromo-5-methyl-4-oxo-4H-3,1-benzoxazin-2-yl)-L-alanine, 1,1-dimethylethyl ester;

N-(6-bromo-5-methyl-4-oxo-4H-3,1-benzoxazin-2-yl)-D-alanine, 1,1-dimethylethyl ester;

N-[6-[[(1,1-dimethylethoxy)carbonyl]amino]-5-methyl-4-oxo-4H-3,1-benzoxazin-2-yl]-L-alanine, 1,1-dimethylethyl ester;

N-[6-[[(1,1-dimethylethoxy)carbonyl]amino]-5-methyl-4-oxo-4H-3,1-benzoxazin-2-yl]-L-phenylalanine, methyl ester;

N-[6-[[(1,1-dimethylethoxy)carbonyl]amino]-5-methyl-4-oxo-4H-3,1-benzoxazin-2-yl]-O-(phenylmethyl)-L-serine, methyl ester;

N-[6-[[(1,1-dimethylethoxy)carbonyl]amino]-5-methyl-4-oxo-4H-3,1-benzoxazin-2yyl]-O-methyl-L-tyrosine, methyl ester;

N-[6-[[(1,1-dimethylethoxy)carbonyl]amino]-5-methyl-4-oxo-4H-3,1-benzoxazin-2-yl]-O-methyl-L-tyrosine, dimethylamide;

N-[6-[[(1,1-dimethylethoxy)carbonyl]amino]-5-methyl-4-oxo-4H-3,1-benzoxazin-2-yl]-L-thiazol-4-yl-alanine, methyl ester;

N-[6-[[(1,1-dimethylethoxy)carbonyl]amino]-5-methyl-4-oxo-4H-3,1-benzoxazin-2-yl]-L-aspartic acid, alpha-methyl ester beta-dimethylamide;

N-[6-[[(1,1-dimethylethoxy)carbonyl]amino]-5-methyl-4-oxo-4H-3,1-benzoxazin-2-yl]-O-methyl-L-tyrosine, N-methyl-N-[2-(1-morpholinyl)ethyl]amide;

N-[6-[[(1,1-dimethylethoxy)carbonyl]amino]-5-methyl-4-oxo-4H-3,1-benzoxazin-2-yl]-O-methyl-L-tyrosine, N-methyl-N-[2-(1-piperidinyl)ethyl]amide;

N-[6-[[(1,1-dimethylethoxy)carbonyl]amino]-5-methyl-4-oxo-4H-3,1-benzoxazin-2-yl]-L-tryptophan, dimethylamide;

N-[6-[[(1,1-dimethylethoxy)carbonyl]amino]-5-methyl-4-oxo-4H-3,1-benzoxazin-2-yl]-O-methyl-L-threonine, methyl ester;

N-[6-[[(1,1-dimethylethoxy)carbonyl]amino]-5-methyl-4-oxo-4H-3,1-benzoxazin-2-yl]-O-methyl-L-serine, methyl ester;

N-[6-[[(1,1-dimethylethoxy) carbonyl]amino]-5-methyl-4-oxo-4H-3,1-benzoxazin-2-yl]-L-phenylglycine, 1,1-dimethylethyl ester;

N-[6-[[(1,1-dimethylethoxy)carbonyl]amino]-5-methyl-4-oxo-4H-3,1-benzoxazin-2-yl]-3,5-diiodo-O-methyl-L-tyrosine, methyl ester;

N-[6-[[(1,1-dimethylethoxy)carbonyl]amino]-5-methyl-4-oxo-4H-3,1-benzoxazin-2-yl]-4-iodo-L-phenylalanine, methyl ester;

N-[6-[[(1,1-dimethylethoxy)carbonyl]amino]-5-methyl-4-oxo-4H-3,1-benzoxazin-2-yl]-L-methionine sulfone, methyl ester;

N-[6-[[(1,1-dimethylethoxy)carbonyl]amino]-5-methyl-4-oxo-4H-3,1-benzoxazin-2-yl]-L-beta-naphthylalanine, methyl ester;

N-[6-[[(1,1-dimethylethoxy)carbonyl]amino]-5-methyl-4-oxo-4H-3,1-benzoxazin-2-yl]-2-aminoisobutyric acid, methyl ester;

N-[6-[[(1,1-dimethylethoxy)carbonyl]amino]-5-methyl-4-oxo-4H-3,1-benzoxazin-2-yl]-1-cyclopropanecarboxylic acid, methyl ester;

N-[6-[[(1,1-dimethylethoxy)carbonyl]amino]-5-methyl-4-oxo-4H-3,1-benzoxazin-2-yl]-L-alanine, N-methyl-N-allylamide;

N-[6-[[(1,1-dimethylethoxy)carbonyl]amino]-5-methyl-4-oxo-4H-3,1-benzoxazin-2-yl]-L-alanine, N-methyl-N-phenylmethylamide;

N-[6[[(1,1-dimethylethoxy)carbonyl]amino]-5-methyl-4-oxo-4H-3,1-benzoxazin-2-yl]-L-alanine, phenyl methyl ester;

N-[6-[[(1,1-dimethylethoxy)carbonyl]amino]-5-methyl-4-oxo-4H-3,1-benzoxazin-2-yl]-3,5-diiodo-L-tyrosine, methyl ester;

N-[6-[[[(1,1-dimethylethoxy)carbonyl]amino]methyl]-5-methyl-4-oxo-4H-3,1-benzoxazin-2-yl]-L-alanine, dimethylamide;

N-[6-[[[(1,1-dimethylethoxy)carbonyl]amino]methyl]-5-methyl-4-oxo-4H-3,1-benzoxazin-2-yl]-O-methyl-L-tyrosine, dimethylamide;

N-[6-[[[(1,1-dimethylethoxy)carbonyl]amino]methyl]-5-methyl-4-oxo-4H-3,1-benzoxazin-2-yl]-L-alanine, methyl ester;

N-[6-amino-5-methyl-4-oxo-4H-3,1-benzoxazin-2-yl]-L-alanine, methyl ester;

N-[6-amino-5-methyl-4-oxo-4H-3,1-benzoxazin-2-yl]-1-phenylalanine, methyl ester;

N-[[6-(dimethylaminomethyl)carbonyl]amino]-5-methyl-4-oxo-4H-3,1-benzoxazin-2-yl]-L-alanine, methyl ester;

5-methyl-N-6-[[(2-pyridyl)carbonyl]amino]-4-oxo-4H-3,1-benzoxazin-2-yl]-L-alanine, methyl ester;

N-[6-[[(5-isoxazolyl)carbonyl]amino]-5-methyl-4-oxo-4H-3,1-benzoxazin-2-yl]-L-alanine, methyl ester;

N-[6-[[(methoxymethyl)carbonyl]amino]-5-methyl-4-oxo-4H-3,1-benzoxazin-2-yl]-L-alanine, methyl ester;

N-[6-[[(methoxymethyl)carbonyl]amino]-5-methyl-4-oxo-4H-3,1-benzoxazin-2-yl]-L-phenylalanine, methyl ester;

N-[6-[[(2-carboxyethyl)carbonyl]amino]-5-methyl-4-oxo-4H-3,1-benzoxazin-2-yl]-L-phenylalanine, methyl ester;

N-[6-[[(cyclobutyl)carbonyl]amino]-5-methyl-4-oxo-4H-3,1-benzoxazin-2-yl]-L-phenylalanine, methyl ester;

N-[6-[[(2-furanyl)carbonyl]amino]-5-methyl-4-oxo-4H-3,1-benzoxazin-2-yl]-L-phenylalanine, methyl ester;

N-[6-[[(2-thienylmethyl)carbonyl]amino]-5-methyl-4-oxo-4H-3,1-benzoxazin-2-yl]-L-phenylalanine, methyl ester;

N-[6-[[[[2-(2-thienyl)ethyl]amino]carbonyl]amino]-5-methyl-4-oxo-4H-3,1-benzoxazin-2-yl]-L-phenylalanine, methyl ester;

N-[6-[[[[2-(2-thienyl)ethyl]amino]carbonyl]amino]-5-methyl-4-oxo-4H-3,1-benzoxazin-2-yl]-L-alanine, methyl ester;

N-[6-[benzenesulfonyl]amino]-5-methyl-4-oxo-4H-3,1-benzoxazin-2-yl]-L-phenylalanine, methyl ester;

N-[6-[benzenesulfonyl]amino]-5-methyl-4-oxo-4H-3,1-benzoxazin-2-yl]-L-alanine, methyl ester; and N-[6-[[(1,1-dimethylethoxy)carbonyl]amino]-5-methyl-4-oxo-4H-3,1-benzoxazin-2-yl]-L-alanine.

30. A method of inhibiting a herpes viral protease in a subject infected with a herpes virus having said protease, said method comprising treating said subject with an effective amount of a compound of Formula II

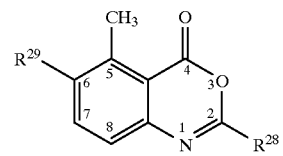

II wherein $R^{28}$ is selected from (a) amino substituted with one or two radicals selected from alkyl, aralkyl, heterocycoalkyl, heterocyclo, and aryl, and (b) amino acid residues and amide or ester derivatives thereof;

wherein $R^{29}$ is selected from alkyl,

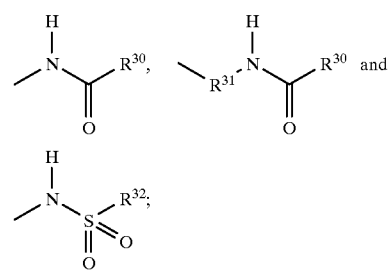

wherein $R^{30}$ is selected from alkyl, alkoxy, alkylamino, carboxyalkyl, alkoxyalkyl, alkylaminoalkyl, cycloalkyl, heterocyclo, heterocycloalkyl, heterocycloalkoxy, alkylaminoalkoxy, alkylaminoalkylamino, heterocycloalkylamino, and N-aralkylamino;

wherein $R^{31}$ is alkylene;

wherein $R^{32}$ is alkyl and aryl;

or a pharmaceutically-acceptable salt thereof.

31. The method of claim 30 wherein $R^{28}$ is selected from (a) amino substituted with one or two radicals selected from lower alkyl, lower aralkyl, lower heterocycoalkyl, heterocyclo, and aryl, and (b) amino acid residues and amide or ester derivatives thereof; wherein $R^{29}$ is selected from lower alkyl,

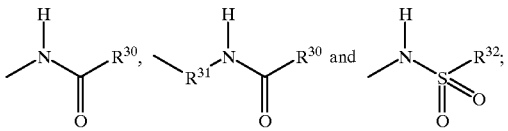

wherein $R^{30}$ is selected from lower alkyl, lower alkoxy, lower alkylamino, lower carboxyalkyl, lower alkoxyalkyl, lower alkylaminoalkyl, lower cycloalkyl, heterocyclo, lower heterocycloalkyl, lower heterocycloalkoxy, lower alkylaminoalkoxy, lower alkylaminoalkylamino, lower heterocycloalkylamino, and lower N-aralkylamino; wherein $R^{31}$ is lower alkyl; wherein $R^{32}$ is lower alkyl and aryl; or a pharmaceutically-acceptable salt thereof.

* * * * *